(12) United States Patent
Honda et al.

(10) Patent No.: US 10,835,559 B2
(45) Date of Patent: Nov. 17, 2020

(54) HUMAN-DERIVED BACTERIA THAT INDUCE PROLIFERATION OR ACCUMULATION OF REGULATORY T CELLS

(71) Applicants: The University of Tokyo, Tokyo (JP); School Corporation, Azabu Veterinary Medicine Educational Institution, Sagamihara-shi, Kanagawa (JP)

(72) Inventors: Kenya Honda, Tokyo (JP); Koji Atarashi, Tokyo (JP); Takeshi Tanoue, Tokyo (JP); Masahira Hattori, Tokyo (JP); Hidetoshi Morita, Sagamihara (JP)

(73) Assignees: The University of Tokyo, Tokyo (JP); School Corporation, Azabu Veterinary Medicine Educational Institution, Sagamihara (JP)

(*) Notice: Subject to any disclaimer, the term of this patent is extended or adjusted under 35 U.S.C. 154(b) by 0 days.

(21) Appl. No.: 16/170,344

(22) Filed: Oct. 25, 2018

(65) Prior Publication Data
US 2019/0046591 A1 Feb. 14, 2019

Related U.S. Application Data

(63) Continuation of application No. 14/362,097, filed as application No. PCT/JP2012/007687 on Nov. 29, 2012, now Pat. No. 10,238,694.

(60) Provisional application No. 61/607,360, filed on Mar. 6, 2012, provisional application No. 61/565,976, filed on Dec. 1, 2011.

(51) Int. Cl.
| | |
|---|---|
| *A61K 35/74* | (2015.01) |
| *C12N 1/20* | (2006.01) |
| *C12Q 1/689* | (2018.01) |
| *A61K 9/00* | (2006.01) |
| *C12R 1/145* | (2006.01) |
| *A61K 35/741* | (2015.01) |
| *A61K 35/742* | (2015.01) |
| *A61K 45/06* | (2006.01) |
| *C12Q 1/04* | (2006.01) |
| *A61K 35/745* | (2015.01) |
| *A61K 35/747* | (2015.01) |
| *A61K 35/00* | (2006.01) |

(52) U.S. Cl.
CPC .......... *A61K 35/74* (2013.01); *A61K 9/0053* (2013.01); *A61K 35/741* (2013.01); *A61K 35/742* (2013.01); *A61K 35/745* (2013.01); *A61K 35/747* (2013.01); *A61K 45/06* (2013.01); *C12N 1/20* (2013.01); *C12Q 1/04* (2013.01); *C12Q 1/689* (2013.01); *C12R 1/145* (2013.01); *A61K 2035/11* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,576,936 A | 3/1986 | MacDonald | |
| 5,599,795 A | 2/1997 | McCann et al. | |
| 5,700,787 A | 12/1997 | Tzianabos et al. | |
| 6,348,452 B1 | 2/2002 | Brown et al. | |
| 6,551,632 B2 | 4/2003 | Borody | |
| 6,645,530 B1 | 11/2003 | Borody | |
| 7,629,330 B2 | 12/2009 | Wang et al. | |
| 7,749,494 B2 | 7/2010 | Renaud et al. | |
| 8,586,029 B2 | 11/2013 | Kasper et al. | |
| 8,906,668 B2 * | 12/2014 | Henn | A61K 38/13 435/252.4 |
| 9,011,834 B1 | 4/2015 | McKenzie et al. | |
| 9,028,841 B2 * | 5/2015 | Henn | A61K 38/13 424/247.1 |
| 9,180,147 B2 | 11/2015 | McKenzie et al. | |
| 9,328,324 B2 | 5/2016 | Mitragotri | |
| 9,415,079 B2 * | 8/2016 | Honda | A61K 45/06 |
| 9,421,230 B2 * | 8/2016 | Honda | A61K 45/06 |
| 9,433,652 B2 * | 9/2016 | Honda | A61K 45/06 |
| 9,446,080 B2 | 9/2016 | McKenzie et al. | |
| 9,533,014 B2 * | 1/2017 | Henn | A61K 38/13 |
| 9,585,921 B2 | 3/2017 | McKenzie et al. | |
| 9,603,878 B2 | 3/2017 | Berry et al. | |
| 9,610,307 B2 * | 4/2017 | Berry | A61K 9/0031 |
| 9,642,281 B1 | 5/2017 | Chen | |
| 9,642,881 B2 * | 5/2017 | Honda | A61K 35/74 |

(Continued)

FOREIGN PATENT DOCUMENTS

| | | |
|---|---|---|
| CA | 2850000 A1 | 4/2013 |
| CN | 101310730 A | 11/2008 |

(Continued)

OTHER PUBLICATIONS

Hayashi et al, Microbiology and Immunology, 2002, 46/8:535-548 (Year: 2002).*

(Continued)

*Primary Examiner* — Nita M. Minnifield

(74) *Attorney, Agent, or Firm* — Wolf, Greenfield & Sacks, P.C.

(57) ABSTRACT

Species of human-derived bacteria belonging to the Clostridia class have been shown to induce accumulation of regulatory T cells (Treg cells) in the colon and suppress immune functions. Pharmaceutical compositions containing these bacteria can be used to prevent and treat immune-mediated diseases such as autoimmune diseases.

15 Claims, 22 Drawing Sheets

Specification includes a Sequence Listing.

(56) References Cited

U.S. PATENT DOCUMENTS

| | | | |
|---|---|---|---|
| 9,642,882 B2* | 5/2017 | Honda | A61K 45/06 |
| 9,649,345 B2* | 5/2017 | Honda | A61K 35/74 |
| 9,662,381 B2* | 5/2017 | Honda | A61K 45/06 |
| 9,764,019 B2 | 9/2017 | Honda et al. | |
| 9,801,933 B2* | 10/2017 | Honda | A61K 45/06 |
| 9,808,519 B2* | 11/2017 | Honda | A61K 45/06 |
| 9,827,276 B2* | 11/2017 | Honda | A61K 45/06 |
| 9,833,483 B2* | 12/2017 | Honda | A61K 45/06 |
| 9,848,853 B2 | 12/2017 | Mitragotri et al. | |
| 9,855,303 B2 | 1/2018 | McKenzie et al. | |
| 9,987,311 B2 | 6/2018 | Mulder et al. | |
| 9,987,312 B2 | 6/2018 | Miyamoto et al. | |
| 9,999,641 B2 | 6/2018 | Schneider et al. | |
| 10,052,353 B2* | 8/2018 | Honda | A61K 35/74 |
| 10,058,578 B2* | 8/2018 | Honda | A61K 35/74 |
| 10,064,900 B2 | 9/2018 | Von Maltzahn et al. | |
| 10,064,901 B2 | 9/2018 | McKenzie et al. | |
| 10,064,904 B2 | 9/2018 | Schneider et al. | |
| 10,076,546 B2 | 9/2018 | Henn et al. | |
| 10,092,603 B2* | 10/2018 | Honda | A61K 35/74 |
| 10,130,695 B2* | 11/2018 | Honda | A61K 38/164 |
| 10,183,045 B2* | 1/2019 | Honda | A61K 35/742 |
| 10,238,694 B2* | 3/2019 | Honda | A61P 31/00 |
| 10,300,137 B2 | 5/2019 | Honda et al. | |
| 10,322,150 B2* | 6/2019 | Honda | A61K 35/17 |
| 10,328,108 B2* | 6/2019 | Honda | A61P 1/12 |
| 10,342,097 B2* | 7/2019 | Kawamata | H05B 47/19 |
| 10,342,832 B2* | 7/2019 | Honda | C12Q 1/689 |
| 10,555,978 B2* | 2/2020 | Honda | A61P 25/00 |
| 10,576,136 B2* | 3/2020 | Honda | A61K 35/742 |
| 10,588,925 B2* | 3/2020 | Honda | A61P 31/04 |
| 10,624,933 B2* | 4/2020 | Honda | A61P 37/06 |
| 10,695,412 B2* | 6/2020 | Honda | A61K 39/114 |
| 2003/0113306 A1 | 6/2003 | Collins et al. | |
| 2004/0028689 A1 | 2/2004 | Borody | |
| 2004/0170617 A1 | 9/2004 | Finegold | |
| 2004/0219160 A1 | 11/2004 | Tzianabos et al. | |
| 2006/0067924 A1 | 3/2006 | Lee et al. | |
| 2006/0240482 A1 | 10/2006 | Kwok et al. | |
| 2007/0258953 A1 | 11/2007 | Duncan et al. | |
| 2008/0003207 A1 | 1/2008 | Cui | |
| 2008/0305089 A1 | 12/2008 | Bufe et al. | |
| 2008/0311080 A1 | 12/2008 | Collins et al. | |
| 2009/0124573 A1 | 5/2009 | Mazmanian et al. | |
| 2009/0317427 A1 | 12/2009 | Kasper et al. | |
| 2010/0119488 A1 | 5/2010 | Huber-Haag et al. | |
| 2010/0275282 A1 | 10/2010 | Round et al. | |
| 2011/0009360 A1 | 1/2011 | Kasper et al. | |
| 2012/0020941 A1 | 1/2012 | Wacklin et al. | |
| 2012/0027734 A1 | 2/2012 | Van Immerseel et al. | |
| 2012/0276149 A1 | 11/2012 | Littman et al. | |
| 2012/0279149 A1* | 11/2012 | Quinn | E06B 9/02 52/173.1 |
| 2013/0149339 A1* | 6/2013 | Honda | A61K 45/06 424/247.1 |
| 2014/0147425 A1* | 5/2014 | Henn | A61K 38/13 424/93.41 |
| 2014/0171339 A1* | 6/2014 | Keku | G01N 33/57419 506/9 |
| 2014/0199281 A1 | 7/2014 | Henn et al. | |
| 2014/0341921 A1* | 11/2014 | Honda | A61K 35/74 424/141.1 |
| 2015/0143557 A1 | 5/2015 | Honda et al. | |
| 2015/0190435 A1 | 7/2015 | Henn et al. | |
| 2015/0224152 A1 | 8/2015 | Littman et al. | |
| 2015/0297642 A1* | 10/2015 | Borody | A61K 35/38 424/487 |
| 2015/0320805 A9 | 11/2015 | Honda et al. | |
| 2016/0040215 A1 | 2/2016 | Henn et al. | |
| 2016/0143960 A1 | 5/2016 | Honda et al. | |
| 2016/0143962 A1 | 5/2016 | Berry et al. | |
| 2016/0144014 A1 | 5/2016 | Honda et al. | |
| 2016/0151430 A1* | 6/2016 | Honda | A61K 45/06 424/93.41 |
| 2016/0158294 A1 | 6/2016 | Von Maltzahn et al. | |
| 2016/0193256 A1* | 7/2016 | Honda | A61K 35/74 424/93.3 |
| 2016/0193257 A1* | 7/2016 | Honda | A61K 35/74 424/93.4 |
| 2016/0199423 A1* | 7/2016 | McKenzie | A61K 35/74 424/93.4 |
| 2016/0199424 A1* | 7/2016 | Berry | A61K 9/0031 424/93.3 |
| 2016/0235792 A1* | 8/2016 | Berry | A61K 9/0031 |
| 2016/0243172 A1* | 8/2016 | Cook | A61K 35/74 |
| 2016/0271188 A1* | 9/2016 | Berry | A61K 9/0031 |
| 2016/0279177 A1* | 9/2016 | Kelly | A61K 35/741 |
| 2017/0007691 A1 | 1/2017 | Riken et al. | |
| 2017/0028061 A1* | 2/2017 | Honda | A61K 39/39 |
| 2017/0087197 A1* | 3/2017 | Honda | A61K 45/06 |
| 2017/0105977 A1* | 4/2017 | Golden | A61K 31/437 |
| 2017/0112915 A1* | 4/2017 | Honda | A61K 45/06 |
| 2017/0142775 A1 | 5/2017 | Kanesalingam et al. | |
| 2017/0143775 A1 | 5/2017 | Mulder et al. | |
| 2017/0165302 A1 | 6/2017 | Henn et al. | |
| 2017/0209502 A1 | 7/2017 | Honda et al. | |
| 2017/0216378 A1 | 8/2017 | Honda et al. | |
| 2017/0232044 A1 | 8/2017 | Honda et al. | |
| 2017/0232045 A1 | 8/2017 | Honda et al. | |
| 2017/0246283 A1 | 8/2017 | Honda et al. | |
| 2017/0354697 A1 | 12/2017 | Schneider et al. | |
| 2018/0000921 A1 | 1/2018 | Honda et al. | |
| 2018/0015130 A1 | 1/2018 | Berry et al. | |
| 2018/0153981 A1 | 6/2018 | Honda et al. | |
| 2018/0169157 A1 | 6/2018 | Schneider et al. | |
| 2018/0243348 A1* | 8/2018 | Honda | A61K 35/74 |
| 2018/0250346 A1 | 9/2018 | Mulder et al. | |
| 2018/0264056 A1 | 9/2018 | Schneider et al. | |
| 2019/0030092 A1 | 1/2019 | Honda et al. | |
| 2019/0030093 A1 | 1/2019 | Honda et al. | |
| 2019/0030098 A1 | 1/2019 | Schneider et al. | |
| 2019/0046591 A1* | 2/2019 | Honda | A61K 35/74 |
| 2019/0046592 A1 | 2/2019 | Honda et al. | |
| 2019/0134179 A1 | 5/2019 | Honda et al. | |
| 2019/0282634 A1 | 9/2019 | Honda et al. | |
| 2019/0282635 A1 | 9/2019 | Honda et al. | |
| 2019/0314426 A1* | 10/2019 | Honda | C12N 1/20 |

FOREIGN PATENT DOCUMENTS

| | | | |
|---|---|---|---|
| CN | 101496819 A | 8/2009 | |
| CN | 103079582 A | 5/2013 | |
| DE | 102006062250 A1 | 6/2008 | |
| EP | 1749538 A1 | 2/2007 | |
| EP | 1955706 A1 | 8/2008 | |
| EP | 2 823 822 A1 | 10/2016 | |
| JP | 2001-112485 A | 4/2001 | |
| JP | 2005-124495 A | 5/2005 | |
| JP | 2009-084215 A | 4/2009 | |
| JP | 2010-129134 | 6/2010 | |
| JP | 5592958 B2 | 8/2014 | |
| KR | 10-0913405 B1 | 8/2009 | |
| WO | WO 2002/007741 A1 | 1/2002 | |
| WO | WO 2009/050486 A2 | 4/2009 | |
| WO | WO 2009/149149 A1 | 12/2009 | |
| WO | WO 2011/005756 A1 | 1/2011 | |
| WO | WO 2011/022542 A2 | 2/2011 | |
| WO | WO 2011/022660 A1 | 2/2011 | |
| WO | WO 2011/027990 A2 | 3/2011 | |
| WO | WO-2011027990 A2 * | 3/2011 | C12P 1/04 |
| WO | WO 2011/151941 A1 | 12/2011 | |
| WO | WO 2011/152566 A2 | 12/2011 | |
| WO | WO-2011151941 A1 * | 12/2011 | A61K 35/74 |
| WO | WO 2012/013861 A2 | 2/2012 | |
| WO | WO 2012/062951 A1 | 5/2012 | |
| WO | WO 2013/080561 A1 | 6/2013 | |
| WO | WO-2013080561 A1 * | 6/2013 | A61K 35/74 |
| WO | WO 2015/156419 A1 | 10/2015 | |
| WO | WO-2015156419 A1 * | 10/2015 | A61K 39/39 |
| WO | WO 2016/194427 A1 | 12/2016 | |

(56) References Cited

FOREIGN PATENT DOCUMENTS

| WO | WO-2016194427 A1 * | 12/2016 | ............. A61P 31/04 |
| WO | WO-2018084172 A1 * | 5/2018 | |
| WO | WO 2019/032572 A1 | 2/2019 | |

OTHER PUBLICATIONS

Ellis et al JAIDS, 2011, 57/5:363-370 (Year: 2011).*
Tanoue et al, Inflammation and Regeneration, 2015, 35/3:99-105 (Year: 2015).*
Favier et al, Anaerobe, 2003, 9:219-229 (Year: 2003).*
Hattori et al, Kagaku Ryoho no Ryoiki, 2011, 27/9:1989-1997, abstract only (Year: 2011).*
Hattori et al, Rinsho Kensa, 2011, 55/2:135-141, abstract only (Year: 2011).*
Hattori et al, Bunchi Shokakibyo, 2011, 8/2:116-121, abstract only (Year: 2011).*
Hattori et al, Bunshi Shokakibyo, 2012, 9/2:130-137, abstract only (Year: 2012).*
U.S. Appl. No. 16/117,054, filed Aug. 30, 2018, Honda et al.
U.S. Appl. No. 16/160,004, filed Oct. 15, 2018, Honda et al.
EP 12854485.5, Mar. 31, 2015, Partial European Search Report.
EP 12854485.5, Jul. 1, 2015, Extended European Search Report.
PCT/JP2012/007687, Jun. 12, 2014, International Preliminary Report on Patentability.
PCT/JP2012/007687, Feb. 12, 2013, International Search Report and Written Opinion.
PCT/JP2011/063302, Dec. 14, 2011, International Search Report.
PCT/JP2011/063302, Dec. 13, 2012, International Preliminary Report on Patentability.
EP 16188203.0, Apr. 26, 2017, Extended European Search Report.
[No Author Listed] Japanese Journal of Bacteriology. 2008;63(1): 166, 3-E-27/p. 43.
[No Author Listed] Ruminococcus. Microbe Wiki. Aug. 2010. Last accessed at https://microbewiki.kenyon.edu/index.php/Ruminococcus on Apr. 19, 2016.
Aas et al., Recurrent Clostridium difficile colitis: case series involving 18 patients treated with donor stool administered via a nasogastric tube. Clin Infect Dis. Mar. 1, 2003;36(5):580-5. Epub Feb. 14, 2003.
Abraham et al., Molecular mechanisms of IL-2 gene regulation following costimulation through LFA-1. J Immunol. Nov. 1, 2001;167(9):5193-201.
Abrams, Open-Label, Uncontrolled Trial of Bowel Sterilization and Repopulation With Normal Bowel Flora for Treatment of Inflammatory Bowel Disease. Current Therapeutic Research. Dec. 1997;58(12):1001-1012.
Andoh et al., Terminal restriction fragment polymorphism analyses of fecal microbiota in five siblings including two with ulcerative colitis. Clin J Gastroenterol. Oct. 2009;2(5):343-345. doi:10.1007/s12328-009-0106-8. Epub Sep. 19, 2009.
Andoh et al., Faecal microbiota profile of Crohn's disease determined by terminal restriction fragment length polymorphism analysis. Aliment Pharmacol Ther. Jan. 2009;29(1):75-82. doi: 10.1111/j.1365-2036.2008.03860.x. Epub Sep. 26, 2008.
Atarashi et al., ATP drives lamina propria T(H)17 cell differentiation. Nature. Oct. 9, 2008;455(7214):808-12. doi: 10.1038/nature07240. Epub Aug. 20, 2008.
Atarashi et al., Induction of Colonic Regulatory T Cells by Indigenous *Clostridium* Species *Science* 331 (2011) 337-341.
Atarashi et al., Induction of Colonic Regulatory T Cells by Indigenous *Clostridium* Species Science 331 (2011) 337-341. Supporting Online Material.
Atarashi et al., Microbiota in autoimmunity and tolerance. Curr Opin Immunol. Dec. 2011;23(6):761-8. doi: 10.1016/j.coi.2011.11.002. Epub Nov. 22, 2011.
Atarashi et al., Microbiotal influence on T cell subset development Seminars in Immunology. Apr. 4, 2011;23(2):146-153.
Atarashi et al., Regulation of colonic regulatory T cells by *Clostridium* species. Poster 064-03. Aug. 25, 2010.
Atarashi et al., Regulation of colonic regulatory T cells by *Clostridium* species. WS/PP-064-03 abstract. 14$^{Th}$ International Congress of Immunology. iii132. Aug. 25, 2010.
Atarashi et al., Treg induction by a rationally selected mixture of Clostridia strains from the human microbiota. Nature. Aug. 8, 2013;500(7461):232-6. doi: 10.1038/nature12331. Epub Jul. 10, 2013.
Autoimmune Disease List. American Autoimmune Related Diseases Association. 2017.
Bakken, Fecal bacteriotherapy for recurrent Clostridium difficile infection. Anaerobe. Dec. 2009;15(6):285-9. doi: 10.1016/j.anaerobe.2009.09.007. Epub Sep. 22, 2009.
Barnes et al., Regulatory T cells reinforce intestinal homeostasis. Immunity. Sep. 18, 2009;31(3):401-11. doi: 10.1016/j.immuni.2009.08.011.
Bassaganya-Riera et al., Punicic acid modulates mucosal immune responses and prevents gut inflammation through PPAR gamma and delta-dependent mechanisms. FASEB J. 2010; 24 (Meeting Abstract Supplement). Abstract.
Bassaganya-Riera et al., Soluble fibers and resistant starch ameliorate disease activity in an experimental model of inflammatory bowel disease. FASEB J. 2010; 24 (Meeting Abstract Supplement). Abstract.
Belkaid et al., Natural regulatory T cells in infectious disease. Nat Immunol. Apr. 2005;6(4):353-60.
Borody et al., Treatment of ulcerative colitis using fecal bacteriotherapy. J Clin Gastroenterol. Jul. 2003;37(1):42-7.
Bouskra et al., Lymphoid tissue genesis induced by commensals through NOD1 regulates intestinal homeostasis. Nature. Nov. 27, 2008;456(7221):507-10. doi: 10.1038/nature07450. Epub Nov. 5, 2008.
Browne et al., Culturing of 'unculturable' human microbiota reveals novel taxa and extensive sporulation. Nature. May 4, 2016. doi: 10.1038/nature17645.
Bueche et al., Quantification of endospore-forming firmicutes by quantitative PCR with the functional gene spo0A. Appl Environ Microbiol. Sep. 2013;79(17):5302-12. doi: 10.1128/AEM.01376-13. Epub Jun. 28, 2013.
Cai Miaoying et al, Names of Bacteria. The 2nd edition, Science Press, Jun. 1996, p. 179.
Cato et al., *Clostridium oroticum* Comb. Nov. Int. J. Syst. Bact. Jan. 1968;17(1):9-13.
Cebra, Influences of microbiota on intestinal immune system development. Am J Clin Nutr. May 1999;69(5):1046S-1051S.
Chandrasekaran et al., Clostridium difficile Toxin B blocks effector T cells proliferation by inhibiting PLD signaling. J. Immunol. Apr. 2010; 184(1): 49.19. Abstract.
Clavel et al., Survival of Bacillus cereus spores and vegetative cells in acid media simulating human stomach. J Appl Microbiol. 2004;97(1):214-9.
Collins et al., The phylogeny of the genus *Clostridium*: proposal of five new genera and eleven new species combinations. Int J Syst Bacteriol. Oct. 1994;44(4):812-26.
Curotto De Lafaille et al., Natural and adaptive foxp3+ regulatory T cells: more of the same or a division of labor? Immunity. May 2009;30(5):626-35. doi: 10.106/j.immuni.2009.05.002.
Dewhirst et al., Phylogeny of the defined murine microbiota: altered Schaedler flora. Appl Environ Microbiol. Aug. 1999;65(8):3287-92.
Di Giacinto et al., Probiotics ameliorate recurrent Th1-mediated murine colitis by inducing IL-10 and IL-10-dependent TGF-beta-bearing regulatory cells. J Immunol. Mar. 15, 2005;174(6):3237-46.
Eeckhaut et al. The anaerobic butyrate-producing strain Butyricicoccus pullicaecorum decreases colonic inflammation and ulceration in a TNBS-induced colitis rat model. In, 5th Probiotics, Prebiotics and New Foods Congress, Rome, Italy (2009).
Ellis et al., Molecular characterization of stool microbiota in HIV-infected subjects by panbacterial and order-level 16S ribosomal DNA (rDNA) quantification and correlations with immune activation. J Acquir Immune Defic Syndr. Aug. 15, 2011;57(5):363-70. doi: 10.1097/QAI.0b013e31821a603c.
European Office Action for Application No. 11 728 077.6, dated Sep. 18, 2015.
Favier et al., Development of bacterial and bifidobacterial communities in feces of newborn babies. Anaerobe. Oct. 2003;9(5):219-29.

(56) References Cited

OTHER PUBLICATIONS

Foditsch et al., Isolation and characterization of Faecalibacterium prausnitzii from calves and piglets. PLoS One. Dec. 31, 2014;9(12):e116465. doi: 10.1371/journal.pone.0116465. eCollection 2014.
Foligne et al., A key role of dendritic cells in probiotic functionality. PLoS One. Mar. 21, 2007;2(3):e313.
Foligne et al., Correlation between in vitro and in vivo immunomodulatory properties of lactic acid bacteria. World J Gastroenterol. Jan. 14, 2007;13(2):236-43.
Frank et al., Molecular-phylogenetic characterization of microbial community imbalances in human inflammatory bowel diseases. Proc Natl Acad Sci U S A. Aug. 21, 2007;104(34):13780-5. Epub Aug. 15, 2007.
Gaboriau-Routhiau et al., The key role of segmented filamentous bacteria in the coordinated maturation of gut helper T cell responses. Immunity. Oct. 16, 2009;31(4):677-89. doi: 10.1016/j.immuni.2009. 08.020.
Garrett et al., Communicable ulcerative colitis induced by T-bet deficiency in the innate immune system. Cell. Oct. 5, 2007;131(1):33-45.
Geuking et al., Intestinal bacterial colonization induces mutualistic regulatory T cell responses. Immunity. May 27, 2011;34(5):794-806. doi: 10.1016/j.immuni.2011.03.021. Epub May 19, 2011.
Grehan et al., Durable alteration of the colonic microbiota by the administration of donor fecal flora. J Clin Gastroenterol. Sep. 2010;44(8):551-61. doi: 10.1097/MCG.0b013e3181e5d06b.
Hart et al., Modulation of human dendritic cell phenotype and function by probiotic bacteria. Gut. Nov. 2004;53(11):1602-9.
Hata et al., Blood group B degrading activity of Ruminococcus gnavus alpha-galactosidase. Artif Cells Blood Substit Immobil Biotechnol. May 2004;32(2):263-74.
Hayashi et al., Fecal microbial diversity in a strict vegetarian as determined by molecular analysis and cultivation. Microbiol Immunol. 2002;46(12):819-31.
Hayashi et al., Phylogenetic analysis of the human gut microbiota using 16S rDNA clone libraries and strictly anaerobic culture-based methods. Microbiol Immunol. 2002;46(8):535-48.
Hazenberg et al., Effects of the human intestinal flora on germ-free mice. J Appl Bacteriol. Feb. 1981;50(1):95-106.
Honda et al., Regulation of T Cell Responses by Intestinal Commensal Bacteria. J Intestinal Microbiol. 2011;25(2):103-104.
ICI Wrap-Up Report. 14th International Congress of Immunology. Aug. 22-27, 2010.
Iizuka et al., Novel evidence suggesting Clostridium difficile is present in human gut microbiota more frequently than previously suspected. Microbiol Immunol. 2004;48(11):889-92.
International Statistical Classification of Diseases and Related Health Problems 10th Revision. WHO (ICD-10). 2016. Chapter 1. Certain infectious and parasitic diseases (A00-B99).
Itoh et al., Characterization of clostridia isolated from faeces of limited flora mice and their effect on caecal size when associated with germ-free mice. Lab Anim. Apr. 1985;19(2):111-8.
Itoh et al., Colonization resistance against Pseudomonas aeruginosa in gnotobiotic mice. Lab Anim. Jul. 1986;20(3):197-201.
Itoh et al., Intestinal bacteria antagonistic to Clostridium difficile in mice. Lab Anim. Jan. 1987;21(1):20-5.
Itoh et al., Production of gnotobiotic mice with normal physiological functions. I. Selection of useful bacteria from feces of conventional mice. Z Versuchstierkd. 1980;22(3):173-8.
Ivanov et al., Induction of intestinal Th17 cells by segmented filamentous bacteria. Cell. Oct. 30, 2009;139(3):485-98. doi: 10.1016/j.cell.2009.09.033.
Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom. 2008.09.009.
Janeway et al., Autoimmune responses are directed against self antigens. Immunobiology: The Immune System in Health and Disease. 5th edition. 2001. New York: Garland Science.
Janeway et al., Immunobiology: The Immune System in Health and Disease. 6th edition. 2005. Chapter 10. 414. Figure 10.4.
Jarry et al., Mucosal IL-10 and TGF-beta play crucial roles in preventing LPS-driven, IFN-gamma-mediated epithelial damage in human colon explants. J Clin Invest. Mar. 2008;118(3):1132-42.
Jawetz et al., Spore-forming gram-positive bacilli: *bacillus* and *clostridium* species. Medical Microbiology. Chapter 11. Nov. 2011.
Kakihana et al., Fecal microbiota transplantation for patients with steroid-resistant acute graft-versus-host disease of the gut. Blood. Oct. 20, 2016;128(16):2083-2088. doi: 10.1182/blood-2016-05-717652. Epub Jul. 26, 2016.
Kamanaka et al., Expression of interleukin-10 in intestinal lymphocytes detected by an interleukin-10 reporter knockin tiger mouse. Immunity. Dec. 2006;25(6):941-52. Epub Nov. 30, 2006.
Karimi et al., Lactobacillus reuteri-induced regulatory T cells protect against an allergic airway response in mice. Am J Respir Crit Care Med. Feb. 1, 2009;179(3):186-93. doi: 10.1164/rccm.200806-951OC. Epub Nov. 21, 2008.
Kelly et al., Commensal gut bacteria: mechanisms of immune modulation. Trends Immunol. Jun. 2005;26(6):326-33.
Keynan et al., The role of regulatory T cells in chronic and acute viral infections. Clin Infect Dis. Apr. 1, 2008;46(7):1046-52. doi: 10.1086/529379.
Khoruts et al., Changes in the composition of the human fecal microbiome after bacteriotherapy for recurrent Clostridium difficile-associated diarrhea. J Clin Gastroenterol. May-Jun. 2010;44(5):354-60. doi: 10.1097/MCG.0b013e3181c87e02.
Kita, Intestinal colonization and transmission of Clostridium difficile among students as a community. J Antibact Antifung Agents. 2004;32(3):105-113.
Krogius-Kurikka et al., Sequence analysis of percent G+C fraction libraries of human faecal bacterial DNA reveals a high number of Actinobacteria. BMC Microbiol. Apr. 8, 2009;9:68. doi: 10.1186/1471-2180-9-68.
Kwon et al., Generation of regulatory dendritic cells and CD4+ Foxp3+ T cells by probiotics administration suppresses immune disorders. Proc Natl Acad Sci U S A. Feb. 2, 2010;107(5):2159-64. doi: 10.1073/pnas.0904055107. Epub Jan. 13, 2010.
Latvala et al., Potentially probiotic bacteria induce efficient maturation but differential cytokine production in human monocyte-derived dendritic cells. World J Gastroenterol. Sep. 28, 2008;14(36):5570-83; discussion 5581-2.
Lau et al., Bacteraemia caused by Anaerotruncus colihominis and emended description of the species. J Clin Pathol. Jul. 2006;59(7):748-52. Epub Feb. 7, 2006.
Lawley et al., Targeted restoration of the intestinal microbiota with a simple, defined bacteriotherapy resolves relapsing Clostridium difficile disease in mice. PLoS Pathog. 2012;8(10):e1002995. doi: 10.1371/journal.ppat.1002995. Epub Oct. 25, 2012.
Lawson et al., Anaerotruncus colihominis gen. nov., sp. nov., from human faeces. Int J Syst Evol Microbiol. Mar. 2004;54(Pt 2):413-7.
Lawson, Anaerotruncus. Bergey's Manual of Systematics of Archaea and Bacteria. Sep. 14, 2015;1-4.
Li et al., Effect of oral feeding with Clostridium leptum on regulatory T-cell responses and allergic airway inflammation in mice. Ann Allergy Asthma Immunol. Sep. 2012;109(3):201-7. doi: 10.1016/j.anai.2012.06.017. Epub Jul. 17, 2012.
Li et al., Symbiotic gut microbes modulate human metabolic phenotypes. Proc Natl Acad Sci U S A. Feb. 12, 2008;105(6):2117-22. doi: 10.1073/pnas.0712038105.
Liu et al., Reclassification of *Clostridium coccoides*, *Ruminococcus hansenii*, *Ruminococcus hydrogenotrophicus*, *Ruminococcus luti*, *Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautai wexlerae* sp. nov., isolated from human faeces. Int J Syst Evol Microbiol. Aug. 2008;58(Pt 8):1896-902. doi: 10.1099/ijs.0.65208-0.
Livingston et al., Gut commensal Lactobacillus reuteri 100-23 stimulates an immunoregulatory response. Immunol Cell Biol. Jan. 2010;88(1):99-102. doi: 10.1038/icb.2009.71. Epub Sep. 29, 2009.

(56) References Cited

OTHER PUBLICATIONS

Lopetuso et al., Commensal Clostridia:leading players in the maintenance of gut homeostasis. Gut Pathog. Aug. 13, 2013;5(1):23. doi: 10.1186/1757-4749-5-23.
Louis et al., Diversity, metabolism and microbial ecology of butyrate-producing bacteria from the human large intestine. FEMS Microbiol Lett. May 2009;294(1):1-8. doi: 10.1111/j.1574-6968.2009.01514.x. Epub Feb. 13, 2009.
Lu et al., Molecular orchestration of differentiation and function of regulatory T cells. Genes Dev. Jun. 1, 2009;23(11):1270-82. doi:10.1101/gad.1791009.
MacPherson et al., Interactions between commensal intestinal bacteria and the immune system. Nat Rev Immunol. Jun. 2004;4(6):478-85.
Maizels et al., Regulatory T cells in infection. Adv Immunol. 2011;112:73-136. doi: 10.1016/B978-0-12-387827-4.00003-6.
Mandalari et al., In vitro evaluation of the prebiotic properties of almond skins (*Amygdalus communis* L.). FEMS Microbiol Lett. Mar. 2010;304(2):116-22. doi: 10.1111/j.1574-6968.2010.01898.x. Epub Jan. 11, 2010.
Mangin et al., Molecular inventory of faecal microflora in patients with Crohn's disease. FEMS Microbiol Ecol. Oct. 1, 2004;50(1):25-36. doi: 10.1016/j.femsec.2004.05.005.
Maslowski et al., Regulation of inflammatory responses by gut microbiota and chemoattractant receptor GPR43. Nature. Oct. 29, 2009;461(7268):1282-6. doi: 10.1038/nature08530.
Maynard et al., Regulatory T cells expressing interleukin 10 develop from Foxp3+ and Foxp3− precursor cells in the absence of interleukin 10. Nat Immunol. Sep. 2007;8(9):931-41. Epub Aug. 12, 2007.
Mazmanian et al., A microbial symbiosis factor prevents intestinal inflammatory disease. Nature. May 29, 2008;453(7195):620-5. doi:10.1038/nature07008.
Mazmanian, Gut immune balance is as easy as S-F-B. Immunity. Oct. 16, 2009;31(4):536-8. doi: 10.1016/j.immuni.2009.09.005.
Miquel et al., Faecalibacterium prausnitzii and human intestinal health. Curr Opin Microbiol. Jun. 2013;16(3):255-61. doi:10.1016/j.mib.2013.06.003. Epub Jul. 3, 2013. Review.
Miyake et al., Dysbiosis in the Gut Microbiota of Patients with Multiple Sclerosis, with a Striking Depletion of Species Belonging to Clostridia XIVa and IV Clusters. PLoS One. Sep. 14, 2015;10(9):e0137429. doi: 10.1371/journal.pone.0137429. eCollection 2015.
Momose et al., 16S rRNA gene sequence-based analysis of clostridia related to conversion of germfree mice to the normal state. J Appl Microbiol. Dec. 1, 2009;107(6):2088-97. doi:10.1111/j.1365-2672.2009.04431.x. Epub Jul. 15, 2009.
Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.
Office Action for Japanese application No. 2017-049543.
O'Garra et al., IL-10-producing and naturally occurring CD4+ Tregs: limiting collateral damage. J Clin Invest. Nov. 2004;114(10):1372-8.
Okada et al., Effects of fecal microorganisms and their chloroform-resistant variants derived from mice, rats, and humans on immunological and physiological characteristics of the intestines of ex-germfree mice. Infect Immun. Dec. 1994;62(12):5442-6.
O'Mahony et al., Commensal-induced regulatory T cells mediate protection against pathogen-stimulated NF-kappaB activation. PLoS Pathog. Aug. 1, 2008;4(8):e1000112. doi: 10.1371/journal.ppat.1000112.
Opposition against EP Patent 2 575 835 B1 dated Apr. 25, 2017. 35 pages. Seres Therapeutics.
Opposition against EP Patent 2 575 835 B1 dated Jul. 18, 2017. 23 pages. Strawman Limited.
Opposition against EP Patent 2 575 835 B1 dated Jul. 18, 2017. 4 pages. Mr. Lars Manke.
Opposition against EP Patent 2 575 835 B1 dated Jul. 19, 2017. 20 pages. Dr. Martin Grund.
Opposition against EP Patent 2 575 835 B1 dated Jul. 19, 2017. 27 pages. Müller Fottner Steineke Part mbB.
Opposition against EP Patent 2 575 835 B1. Seres Therapeutics, Inc. Annexure; dated May 25, 2018.
Opposition against EP Patent 2 575 835 B1. Summary of File History for Information; dated Jun. 7, 2018.
Opposition against EP Patent No. 2 575 835 B1 dated Jul. 19, 2017. 37 pages. Nestec S.A.
Paredes-Sabja et al., Clostridium difficile spore biology:sporulation, germination, and spore structural proteins. Trends Microbiol. Jul. 2014;22(7):406-16. doi: 10.1016/j.tim.2014.04.003. Epub May 7, 2014.
Qin et al., A human gut microbial gene catalogue established by metagenomic sequencing. Nature. Mar. 4, 2010;464(7285):59-65. doi: 10.1038/nature08821.
Qiu et al., C. Faecalibacterium prausnitzii upregulates regulatory T cells and anti-inflammatory cytokines in treating TNBS-induced colitis. J Crohns Colitis. Dec. 1, 2013;7(11):e558-68. doi: 10.1016/j.crohns.2013.04.002. Epub May 2, 2013.
Reeck et al., "Homology" in proteins and nucleic acids: a terminology muddle and a way out of it. Cell. Aug. 28, 1987;50(5):667.
Reexamination Decision for Chinese application No. 201180037900.8 dated Mar. 19, 2018.
Rehman et al., Transcriptional activity of the dominant gut mucosal microbiota in chronic inflammatory bowel disease patients. J Med Microbiol. Sep. 2010;59(Pt 9):1114-22. doi:10.1099/jmm.0.021170-0. Epub Jun. 3, 2010.
Response to European Office Action for Application No. 11 728 077.6, dated Feb. 25, 2014.
Response to European Office Action for Application No. 11 728 077.6, dated Jan. 28, 2015.
Response to European Office Action for Application No. 11 728 077.6, dated Nov. 18, 2015.
Roberts, CSO Vedanta Biosciences Presentation. $1^{st}$ Microbiome Drug Development Summit. Jun. 28, 2016.
Rohlke et al., Fecal flora reconstitution for recurrent Clostridium difficile infection: results and methodology. J Clin Gastroenterol. Sep. 2010;44(8):567-70. doi: 10.1097/MCG.0b013e3181dadb10.
Rosero et al., Reclassification of Eubacterium rectale (Prévot et al., 1967) in a new genus *Agathobacter* gen. nov., as *Agathobacter rectalis* comb. nov., within the family Lachnospiraceae, and description of *Agathobacter ruminis* sp. nov., from the rumen. Int J Syst Evol Microbiol. Nov. 30, 2015. doi: 10.1099/ijsem.0.000788.
Rossi et al., Faecalibacterium prausnitzii A2-165 has a high capacity to induce IL-10 in human and murine dendritic cells and modulates T cell responses. Sci Rep. Jan. 4, 2016;6:18507. doi:10.1038/srep18507.
Round et al., Inducible Foxp3+ regulatory T-cell development by a commensal bacterium of the intestinal microbiota. Proc Natl Acad Sci U S A. Jul. 6, 2010;107(27):12204-9. doi: 10.1073/pnas.0909122107. Epub Jun. 21, 2010.
Round et al., The gut microbiota shapes intestinal immune responses during health and disease. Nat Rev Immunol. May 2009;9(5):313-23. doi:10.1038/nri2515. Review. Erratum in: Nat Rev Immunol. Aug. 2009;9(8):600.
Rubtsov et al., Regulatory T cell-derived interleukin-10 limits inflammation at environmental interfaces. Immunity. Apr. 2008;28(4):546-58. doi: 10.1016/j.immuni.2008.02.017.
Sakaguchi et al., Regulatory T cells and immune tolerance. Cell. May 30, 2008;133(5):775-87. doi: 10.1016/j.cell.2008.05.009.
Salzman et al., Enteric defensins are essential regulators of intestinal microbial ecology. Nat Immunol. Jan. 2010;11(1):76-83. doi:10.1038/ni.1825. Epub Oct. 22, 2009.
Sanchez et al., The role of natural regulatory T cells in infection. Immunol Res. Apr. 2011;49(1-3):124-34. doi: 10.1007/s12026-010-8176-8.
Sanos et al., RORgammat and commensal microflora are required for the differentiation of mucosal interleukin 22-producing NKp46+ cells. Nat Immunol. Jan. 2009;10(1):83-91. doi: 10.1038/ni.1684. Epub Nov. 23, 2008.

(56) References Cited

OTHER PUBLICATIONS

Sartor, Therapeutic correction of bacterial dysbiosis discovered by molecular techniques. Proc Natl Acad Sci U S A. Oct. 28, 2008;105(43):16413-4. doi:10.1073/pnas.0809363105. Epub Oct. 23, 2008.

Schloss et al., The dynamics of a family's gut microbiota reveal variations on a theme. Microbiome. Jul. 21, 2014;2:25. doi:10.1186/2049-2618-2-25. eCollection 2014.

Schouten et al., Oligosaccharide-induced whey-specific CD25(+) regulatory T-cells are involved in the suppression of cow milk allergy in mice. J Nutr. Apr. 2010;140(4):835-41. doi: 10.3945/jn.109.116061. Epub Feb. 17, 2010.

Screenshot of https://academic.oup.com/intimm/issue/22/Suppl_1_Pt3 showing the publication of Warren et al. at the Workshop abstract WS64 of XIVth International congress of Immunology held in Kobe in Japan on Aug. 2010.

Segain et al., Butyrate inhibits inflammatory responses through NFkappaB inhibition: implications for Crohn's disease. Gut. Sep. 2000;47(3):397-403.

Sequence listing of WO 2011/152566.

Sghir et al., Quantification of bacterial groups within human fecal flora by oligonucleotide probe hybridization. Appl Environ Microbiol. May 2000;66(5):2263-6.

Shen et al., Molecular profiling of the Clostridium leptum subgroup in human fecal microflora by PCR-denaturing gradient gel electrophoresis and clone library analysis. Appl Environ Microbiol. Aug. 2006;72(8):5232-8.

So et al., Lactobacillus casei potentiates induction of oral tolerance in experimental arthritis. Mol Immunol. Nov. 2008;46(1):172-80. doi: 10.1016/j.molimm.2008.07.038. Epub Sep. 19, 2008.

So et al., Lactobacillus casei suppresses experimental arthritis by down-regulating T helper 1 effector functions. Mol Immunol. May 2008;45(9):2690-9. doi:10.1016/j.molimm.2007.12.010. Epub Feb. 19, 2008.

Sokol et al., Faecalibacterium prausnitzii is an anti-inflammatory commensal bacterium identified by gut microbiota analysis of Crohn disease patients. Proc Natl Acad Sci U S A. Oct. 28, 2008;105(43):16731-6. doi: 10.1073/pnas.0804812105. Epub Oct. 20, 2008.

Sokol et al., Low counts of Faecalibacterium prausnitzii in colitis microbiota. Inflamm Bowel Dis. Aug. 2009;15(8):1183-9. doi:10.1002/ibd.20903.

Song et al., *Clostridium bartlettii* sp. nov., isolated from human faeces. Anaerobe. Jun. 2004;10(3):179-84.

Sydora et al. CD4+CD25+ regulatory T cells have divergent effects on intestinal inflammation in IL-10 gene-deficient mice. Dig Dis Sci. Jun. 2008;53(6):1544-52.

Takaishi et al., Imbalance in intestinal microflora constitution could be involved in the pathogenesis of inflammatory bowel disease. Int J Med Microbiol. Jul. 2008;298(5-6):463-72. Epub Sep. 25, 2007.

Tanoue et al., Immune responses to gut microbiota-commensals and pathogens *Gut Microbes*. Jul.-Aug. 2010; 1(4): 224-233.

Tanoue et al., Regulation of intestinal Th17 and Treg cells by gut microbiota. Inflammation Regeneration. May 2015;35(3):99-105.

Tao et al., Deacetylase inhibition promotes the generation and function of regulatory T cells. Nat Med. Nov. 2007;13(11):1299-307. Epub Oct. 7, 2007.

Thibault et al., Butyrate utilization by the colonic mucosa in inflammatory bowel diseases: a transport deficiency. Inflamm Bowel Dis. Apr. 2010;16(4):684-95. doi:10.1002/ibd.21108.

Third Party Observations filed in European Patent Application No. 11728077.6 on Jan. 29, 2016.

Umesaki et al., Differential roles of segmented filamentous bacteria and clostridia in development of the intestinal immune system. Infect Immun. Jul. 1999;67(7):3504-11.

Valcheva et al., Prebiotics Prevent Loss of Intestinal Biodiversity and Reduce Colitis in Hla-B27 Transgenic Rats. Canadian Digestive Diseases Week. Feb. 2009. Poster Session 2—Immunology and Inflammatory Bowel Disease. Abstract 168.

Van Immerseel et al., Butyric acid-producing anaerobic bacteria as a novel probiotic treatment approach for inflammatory bowel disease. J Med Microbiol. Feb. 2010;59(Pt 2):141-3. doi: 10.1099/jmm.0.017541-0. Epub Nov. 26, 2009.

Van'T Land et al., Regulatory T-cells have a prominent role in the immune modulated vaccine response by specific oligosaccharides. Vaccine. Aug. 9, 2010;28(35):5711-7. doi: 10.1016/j.vaccine.2010.06.046. Epub Jun. 26, 2010.

Wachsman et al., Characterization of an orotic acid fermenting bacterium, *Zymobacterium oroticum*, nov. gen., nov. spec. J Bacteriol. Oct. 1954;68(4):400-4.

Wang et al., Analysis of the germination of individual Clostridium perfringens spores and its heterogeneity. J Appl Microbiol. Nov. 2011;111(5):1212-23. doi:10.1111/j.1365-2672.2011.05135.x. Epub Sep. 14, 2011.

Warren et al., *Clostridium aldenense* sp. nov. and *Clostridium citroniae* sp. nov. isolated from human clinical infections. J Clin Microbiol. Jul. 2006;44(7):2416-22.

Wells et al., Clostridia: Sporeforming Anaerobic Bacilli. Medical Microbiology.4$^{th}$ edition. Ed:Baron. 1996. University of Texas Medical Branch at Galveston. Mar. 7, 2017.

Zhang et al., Therapeutic effects of Clostridium butyricum on experimental colitis induced by oxazolone in rats. World J Gastroenterol. Apr. 21, 2009;15(15):1821-8.

Zhou et al., Total fecal microbiota transplantation alleviates high-fat diet-induced steatohepatitis in mice via beneficial regulation of gut microbiota. Sci Rep. May 8, 2017;7(1):1529. doi: 10.1038/s41598-017-01751-y.

[No Author Listed] Poster Presentation Schedule 14$^{th}$ International Congress of Immunology. Aug. 25, 2010. Kyoto, Japan.

[No Author Listed] Screenshot—pre-conference itinerary tool for the XIVth International Congress of Immunology held in Kobe, Japan, Aug. 22-27, 2010.

Abbas et al., Regulatory T cells: recommendations to simplify the nomenclature. Nat Immunol. Apr. 2013;14(4):307-8. doi: 10.1038/ni.2554.

Arpaia et al., A Distinct Function of Regulatory T Cells in Tissue Protection. Cell. Aug. 27, 2015;162(5):1078-89. doi: 10.1016/j.cell.2015.08.021. Supplemental Information.

Bag et al., Complete Genome Sequence of *Faecalibacterium prausnitzii* Isolated from the Gut of a Healthy Indian Adult. Genome Announc. Nov. 16, 2017;5(46). pii: e01286-17. doi: 10.1128/genomeA.01286-17.

Bergey et al., (2009). Bergey's manual of systematic bacteriology: vol. 3. New York: Springer. 795, 814-815 and 820. (17 pages).

Declaration by Marin Vuliè, Ph.D. Concerning European Patent 2575835. Dec. 17, 2018.

Declaration of Alexander Sudensky, Ph.D. Concerning European Patent 2575835. Dec. 16, 2018.

Declaration of Dr. James Dooley regarding abstracts of the XIVth International Congress of Immunology in Kobe in Aug. 2010, cited in EP Opposition 2575835.

Declaration of Joseph Sorg, Ph.D. Concerning European Patent 2575835. Dec. 16, 2018.

Eiseman B et al.; Fecal Enema as an Adjunct in the Treatment of Pseudomembranous Enterocolitis; Surgery vol. 44 No. 5; Nov. 1958.

Fontenot et al., Regulatory T Cell Lineage Specification by the Forkhead Transcription Factor Foxp3. Immunity. Mar. 2005;22(3):329-41.

Hsu et al., IL-10 Potentiates Differentiation of Human Induced Regulatory T Cells via STAT3 and Foxo1. J Immunol. Oct. 15, 2015;195(8):3665-74. doi: 10.4049/jimmunol.1402898. Epub Sep. 11, 2015.

Jordan et al., Thymic selection of CD4+CD25+ regulatory T cells induced by an agonist self-peptide. Nat Immunol. Apr. 2001;2(4):301-6.

Kuswanto et al., Poor Repair of Skeletal Muscle in Aging Mice Reflects a Defect in Local, Interleukin-33-Dependent Accumulation of Regulatory T Cells. Immunity. Feb. 16, 2016;44(2):355-67. doi: 10.1016/j.immuni.2016.01.009. Epub Feb. 9, 2016. Supplemental Information.

(56) References Cited

OTHER PUBLICATIONS

Lafaille et al., High Incidence of Spontaneous Autoimmune Encephalomyelitis in Immunodeficient Anti-Myelin Basic Protein T cell Receptor Transgenic Mice. Cell. Aug. 12, 1994;78(3):399-408.
Leber et al., Systems Modeling of Interactions between Mucosal Immunity and the Gut Microbiome during *Clostridium difficile* Infection. PLoS One. Jul. 31, 2015;10(7):e0134849. doi: 10.1371/journal.pone.0134849. eCollection 2015.
Levine et al., Continuous requirement for the TCR in regulatory T cell function. Nat Immunol. Nov. 2014;15(11):1070-8. doi: 10.1038/ni.3004. Epub Sep. 28, 2014.
Levine et al., Suppression of lethal autoimmunity by regulatory T cells with a single TCR specificity. J Exp Med. Mar. 6, 2017;214(3):609-622. doi: 10.1084/jem.20161318. Epub Jan. 27, 2017.
Martín et al., The Commensal Bacterium *Faecalibacterium prausnitzii* is Protective in DNBS-induced Chronic Moderate and Severe Colitis Models; Inflamm Bowel Dis 2014;20:417-430.
Murai et al., Interleukin 10 acts on regulatory T cells to maintain expression of the transcription factor Foxp3 and suppressive function in mice with colitis. Nat Immunol. Nov. 2009;10(11):1178-84. doi: 10.1038/ni.1791. Epub Sep. 27, 2009.
Opposition against European Patent No. 2575835/The University of Tokyo dated Dec. 18, 2018. Muller Fottner Steinecke.
Opposition to European Patent No. 2575835 dated Dec. 18, 2018. Mathys & Squire.
Panduro et al., Tissue Tregs. Annu Rev Immunol. May 20, 2016;34:609-33. doi: 10.1146/annurev-immunol-032712-095948. Author manuscript.
Povoleri et al., Human retinoic acid-regulated CD161+ regulatory T cells support wound repair in intestinal mucosa. Nat Immunol. Dec. 2018;19(12):1403-1414. doi: 10.1038/s41590-018-0230-z. Epub Nov. 5, 2018.
Pre-Hearing Submission Opponent 5 for EP Patent 2575835. Dec. 18, 2018.
Rautava, Potential uses of probiotics in the neonate. Semin Fetal Neonatal Med. Feb. 2007;12(1):45-53. Epub Nov. 29, 2006.
Response to the Summons to attend oral proceedings pursuant to Rule 115(1) EPC, dated Jun. 7, 2018. Mailed Nov. 16, 2018. EP Patent 2575835.
Solomon et al., Mortality in patients with *Clostridium difficile* infection correlates with host pro-inflammatory and humoral immune responses. J Med Microbiol. Sep. 2013;62(Pt 9):1453-60. doi: 10.1099/jmm.0.058479-0. Epub May 30, 2013.
Stackebrandt et al., Phylogenetic basis for a taxonomic dissection of the genus *Clostridium*. FEMS Immunol Med Microbiol. Jul. 1999;24(3):253-8.
Steer et al., *Clostridium hathewayi* sp. nov., from human faeces. Syst Appl Microbiol. Nov. 2001;24(3):353-7. Abstract only.
Van Den Elsen et al., Embracing the gut microbiota: the new frontier for inflammatory and infectious diseases. Clin Transl Immunology. Jan. 20, 2017;6(1):e125. doi: 10.1038/cti.2016.91. eCollection Jan. 2017.
Varanasi et al., Role of IL-18 induced Amphiregulin expression on virus induced ocular lesions. Mucosal Immunol. Nov 2018;11(6):1705-1715. doi: 10.1038/s41385-018-0058-8. Epub Aug. 7, 2018.
Vidhyalakshmi et al.; Encapsulation "The Future of Probiotics"—A Review; Advances in Biological Research 3 (3-4): 96-103, 2009.
Wan et al., Identifying Foxp3-expressing suppressor T cells with a bicistronic reporter. Proc Natl Acad Sci U S A. Apr. 5, 2005;102(14):5126-31. Epub Mar. 28, 2005.
Workman et al.; The Development and Function of Regulatory T Cells. Cell Mol Life Sci., 66(16), 2603-2622.
Written Submission for EP 2575835 on behalf of proprietor dated Dec. 18, 2018. Hoffmann Eitle.
Honda et al. Immune regulation by intestinal microflora. Presentation, Dec. 4, 2009. 28 pages.
Kumar et al., Probiotic administration alters the gut flora and attenuates colitis in mice administered dextran sodium sulfate. J. Gastroenterology and Hepatology. Dec. 2008;23(12):1834-9. Epub Nov. 28, 2008. https://doi.org/10.1111/j.1440-1746.2008.05723.x.
U.S. Appl. No. 16/427,899, filed May 31, 2019, Honda et al.
U.S. Appl. No. 16/389,380, filed Apr. 19, 2019, Honda et al.
U.S. Appl. No. 16/425,030, filed May 29, 2019, Honda et al.
EP 19178787.8, Aug. 12, 2019, Extended European Search Report.
EP 19168383.8, Jul. 26, 2019, Extended European Search Report.
EP 19174499.4, Jul. 26, 2019, Extended European Search Report.

\* cited by examiner

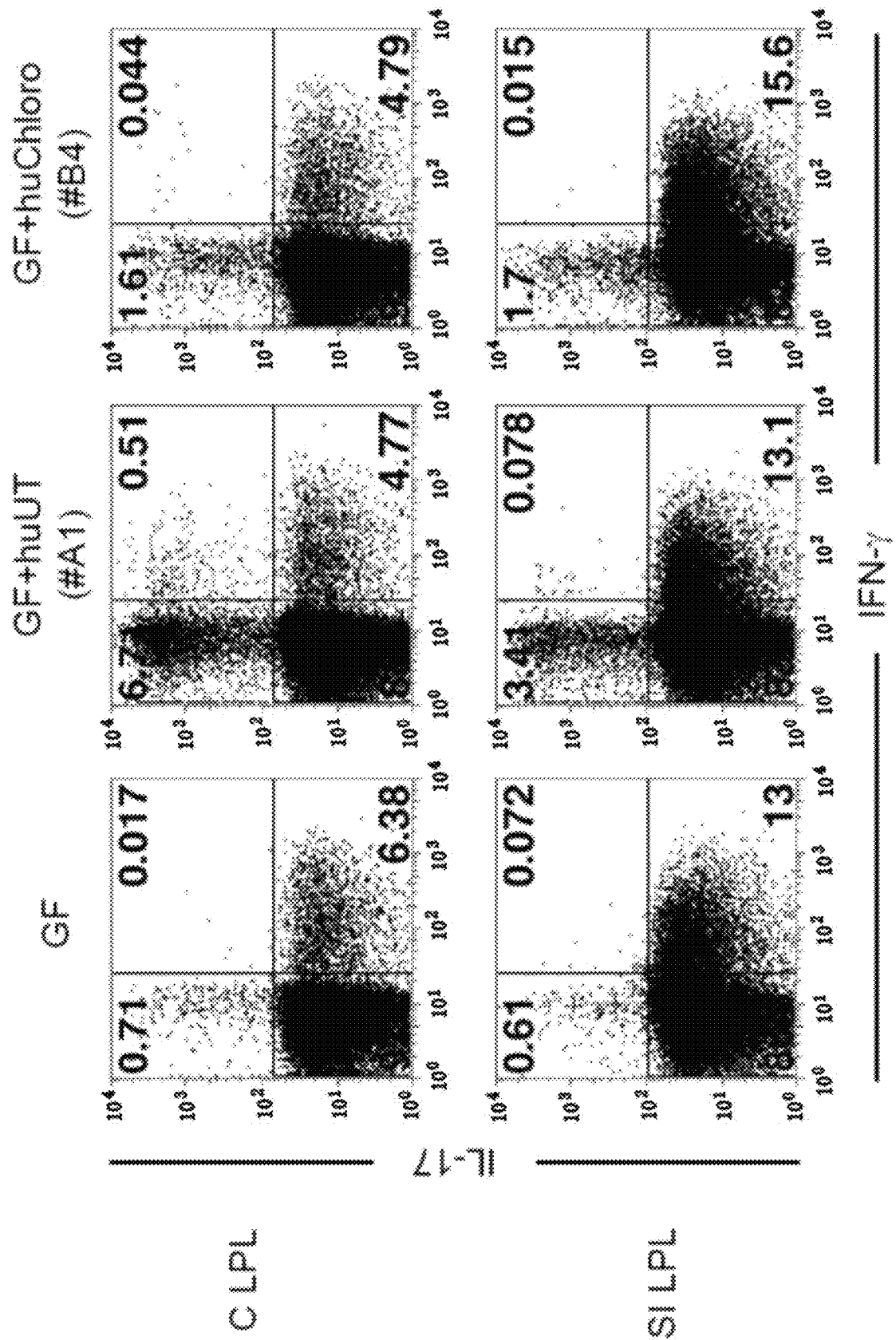

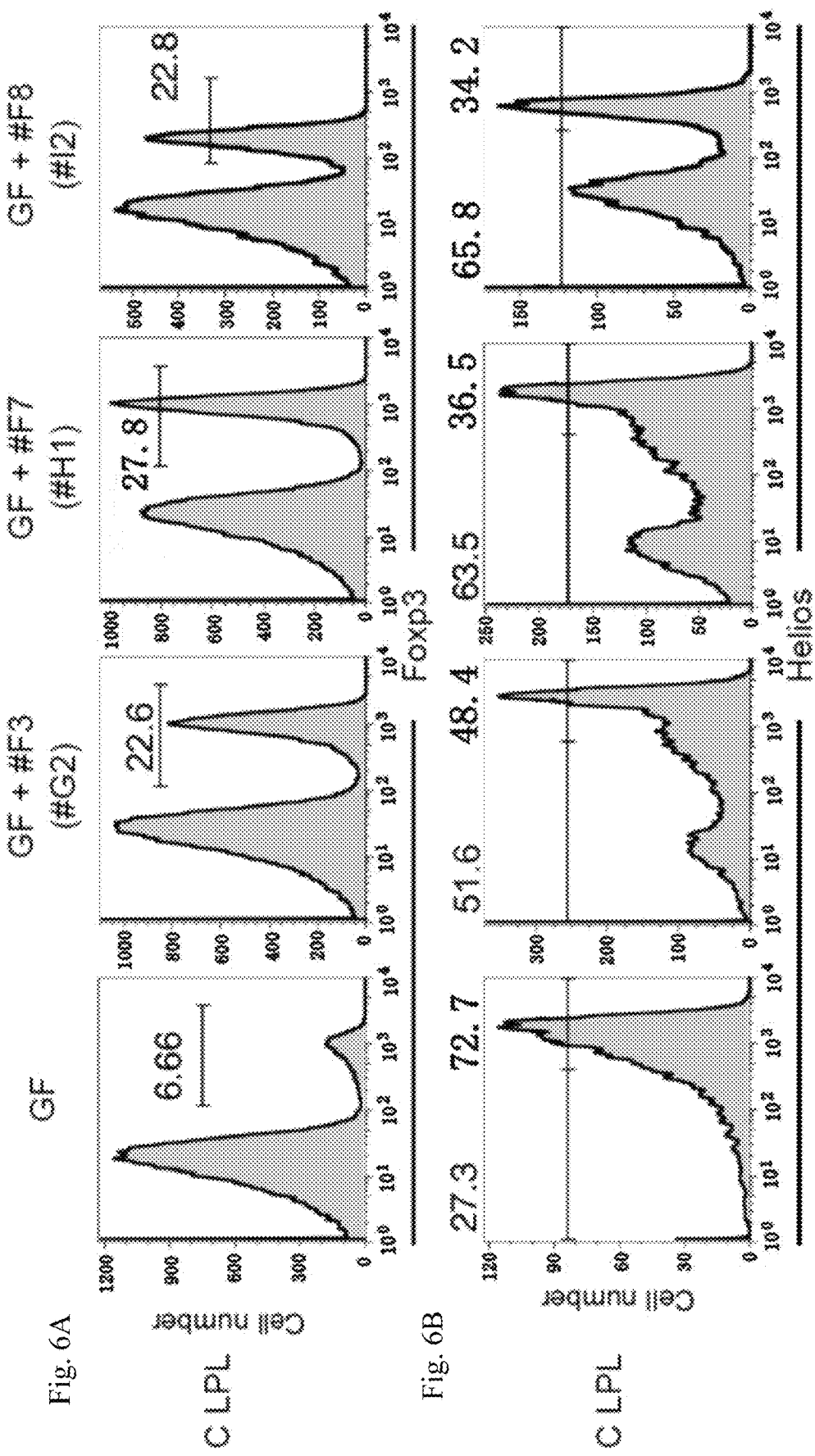

HUMAN-DERIVED BACTERIA THAT INDUCE PROLIFERATION OR ACCUMULATION OF REGULATORY T CELLS

RELATED APPLICATIONS

This application is a continuation of U.S. application Ser. No. 14/362,097, filed May 30, 2014, which is a national stage filing under 35 U.S.C. § 371 of International Application PCT/JP2012/007687, filed Nov. 29, 2012, which claims the benefit under 35 U.S.C. 119(e) of U.S. Provisional Application No. 61/565,976, filed Dec. 1, 2011 and U.S. Provisional Application No. 61/607,360, filed Mar. 6, 2012. The entire teachings of the referenced applications are incorporated herein by reference.

TECHNICAL FIELD

The subject matter described herein relates to a composition of human-derived bacteria that induces proliferation, accumulation, or proliferation and accumulation of regulatory T cells and which comprises, as an active component, (a) one or more (a, at least one) human-derived bacteria that belongs to the Clostridia class, (b) culture supernatant of one or more (a, at least one) of the bacteria; (c) a physiologically active substance derived from one or more of the bacteria or (d) a combination of any two or more of the foregoing. It also relates to a method for inducing proliferation, accumulation or proliferation and accumulation of regulatory T cells. The composition, which comprises any of (a)-(d) above, is referred to as a bacterial composition. Moreover, the subject matter relates to a method for treating or preventing at least one disease or condition that is responsive to induction of regulatory T cells, such as autoimmune diseases, inflammatory diseases, and infectious diseases, by administering the bacterial composition to an individual in need thereof.

BACKGROUND

Hundreds of species of commensal microorganisms are harbored in the gastrointestinal tracts of mammals, where they interact with the host immune system. Research using germ-free (GF) animals has shown that the commensal microorganisms influence the development of the mucosal immune system, such as histogenesis of Peyer's patches (PPs) and isolated lymphoid follicles (ILFs), secretion of antimicrobial peptides from the epithelium, and accumulation of unique lymphocytes in mucosal tissues, including immunoglobulin A-producing plasma cells, intraepithelial lymphocytes, IL-17-producing CD4-positive T cells (Th 17), and IL-22-producing NK-like cells (Non-Patent Literature (NPL) 1 to 7). Consequently, the presence of intestinal bacteria enhances protective functions of the mucous membranes, enabling the host to mount robust immune responses against pathogenic microbes invading the body. On the other hand, the mucosal immune system maintains unresponsiveness to dietary antigens and harmless microbes (NPL Document 3). Abnormality in the regulation of cross-talk between commensal bacteria and the immune system (intestinal dysbiosis) may lead to overly robust immune response to environmental antigens and inflammatory bowel disease (IBD) may result (NPL 8 to 10).

Recent studies have shown that individual commensal bacteria control differentiation of their specific immune cells in the mucosal immune system. For example, *Bacteroides fragilis*, which is a commensal bacterium in humans, specifically induces a systemic Th1 cell response and a mucosal IL-10-producing T cell response in mice, and plays a role in protecting the host from colitis, which is caused by a pathogen (NPL 3). Segmented filamentous bacteria, which are intestinal commensal bacteria in mice, induce mucosal Th17 cell response and enhance resistance against infection of gastrointestinal tracts of the host with a pathogen (NPL 11 to 13). In addition, short-chain fatty acids derived from several commensal bacteria are known to suppress intestinal inflammation (NPL 14). Moreover, it has been observed that the presence of some species of intestinal microbiota greatly influences the differentiation of regulatory T cells (hereafter referred to as "Treg cells") which help maintain homeostasis of the immune system. Although specific species of murine bacterial commensals that can strongly stimulate Tregs have been identified (NPL 15), it is still unknown whether species of human commensal bacteria exert an equivalent influence on the human immune system. Furthermore, the human intestinal tract harbors more than a thousand bacterial species, many of which have not yet been cultured (NPL 16). It is not feasible to guess a priori which ones, if any, might have an effect on Tregs.

In order to develop drugs, dietary supplements, or foods with beneficial immune functions for human use, it is desirable to identify commensal microorganisms that naturally colonize humans and have immune-modulating properties. Furthermore, since many of the commensals in the human microbiome have yet to be cultured, it is necessary to develop methods to cultivate them so that they can be produced by traditional industrial fermentation processes and subsequently incorporated in pharmaceutical or food formulations.

$CD4^+$ T cells are regulatory T cells that have been identified as a cell subset that suppresses immunity. A transcription factor, Foxp3, is expressed in $CD4^+$ T cells, which are known to play an important role in maintaining immunological homeostasis (NPL 8, 9, 17, and 18). Foxp3-expressing cells are present in large numbers in the colon and only Treg cells present locally in the colon constantly express IL-10, an immunosuppressive cytokine, at a high level (NPL 19). Animals having $CD4^+$ $Foxp3^+$ cells from which IL-10 is specifically removed develop inflammatory bowel disease (NPL 20).

Accordingly, there is a need to identify human-derived commensal bacterial species with the ability to strongly induce Treg cells to produce IL-10 in the colon at a high level and to develop methods to culture such species. Such species could be used to enhance immunosuppression, which, in turn, can be applied to treatment of autoimmune diseases, such as inflammatory bowel disease, inflammatory diseases, allergies, or organ transplantation, among other diseases and conditions.

Non Patent Literature

[NPL 1] J. J. Cebra, "Am J Clin Nutr", May, 1999, 69, 1046S
[NPL 2] A. J. Macpherson, N. L. Harris, "Nat Rev Immunol", June 2004, 4, 478
[NPL 3] J. L. Round, S. K. Mazmanian, "Nat Rev Immunol", May 2009, 9, 313
[NPL 4] D. Bouskra et al., "Nature", Nov. 27, 2008, 456, 507
[NPL 5] K. Atarashi et al., "Nature", Oct. 9, 2008, 455, 808
[NPL 6] Ivanov, II et al., "Cell Host Microbe", Oct. 16, 2008, 4, 337
[NPL 7] S. L. Sanos et al., "Nat Immunol", January 2009, 10, 83

[NPL 8] M. A. Curotto de Lafaille, J. J. Lafaille, "Immunity", May 2009, 30, 626
[NPL 9] M. J. Barnes, F. Powrie, "Immunity", Sep. 18, 2009, 31, 401
[NPL 10] W. S. Garrett et al., "Cell", Oct. 5, 2007, 131, 33
[NPL 11] Ivanov, II et al., "Cell", Oct. 30, 2009, 139, 485.
[NPL 12] V. Gaboriau-Routhiau et al., "Immunity", Oct. 16, 2009, 31, 677
[NPL 13] N. H. Salzman et al., "Nat Immunol", 11, 76.
[NPL 14] K. M. Maslowski et al., "Nature", Oct. 29, 2009, 461, 1282
[NPL 15] K. Atarashi et al., "Science", Jan. 21, 2011, 331, 337
[NPL 16] J. Quin et al., "Nature", Mar. 4, 2010, 464, 59
[NPL 17] L. F. Lu, A. Rudensky, "Genes Dev", Jun. 1, 2009, 23, 1270
[NPL 18] S. Sakaguchi, T. Yamaguchi, T. Nomura, M. Ono, "Cell", May 30, 2008, 133, 775
[NPL 19] C. L. Maynard et al., "Nat Immunol", September 2007, 8, 931
[NPL 20] Y. P. Rubtsov et al., "Immunity", April 2008, 28, 546

SUMMARY

The present compositions and methods have been made in view of the above-described problems in the art. Described herein are methods of identifying and culturing intestinal commensal bacteria, isolated from humans, which induce, preferably strongly induce, the proliferation, accumulation, or proliferation and accumulation of regulatory T cells. Described are compositions, also referred to as bacterial compositions, that (1) comprise (a) one or more of the identified intestinal commensal (human-derived) bacteria; (b) a culture supernatant of one or more of the bacteria; (c) one or more physiologically active substance derived from one or more of the bacteria or from one or more of the culture supernatant; (d) or a combination of any two or three of (a)-(c) and (2) induce the proliferation and/or accumulation of regulatory T cells (Treg cells). Alternatively, a composition comprises (a) one or more of the identified intestinal commensal (human-derived) bacteria; (b) a culture supernatant of one or more of the bacteria; or (c) one or more physiologically active substance derived from the bacteria or from the culture supernatant, wherein the composition induces proliferation and/or accumulation of regulatory cells. In some embodiments, the composition comprises one or more of the identified intestinal commensal (human-derived) bacteria. In some embodiments, the composition comprises a culture supernatant of one or more of the bacteria. In some embodiments, the composition comprises one or more physiologically active substance derived from the bacteria or from the culture supernatant. In some embodiments, the one or more bacteria or one or more physiologically active substance derived from the bacteria is three or more. In some embodiments, the one or more bacteria or one or more physiologically active substance derived from the bacteria is five or more. In some embodiments, the one or more bacteria or one or more physiologically active substance derived from the bacteria is seventeen or more. In some embodiments, the one or more bacteria or one or more physiologically active substance derived from the bacteria is twenty-three or more. In some embodiments, the one or more bacteria or one or more physiologically active substance derived from the bacteria is 23. In specific embodiments, the bacterial compositions induce, and preferably strongly induce, proliferation, accumulation, or proliferation and accumulation of regulatory T cells that produce an immunosuppressive cytokine, such as IL-10, in the colon (e.g., the human colon) at high levels. Such bacterial compositions are useful, for example, to enhance immunosuppression and, as a result, to treat autoimmune diseases. Bacterial compositions comprise, as an active component, at least one organism and/or at least one substance selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662.; a culture supernatant of at least one (a, one or more) of the bacteria described/listed herein; a physiologically active substance derived from (a, one or more) bacteria described/listed herein or any combination of two or three of the foregoing. Alternatively, bacterial compositions comprise, as an active component, at least one organism or at least one substance selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662.; a culture supernatant of at least one (a, one or more) of the bacteria described/listed herein; a physiologically active substance derived from (a, one or more) bacteria described/listed herein. In some embodiments, a bacterial composition comprises at least one organism selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lach-* nospiraceae bacterium 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662. In some embodiments, a bacterial composition comprises a culture supernatant of at least one (a, one or more) of the bacteria described/listed herein. In some embodiments, a bacterial composition comprises a physiologically active substance derived from (a, one or more) bacteria described/listed herein. In some embodiments, the one or more bacteria or one or more physiologically active substance derived from the bacteria is three or more. In some embodiments, the one or more bacteria or one or more physiologically active substance derived from the bacteria is five or more. In some embodiments, the one or more bacteria or one or more physiologically active substance derived from the bacteria is 17 or more. In some embodiments, the one or more bacteria or one or more physiologically active substance derived from the bacteria is 23 or more. In some embodiments, the one or more bacteria or one or more physiologically active substance derived from the bacteria is 23. Bacterial compositions can comprise any bacteria (Clostridia or other bacteria) that contain DNA comprising a nucleotide sequence having sufficient homology with sequences provided herein and that exhibit substantially the same effect on regulatory T cells as that exerted by any one of the following: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides*, and *Anaerostipes caccae* DSM 14662. In some embodiments, bacteria present in bacterial compositions have at least 90% (90%, 91%, 92%, 93%, 94%, 95%, 96%, 97%, 98%, 99% or 100%) homology with sequences provided herein, such as, but not limited to, the nucleotide sequences designated OTU herein and listed, for example, at the pages following the last Example. In specific embodiments, such bacteria contain DNA comprising a nucleotide sequence that has at least 90% (90%, 91%, 92%, 93%, 94%, 95%, 96%, 97%, 98%, 99% or 100%) homology with one or more DNA sequence designated herein as follows: OTU136; OTU46; OTU221; OTU9; OTU296; OTU21; OTU166; OTU73; OTU174; OTU14; OTU55; OTU337; OTU314; OTU195; OTU306; OTU87; OTU86; OTU152; OTU253; OTU259; OTU281; OTU288; OTU334; OTU359; OTU362; or OTU367. Alternatively, bacteria contain DNA comprising a nucleotide sequence that has at least 90% (90%, 91%, 92%, 93%, 94%, 95%, 96%, 97%, 98%, 99% or 100%) homology with DNA of one or more of the following: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides*, and *Anaerostipes caccae* DSM 14662. In specific embodiments, bacterial compositions comprise bacteria (such as human-derived bacteria) that contain DNA comprising a nucleotide sequence having at least 97%, 98% or 99% homology with sequences provided herein, such as, but not limited to, the nucleotide sequences designated OTU herein and listed, for example, at the pages following the last Example. In specific embodiments, the bacteria in bacterial compositions contain DNA comprising a nucleotide sequence that has at least 97%, 98% or 99% homology with one or more DNA sequence designated herein as follows: OTU136; OTU46; OTU221; OTU9; OTU296; OTU21; OTU166; OTU73; OTU174; OTU14; OTU55; OTU337; OTU314; OTU195; OTU306; OTU87; OTU86; OTU152; OTU253; OTU259; OTU281; OTU288; OTU334; OTU359; OTU362; or OTU367. Alternatively, the bacteria contain DNA comprising a nucleotide sequence that has at least 97%, 98% or 99% homology with DNA of one or more of the following: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662. Any of the bacteria of the Clostridia class can be present in spore form or vegetative form.

Solution of Problem

As described herein, among the more than a thousand species of bacteria in the human microbiome, there are several species that strongly induce the accumulation of Tregs in the colon. As also described, although most bacterial species present in fecal samples from healthy individuals do not have the ability to stimulate Tregs, species that belong to the Clostridia class have the ability to cause a robust induction of Tregs in the colon. Moreover, the inventors have obtained in vitro cultures of each of the bacterial species identified and shown that inoculating mice with the in vitro cultured species also leads to a robust accumulation of Tregs in the colon.

As described herein, compositions that comprise, as an active component, (a) one or more of certain species of bacteria that belong to the Clostridia class or bacteria that contain DNA comprising a nucleotide sequence having at least 90% homology with sequences provided herein, in spore form or in vegetative form; (b) a culture supernatant of one or more such bacteria; (c) one or more physiologically active substance derived from (a) or (b); or (d) a combination of any two or three of (a), (b) and (c) and induce the proliferation and/or accumulation of regulatory T cells (Treg cells) suppress immune functions.

More specifically:

One embodiment is a composition that induces proliferation, accumulation or both proliferation and accumulation of regulatory T cells, the composition comprising, as an active component, at least one organism and/or at least one substance selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662.; a culture supernatant of at least one of the bacteria described/listed herein, and a physiologically active substance derived from a bacterium described/listed herein.

In some embodiments, the active component is one or more of *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662. In some embodiments, the active component is a culture supernatant of one or more of the bacteria described/listed herein. In some embodiments, the active component is one or more physiologically active substances derived from a bacterium described/listed herein. In some embodiments, the one or more bacteria or one or more physiologically active substance derived from the bacteria is three or more. In some embodiments, the one or more bacteria or one or more physiologically active substance derived from the bacteria is five or more. In some embodiments, the one or more bacteria or one or more physiologically active substance derived from the bacteria is 17 or more. In some embodiments, the one or more bacteria or one or more physiologically active substance derived from the bacteria is 23 or more. In some embodiments, the one or more bacteria or one or more physiologically active substance derived from the bacteria is 23.

A bacterial composition as described herein comprises at least one of the following: one bacteria as described herein; at least one culture supernatant obtained from culture in which one (or more) of the bacteria was present (grown or maintained) or a fraction of such a supernatant; one or more physiologically active substance derived from one or more bacteria (such as from the bacteria named herein) or a combination of any two or three of the foregoing. The term composition/bacterial composition refers to all such combinations.

The bacteria in the composition can be, for example, *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662 or any bacteria (such as human-derived bacteria) that contain DNA comprising at least 90% homology (e.g., 90%, 91%, 92%, 93%, 94%, 95%, 96%, 97%, 98%, 99% or 100% homology) with sequences provided herein, such as, but not limited to, the nucleotide sequences designated OTU herein and listed, for example, at the pages following the last Example. In specific embodiments, the bacteria contain DNA comprising a nucleotide sequence that has at least 97%, at least 98% or at least 99% homology with one or more DNA sequence designated herein as follows: OTU136; OTU46; OTU221; OTU9; OTU296; OTU21; OTU166; OTU73; OTU174; OTU14; OTU55; OTU337; OTU314; OTU195; OTU306; OTU87; OTU86; OTU152; OTU253; OTU259; OTU281; OTU288; OTU334; OTU359; OTU362; or OTU367. Alternatively, the bacteria contain DNA comprising a nucleotide sequence that has at least 97% (97%, 98%, 99%, 100%) homology with DNA of one or more of the following: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides*, and *Anaerostipes caccae* DSM 14662.

In one embodiment, the composition induces regulatory T cells that are transcription factor Foxp3-positive regulatory T cells or IL-10-producing regulatory T cells. In another embodiment, the composition has an immunosuppressive effect.

One embodiment is a pharmaceutical composition that induces proliferation, accumulation or both proliferation and/or accumulation of regulatory T cells and suppresses immune function. The pharmaceutical composition comprises a bacterial composition described herein and a pharmaceutically acceptable component, such as a carrier, a solvent or a diluent. In specific embodiments, such a pharmaceutical composition comprises (a) (1) one or more species of bacteria belonging to the Clostridia class, as described herein, in spore form or in vegetative form, (2) a culture supernatant of such bacteria, (3) a physiologically active substance derived therefrom or (4) a combination of any two or three of (1), (2) and (3) and (b) a pharmaceutically acceptable component, such as carrier, a solvent or a diluent. In specific embodiments, (a) above is at least one organism or substance selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662, a culture supernatant of one or more of the bacteria, and a physiologically active substance derived from one or more of the bacteria. In some embodiments, (a) above is at least one organism selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662. In some embodiments, (1) above is a culture supernatant of one or more of the bacteria. In some embodiments, (1) above is a physiologically active substance derived from one or more of the bacteria. In some embodiments, the at least one organism or substances is three or more. In some embodiments, the at least one organism or substances is five or more. In some embodiments, the at least one organism or substances is 17 or more. In some embodiments, the at least one organism or substances is 23 or more. In some embodiments, the at least one organism or substances is 23. In further embodiments, (a)(1) above is bacteria (such as human-derived bacteria) that contain DNA comprising at least 90% homology (e.g., 90%, 91%, 92%, 93%, 94%, 95%, 96%, 97%, 98%, 99% or 100% homology) with sequences provided herein, such as, but not limited to, the nucleotide sequences designated OTU herein and listed, for example, at the pages following the last Example. In specific embodiments of the pharmaceutical composition, the bacteria contain DNA comprising a nucleotide sequence that has at least 97%, at least 98% or at least 99% homology with one or more DNA sequence designated herein as follows: OTU136; OTU46; OTU221; OTU9; OTU296; OTU21; OTU166; OTU73; OTU174; OTU14; OTU55; OTU337; OTU314; OTU195; OTU306; OTU87; OTU86; OTU152; OTU253; OTU259; OTU281; OTU288; OTU334; OTU359; OTU362; or OTU367. Alternatively, the bacteria in the pharmaceutical composition contain DNA comprising a nucleotide sequence that has at least 97% (97%, 98%, 99%, 100%) homology with DNA of one or more of the following: *Clostridium saccharogumia,*

*Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium 5_1_57FAA, Lachnospiraceae bacterium 6_1_63FAA, Clostridium* sp. 14616, *Clostridium bolteae* ATCC BAA-613, cf. *Clostridium* sp. MLG055, *Erysipelotrichaceae bacterium 2_2_44A, Clostridium indolis, Anaerostipes caccae, Clostridium bolteae, Lachnospiraceae bacterium DJF_VP30, Lachnospiraceae bacterium 3_1_57FAA_CT1, Anaerotruncus colihominis, Anaerotruncus colihominis* DSM 17241, *Ruminococcus* sp. ID8, *Lachnospiraceae bacterium 2_1_46FAA, Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium 1_7_47FAA, Blautia cocoides, Anaerostipes caccae* DSM 14662.

The pharmaceutical composition induces the proliferation and/or accumulation of regulatory T cells (Treg cells) and suppresses immune function.

Also provided is a method of inducing proliferation, accumulation or both proliferation and accumulation of regulatory T cells in an individual (e.g., an individual in need thereof, such as an individual in need of induction of proliferation and/or accumulation of regulatory T cells). The method comprises administering to the individual a bacterial composition described herein or a pharmaceutical composition comprising a bacterial composition described herein. In the method at least one organism or substance selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium 5_1_57FAA, Lachnospiraceae bacterium 6_1_63FAA, Clostridium* sp. 14616, *Clostridium bolteae* ATCC BAA-613, cf. *Clostridium* sp. MLG055, *Erysipelotrichaceae bacterium 2_2_44A, Clostridium indolis, Anaerostipes caccae, Clostridium bolteae, Lachnospiraceae bacterium DJF_VP30, Lachnospiraceae bacterium 3_1_57FAA_CT1, Anaerotruncus colihominis, Anaerotruncus colihominis* DSM 17241, *Ruminococcus* sp. ID8, *Lachnospiraceae bacterium 2_1_46FAA, Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium 1_7_47FAA, Blautia cocoides, Anaerostipes caccae* DSM 14662; a culture supernatant of one or more of the bacteria or one or more component of the culture supernatant; a physiologically active substance derived from one or more of the bacteria or a combination of two or three of the foregoing is administered to an individual (also referred to as an individual in need thereof) who can be a healthy individual or an individual in need of prevention, reduction or treatment of a condition or disease. For example, the compositions described may be administered to an individual in need of treatment, reduction in the severity of or prevention of a disease or condition such as an autoimmune disease, an inflammatory disease, an allergic disease, and an infectious disease Optionally, administration of the bacterial composition may be in combination with, or preceded by, a course of one or more antibiotics.

Optionally, administration of the bacterial composition may be in combination with administration of at least one prebiotic substance that preferentially favors the growth of the species in the bacterial composition over the growth of other human commensal bacterial species. In one embodiment, the prebiotic substance(s) is, for example, a nondigestible oligosaccharide. In specific embodiments, the one or more prebiotic substance(s) is selected from the group consisting of almond skin, inulin, oligofructose, raffinose, lactulose, pectin, hemicellulose, amylopectin, acetyl-Co A, biotin, beet molasses, yeast extracts, and resistant starch. Also contemplated herein is a composition that comprises the bacterial composition and at least one prebiotic substance.

The bacterial composition may be administered in combination with a substance selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, anti-TNF inhibitors such as infliximab, adalimumab, certolizumab pegol, golimumab, or etanercept, and combinations thereof. Also described herein is a composition that comprises the bacterial composition and at least one substance selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, anti-TNF inhibitors such as infliximab, adalimumab, certolizumab pegol, golimumab, or etanercept, and combinations thereof.

In a further embodiment, the bacterial composition can be used as an adjuvant to improve the efficacy of a vaccine formulation. For example, the bacterial composition can be used as an adjuvant to a vaccine for the prophylaxis or treatment of an autoimmune disease or an allergic disease. In some embodiments, a method for prophylaxis or treatment is provided, the method comprising administering the bacterial composition and adminstering a vaccine.

Assessment of the extent of induction of proliferation or accumulation of regulatory T cells that results from administration of a composition described herein can be carried out by a variety of approaches, such as by measurement of the number of Foxp3-expressing Tregs in a patient sample (such as a biopsy or a blood sample), promotion of IL-10 expression, promotion of CTLA4 expression, promotion of IDO expression, suppression of IL-4 expression, or colonization of an individual with the bacterial composition. The results of such assessments are used as an index of the induction of proliferation or accumulation of regulatory T cells in the individual.

In one embodiment, administration of a composition described herein causes induction of the regulatory T cells that are transcription factor Foxp3-positive regulatory T cells or IL-10-producing regulatory T cells.

The composition described herein can be administered by a variety of routes and in one embodiment, is administered orally to an individual in need thereof, such as a patient in need thereof. The composition may be administered in a number of oral forms, such as in spore-form (in a dry powder or dissolved in a liquid formulation), in enteric capsules, in sachets, or in a food matrix, such as yogurt, or a drink.

Also provided is a method to predict a subject's response to treatment (predict whether the subject will or will not respond to treatment) with compositions of the invention. The method comprises (a) obtaining a (at least one, one or more) sample, such as a fecal sample or a colonic biopsy, from a patient before he or she is treated with a bacterial composition described herein; (b) measuring or determining the percentage or absolute counts in the sample of at least one bacterial species selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides*, and *Anaerostipes caccae* DSM 14662, thereby producing a percentage or count, and (c) comparing the resulting percentage or count (measurement) to a baseline value of the same measurement in a healthy subject, wherein a percentage or count in the sample obtained from the patient that is lower than the baseline value indicates that the subject may respond favorably to administration of the bacterial composition. In some embodiments, the method further comprises (d) administering the bacterial composition to the patient if the percentage or count in the sample obtained from the patient is lower than the baseline value. Optionally, the method may further comprise measuring in a patient's sample (e.g., a fecal sample or a colonic biopsy) the percentages or absolute counts of other commensal species that belong to *Clostridium* Clusters IV and XIVa, but are not present in the bacterial composition, wherein a value of the percentage or absolute count (measurement) lower than baseline further indicates that the subject may respond favorably to administration of the bacterial compositions. In some embodiments, the method further comprises administering the bacterial composition to the patient if the value of the percentage or absolute count (measurement) is lower than baseline. In one embodiment, the patient being assessed suffers from inflammatory bowel disease or a *C. difficile* infection.

Also provided is a method of monitoring a subject's response to treatment with the bacterial compositions of the invention, comprising: (a) obtaining a (at least one) sample, such as a fecal sample or a colonic biopsy from a patient before treatment with a bacterial composition described herein; (b) obtaining, a (at least one) corresponding sample from the patient after treatment with a bacterial composition described herein; and (c) comparing the percentage or absolute counts of at least one bacterial species selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662 in the sample obtained in (a) with the percentage or absolute counts of the same at least one bacterial species in the sample obtained in (b), wherein a higher value in the sample obtained in (b) (after treatment with the bacterial composition) than in the sample obtained in (a) (before treatment) indicates that the subject has responded favorably to treatment (e.g. is a positive indicator of enhanced immunosuppression in the subject). In some embodiments, the method further comprises (d) further administering the bacterial composition to the patient or ceasing administration of the bacterial composition to the patient based on the comparison in (c). Optionally, the method may further comprise measuring in the subject's samples the percentages or absolute counts of other commensal species that belong to *Clostridium* Clusters IV and XIVa, but are not present in the bacterial composition, wherein a higher value after treatment than before treatment indicates that the subject has responded favorably to treatment.

Effects of Compositions and Methods Described Herein

The compositions described herein, which contain, as an active component, selected bacteria belonging to the Clostridia class or other bacteria, as described herein; a culture supernatant of such bacteria; a physiologically active substance derived from such bacteria; or a combination of two or three of the foregoing are excellent at inducing the proliferation or accumulation of regulatory T cells (Treg cells).

Immunity in an individual can be suppressed through administration of the subject composition, such as through ingestion of the bacterial composition in a food or beverage or as a dietary supplement or through administration of a pharmaceutical composition comprising the bacterial composition. The subject composition can be used, for example, to prevent or treat autoimmune diseases, allergic diseases, infectious diseases, as well as to suppress immunological rejection in organ transplantation or the like. In addition, if a food or beverage, such as a health food, comprises the subject composition, healthy individuals can ingest the composition easily and routinely. As a result, it is possible to induce the proliferation and/or accumulation of regulatory T cells and thereby to improve immune functions.

The composition described herein provides for a natural, long-lasting, patient-friendly, and benign treatment alternative for immune-mediated conditions. For example, inflammatory bowel disease is currently managed with synthetic drugs that may have severe side effects (such as corticosteroids, TNF inhibitors), cannot be administered orally (such as TNF inhibitors), have inconvenient dosing involving several pills a day (such as mesalazine or sulfasalazine) or have limited efficacy and short-lived effects (such as currently marketed probiotics, e.g. *Lactobacillus* GG, *Lactobacillus acidophilus*, *Bifidobacterium longum*, etc).

BRIEF DESCRIPTION OF DRAWINGS

FIG. 1D represents a separate animal, and error bars indicate the SD. *$P<0.05$; **$P<0.001$, unpaired t test.

FIG. 1E shows representative flow cytometry dot plots for the intracellular expressions of IL-17 and IFN- in CD4$^+$ cells from colonic lamina propia (upper panel) and small intestinal lamina propria (lower panel) of GF mice or GF mice colonized with untreated (+huUT) or chloroform-treated (+huChloro) human feces. The number in each quadrant indicates the percentage of the population.

FIG. 1G represents a separate animal, and error bars indicate the SD. *$P<0.05$; ns, not significant ($P>0.05$), unpaired t test.

FIG. 2C represents a separate animal, and error bars indicate the SD. ns, not significant ($P>0.05$), unpaired t test.

FIG. 5C represents a separate animal, and error bars indicate the SD. *$P<0.05$; **$P<0.001$, unpaired t test.

FIGS. 6A-6D shows representative plots (FIGS. 6A, 6B) and combined data (FIGS. 6C, 6D) for Foxp3 expression in CD4$^+$ cells (FIGS. 6A, 6C), or Helios expression in Foxp3$^+$CD4$^+$ cells (FIGS. 6B, 6D) from colonic lamina propria (C LPL) and small intestinal lamina propria (SI LPL) for GF mice, and GF mice that were inoculated with fecal suspension of # F3 (n=5), # F7 (n=4) or # F8 (n=4) mouse. Numbers above bracketed lines in FIG. 6A and FIG. 6B indicate the percentage of the population. Each circle in FIG. 6C and FIG. 6D represents a separate animal, and error bars indicate the SD. *$P<0.05$; **$P<0.001$, unpaired t test.

FIG. 7C represents a separate animal, and error bars indicate the SD. ns, not significant ($P>0.05$), unpaired t test.

FIG. 10C represents a separate animal, and error bars indicate the SD. *P<0.05; **P<0.001, unpaired t test.

Figures 1A, 1B:
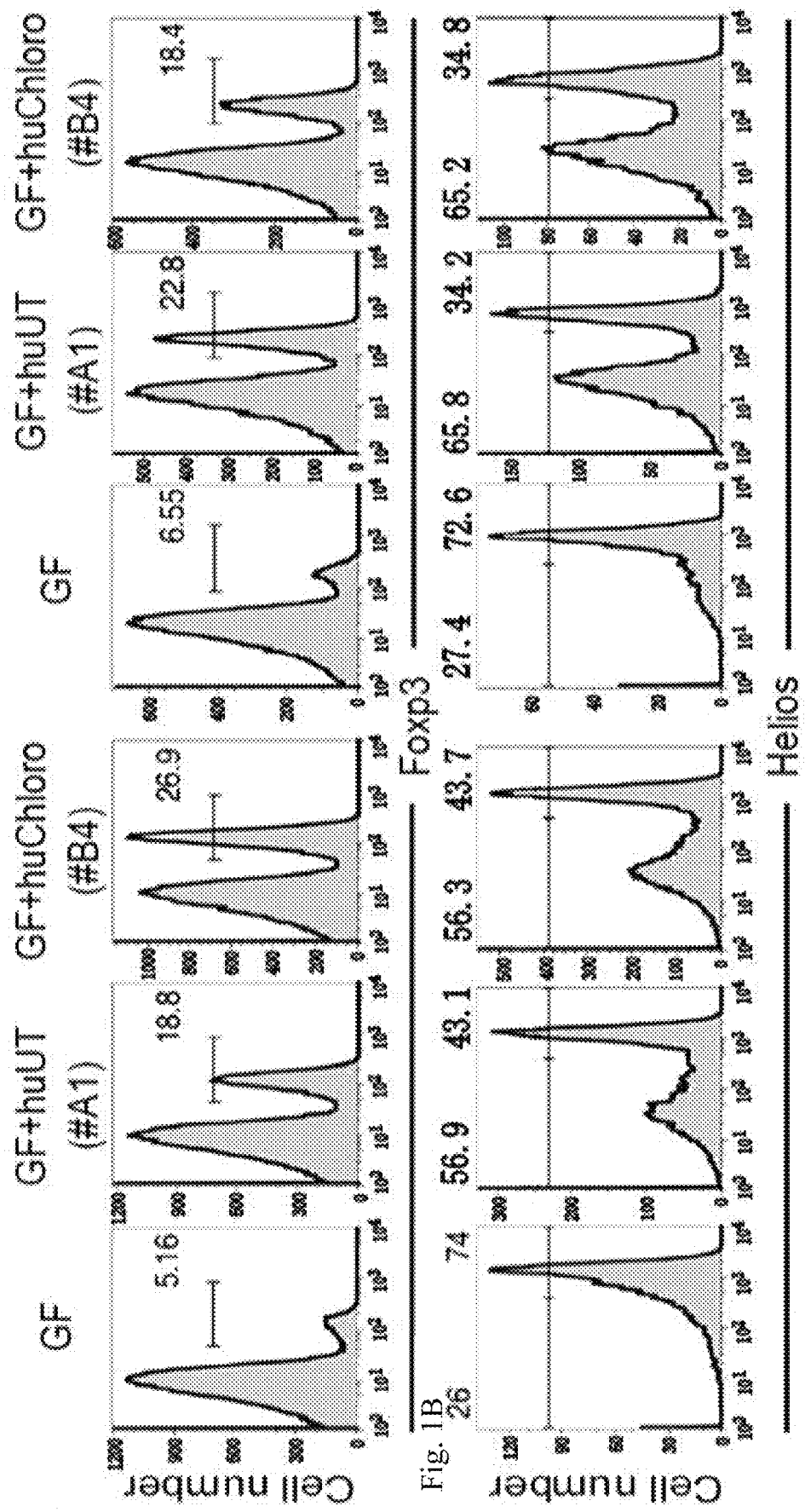
FIG. 1A is a histogram showing Foxp3 expression gated CD4 cells from colonic lamina propia (C LPL, left panel) and small intestinal lamina propria (SI LPL, right panel) of GF mice or GF mice colonized with untreated (+huUT, n=4, numbering from # A1 to # A4) or chloroform-treated (+huChloro, n=4, numbering from # B1 to # B4) human feces. Numbers above bracketed lines indicate the percentage of the population.
FIG. 1B is a histogram showing Helios expression in Foxp3$^+$CD4$^+$ cells from colonic lamina propia (left panel) and small intestinal lamina propria (right panel) of GF mice or GF mice colonized with untreated (+huUT) or chloroform-treated (+huChloro) human feces. Numbers above bracketed lines indicate the percentage of the population.
Figure 1C:
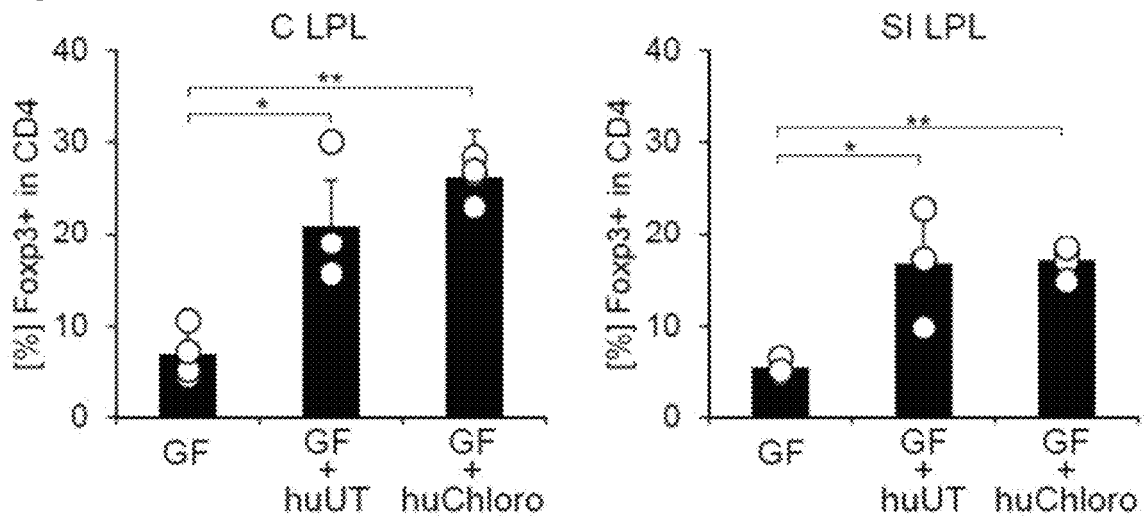
FIGS. 1C-1D are graphs showing, respectively, combined data for Foxp3 expression in CD4$^+$ cells, and for Helios expression in Foxp3$^+$CD4$^+$ cells, from colonic lamina propia (left panel) and small intestinal lamina propria (right panel) of GF mice or GF mice colonized with untreated (+huUT) or chloroform-treated (+huChloro) human feces. Each circle in FIG. 1C
Figure 1D:
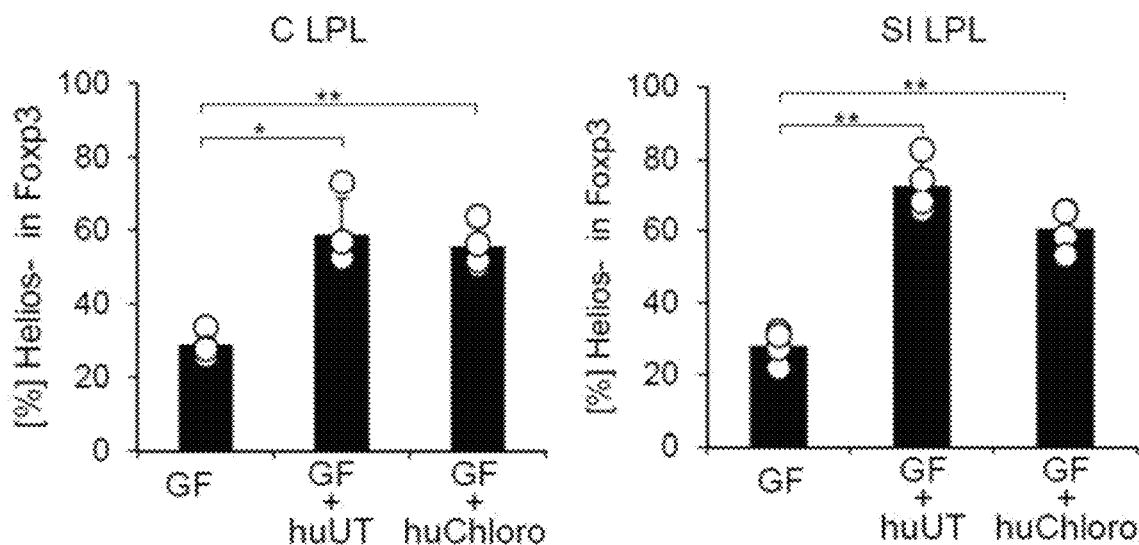
Figure 1F:
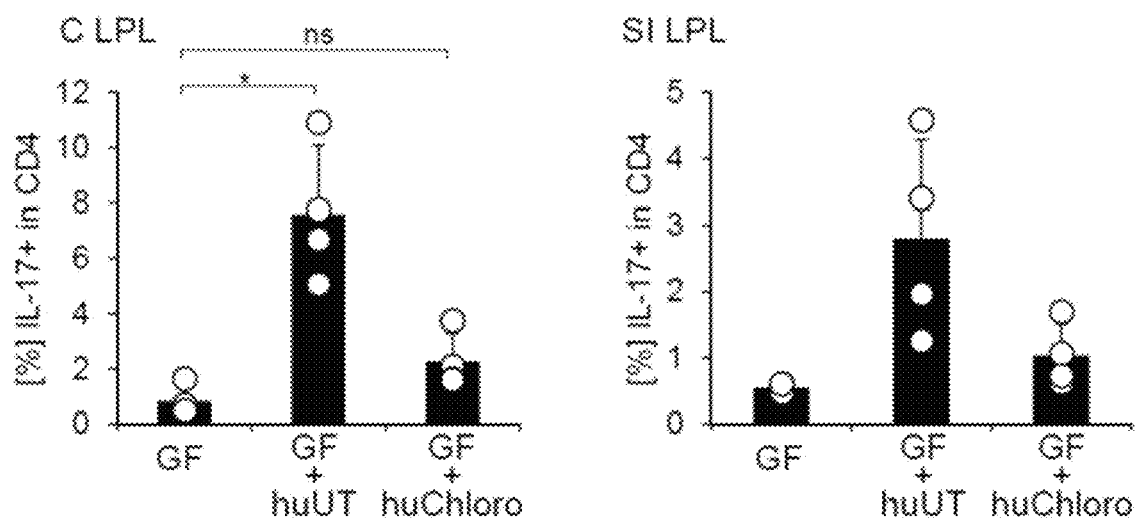
FIGS. 1F-1G show, respectively, combined data of all mice for IL-17 and IFN-expression in CD4$^+$ cells from colonic lamina propia (left panel) and small intestinal lamina propria (right panel) of GF mice or GF mice colonized with untreated (+huUT) or chloroform-treated (+huChloro) human feces. Each circle in FIG. 1F
Figure 1G:
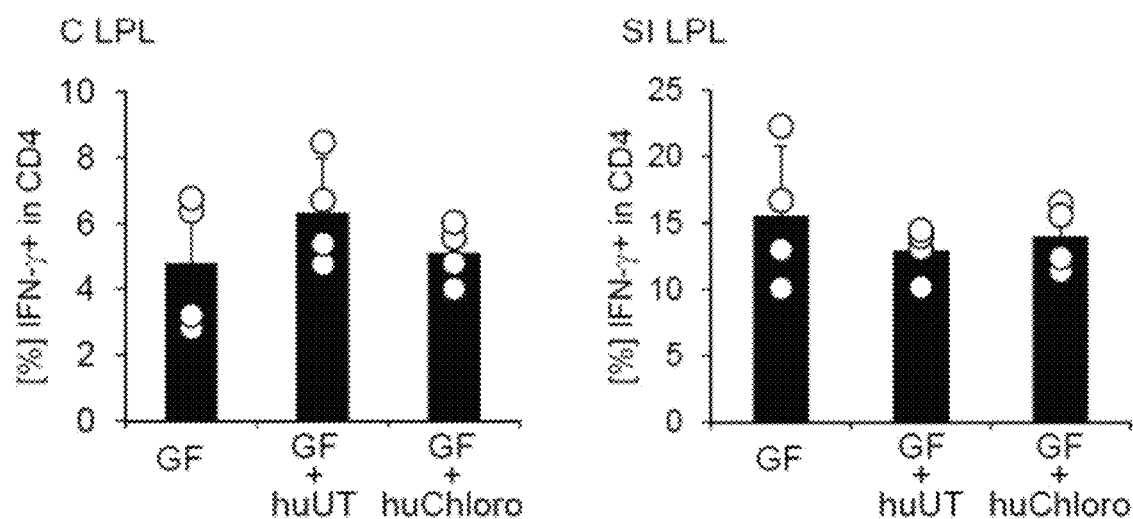

Table 1 shows the numbers of detected reads and the closest relatives for each OTU obtained from classification of sequences (3400 reads for each sample) resulting from 16srRNA coding gene amplification and PCR metasequencing of bacterial DNA extracted from the cecal contents of mouse # A1, # C4, # F8, # G2, # H3, # I3, # J3 and # K3 (classification on the basis of sequence similarity, >97% identity to sequences in nucleic acid databases using BLAST)

Table 2 shows, for each of seventeen bacterial strains isolated from the cecal contents of mouse # F8, # G2, # I1 and # K3 using BL agar or EG agar plates, the closest relative in known species, the maximum similarity with the closest relative, its classification in the Clostridiaceae cluster, origin of mouse ID, and culture medium for isolation.

Table 3 shows, for each of 31 bacterial strains isolated from the caecal contents of mouse # F8, # G2, # I1 and # K3 using BL agar or EG agar plates, the closest relative in known species, the maximum similarity with the closest relative, the database used for BLAST search, and similarity between strains.

Table 4 shows 16S rDNA analysis for each of 31 strains that were isolated. Bacterial DNA was isolated from each of the 31 strains and the 16S rDNA of the isolates was amplified by colony-PCR. Each amplified DNA was purified, sequenced, and aligned using the ClustalW software program. Based on the sequence of 16S rDNA for each strain, their closest species, % similarity with the closest species, and the similarity to other strains are shown. Strains that were included in the 23-mix, 17-mix, 5-mixA, 5-mixB, 5-mixC, and 3-mix are marked in the right hand column.

DETAILED DESCRIPTION

<Composition Having Effect of Inducing Proliferation or Accumulation of Regulatory T Cells>

Described herein is a composition that induces proliferation, accumulation of regulatory T cells or both proliferation and accumulation of regulatory T cells. The composition comprises, as an active ingredient, one or more of the following: a (at least one, one or more) organism selected from the group consisting of: *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium*

*contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662, a culture supernatant of one or more of the bacteria, a component of culture medium in which a (at least one, one or more) bacterium described herein has grown, a physiologically active substance derived from a (at least one; one or more) bacterium described herein; and a (at least one; one or more) bacterium containing DNA comprising a nucleotide sequence having at least 97% homology to the nucleotide sequence of DNA of any of the bacterial species described herein, such as those listed above. Bacteria described herein were isolated from human fecal samples using the methods outlined in Examples 19 to 28.

The term "regulatory T cells" refers to T cells that suppress an abnormal or excessive immune response and play a role in immune tolerance. The regulatory T cells are typically transcription factor Foxp3-positive CD4-positive T cells. The regulatory T cells of the present invention also include transcription factor Foxp3-negative regulatory T cells that are IL-10-producing CD4-positive T cells.

The term "induces proliferation or accumulation of regulatory T cells" refers to an effect of inducing the differentiation of immature T cells into regulatory T cells, which differentiation leads to the proliferation and/or the accumulation of regulatory T cells. Further, the meaning of "induces proliferation or accumulation of regulatory T cells" includes in-vivo effects, in vitro effects, and ex vivo effects. All of the following effects are included: an effect of inducing in vivo proliferation or accumulation of regulatory T cells through administration or ingestion of the aforementioned bacteria belonging to the Clostridia class, a culture supernatant of the bacteria or supernatant component(s), or a physiologically active substance derived from the bacteria; an effect of inducing proliferation or accumulation of cultured regulatory T cells by causing the aforementioned bacteria belonging to the Clostridia class, a culture supernatant of the bacteria or supernatant component(s), or a physiologically active substance derived from the bacteria to act on the cultured regulatory T cells; and an effect of inducing proliferation or accumulation of regulatory T cells which are collected from a living organism and which are intended to be subsequently introduced into a living organism, such as the organism from which they were obtained or another organism, by causing the aforementioned bacteria belonging to the Clostridia class, a culture supernatant of the bacteria or supernatant component(s), or the physiologically active substance derived from the bacteria to act on the regulatory T cells. The effect of inducing proliferation or accumulation of regulatory T cells can be evaluated, for example, as follows. Specifically, the aforementioned bacteria belonging to the Clostridia class, a culture supernatant of the bacteria or supernatant component(s), or a physiologically active substance derived from the bacteria is orally administered to an experimental animal, such as a germ-free mouse, then CD4-positive cells in the colon are isolated, and the ratio of regulatory T cells contained in the CD4-positive cells is measured by flow cytometry (refer to Example 7).

The regulatory T cells whose proliferation or accumulation is induced by the composition of the present invention are preferably transcription factor Foxp3-positive regulatory T cells or IL-10-producing regulatory T cells.

In the present invention, "human-derived bacteria" means bacterial species that have been isolated from a fecal sample or from a gastrointestinal biopsy obtained from a human individual or whose ancestors were isolated from a fecal sample or from a gastrointestinal biopsy obtained from a human (e.g., are progeny of bacteria obtained from a fecal sample or a gastrointestinal biopsy). For example, the bacterial species may have been previously isolated from a fecal sample or from a gastrointestinal biopsy obtained from a human and cultured for a sufficient time to generate progeny. The progeny can then be further cultured or frozen. The human-derived bacteria are naturally occurring commensals that populate the gastrointestinal tract of human individuals, preferably healthy human individuals.

In the present invention, the term "Clostridia class" (as in "compositions containing bacteria belonging to the Clostridia class") refers to a class of Gram+, obligate anaerobic bacteria belonging to the Firmicutes phylum that have the ability to form spores. It is important to note that while currently most bacteria in this class are included in the *Clostridiales* order, this categorization is still partly based on old methods and is likely to be redefined in the future based on new advances in sequencing technologies that are enabling sequencing of the full genomes of bacteria in this class. Table 2 provides a summary of the categorization of 17 abundant species belonging to the Clostridia class which have been identified by the inventors as strong Treg-inducers and cultured in vitro. All of these species fall, under current categorization rules, in the Clostridiaceae family, and belong to clusters IV, XIVa, XVI, and XVIII.

The composition of the present invention may include one strain alone (only one strain) of any of the aforementioned bacterial species, but two or more strains of the bacteria can be used together. For example, one, two, three, four, five, six, seven, eight, nine, ten, eleven, twelve, thirteen, fourteen, fifteen, sixteen or seventeen of the strains listed in Table 2 or Table 4, in any combination, can be used together to affect regulatory T cells. In some embodiments, the 23, 17, 5, or 3 species mixes listed in Table 4 can be used together (and administered in one or several compositions) to affect regulatory T cells. In some embodiments, the following strains can be combined (the composition comprises): strain 1 (OTU136, closest species: *Clostridium saccharogumia, Clostridium ramosum* JCM1298), strain 3 (OTU221, closest species: *Flavonifractor plautii, Pseudoflavonifractor capillosus* ATTC 29799), strain 4 (OTU9, closest species: *Clostridium hathewayi, Clostridium saccharolyticum* WM1), strain 5 (OTU296, closest species: *Clostridium scindens, Lachnospiraceae bacterium* 5_1_57FAA), strain 6 (OTU21, closest species: *Blautia coccoides, Lachnospiraceae bacterium* 6_1_63FAA), strain 7 (OUT 166, closest species: *Clostridium* sp., *Clostridium bolteae* ATCC BAA-613), strain 8 (OTU73, closest species: cf. *Clostridium* sp. MLG055, *Erysipelotrichaceae bacterium* 2_2_44A), strain 9 (OTU174, closest species: *Clostridium indolis, Anaerostipes caccae* DSM 14662), strain 10 (OTU166, closest species: *Clostridium bolteae, Clostridiu bolteae* ATCC BAA-613), strain 12 (OTU55, closest species: *Lachnospiraceae bacterium* DJF_VP30, *Lachnospiraceae bacterium* 3_1_57FAA_CT1), strain 13 (OTU337, closest species: *Anaerotruncus colihominis, Anaerotruncus colihominis* DSM 17241), strain 14 (OTU314, closest species: *Ruminococcus* sp. ID8, *Lachnospiraceae bacterium* 2_1_46FAA), strain 15 (OTU195, closest species: *Clostridium lavalense, Clostridium asparagiforme* DSM 15981), strain 16 (OTU306, closest species: *Clostridium symbiosum, Clostridium symbiosum* WAL-14163), strain 18 (OTU46, closest species: *Clostridium ramosum, Clostridium ramosum*), strain 21 (OTU87, closest species: *Eubacterium contortum, Clostridium* sp. D5), strain 23 (OTU152, closest species: *Lachnospiraceae bacterium*

DJF_VP30, Lachnospiraceae bacterium 3_1_57FAA_CT1), strain 24 (OTU253, closest species: Oscillospiraceae bacterium NML 061048, Oscillibacter valericigenes), strain 25 (OTU259, closest species: Eubacterium contortum, Clostridium sp. D5), strain 26 (OTU281, closest species: Clostridium scindens, Lachnospiraceae bacterium 5_1_57FAA), strain 27 (OTU288, closest species: Lachnospiraceae bacterium A4, Lachnospiraceae bacterium 3_1_57FAA_CT1), strain 28 (OTU344, closest species: Clostridium sp. 316002/08, Clostridiales bacterium 1_7_47FAA), and strain 29 (OTU359, closest species: Lachnospiraceae bacterium A4, Lachnospiraceae bacterium 3_1_57FAA_CT1) as described in Table 4.

In some embodiments, the following strains can be combined (the composition comprises: strain 1 (OTU136, closest species: Clostridium saccharogumia, Clostridium ramosum JCM1298), strain 3 (OTU221, closest species: Flavonifractor plautii, Pseudoflavonifractor capillosus ATTC 29799), strain 4 (OTU9, closest species: Clostridium hathewayi, Clostridium saccharolyticum WM1), strain 6 (OTU21, closest species: Blautia coccoides, Lachnospiraceae bacterium 6_1_63FAA), strain 7 (OUT 166, closest species: Clostridium sp., Clostridium bolteae ATCC BAA-613), strain 8 (OTU73, closest species: cf. Clostridium sp. MLG055, Erysipelotrichaceae bacterium 2_2_44A), strain 9 (OTU174, closest species: Clostridium indolis, Anaerostipes caccae DSM 14662), strain 13 (OTU337, closest species: Anaerotruncus colihominis, Anaerotruncus colihominis DSM 17241), strain 14 (OTU314, closest species: Ruminococcus sp. ID8, Lachnospiraceae bacterium 2_1_46FAA), strain 15 (OTU195, closest species: Clostridium lavalense, Clostridium asparagiforme DSM 15981), strain 16 (OTU306, closest species: Clostridium symbiosum, Clostridium symbiosum WAL-14163), strain 18 (OTU46, closest species: Clostridium ramosum, Clostridium ramosum), strain 21 (OTU87, closest species: Eubacterium contortum, Clostridium sp. D5), strain 26 (OTU281, closest species: Clostridium scindens, Lachnospiraceae bacterium 5_1_57FAA), strain 27 (OTU288, closest species: Lachnospiraceae bacterium A4, Lachnospiraceae bacterium 3_1_57FAA_CT1), strain 28 (OTU344, closest species: Clostridium sp. 316002/08, Clostridiales bacterium 1_7_47FAA), and strain 29 (OTU359, closest species: Lachnospiraceae bacterium A4, Lachnospiraceae bacterium 3_1_57FAA_CT1) as described in Table 4.

In some embodiments, the following strains can be combined (the composition comprises): strain 1 (OTU136, closest species: Clostridium saccharogumia, Clostridium ramosum JCM1298), strain 4 (OTU9, closest species: Clostridium hathewayi, Clostridium saccharolyticum WM1), strain 16 (OTU306, closest species: Clostridium symbiosum, Clostridium symbiosum WAL-14163), strain 27 (OTU288, closest species: Lachnospiraceae bacterium A4, Lachnospiraceae bacterium 3_1_57FAA_CT1), and strain 29 (OTU359, closest species: Lachnospiraceae bacterium A4, Lachnospiraceae bacterium 3_1_57FAA_CT1) as described in Table 4. In some embodiments, the following strains can be combined: strain 6 (OTU21, closest species: Blautia coccoides, Lachnospiraceae bacterium 6_1_63FAA), strain 8 (OTU73, closest species: cf. Clostridium sp. MLG055, Erysipelotrichaceae bacterium 2_2_44A), strain 13 (OTU337, closest species: Anaerotruncus colihominis, Anaerotruncus colihominis DSM 17241), strain 14 (OTU314, closest species: Ruminococcus sp. ID8, Lachnospiraceae bacterium 2_1_46FAA), and strain 26 (OTU281, closest species: Clostridium scindens, Lachnospiraceae bacterium 5_1_57FAA) as described in Table 4. In some embodiments, the following strains can be combined: strain 3 (OTU221, closest species: Flavonifractor plautii, Pseudoflavonifractor capillosus ATTC 29799), strain 7 (OUT 166, closest species: Clostridium sp., Clostridium bolteae ATCC BAA-613), strain 9 (OTU174, closest species: Clostridium indolis, Anaerostipes caccae DSM 14662), strain 15 (OTU195, closest species: Clostridium lavalense, Clostridium asparagiforme DSM 15981), and strain 28 (OTU344, closest species: Clostridium sp. 316002/08, Clostridiales bacterium 1_7_47FAA) as described in Table 4 In some embodiments, the following strains can be combined: strain 1 (OTU136, closest species: Clostridium saccharogumia, Clostridium ramosum JCM1298), strain 2 (OTU46, closest species: Flavonifractor plautii, Pseudoflavonifractor capillosus ATCC 29799) and strain 3 (OTU221, closest species: Flavonifractor plautii, Pseudoflavonifractor capillosus ATTC 29799) as described in Table 4. The use of multiple strains of the aforementioned species of bacteria, preferably belonging to the Clostridium cluster XIVa or the cluster IV in combination can bring about an excellent effect on regulatory T cells. In addition to the bacteria belonging to clusters XIVa and IV, Clostridium ramosum, Clostridium saccharogumia (belonging to cluster XVIII) and cf. Clostridium sp. MLG055 (belonging to cluster XVI) can also be used. If more than one strain of bacteria is used (e.g., one or more strain belonging to cluster XIVa, one or more strain belonging to cluster IV, one or more strain belonging to clusters XVIII or XVI or a combination of any of the foregoing), the number and ratio of strains used can vary widely. The number and ratio to be used can be determined based on a variety of factors (e.g., the desired effect, such as induction or inhibition of proliferation or accumulation of regulatory T cells; the disease or condition to be treated, prevented or reduced in severity; the age or gender of the recipient; the typical amounts of the strains in healthy humans). The strains can be present in a single composition, in which case they can be consumed or ingested together (in a single composition), or can be present in more than one composition (e.g., each can be in a separate composition), in which case they can be consumed individually or the compositions can be combined and the resulting combination (combined compositions) consumed or ingested. Any number or combination of the strains that proves effective (e.g., any number from one to 22, such as 1 to 20, 1 to 15, 1 to 10, 1 to 5, 1 to 3, 1 to 2, and any number therebetween or one to 23, such as 1 to 23, 3 to 23, 5 to 23, 1 to 20, 1 to 17, 3 to 17, 5 to 17, 1 to 15, 1 to 10, 1 to 5, 3 to 5, 1 to 3, 1 to 2, and any number therebetween) can be administered. In certain embodiments of the present invention, a combination of some or all of the 22 or 23 (e.g., the 23 strains in Example 32 and Table 4) strains described in the present disclosure is used. For example, at least one, two or more, three, three or more, four, four or more, five, five or more, six, six or more or any other number of the 22 or 23 described strains, including 22 or 23 strains, can be used. In some embodiments, the specific combinations of 3, 5, 17, or 23 strains described in Table 4 can be used (the composition comprises combinations of 3, 5, 17 or 23 strains described in Table 4). They can be used in combination with one another and in combination with strains not described in the cited reference.

Cells of bacteria belonging to the Clostridia class, such as these specifically described herein, can be used in spore form or in vegetative form. From the viewpoint of stability to high temperature and pressure conditions, extended shelf life, ease of handling, resistance to antibiotics, and lack of need for a cold chain storage and distribution, the bacteria may be preferably in the form of spore. From the viewpoint of abiding by the directives of certain manufacturing organizations that do not tolerate spore contamination in their facilities, the bacteria may alternatively be produced (and later administered) in the form of vegetative cells.

The term the "physiologically active substance derived from bacteria belonging to the Clostridia class" of the present invention includes substances contained in the bacteria, secretion products of the bacteria, and metabolites of the bacteria. Such a physiologically active substance can be identified by purifying an active component from the bacteria, a culture supernatant thereof, or intestinal tract contents in the intestinal tract of a mouse in which only bacteria belonging to the Clostridia class are colonized by an already known purification method.

"Chloroform treatment" of a fecal sample obtained from a human is a method that isolates the bacteria in the fecal sample that have the ability to form spores, and is not particularly limited, as long as the spore-forming fraction is obtained by treating feces of a human with chloroform (for example, 3% chloroform), and has the effect of inducing proliferation or accumulation of regulatory T cells, including mammalian regulatory T cells such as murine regulatory T cells and human regulatory T cells.

When the aforementioned "bacteria belonging to the Clostridia class" are cultured in a medium, substances contained in the bacteria, secretion products and metabolites produced by the bacteria are released from the bacteria. The meaning of the active ingredient "culture supernatant of the bacteria" in the composition of the present invention includes such substances, secretion products, and metabolites. The culture supernatant is not particularly limited, as long as the culture supernatant has the effect of inducing proliferation or accumulation of regulatory T cells. Examples of the culture supernatant include a protein fraction of the culture supernatant, a polysaccharide fraction of the culture supernatant, a lipid fraction of the culture supernatant, and a low-molecular weight metabolite fraction of the culture supernatant.

The bacterial composition may be administered in the form of a pharmaceutical composition, a dietary supplement, or a food or beverage (which may also be an animal feed), or may be used as a reagent for an animal model experiment. The pharmaceutical composition, the dietary supplement, the food or beverage, and the reagent induce proliferation or accumulation of regulatory T cells. An example presented herein revealed that regulatory T cells (Treg cells) induced by bacteria or the like belonging to the Clostridia class suppressed the proliferation of effector T-cells. The composition of the present invention can be used suitably as a composition having an immunosuppressive effect. The immunosuppressive effect can be evaluated, for example, as follows. Regulatory T cells isolated from an experimental animal, such as a mouse, to which the composition of the present invention is orally administered are caused to act on effector T-cells ($CD4^+$ $CD25^-$ cells) isolated from the spleen, and the proliferation ability thereof is measured by using the intake amount of $[^3H]$-thymidine as an index (refer to Example 14).

The bacterial composition of the present invention can be used, for example, as a pharmaceutical composition for preventing or treating (reducing, partially or completely, the adverse effects of) an autoimmune disease. such as chronic inflammatory bowel disease, systemic lupus erythematosus, rheumatoid arthritis, multiple sclerosis, or Hashimoto's disease; an allergic disease, such as a food allergy, pollenosis, or asthma; an infectious disease, such as an infection with *Clostridium difficile*; an inflammatory disease such as a TNF-mediated inflammatory disease (e.g., an inflammatory disease of the gastrointestinal tract, such as pouchitis, a cardiovascular inflammatory condition, such as atherosclerosis, or an inflammatory lung disease, such as chronic obstructive pulmonary disease); a pharmaceutical composition for suppressing rejection in organ transplantation or other situations in which tissue rejection might occur; a supplement, food, or beverage for improving immune functions; or a reagent for suppressing the proliferation or function of effector T-cells.

More specific examples of target diseases for which the composition is useful for treatment (reducing adverse effects or prevention) include autoimmune diseases, allergic diseases, infectious diseases, and rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondy loarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and salmonella associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondy litis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with *acanthosis nigricans*, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulindependent diabetes mellitus, sympathetic ophthalmia, pulmonary hypertension secondary to connective tissue disease, Goodpasture's syndrome, pulmonary manifestation of *polyarteritis nodosa*, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, and diarrhea.

Additional examples of target diseases for which the composition is useful for treatment include colon cancer, cystic fibrosis, celiac disease, Type 2 diabetes, and autism-related immunopathologies. These diseases are characterized by a reduction of *Clostridium* Clusters IV and XIV in the gastrointestinal microbiota.

Compositions described herein can also be used as a pharmaceutical composition for preventing or treating infectious diseases in an individual whose resistance to the infectious diseases is impaired, for example because of damage due to excessive inflammation caused by the immunity or due to an alteration of the patient's microbiome. Examples of infectious pathogens that impair maintenance or recovery of homeostasis of a host, and which eventually bring about such immunopathological tissue damage include *Salmonella, Shigella, Clostridium difficile, Mycobacterium* (which cause the disease tuberculosis), protozoa (which cause malaria), filarial nematodes (which cause the disease filariasis), *Schistosoma* (which cause schistosomiasis), *Toxoplasma* (which cause the disease toxoplasmosis), *Leishmania* (which cause the disease leishmaniasis), HCV and HBV (which cause the disease hepatitis C and hepatitis B), and herpes simplex viruses (which cause the disease herpes).

Pharmaceutical preparations can be formulated from the bacterial compositions described by drug formulation methods known to those of skill in the art. For example, the composition can be used orally or parenterally in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

For formulating these preparations, the bacterial compositions can be used in appropriate combination with carriers that are pharmacologically acceptable or acceptable for ingestion, such as in a food or beverage, including one or more of the following: sterile water, physiological saline, vegetable oil, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, a flavor corrigent, a solubilizer, and other additives.

A pharmaceutical preparation or formulation and particularly a pharmaceutical preparation for oral administration, comprises an additional component that enables efficient delivery of the bacterial composition of the present invention to the colon, in order to more efficiently induce proliferation or accumulation of regulatory T cells in the colon. A variety of pharmaceutical preparations that enable the delivery of the bacterial composition to the colon can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon.

Another embodiment of a pharmaceutical preparation useful for delivery of the bacterial composition to the colon is one that ensures the delivery to the colon by delaying the release of the contents (e.g., the bacterial composition) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Examples of the composition enabling the delivery to the colon further include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

An example of a system enabling the delivery to the colon is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

Another example of the system enabling the delivery to the colon is a system of delivering a composition to the colon, the system being specifically decomposed by an enzyme (for example, a carbohydrate hydrolase or a carbohydrate reductase) present in the colon. Such a system is not particularly limited, and more specific examples thereof include systems which use food components such as non-starch polysaccharides, amylose, xanthan gum, and azopolymers.

When used as a pharmaceutical preparation, the bacterial composition may be used in combination with an already known pharmaceutical composition for use in immunosuppression. In some embodiments, the pharmaceutical preparation can comprise both the bacterial composition and the already known pharmaceutical composition. Such a known pharmaceutical composition is not particularly limited, and may be at least one therapeutic composition selected from the group consisting of corticosteroids, mesalazine, mesalamine, sulfasalazine, sulfasalazine derivatives, immunosuppressive drugs, cyclosporin A, mercaptopurine, azathioprine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines (preferably vaccines used for vaccination where the amount of an allergen is gradually increased), anti-TNF inhibitors such as infliximab, adalimumab, certolizumab pegol, golimumab, or etanercept, and combinations thereof. It is preferable to use these therapeutic compositions in combination with the bacterial composition described herein. The bacterial composition can also be used as an adjuvant to improve the efficacy of a vaccine formulation such as a vaccine for the prophylaxis or treatment of an autoimmune disease or an allergic disease.

The bacterial composition can be used as a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, creme caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies. The composition of the present invention can be used for animals, including humans. The animals, other than humans, are not particularly limited, and the composition can be used for various livestock, poultry, pets, experimental animals, and the like. Specific examples of the animals include pigs, cattle, horses, sheep, goats, chickens, wild ducks, ostriches, domestic ducks, dogs, cats, rabbits, hamsters, mice, rats, monkeys, and the like, but the animals are not limited thereto.

Without wishing to be bound by theory, individuals in whom bacteria belonging to the group Firmicutes (the group to which the *Clostridium* clusters IV and XIVa belong) are relatively abundant gain more body weight than individuals in whom bacteria belonging to the group Bacteroidetes are relatively abundant is large. The bacterial composition is capable of conditioning absorption of nutrients and improving feed efficiency. From such a viewpoint, the bacterial composition can be used for promoting body weight gain, or for a high efficiency animal feed. Diseases and conditions that would benefit from body weight gain include, e.g., starvation, cancer, AIDS, gastrointestinal disorders (e.g., celiac disease, peptic ulcer, inflammatory bowel disease (Crohns' disease and ulcerative colitis), pancreatitis, gastritis, diarrhea), hyperthyroidism, infection, renal disease, cardiac disease, pulmonary disease, connective tissue disease, weight loss caused by medications, anorexia, Addison's disease, dementia, depression, hypercalcemia, Parkinson's disease and tuberculosis.

The addition of the bacterial composition to an antibiotic-free animal feed makes it possible to increase the body weight of an animal that ingests the animal feed to a level equal to or higher than that achieved by animal ingesting antibiotic-containing animal feeds, and also makes it possible to reduce pathogenic bacteria in the stomach to a level equal to those in animals consuming typical antibiotic-containing animal feeds. The bacterial composition can be used as a component of an animal feed that does not need the addition of antibiotics.

In addition, unlike conventional bacteria (*Lactobacillus* and Bifidobacteria) in commercial use, which are not easy to incorporate into the livestock production, the present bacterial composition in spore form can be pelletized, sprayed, or easily mixed with an animal feed and can also be added to drinking water.

Animal feed comprising the bacterial composition can be fed to a wide variety of types of animals and animals of a varying ages and can be fed at regular intervals or for a certain period (for example, at birth, during weaning, or when the animal is relocated or shipped).

The bacterial composition can be used to promote weight gain and enhance energy absorption in humans and nonhumans (e.g., farm or other food animals).

The bacterial active components of the bacterial composition can be manufactured using fermentation techniques well known in the art. In one embodiment, the active ingredients are manufactured using anaerobic fermentors, which can support the rapid growth of bacterial species belonging to the Clostridia class. The anaerobic fermentors may be, for example, stirred tank reactors or disposable wave bioreactors. Culture media such as BL media and EG media, or similar versions of these media devoid of animal components can be used to support the growth of the bacterial species. The bacterial product can be purified and concentrated from the fermentation broth by traditional techniques, such as centrifugation and filtration, and can optionally be dried and lyophilized by techniques well known in the art.

A food or beverage comprising a bacterial composition described herein can be manufactured by manufacturing techniques well known in the technical field. One or more components (for example, a nutrient) which are effective for the improvement of an immune function by an immunosuppressive effect may be added to the food or beverage. In addition, the food or beverage may be combined with another component or another functional food exhibiting a function other than the function of the improvement of an immune function to thereby serve as a multi-functional food or beverage.

Moreover, the bacterial composition can be incorporated into foods requiring a processing step which may destroy ordinary probiotic strains. Specifically, most commercially usable probiotic strains cannot be incorporated into foods that need to be processed, for example, by heat treatment, long term storage, freezing, mechanical stress, or high-pressure treatment (for example, extrusion forming or roll forming). On the other hand, because of the advantageous nature of forming spores, the bacterial composition described herein can be easily incorporated into such processed foods. For example, the bacterial composition in the form of spores can survive even in a dried food, and can remain living even after being ingested. The bacterial composition can withstand low-temperature sterilization processes, typically processes carried out at a temperature from about 70° C. to about 100° C., both inclusive. The bacterial composition can be incorporated into dairy products that require a pasteurization step. Furthermore, the bacterial composition can withstand long-term storage of many years; high-temperature processing such as baking and boiling; low-temperature processing such as freezing and cold storage; and high-pressure treatments such as extrusion forming and roll forming.

Many types of foods that need to be processed under such harsh conditions include foods which need to be processed in a microwave oven to be edible (for example, oatmeal), foods which need to be baked to be edible (for example, a muffin), foods which need to be subjected to a sterilization high-temperature treatment for a short period of time to be edible (for example, milk), and foods which need to be heated to be drinkable (for example, hot tea).

The amount of the bacterial composition to be administered or ingested can be determined empirically, taking into consideration such factors as the age, body weight, gender, symptoms, health conditions, of an individual who will receive it, as well as the kind of bacterial composition (a pharmaceutical product, a food or beverage) to be administered or ingested. For example, the amount per administration or ingestion is generally 0.01 mg/kg body weight to 100 mg/kg body weight, and, in specific embodiments, 1 mg/kg body weight to 10 mg/kg body weight. Also described herein is a method for suppressing the immunity (reducing the immune response) of a subject, the method being characterized in that the bacteria belonging to the Clostridia class or the physiologically active substance derived from the bacteria is administered to or ingested by the subject as described above.

The bacterial composition may be administered to an individual once, or it may be administered more than once. If the composition is administered more than once, it can be administered on a regular basis (for example, once a day, once every two days, once a week, once every two weeks, once a month, once every 6 months, or once a year) or on an as needed or irregular basis. The appropriate frequency of administration (which may depend on host genetics, age, gender, and health or disease status of the subject, among other factors) may be determined empirically. For example, a patient can be administered one dose of the composition, and the levels of the bacterial strains of the composition in fecal samples obtained from the patient can be measured at different times (for example after 1 day, after 2 days, after 1 week, after 2 weeks, after 1 month). When the levels of the bacteria fall to, for example, one half of their maximum value, a second dose can be administered, and so on.

A product comprising the bacterial composition (a pharmaceutical product, a food or beverage, or a reagent) or a manual thereof may be accompanied by document or statement explaining that the product can be used to suppress the immunity (including a statement that the product has an immunosuppressive effect and a statement that the product has an effect of suppressing the proliferation or function of effector T-cells). Here, the "provision to the product or the manual thereof with the note" means that the document or statement is provided to a main body, a container, a package, or the like of the product, or the note is provided to a manual, a package insert, a leaflet, or other printed matters, which disclose information on the product.

<Method for Inducing Proliferation or Accumulation of Regulatory T Cells>

As described above, and as shown in Examples, administration of the bacterial composition to an individual makes it possible to induce proliferation or accumulation of regulatory T cells in the individual. This provides a method of inducing proliferation or accumulation of regulatory T cells in an individual, the method comprising: administering, to the individual, at least one substance selected from the group consisting of: (a) *Clostridium saccharogumia, Clostridium ramosum* JCM1298, *Clostridium ramosum, Flavonifractor plautii, Pseudoflavonifractor capillosus* ATCC 29799, *Clostridium hathewayi, Clostridium saccharolyticum* WM1, *Bacteroides* sp. MANG, *Clostridium saccharolyticum, Clostridium scindens, Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis, Anaerostipes caccae, Clostridium bolteae, Lachnospiraceae bacterium* DJF_VP30, *Lachnospiraceae bacterium* 3_1_57FAA_CT1, *Anaerotruncus colihominis, Anaerotruncus colihominis* DSM 17241, *Ruminococcus* sp. ID8, *Lachnospiraceae bacterium* 2_1_46FAA, *Clostridium lavalense, Clostridium asparagiforme* DSM 15981, *Clostridium symbiosum, Clostridium symbiosum* WAL-14163, *Eubacterium contortum, Clostridium* sp. D5, *Oscillospiraceae bacterium* NML 061048, *Oscillibacter valericigenes, Lachnospiraceae bacterium* A4, *Clostridium* sp. 316002/08, and *Clostridiales bacterium* 1_7_47FAA, *Blautia cocoides, Anaerostipes caccae* DSM 14662; (b) a culture supernatant of at least one (a, one or more) of the bacteria described/listed herein; (c) a physiologically active substance derived from a (one or more, at least one) bacterium described/listed herein; or a combination of any two or three of (a), (b) and (c). The bacterial composition is administered (provided) to the individual in sufficient quantity to produce the desired effect of inducing proliferation, accumulation or both proliferation and accumulation of regulatory T cells. It may be administered to an individual in need of treatment, reduction in the severity of or prevention of at least one disease selected from an autoimmune disease, an inflammatory disease, an allergic disease, and an infectious disease.

Note that, the "individual" or "subject" may be in a healthy state or a diseased state. The method may further comprise the optional step of administering at least one (a, one or more) antibiotic preceding, or in combination with, the bacterial composition. The antibiotic administered can be, for example, one which facilitates recolonization of the gut by Gram-positive bacteria of the Clostridia class, such as an antibiotic that reduces Gram-negative bacteria. Examples of such antibiotics include aminoglycoside antibiotics (amikacin, gentamicin, kanamycin, neomycin, netilmicin, tobramycin, and paromomycin), cephalosporin antibiotics (cefaclor, cefamandole, cefoxitin, cefprozil, cefuroxime, cefixime, cefdinir, cefditoren, cefoperazone, cefotaxime, ceftazidime, ceftibuten, ceftizoxime, ceftriaxone, and cefoxotin), sulfonamides, ampicillin, and streptomycin.

Moreover, a prebiotic composition such as almond skin, inulin, oligofructose, raffinose, lactulose, pectin, hemicellulose (such as xyloglucan and alpha-glucans), amylopectin, and resistant starch which are not decomposed in the upper gastrointestinal tract and promote the growth of intestinal microbes in the intestinal tract, as well as growth factors such as acetyl-Co A, biotin, beet molasses, and yeast extracts, preferentially contributes to the proliferation of the bacterial species in the composition belonging to the Clostridia class. A method of inducing proliferation and/or accumulation of regulatory T cells in an individual can comprise administering, to the individual, at least one substance selected from the above in combination with the bacterial composition. Also contemplated herein is a composition comprising the bacterial composition and a prebiotic composition.

The above-described antibiotic, and the above-described prebiotic composition or growth factor may be used in combination. Moreover, a therapeutic composition may be administered to an individual together with at least one substance selected from the group consisting of the bacterial composition, an antibiotic, and a prebiotic composition or growth factor.

A therapeutic composition can be, for example, one therapeutic composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines (preferably, vaccines used for vaccination where the amount of an allergen is gradually increased), anti-TNF inhibitors such as infliximab, adalimumab, certolizumab pegol, golimumab, or etanercept, and combinations thereof. These therapeutic compositions can be administered prior to, in combination with or following administration of the bacterial composition and optionally, also in combination with an antibiotic, a prebiotic composition, a growth factor or any combination of an antibiotic, a prebiotic composition and a growth factor.

There is no particular limitation imposed on the combined use of the therapeutic composition with at least one substance selected from the group consisting of the bacterial composition, the "antibiotic", and the "prebiotic composition or growth factor". For example, the "one substance" and the therapeutic composition are administered orally or parenterally to an individual simultaneously or sequentially/individually at any appropriate time.

Whether administration of the bacterial composition induces the proliferation and/or accumulation of regulatory T cells can be determined by using, as an index, increase or reinforcement of at least one of the following: the number of regulatory T cells, the ratio of regulatory T cells in the T cell group of the colon, a function of regulatory T cells, or expression of a marker of regulatory T cells. A specific approach is measurement counts or percentage of Foxp3-expressing Tregs in a patient sample, such as a biopsy or a blood sample, promotion (enhancement) of IL-10 expression, promotion (enhancement) of CTLA4 expression, promotion (enhancement) of IDO expression, suppression of IL-4 expression, or colonization of an individual with the bacterial composition administered as the index of the induction of proliferation or accumulation of regulatory T cells.

Methods for detecting such expression include northern blotting, RT-PCR, and dot blotting for detection of gene expression at the transcription level; ELISA, radioimmunoassays, immunoblotting, immunoprecipitation, and flow cytometry for detection of gene expression at the translation level.

Samples that may be used for measuring such an index include tissues and fluids obtained from an individual, such as blood, obtained in a biopsy, and a fecal sample.

<Method for Predicting Response of an Individual to the Bacteria Composition by Monitoring the Individual's Response to Treatment with the Composition>

Also described is a method in which an amount (e.g. count) or the percentage of at least one bacterial species selected from the group consisting of: *Clostridium saccharogumia*, *Clostridium ramosum* JCM1298, *Clostridium ramosum*, *Flavonifractor plautii*, *Pseudoflavonifractor capillosus* ATCC 29799, *Clostridium hathewayi*, *Clostridium saccharolyticum* WM1, *Bacteroides* sp. MANG, *Clostridium saccharolyticum*, *Clostridium scindens*, *Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis*, *Anaerostipes caccae*, *Clostridium bolteae*, *Lachnospiraceae bacterium* DJF_VP30, *Lachnospiraceae bacterium* 3_1_57FAA_CT1, *Anaerotruncus colihominis*, *Anaerotruncus colihominis* DSM 17241, *Ruminococcus* sp. ID8, *Lachnospiraceae bacterium* 2_1_46FAA, *Clostridium lavalense*, *Clostridium asparagiforme* DSM 15981, *Clostridium symbiosum*, *Clostridium symbiosum* WAL-14163, *Eubacterium contortum*, *Clostridium* sp. D5, *Oscillospiraceae bacterium* NML 061048, *Oscillibacter valericigenes*, *Lachnospiraceae bacterium* A4, *Clostridium* sp. 316002/08, and *Clostridiales bacterium* 1_7_47FAA, *Blautia cocoides*, *Anaerostipes caccae* DSM 14662 in a patient's sample (e.g. a colonic biopsy or a fecal sample) is determined. When the percentage or the count of the bacteria selected from the list above is lower in an individual than a base line value obtained by performing a similar determination on a healthy individual (e.g., an individual who does not have/has not been identified as having a disease or condition for which the bacterial composition is a potential treatment such as an auto-immune disease, an allergic condition, cancer, organ rejection), it is determined that the individual is likely to be responsive to the bacterial composition. This determination can be used, for example, by a clinician to determine whether an individual or a patient is likely to benefit from treatment with the bacterial composition, or to select an individual or a patient for inclusion in a clinical trial. The clinician can then administer the bacterial composition to the individual or patient based on the determination that the individual or patient is likely to benefit from treatment. This determination can also be used as a method to monitor an individual's response to treatment with the bacterial compositions described, wherein a higher value of the determination after treatment with the bacterial composition (compared to a determination before treatment)

indicates that the individual has responded favorably to treatment (e.g. is a positive indicator of successful colonization and enhanced immunosuppression in the individual). Optionally, the prognosis and monitoring methods described here may further comprise the step of measuring in the individual's samples the percentages or absolute counts of other commensal species belonging to Clostridium Clusters IV and XIVa that are not present in the bacterial composition, wherein lower than baseline values before treatment indicate a higher likelihood of a positive response to treatment, and wherein an increased value after treatment indicates that the individual has responded favorably to treatment. In the prognosis and monitoring methods described here, a variety of known methods can be used for determining the composition of the microbiota. For example, 16S rRNA sequencing can be used <Vaccine Adjuvant Composition and Method for Treating or Preventing Infectious Disease or Autoimmune Disease by Using the Vaccine Composition>

As described above, and as shown in the Examples, the induction of Treg cells in the colon by bacteria belonging to the Clostridia class has an important role in local and systemic immune responses. The bacterial composition can also be used as an adjuvant to improve the efficacy of a vaccine formulation. In one embodiment, the bacterial composition can be used as an adjuvant to a vaccine for the prophylaxis or treatment of an autoimmune disease or an allergic disease (for example, as an adjuvant for a vaccination protocol where the amount of an allergen is gradually increased).

Example of autoimmune diseases and allergic diseases include those described as the "specific examples of target diseases" in <Composition Having Effect of Inducing Proliferation or Accumulation of Regulatory T cells>.

Other Embodiment

The bacterial composition can also be administered to an individual who is also receiving antibiotic treatment. The present inventors have demonstrated that antibiotics that act against Gram+ bacteria, such as vancomycin or metronidazole, can effectively eliminate or greatly reduce bacterial species belonging to the Clostridia class from the gastrointestinal tract of mammals and subsequently decrease the levels of regulatory T cells (Example 5, FIG. 30). Without wishing to be bound by theory, the key role of bacteria belonging to the Clostridia class in preserving immune tolerance strongly indicates that their absence or reduced levels can play a key role in autoimmune diseases characterized by failures of immune tolerance. Accordingly, individuals undergoing courses of antibiotics against Gram+ bacteria (for example, individuals being treated for infections with pathogens such as C. difficile and Giardia), who are at a high risk of experiencing a loss of the bacteria belonging to the Clostridia class and thus experience immune tolerance deficits, can be preventively "repopulated" through use of the bacterial composition. The bacterial composition can be administered before, simultaneously with, or after the antibiotic treatment, but preferably it is administered simultaneously or after the antibiotic treatment. The bacterial composition is preferably administered in spore form, to improve its resistance to residual antibiotics. Antibiotics against Gram-positive bacteria include, but are not limited to, vancomycin, metronidazole, linezolid, ramoplanin, fidaxomicin, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

<Methods to Select Treg-Inducing Organisms>

Also described is a method of obtaining bacteria capable of inducing Tregs, comprising (1) isolating the bacterial spore-forming fraction from a fecal or biopsy sample obtained from a mammal, preferably a human (e.g. by chloroform treatment or by heat treatment), (2) optionally, orally administering the spore-forming fraction to a non-human mammal, preferably a germ-free non-human mammal; (3) optionally, obtaining a fecal sample from the non-human mammal, diluting the fecal sample (for example diluting it by volume by a factor of 10, 100, 1,000, or 10,000), thereby producing a diluted fecal sample, and orally administering the diluted sample to a second germ-free non-human mammal, wherein optional step (3) can be repeated more than one time, (4) plating serial dilutions, under aerobic condition or strictly anaerobic conditions, of either the spore-forming fraction obtained in (1) or a sample of intestinal contents of the non-human mammal of (3), and (5) picking a single colony from the culture plate. The colony can be further assessed for the ability of bacteria to induce proliferation of regulatory T cells and/or accumulation of regulatory T cells using known methods, such as those described in the examples.

Following are examples, which describe specific aspects. They are not intended to be limiting in any way.

Note that mice used in Examples were prepared or produced as follows. In the following description, mice may be referred to as "SPF" or "GF". These "SPF" and "GF" indicate that the mice were maintained in the absence of specific pathogenic bacteria (specific pathogen-free, SPF), and that the mice were maintained under Germ-Free (GF) conditions, respectively.

<Mice>

C57BL/6, Balb/c, and IQI mice maintained under SPF or GF conditions were purchased from Sankyo Labo Service Corporation, Inc. (Japan), JAPAN SLC, INC. (Japan), CLEA Japan, Inc. (Japan), or The Jackson Laboratory (USA). GF mice and gnotobiotic mice were bred and maintained within the gnotobiotic facility of The University of Tokyo, Yakult Central Institute for Microbiological Research, or Sankyo Labo Service Corporation, Inc. Myd88$^{-/-}$, Rip2$^{-/-}$, and Card9$^{-/-}$ mice were produced as described in NPL 1 to 3, and backcrossed for 8 generations or more, so that a C57BL/6 genetic background was achieved. Foxp3$^{eGFP}$ mice were purchased from the Jackson Laboratory.

<Il10$^{venus}$ Mice>

To form a bicistronic locus encoding both Il10 and Venus under control of an Il10 promoter, a targeting construct was first created. Specifically, a cassette (IRES-Venus-SV40 polyA signal cassette, refer to Non-Patent Document 4) which was made of an internal ribosome entry site (IRES), a yellow fluorescent protein (Venus), and a SV40 polyA signal (SV40 polyA) and which was arranged next to a neomycin-resistant gene (neo), was inserted between a stop codon and a polyA signal (Exon 5) of a Il10 gene. Next, the obtained targeting construct was used to cause homologous recombination with the Il10 gene region in the genome of mice. Thus, Il10$^{venus}$ mice having an Il10$^{venus}$ alleles were produced (refer to FIG. 1). Note that in FIG. 1 "tk" represents a gene coding thymidine kinase, "neo" represents the neomycin-resistant gene, and "BamH1" represents a cleavage site by the restriction enzyme BamH1.

Figure 2A:
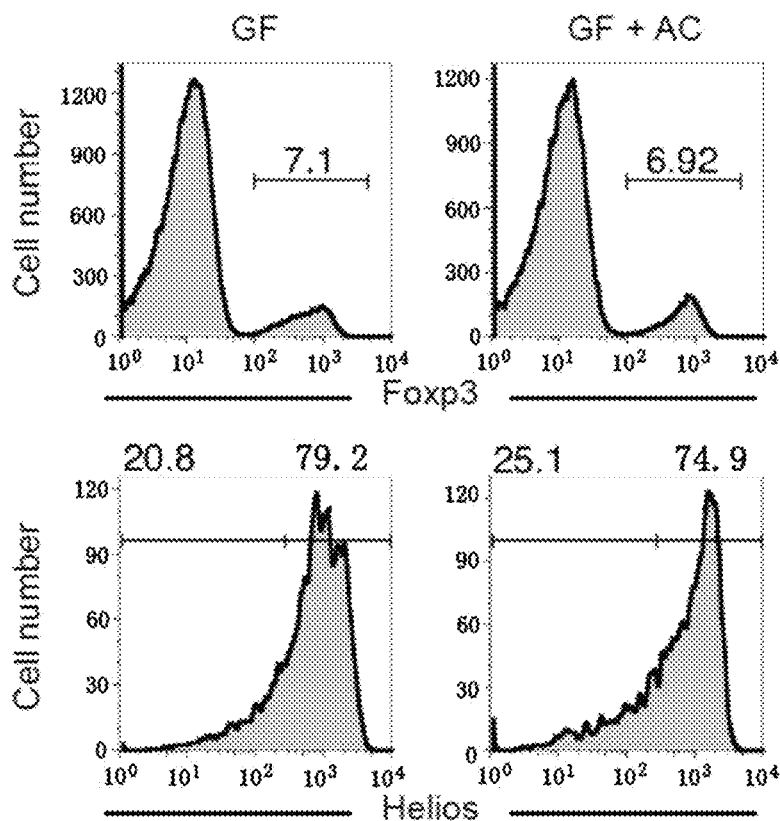
FIGS. 2A-2C shows representative plots (FIG. 2A) and combined data (FIGS. 2B-2C) for Foxp3 expression in CD4+ cells (upper panel in FIG. 2A, left panel in FIG. 2B), or Helios expression in Foxp3+CD4+ cells (lower panel in FIG. 2A, right panel in FIG. 2C) for GF mice and GF mice orally inoculated (once a week for 4 weeks) with a suspension of chloroform-treated human feces that had been previously autoclaved. Numbers above bracketed lines in FIG. 2A indicate the percentage of the population. Each circle in FIG. 2B
Figure 2B:
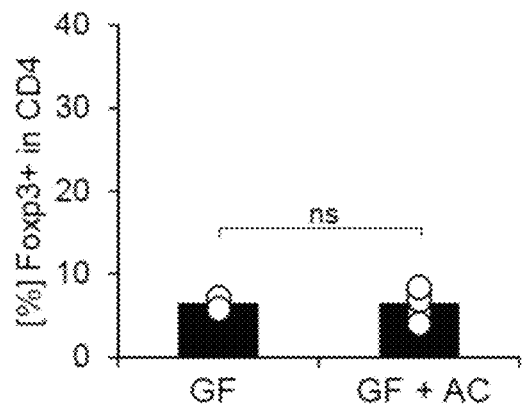
Figure 2C:
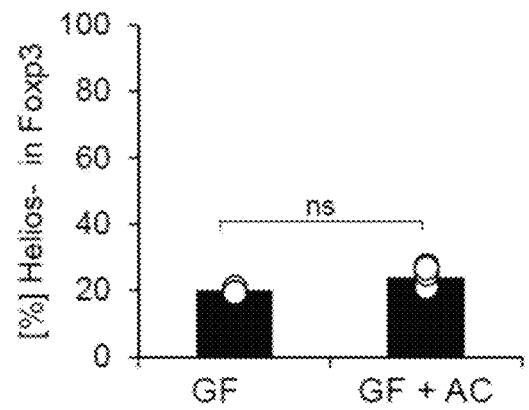

Genomic DNAs were extracted from the Il10$^{venus}$ mice, treated with BamH1, and Southern blotted by use of a probe shown in FIG. 1. FIG. 2 shows the obtained results. Wild-type and Il10$^{venus}$ alleles were detected as bands having sizes of 19 kb and 5.5 kb, respectively. Hence, as is apparent from the results obtained, the homologous recombination occurred in the genome of the Il10$^{venus}$ mice.

Further, CD4$^+$ Venus$^-$ cells or CD4$^+$ Venus$^+$ cells in the colonic lamina propria of the Il10$^{venus}$ mice were sorted by use of a FACSAria. Then, real-time RT-PCR was carried out on an ABI 7300 system by a method to be described later, to determine the amount of IL-10 mRNA expressed. It was found that, since the development of the IL-10 mRNA was detected only in the CD4$^+$ Venus$^+$ cells, the expression of IL-10 mRNA in the Il10$^{venus}$ mice was correctly reflected in the expression of Venus. Note that the germ-free states of such Il10$^{venus}$ mice were established in Central Institute for Experimental Animals (Kawasaki, Japan). The Il10$^{venus}$ mice in the germ-free states were maintained in vinyl isolators in Sankyo Labo Service Corporation, Inc. (Tokyo, Japan), and used in the following Examples.

Experiments and analyses in Examples were carried out as follows.

<Method for Colonization of Mice with Murine Bacteria and Analysis Thereof>

According to the description in NPL 5 and 6, mice in which SFB or *Clostridium* were colonized were produced. Cecal contents or feces of the obtained gnotobiotic mice were dissolved in sterile water or an anaerobic dilution solution. The dissolved cecal contents or feces as they were or after a chloroform treatment were orally administered to GF mice. Three strains of the *Lactobacillus* and 16 strains of the *Bacteroides* were cultured separately from each other in a BL or EG agar medium in an anaerobic manner. The cultured bacteria were harvested, suspended in an anaerobic TS broth, and orally administrated forcibly to GF mice. The state of the colonization of the bacteria in the mice was assessed by microscopic observation conducted on a smear preparation of fecal pellets.

<Isolation of Intestinal Lamina Propria Lymphocytes and Flow Cytometry>

The small intestine and colon were collected and opened longitudinally. The cecum was also isolated and cecal content was directly frozen at −80° C. or suspended in 2 ml PBS, then added 40% glycerol (final concentration 20%), snap-frozen in liquid nitrogen and stored at −80° C. until use. The colon and small intestine were washed in PBS to remove all luminal contents and shaken in Hanks' balanced salt solution (HBSS) containing 5 mM EDTA for 20 min at 37° C. After removing epithelial cells, muscle layers and fat tissue using tweezers, the lamina propria layers were cut into small pieces and incubated with RPMI1640 containing 4% fetal bovine serum, 1 mg/ml collagenase D, 0.5 mg/ml dispase and 40 μg/ml DNase I (all Roche Diagnostics) for 1 h at 37° C. in a shaking water bath. The digested tissues were washed with HBSS containing 5 mM EDTA, resuspended in 5 ml of 40% Percoll (GE Healthcare) and overlaid on 2.5 ml of 80% Percoll in a 15-ml Falcon tube. Percoll gradient separation was performed by centrifugation at 800 g for 20 min at 25° C. The lamina propria lymphocytes were collected from the interface of Percoll gradient and suspended in ice-cold PBS. For analysis of regulatory T cells, isolated lymphocytes were labeled with the LIVE/DEAD fixable violet dead cell stain kit (Invitrogen) to exclude dead cells in the analysis. The cells were washed with staining buffer containing PBS, 2% FBS, 2 mM EDTA and 0.09% NaN3 and stained surface CD4 with PECy7-labeled anti-CD4 Ab (RM4-5, BD Biosciences). Intracellular staining of Foxp3 and Helios was performed using the Alexa700-labeled anti-Foxp3 Ab (FJK-16s, eBioscience), Alexa647-labeled anti-Helios (22F6, eBioscience) and Foxp3 Staining Buffer Set (eBioscience). For analysis of Th1 and Th17 cells, isolated lymphocytes were stimulated for 4 hours with 50 ng/ml phorbol 12-myristate 13-acetate (PMA, Sigma) and 1 μg/ml ionomycin (Sigma) in the presence of GolgiStop (BD Biosciences). After incubation for 4 hours, cells were washed in PBS, labeled with the LIVE/DEAD fixable violet dead cell stain kit and stained surface CD4 with PECy7-labeled anti-CD4 Ab. Cells were washed, fixed in Cytofix/Cytoperm, permeabilized with Perm/Wash buffer (BD Biosciences), and stained with the APC-labeled anti-IL-17 Ab (eBio17B7, eBioscience) and FITC-labeled anti-IFN-γ Ab (XMG1.2, BD Biosciences). The Ab stained cells were analyzed with a LSR Fortessa (BD Biosciences), and data were analyzed using Flow Jo software (Treestar).

<Real-Time RT-PCR>

From an RNA prepared by using RNeasy Mini Kit (Qiagen), a cDNA was synthesized by use of a MMV reverse transcriptase (Promega KK). The cDNA obtained was analyzed by real-time RT-PCR using Power SYBR Green PCR Master Mix (Applied Biosystems) and ABI 7300 real time PCR system (Applied Biosystems), or real-time RT-PCR using SYBR Premix Ex Taq (TAKARA) and Light Cycler 480. For each sample, a value obtained was normalized for the amount of GAPDH. A primer set was designed by using Primer Express Version 3.0 (Applied Biosystems), and those exhibiting a 90% or higher sequence identity at an initial evaluation were selected. The primer set used was as follows:

```
Foxp3
                                         (SEQ ID NO: 1)
5'-GGCAATAGTTCCTTCCCAGAGTT-3'

(SEQ ID NO: 2)
5'-GGGTCGCATATTGTGGTACTTG-3'

CTLA4
                                         (SEQ ID NO: 3)
5'-CCTTTTGTAGCCCTGCTCACTCT-3'

(SEQ ID NO: 4)
5'-GGGTCACCTGTATGGCTTCAG-3'

GITR
                                         (SEQ ID NO: 5)
5'-TCAGTGCAAGATCTGCAAGCA-3'

(SEQ ID NO: 6)
5'-ACACCGGAAGCCAAACACA-3'

IL-10
                                         (SEQ ID NO: 7)
5'-GATTTTAATAAGCTCCAAGACCAAGGT-3'

(SEQ ID NO: 8)
5'-CTTCTATGCAGTTGATGAAGATGTCAA-3'

GAPDH
                                         (SEQ ID NO: 9)
5'-CCTCGTCCCGTAGACAAAATG-3'

(SEQ ID NO: 10)
5'-TCTCCACTTTGCCACTGCAA-3'
```

-continued

Mmp2

5'-GGACATTGTCTTTGATGGCA-3' (SEQ ID NO: 11)

5'-CTTGTCACGTGGTGTCACTG-3' (SEQ ID NO: 12)

Mmp9

5'-TCTCTGGACGTCAAATGTGG-3' (SEQ ID NO: 13)

5'-GCTGAACAGCAGAGCCTTC-3' (SEQ ID NO: 14)

Mmp13

5'-AGGTCTGGATCACTCCAAGG-3' (SEQ ID NO: 15)

5'-TCGCCTGGACCATAAAGAA-3' (SEQ ID NO: 16)

Ido1

5'-AGAGGATGCGTGACTTTGTG-3' (SEQ ID NO: 17)

5'-ATACAGCAGACCTTCTGGCA-3'. (SEQ ID NO: 18)

<Preparation and Culturing of Large Intestinal Epithelial Cells (IECs)>

First, the colon was collected, cut open longitudinally, and rinsed with PBS. Subsequently, the colon was treated with 1 mM dithiothreitol (DTT) at 37° C. for 30 minutes on a shaker, and then vortexed for one minute to disrupt the epithelial integrity. The released intestinal epithelial cells (IECs) were collected, and suspended in 5 ml of 20% percoll. The suspension was overlayered on 2.5 ml of 80% percoll in a 15-ml Falcon tube. Then, the tube was centrifuged at 25° C. and 780 g for 20 minutes to conduct cell separation by percoll density gradient centrifugation. Cells at the interface were collected, and used as colonic IECs (purity: 90% or higher, viability: 95%). The IECs obtained collected were suspended in RPMI containing 10% FBS, and $1 \times 10^5$ cells of the IECs were cultured in a 24-well plate for 24 hours. Thereafter, the culture supernatant was collected, and measured for active TGF-β1 level by ELISA (Promega).

Meanwhile, for culturing T cells in vitro, $1.5 \times 10^5$ MACS-purified splenic CD4$^+$ T cells were cultured in each well of a round-bottomed 96-well plate, together with a 50% conditioned medium in which IECs isolated from GF mice or Clostridium-colonized mice were cultured, and with 25 ng/ml of hIL-2 (Peprotech), in the presence or absence of 25 μg/ml of an anti-TGF-β antibody (R&D). Note that 10 μg/ml of an anti-CD3 antibody and an anti-CD28 antibody (BD Bioscience) were bound to the round-bottomed plate. After a 5-day culture, the CD4$^+$ T cells were collected, and subjected to a real-time PCR.

<Colitis Experimental Model>

A fecal suspension from Clostridium-colonized mice was orally administered to C57BL/6 mice (2-week old), which were grown in a conventional environment for six weeks.

For preparing a DSS-induced colitis model, 2% (wt/vol) DSS (reagent grade, DSS salt, molecular weight=36 to 50 kD, manufactured by MP Biomedicals), together with drinking water, was given to the mice for six days.

Meanwhile, for preparing an oxazolone-induced colitis model, the mice were presensitized by transdermally applying, onto the mice, 150 μl of a 3% oxazolone (4-ethoxymethylene-2-phenyl-2-oxazolin-5-one, Sigma-Aldrich)/100% ethanol solution. Five days after that, 150 μl of a 1% oxazolone/50% ethanol solution was intrarectally administered again to the presensitized mice under a light anesthesia. Note that the intrarectal administration was conducted by using a 3.5 F catheter.

Each mouse was analyzed daily for body weight, occult blood, bleeding visible with the naked eyes (gross blood), and the hardness of stool. Moreover, the body weight loss percentage, intestinal bleeding (no bleeding, occult blood (hemoccult+), or bleeding visible with the naked eyes), and the hardness of stool (normal stool, loose stool, or diarrhea) were evaluated numerically, and the disease activity index (DAI) was calculated in accordance with the description in "S. Wirtz, C. Neufert, B. Weigmann, M. F. Neurath, Nat Protoc 2, 541 (2007)."

<OVA Specific IgE Reaction>

BALB/c SPF mice were inoculated with a fecal suspension from Clostridium-colonized mice (2-week old), and grown in a conventional environment. Then, 1 μg of OVA (grade V, Sigma) and 2 mg of alum (Thermo Scientific), 0.2 ml in total, were intraperitoneally injected to the mice (at their ages of 4 weeks and 6 weeks). Sera were collected every week from the mice at the root of their tail, and OVA-specific IgE was measured by ELISA (Chondrex). Then, at their ages of 8 weeks, splenic cells were collected, inoculated in a 96-well plate at $1 \times 10^6$ cells per well, and stimulated with OVA (100 μg/ml) for three days. Thereafter, the culture supernatant was collected, and measured for IL-4 and IL-10 levels by ELISA (R&D).

<Statistical Analysis>

The difference between control and experimental groups was evaluated by the Student's t-test.

<Chloroform Treatment and Oral Inoculation with Fecal Samples into GF Mice>

Human stool (2 g) from a healthy volunteer (Japanese, male, 29 y old) was suspended with 20 ml phosphate-buffered saline (PBS) and passed through a 70 μm cell strainer to eliminate clumps and debris. Then fecal suspension was mixed with or without chloroform (final concentration 3%), and incubated in a shaking water bath for 60 min. The fecal suspensions without chloroform treatment were orally inoculated into germ-free (GF) mice (250 μl/mouse). After evaporation of chloroform by bubbling with N2 gas for 30 min, the aliquots containing chloroform-resistant (spore-forming) fraction of human intestinal bacteria were inoculated into IQI GF mice. Each group of ex-GF mice was separately kept in a vinyl isolator for 3 or 4 weeks.

<Co-Housing Experiment>

To evaluate whether Treg-inducing human bacteria can be transmitted horizontally, IQI GF mice were co-housed for 4 weeks with ex-GF mice colonized with chloroform-treated human feces (Example 21 mice) in a vinyl isolator (6 mice, designated as mouse # D1 to # D6

<Inoculation with Diluted Cecal Contents into GF Mice>

The frozen cecal content from ex-GF mice inoculated with chloroform-treated human feces (# C 4) was suspended in 10 times volume (w/v) of PBS, passed through a 70 μm cell strainer and treated 3% chloroform. Then the suspension was diluted 2000 (for 4 mice, designated as mouse # E1 to # E4) or 20000 (for 8 mice, designated as mouse # F1 to # F8)-fold with PBS and orally inoculated into GF IQI mice ($2.5 \times 10^5$ or $2.5 \times 10^4$ cells/250 μl/mouse). After 4 weeks, lymphocytes were collected from colon and small intestine and analyzed for Foxp3+ Treg cell proportion and their Helios expression. Cecal contents were frozen and stored at −80° C. until use.

<Re-Colonization Experiments>

The frozen cecal content from ex-GF mice inoculated with 20000-fold dilution (# F3, 7 and 8) was suspended in 10 times volume (w/v) of PBS, passed through a 70 µm cell strainer and treated 3% chloroform. The suspensions were orally inoculated into GF IQI mice (5, 4 or 4 mice; designated as mouse # G1 to # G5, # H1 to # H4 or # I1 to # I4, respectively). After 4 weeks, colon and small intestine were collected and analyzed for Foxp3+ Treg cell proportion and their Helios expression. Cecal contents were suspended in 20% glycerol solution, snap-frozen in liquid nitrogen and stored at −80° C.

<Cultured Bacteria-Colonization Experiments>

The glycerol stock of cecal content from # G2 mouse was diluted with PBS and seeded onto BL agar plate. After 48 hours, all bacterial colonies were collected by scraping the plates with a plate scraper and inoculated into GF IQI mice (4 mice, designated as mouse # K1 to # K 4). Six bacterial strains were isolated from the freeze stock of cecal content from # F8 mouse using BL agar plate. These isolated strains were inoculated into GF IQI mice (4 mice, designated as mouse # J1 to # J4). (Details of the culture method are described below.)

<16S rRNA Gene Quantitative PCR Analysis

Using a QIAamp DNA Stool mini kit (QIAGEN), bacterial genomic DNA was isolated from the human stool from a healthy volunteer as described above (human stool), cecal contents from GF mice gavaged with chloroform-treated human stool (cecal content of B-4 mouse) or feces from SPF ICR mouse (feces of SPF mouse). The isolated DNA was used as template for quantitative PCR. The amplification program consisted of one cycle at 95° C. for 1 min, followed by 50 cycles at 95° C. for 10 s and 60° C. for 30 s. Quantitative PCR analysis was carried out using a Light-Cycler 480 (Roche). Relative quantity was calculated by the ΔCt method and normalized to the amount of total bacteria. The following primer sets were used: total bacteria, 5'-GGTGAATACGTTCCCGG-3'(SEQ ID NO.: 45) and 5'-TACGGCTACCTTGTTACGACTT-3'(SEQ ID NO.: 46); *Clostridium* cluster XIVa (*Clostridium coccoides* subgroup), 5'-AAATGACGGTACCTGACTAA-3' (SEQ ID NO.: 47) and 5'-CTTTGAGTTTCATTCTTGCGAA-3'(SEQ ID NO.: 48); *Clostridium* cluster IV (*Clostridium leptum*) 5'-CCTTCCGTGCCGSAGTTA-3'(SEQ ID NO.: 49) and 5'-GAATTA AACCACATACTCCACTGCTT-3'(SEQ ID NO.: 50); *Bacteroides*, 5'-GAGAGGAAGGTCCCCCAC-3' (SEQ ID NO.: 51) and 5'-CGCTACTTGGCTGGTTCAG-3'(SEQ ID NO.: 52); *Bifidobacterium*, 5'-CGGGTGAG-TAATGCGTGACC-3' (SEQ ID NO.: 53) and 5'-TGATAGGACGCGACCCCA-3'(SEQ ID NO.: 54). Note that mice gavaged with chloroform-treated human stool exhibited high levels of spore-forming bacteria, such as *Clostridium* clusters XIVa and IV, and a severe decrease of non-spore-forming bacteria, such as *Bacteroides* and *Bifidobacterium*, compared with the human stool before chloroform treatment.

<Isolation of DNA from Cecal Contents for 16S rRNA Gene Metasequence Analysis>

The cecal contents of A1-1, A2-4, B-4, E-3, E-7, E-8, F-2, G-3, H-3, I-3 and J-3 were collected by centrifugation at 5000×g for 10 min at 4° C., suspended in 10 ml of Tris-EDTA containing 10 mM Tris-HCl and 1 mM EDTA (pH 8), and then used for DNA isolation. Lysozyme (SIGMA, 15 mg/ml) was added to the cell suspension. After incubation at 37° C. for 1 h with gentle mixing, a purified achromopeptidase (Wako) was added (final 2000 unit/ml) and incubated at 37° C. for 30 min. Then, sodium dodecyl sulfate (final 1%) was added to the cell suspension and mixed well. Subsequently, proteinase K (Merck) was added (final 1 mg/ml) to the suspension and the mixture was incubated at 55° C. for 1 h. High-molecular-weight DNA was isolated and purified by phenol/chloroform extraction, ethanol, and finally polyethyleneglycol precipitation.

<16S rRNA Gene Metasequence>

An aliquot of the DNA was used for PCR amplification and sequencing of bacterial 16S rRNA genes. ~330 bp amplicons, spanning variable region 1-2 (V1-2) of the gene were generated by using (i) modified primer 8F (5'-CCATCTCATCCCTGCGTGTCTCCGACTCAG+Barcode+agrgtttgatymtggctcag-3' (SEQ ID NO.: 55)) which consists of 454 adaptor sequence (underlined), a sample specific, error correcting barcode (10 bases, bold) and the universal bacterial primer 8F and (ii) modified primer 338R (5'-CCTATCCCCTGTGTGCCTTGGCAGTCTCAG+tgctgcctcccgtaggagt-3'(SEQ ID NO.: 56)) which contains 454 adaptor sequence (underlined) and the bacterial primer 338R. Polymerase chain reactions were performed for each fecal DNA sample: each 50-µL reaction contained 40 ng of DNA, 5 µl of 10×Ex Taq buffer (TAKARA), 5 µl of 2.5 mM dNTP mixture, 0.2 µl Ex Taq and 0.2 µM of each primer. PCR conditions consisted of an initial denaturation step performed at 96° C. for 2 min, followed by 20 cycles of denaturation (96° C., 30 s), annealing (55° C., 45 s) and amplification (72° C., 1 min) and final amplification step performed at 72° C. for 10 min. Amplicons generated from each sample were subsequently purified using AMPur XP (Beckman Coulter). The amount of DNA was quantified using Quant-iT Picogreen dsDNA Assay Kit (Invitrogen) and TBS-380mini Fluorometer (Turner Biosystems). The amplified DNA were used as template for 454 GS Junior (Roche) pyrosequencing. The sequences were performed using GS Junior Titanium emPCR Kit-Lib-L, GS Junior Titanium Sequencing Kit and GS Junior Titanium PicoTiterPlate Kit (all Roche) according to the manufacturer's manuals (GS Junior Titanium Series, emPCR Amplification Method Manual—Lib-L and Sequencing Method Manual). Resulting sequences (3400 reads were produced for each sample) were classified into OTU on the basis of sequence similarity (>97% identity). Representative sequences from each OTU were compared with sequences in nucleic acid databases (Ribosomal Database Project) using BLAST to determine the closest relatives. Then, OTUs were classified into species on the basis of the closest relatives. All data of close relatives and the number of reads are shown in Table. 1.

<Isolation of Bacterial Strains>

Bacterial strains were isolated from the cecal contents of # F8, # G2, # I1 and # K3 by plating serial dilutions of the cecal samples under aerobic condition or strictly anaerobic conditions (80% N2 10% H2 10% CO2) onto BL agar (Eiken Chemical) or EG agar plates containing medium with the following components (quantities expressed per liter): Meat extract 500 ml; Proteose peptone No. 3 (10.0 g, Difco); Yeast Extract (5.0 g, Difco); Na2HPO4 (4.0 g); D(+)-Glucose (1.5 g); Soluble Starch (0.5 g); L-cystine (0.2 g), L-cysteine-HCl—H2O (0.5 g); Tween80 (0.5 g); Bacto Agar (16.0 g, Difco); defibrinated horse blood (50 ml). After culture at 37° C. for 2 or 4 days, each single colony was picked up and cultured for additional 2 or 4 days at 37° C. by ABCM broth or EG agar plate. The isolated strains were collected into EG stock medium (10% DMSO) and stored at −80° C. For suspension of isolated strains to re-inoculate mice, TS medium (27.5 g of trypticase soy broth w/o dextrose, 0.84 g of Na2CO3, 0.5 g of L-cysteine-HCl—

H2O, 1000 ml of distilled water, pH adjusted to 7.2+/−0.2 with NaOH, then autoclaved for 15 minutes at 115 degrees Celsius). To identify the isolated strains, 16SrRNA coding gene sequences were performed. The 16S rRNA genes were amplified by colony-PCR using KOD FX (TOYOBO), 16S rRNA gene-specific primer pairs: 8F (5'-AGAGTTTGATC-MTGGCTCAG-3'(SEQ ID NO.: 57)) and 519R (5'-ATTAC-CGCGGCKGCTG-3'(SEQ ID NO.: 58)) for *C. indolis, C. bolteae, Bacteroides* sp. MANG, *L. bacterium* DJF_VP30, *A. colihominis, Ruminococcus* sp. ID8, *C. lavalense, C. symbiosum* and *E. contortum* or 1513R (5'-ACGGCTAC-CTTGTTACGACTT-3'(SEQ ID NO.: 59)) for *C. saccharogumia, C. ramosum, F. plautii, C. hathewayi, C. scindens, Clostridium* sp. 2335, *Clostridium* sp. 14616 and cf *Clostridium* sp. MLG055 and GeneAmp PCR System9700 (Applied Biosystems). The amplification program consisted of one cycle at 98° C. for 2 min, followed by 40 cycles at 98° C. for 10 s, 57° C. for 30s and 68° C. for 40 s. Each amplified DNA was purified from the reaction mixture using Illustra GFX PCR DNA and Gel Band Purification Kit (GE Healthcare). Sequence analysis was performed using BigDye Terminator V3.1 Cycle Sequencing Kit (Applied Biosystems) and Applied Biosystems 3730xl DNA analyzer (Applied Biosystems). The resulting sequences were compared with sequences in nucleic acid databases using BLAST to determine the closest relatives. The closest relatives and % identity of all isolated strains, information for genus-species of the closest relatives, *Clostridium* cluster, ID of mouse from which was derived, maximum similarity and culture medium of isolated strains were summarized in Table 2.

Example 1

First, it was investigated whether or not accumulation of regulatory T cells (Treg cells) in the colonic lamina propria was dependent on commensal bacteria. Specifically, lymphocytes were isolated from peripheral lymph nodes (pLN) of Balb/c mice bred in the absence of specific pathogenic bacteria (SPF) or from lamina propria of the colon or the small intestine (SI) of the mice. The CD4 and Foxp3 were stained by antibodies. Then, the ratio of Foxp3$^+$ cells in CD4$^+$ lymphocytes was analyzed by flow cytometry. The results showed that Foxp3$^+$ Treg cells were present at a high frequency in the lamina propria of the gastrointestinal tracts, especially in the colonic lamina propria, of the mice kept under the environment free from specific pathogenic microorganisms (SPF). In addition, it was also found that the number of the Foxp3$^+$ Treg cells in the colonic lamina propria gradually increased up to three months after their birth, whereas the number of the Foxp3$^+$ Treg cells in the peripheral lymph nodes was basically constant from the time of two weeks after their birth.

Example 2

Next, it was investigated whether or not the temporal accumulation of the Treg cells in the colon as found in Example 1 had a relationship with the colonization of intestinal commensal microbiota. Specifically, the expression of CD4 and the expression of Foxp3 in lymphocytes isolated from the small intestine, the colon, and the peripheral lymph nodes of mice bred under a germ-free (GF) or SPF environment (8 weeks old: Balb/c mice, IQI mice, and C57BL/6 mice) were analyzed. Similar results were obtained in three or more independent experiments.

In addition, lamina propria lymphocytes were collected from SPF mice and GF mice (Balb/c mice or C57BL/6 mice). CD4 and Foxp3 were stained with antibodies. Then, the lamina propria lymphocytes were analyzed by FACS.

Further, lymphocytes were isolated from the lamina propria of the colon, the lamina propria of the small intestine (SI), Peyer's patches (PPs), and mesenteric lymph nodes (MLNs) of mice (SPF C57BL/6 mice) to which antibiotics were orally administered with water for eight weeks. CD4 and Foxp3 were stained with antibodies. Then, the lymphocytes were analyzed by FACS. Similar results (the ratio of the Foxp3$^+$ cells in the CD4$^+$ cells of an individual mouse) were obtained in two or more independent experiments.

Note that the following antibiotics were used in combination in accordance with the description in the following document:
ampicillin (A; 500 mg/L, Sigma)
vancomycin (V; 500 mg/L, NACALAI TESQUE, INC.)
metronidazole (M; 1 g/L, NACALAI TESQUE, INC.)
neomycin (N; 1 g/L, NACALAI TESQUE, INC.)
Rakoff-Nahoum, J. Paglino, F. Eslami-Varzaneh, S. Edberg, R. Medzhitov, Cell 118, 229 (Jul. 23, 2004)
Fagarasan et al., Science 298, 1424 (Nov. 15, 2002)

As is apparent from the results the frequencies and the absolute numbers of Foxp3$^+$ CD4$^+$ cells in the small intestine and the peripheral lymph nodes of the GF mice were equal to or greater than those of the SPF mice. In addition, the numbers of the Treg cells in the small intestinal lamina propria, Peyer's patches, and mesenteric lymph nodes of the SPF mice to which the antibiotics were orally administered for eight weeks were equal to or greater than those of the SPF mice that had not received antibiotics. Meanwhile, the number of the Foxp3$^+$ CD4$^+$ cells in the colonic lamina propria of the GF mice was decreased significantly in comparison with that of the SPF mice. This decrease was commonly observed among mice of different genetic backgrounds (Balb/c, IQI, and C57BL/6), as well as among mice bred in different animal facilities. In addition, it was also shown that the number of Treg cells in the colonic lamina propria of the SPF C57BL/6 mice to which the antibiotics were administered was decreased significantly.

Example 3

Next, it was directly checked whether or not the decrease in the number of the Treg cells in the colonic lamina propria of the GF mice shown in Example 2 was attributed to the absence of microbiota. Specifically, a fecal suspension of B6 SPF mice purchased from The Jackson Laboratory was orally administered to GF-IQI mice (conventionalization). Three weeks after the administration, lymphocytes were isolated from the colonic lamina propria, and the expression of Foxp3 in CD4$^+$ lymphocytes was analyzed. The results showed that the number of Treg cells in the small intestinal lamina propria did not change. However, the number of the Treg cells in the colonic lamina propria increased significantly. Hence, it was shown that host-microbial interaction played an important role in the accumulation of Foxp3$^+$ Treg cells in the colonic lamina propria, while the accumulation of the Treg cells in the small intestinal lamina propria had a different mechanism.

Example 4

Next, the relationship between the gut-associated lymphoid tissues of mice and the number of Foxp3$^+$ cells in the colonic lamina propria of the mice was investigated in accordance with the method described in M. N. Kweon et al., J Immunol 174, 4365 (Apr. 1, 2005). Specifically, 100 µg of an extracellular domain recombinant protein (a fusion protein (LTβR-Ig) between a lymphotoxin β receptor (LTβR) and a Fc region of human IgG1, refer to Honda et al., J Exp Med 193, 621 (Mar. 5, 2001)) was injected intraperitoneally into pregnant C57BL/6 mice 14 days after conception. The LTβR-Ig was again injected intraperitoneally into fetuses obtained from such mice, so that mice from which isolated lymphoid follicles (ILFs), Peyer's patches (PPs), and colonic-patches (CPs) were completely removed were produced. Then, the ratios of Foxp3$^+$ cells in CD4$^+$ cells in the colonic lamina propria of the mice treated with the LTβR-Ig, and mice treated with rat IgG (control) were analyzed by FACS. The results show that the ratio of the Foxp3$^+$ cells in the colonic lamina propria of the mice deficient in isolated lymphoid follicles, Peyer's patches, and the colonic-patches (the mice treated with the LTβR-Ig) rather increased. Accordingly, it was suggested that the decrease in the number of the Treg cells in the colonic lamina propria of the GF mice and the mice treated with the antibiotics was caused because the transmission of specific signals which promotes the accumulation of Treg cells in the colonic lamina propria and which is caused by the intestinal microbes did not occur, rather than simply because of a secondary effect of disorganized gut-associated lymphoid tissues.

Example 5

To investigate whether or not a specific intestinal flora induced the accumulation of colonic Treg cells, vancomycin as an antibiotic against Gram-positive bacteria or polymyxin B as an antibiotic against Gram-negative bacteria was administered to SPF mice (from 4 weeks of age) for four weeks, and analyzed for the ratio of Foxp3$^+$ cells in the CD4$^+$ cell group ([%] Foxp3$^+$ in CD4).

The results show that the number of Treg cells in the colon of the mice to which vancomycin was administered was markedly decreased in comparison with that of the control. In contrast, no influence was observed on the number of Treg cells of the mice to which polymyxin B was administered. Those facts suggested that Gram-positive commensal bacteria played a major role in accumulation of Treg cells.

Example 6

A recent report has suggested that spore-forming bacteria play an important role in intestinal T cells response (see V. Gaboriau-Routhiau et al., Immunity 31, 677 (Oct. 16, 2009)). In this respect, fecal microorganisms (spore-forming fraction) resistant to 3% chloroform were orally administered to GF mice, which were then analyzed for the ratio of Foxp3$^+$ cells in the CD4$^+$ cell group ([%] Foxp3$^+$ in CD4).

Three weeks after the administration of the chloroform-treated feces, the number of Treg cells in the administered mice was markedly increased to the same level as those of the SPF mice and the GF mice to which the untreated feces was forcibly administered.

Accordingly, considering the results shown in Example 5 in combination, it was revealed that the specific components of the indigenous microbiota were highly likely to belong to the Gram-positive group, and that the spore-forming fraction played an important role in the induction of Treg cells.

Example 7

Next, the species of the intestinal microbiota which induced the accumulation of Treg cells in the colon as suggested in Examples 4 to 6 were identified. Specifically, segmented filamentous bacteria (SFB), 16 strains of the *Bacteroides* spp. (Bactero. (6 strains of *B. vulgatus*, 7 of the *B. acidifaciens* group 1, and 3 of the *B. acidifaciens* group 2)), 3 strains of the *Lactobacillus* (Lacto. (*L. acidophilus*, *L. fermentum*, and *L. murinum*)), and 46 strains of *Clostridium* spp. (Clost., refer to "Itoh, K., and Mitsuoka, T. Characterization of clostridia isolated from faeces of limited flora mice and their effect on caecal size when associated with germ-free mice. Lab. Animals 19: 111-118 (1985))"), or microbiota collected from mice (SPF) bred under a conventional environment was orally administered to GF-Balb/c mice or GF-IQI mice. The mice were maintained in vinyl isolators for three weeks. Then, CD4 cells were isolated from the colon and the small intestine of these mice. The numbers of Treg cells in the colon and the small intestine were analyzed by flow cytometry.

The bacteria belonging to the genus *Clostridium* are classified by sequencing of 16S rRNA gene, as follows. Specifically, the 16S rRNA genes of the bacteria were amplified by PCR using 16S rRNA gene-specific primer pairs: 5'-AGAGTTTGATCMTGGCTCAG-3' (SEQ ID NO: 60) and 5'-ATTACCGCGGCKGCTG-3' (SEQ ID NO: 61) (see T. Aebischer et al., Vaccination prevents *Helicobacter pylori*-induced alterations of the gastric flora in mice. FEMS Immunol. Med. Microbiol. 46, 221-229(2006)). The 1.5-kb PCR product was then introduced into pCR-Blunt Vector. The inserts were sequenced and aligned using the ClustalW software program. The resulting sequences of 16S rRNA genes derived from strain 1-41 of 46 strains of *Clostridium* spp. were shown in SEQ ID NO: 21-61. A phylogenetic tree was constructed by the neighbor-joining method with the resulting sequences of the 41 strains of *Clostridium* and those of known bacteria obtained from Genbank database using Mega software.

The results showed no effect on the number of the Treg cells in the colon was observed in the GF mice in which the segmented filamentous bacteria (SFB) were colonized. Moreover, mice in which the cocktail of three strains of *Lactobacillus* was colonized gave similar results. On the other hand, it was shown that the accumulation of Foxp3$^+$ cells in the colonic lamina propria was strongly induced in the mice in which 46 strains of *Clostridium* spp. were colonized. Importantly, such accumulation was promoted irrespective of the genetic backgrounds of the mice, and led to the increase in number similar to that in the SPF mice although intestinal microbiota of only a single genus were colonized. It was also shown that the colonization of the *Clostridium* did not change the number of Treg cells in the small intestinal lamina propria. Note that, when the 16 strains of Bactericides spp. were colonized, the number of Treg cells in the colon was increased significantly. However, the extent of the increase varied depending on the genetic background of the mice in which the bacteria were colonized.

Example 8

Next, CD4 expression, Foxp3 expression, and Helios expression in LP lymphocytes of the thymuses and the colons of SPF mice, GF mice, *Lactobacillus*-colonized mice, and *Clostridium*-colonized mice were analyzed by flow cytometry.

The results show that most Foxp3$^+$ cells found in the SPF mice or the *Clostridium*-colonized mice did not express Helios. Note that Helios is a transcription factor known to be expressed in thymic-derived natural Treg cells (see A. M.

Thornton et al., J Immunol 184, 3433 (Apr. 1, 2010)). Accordingly, it was suggested that most of the Treg cells in the SPF mice and the *Clostridium*-colonized mice were Treg cells induced in peripheral portions (so-called iTreg cells).

Example 9

Next, it was investigated whether or not the colonization of the *Clostridium* or the like had an influence on other T cells. Specifically, SFB, 16 strains of *Bacteroides* spp. (Bactero.), 46 strains of *Clostridium* spp. (Clost.), or microbiota collected from mice bred under a conventional environment (SPF) was colonized in GF IQI mice. Three weeks later, lymphocytes in the colonic lamina propria were isolated from these mice, and stimulated with PMA (50 ng/ml) and ionomycin (1 µg/ml) for four hours in the presence of Golgistop (BD Bioscience). After the stimulation was given, intracellular cytokines were stained by using an anti-IL-17 PE antibody (TC11-18H10) and an anti-IFN-g FITC antibody (BD Bioscience) in accordance with the manual of a cytofix/cytoperm kit (BD Bioscience). Then, the ratio of IFN-$\gamma^+$ cells or IL-17$^+$ cells in CD4$^+$ leucocytes was analyzed by flow cytometry. The results show that the colonization of the *Clostridium* did not have any influence on Th1 cells (CD4$^+$ IFN-$\gamma^+$ cells) in the colon, and caused only a slight increase of Th17 cells (CD4$^+$ IL-17$^+$ cells). Accordingly, it was suggested that the genus *Clostridium* was a genus of bacteria which specifically induced Treg cells.

Example 10

It has been reported that 46 strains of *Clostridium* spp. exert an influence on the accumulation of CD8$^+$ intestinal tract intraepithelial lymphocytes (IELs) in the colon. Accordingly, it is conceivable that *Clostridium* regulates the immune system in various aspects, and that *Clostridium* exhibits a marked ability to induce and maintain Treg cells especially in the colon, as described above. In addition, a kind of cytokines, transforming growth factor-β(TGF-β), is known to play an important role in regulation of Treg cell generation.

In this respect, it was examined whether or not the colonization of *Clostridium* provided a colonic environment rich in TGF-β. Specifically, first, the whole colons of GF mice, *Clostridium*-colonized mice, and *Lactobacillus*-colonized mice were cultured for 24 hours, and the culture supernatants thereof were measured for the concentration of active TGF-β (TGF-β1) by ELISA (the number of mice analyzed was four per group).

The results show that the amount of TGF-β produced in the colons of the *Clostridium*-colonized mice was significantly greater than that in colons of the GF mice and the *Lactobacillus*-colonized mice.

Next, intestinal epithelial cells (IECs) of GF mice and *Clostridium*-colonized mice were cultured for 24 hours, and the culture supernatants thereof were measured for the concentration of active TGF-β (TGF-β1) by ELISA (the number of mice analyzed was four per group).

The results show that TGF-β was detected in the culture supernatant of the IECs isolated from the *Clostridium*-colonized mice, whereas no TGF-β was detected in the culture supernatant of the IECs isolated from the GF mice.

Next, as described above, splenic CD4$^+$ T cells were cultured for five days together with a 50% conditioned medium in which IECs isolated from the GF mice or the *Clostridium*-colonized mice were cultured, and with the anti-CD3 antibody, in the presence or absence of an anti-TGF-β antibody. Then, the T cells were collected, and analyzed for expression of Foxp3 by real-time RT-PCR.

The results show that when the culture supernatant of the IECs derived from the *Clostridium*-colonized mice was added to the splenic CD4$^+$ T cells, differentiation into Foxp3-expressing cells was accelerated. Meanwhile, differentiation into Treg cells was inhibited by the anti-TGF-β antibody.

The expression of MMP2, MMP9, and MMP13, which are thought to contribute to the activation of latent TGF-β was investigated. The expression of indoleamine 2,3-dioxygenase (IDO), which is thought to be involved in the induction of Treg cells, was also investigated. Specifically, 46 bacterial strains of the genus *Clostridium* (Clost.), or three bacterial strains of the genus *Lactobacillus* (Lacto.) were orally administered to C57BL/6 germ-free mice. Three weeks after administration, IECs were collected, and analyzed for relative mRNA expression levels of MMP2, MMP9, MMP13, and IDO genes by real-time RT-PCR (the number of mice analyzed was three per group).

For the relationship between the activation of latent TGF-β and the above-describe MMP, see D'Angelo et al., J. Biol. Chem. 276, 11347-11353, 2001; Heidinger et al., Biol. Chem. 387, 69-78, 2006; Yu et al., Genes Dev. i4, 163-176, 2000. For the relationship between IDO and the induction of Treg cells, see G. Matteoli et al., Gut 59, 595 (May, 2010).

The results show in agreement with the production of TGF-β described above, that transcription products of the genes encoding MMP2, MMP9, and MMP13 were expressed at higher levels in the IECs derived from the *Clostridium*-colonized mice than in those in the GF mice and in the *Lactobacillus*-colonized mice.

Moreover, IDO was expressed only in the *Clostridium*-colonized mice.

Accordingly, it was revealed that the *Clostridium* activated the IECs, and led to the production of TGF-β and other Treg cell-inducing molecules in the colon.

Example 11

Next, it was investigated whether or not the Treg cell accumulation induced by the colonization of the *Clostridium* was dependent on signal transmission by pathogen-associated molecular pattern recognition receptors. Specifically, the numbers of Treg cells in the colonic lamina propria of each SPF mice of Myd88$^{-/-}$ (deficient in Myd88 (signaling adaptor for Toll-like receptor)), Rip2$^{-/-}$ (deficient in Rip2 (NOD receptor adaptor)), and Card9$^{-/-}$ (deficient in Card9 (essential signal transmission factor for Dectin-1 signal transmission)) were examined. In addition, *Clostridium* spp. were caused to be colonized in the Myd88$^{-/-}$GF mice, and the change in the number of Treg cells was investigated. The results show that the number of Treg cells of each kind of the SPF mice deficient in the associated factors of the pathogen-associated molecular pattern recognition receptors did not change relative to that of wild-type mice of the same litter, which served as a control. In addition, it was found that when *Clostridium* spp. were colonized in GF mice deficient in Myd88, the accumulation of Treg cells in the colonic lamina propria was induced. Accordingly, it has been suggested that the mechanism of inducing the accumulation of Treg cells in the colonic lamina propria relies not on activation of recognition pathway for major pathogen-associated molecular patterns as is caused by most bacteria, but on specific commensal bacterial species.

Example 12

Intestinal tract Foxp3$^+$ Treg cells are known to exert some immunosuppressive functions through IL-10 production (refer to NPL 9). Meanwhile, animals having CD4$^+$ Foxp3$^+$ cells from which IL-10 is specifically removed are known to develop inflammatory bowel disease (refer to NPL 18). In this respect, first, the expression of IL-10 in lymphocytes of various tissues was examined Specifically, lymphocytes were isolated from various tissues of SPF Il10$^{venus}$ mice, and the expression of CD4 and the expression of Venus were analyzed by flow cytometry.

Lymphocytes in the colonic lamina propria were isolated from Il10$^{venus}$ mice, and the expression of T cell receptor β chain (TCRβ) on the surfaces of the cells was detected by FACS.

Lymphocytes in the colonic lamina propria were isolated from Il10$^{venus}$ mice. The lymphocytes were stimulated with PMA (50 ng/ml) and ionomycin (1 μg/ml) for four hours in the presence of Golgistop (BD Bioscience). Then, after the stimulation was given, intracellular cytokines were stained by using an anti-IL-17 PE antibody, an anti-IL-4 APC antibody (11B11), and an anti-IFN-g FITC antibody (BD Bioscience) in accordance with the manual of a cytofix/cytoperm kit (BD Bioscience).

In addition, Foxp3$^+$ CD4$^+$ cells and Foxp3$^-$ CD4$^+$ cells were isolated from the spleen (Spl) of Foxp3$^{eGFP}$ reporter mice, and Venus$^+$ cells were isolated from the colonic lamina propria and the small intestine (SI) lamina propria of Il10$^{venus}$ mice. The obtained cells were analyzed in terms of expression of predetermined genes. The gene expression was analyzed by real-time RT-PCR using a Power SYBR Green PCR Master Mix (Applied Biosystems) and an ABI 7300 real time PCR system (Applied Biosystems). Here, the value for each cell was normalized for the amount of GAPDH.

The results show that almost no Venus$^+$ cells (IL-10-producing cells) were detected in the cervical lymph nodes (peripheral lymph nodes), thymus, peripheral blood, lung, and liver of mice kept under the SPF conditions. Meanwhile, in the spleen, Peyer's patches, and mesenteric lymph nodes thereof, Venus$^+$ cells were slightly detected. On the other hand, many Venus$^+$ cells were found in the lymphocytes in the small intestine lamina propria and colonic lamina propria. In addition, most of the Venus$^+$ cells in the intestines were positive for CD4, and also positive for T cell receptor β chain (TCRβ). It was found that the Venus' CD4$^+$ T cells expressed Foxp3 and other Treg cell-associated factors such as a cytotoxic T-Lymphocyte antigen (CTLA-4) and a glucocorticoid-induced TNFR-associated protein (GITR), although the Venus$^+$ CD4$^+$ T cells showed none of the phenotypes of Th2 (IL-4-producing) and Th17 (IL-17-producing). It was shown that the expression level of CTLA-4 in the intestinal Venus$^+$ cells was higher than that in the splenic GFP$^+$ Treg cells isolated from the Foxp3$^{eGFP}$ reporter mice.

Example 13

Venus$^+$ cells can be classified into at least two subsets, namely, Venus$^+$ Foxp3$^+$ double positive (DP) Treg cells and Venus$^+$ Foxp3$^-$ Treg cells on the basis of intracellular Foxp3 expression. Cells of the latter subset correspond to type 1 regulatory T cells (Tr1) (refer to NPL 8 and 9). In this respect, the Venus$^+$ cells (IL-10-producing cells) observed in Example 8 were investigated in terms of the expression of Foxp3. Specifically, the expression of CD4, Foxp3, and Venus in the lamina propria of the colon and the lamina propria of the small intestine of Il10$^{venus}$ mice kept under GF or SPF conditions was analyzed by FACS, and the numbers of Venus$^+$ cells in the intestinal tract lamina propria were compared between SPF and GF Il10$^{Venus}$ mice.

In addition, the intracellular expression of Venus and Foxp3 in CD4 cells in various tissues of SPF Il10$^{venus}$ mice was analyzed by flow cytometry.

In order to investigate whether or not the presence of commensal bacteria had any influence on the expression of IL-10 in regulatory cells in the gastrointestinal tracts, germ-free (GF) Il10$^{Venus}$ mice were prepared. Then, predetermined species of bacteria were caused to be colonized in the obtained GF Il10$^{venus}$ mice. Three weeks after the species of bacteria were colonized, a CD4$^+$ cell group (V$^+$F$^-$, Venus$^+$ Foxp3$^-$ cells; V$^+$F$^+$, Venus$^+$ Foxp3$^+$ cells; and V$^-$F$^+$, Venus$^-$ Foxp3$^+$ cells) in which Foxp3 and/or Venus were expressed in the colon and the small intestine was analyzed by flow cytometry.

In order to check whether or not the presence of commensal bacteria had any influence on the expression of IL-10 in regulatory cells in the gastrointestinal tracts, antibiotics were orally given with water to five or six Il10$^{venus}$ mice per group for 10 weeks. The following antibiotics were used in combination.

ampicillin (A; 500 mg/L Sigma)
vancomycin (V; 500 mg/L NACALAI TESQUE, INC.)
metronidazole (M; 1 g/L NACALAI TESQUE, INC.)
neomycin (N; 1 g/L NACALAI TESQUE, INC.)

Then, CD4 and Foxp3 of lymphocytes in the lamina propria of the colon, the lamina propria of the small intestine (SI), mesenteric lymph nodes (MLN), and Peyer's patches (PPs) were stained with antibodies, and analyzed by FACS. The results were obtained from two or more independent experiments which gave similar results.

The results show that the small intestinal lamina propria was rich in Venus$^+$ Foxp3$^-$ cells, namely, Tr1-like cells, and that the Venus$^+$ Foxp3$^+$ DP Treg cells were present at a high frequency in the colon of the SPF mice. In contrast, although sufficient numbers of Foxp3$^+$ cells were observed also in other tissues, the expression of Venus was not observed in almost all of the cells.

In addition, it was shown that all regulatory T cell fractions of Venus$^+$ Foxp3$^-$, Venus$^+$ Foxp3$^+$, and Venus$^-$ Foxp3$^+$ in the colon significantly decreased under the GF conditions. Moreover, similar decrease in Venus$^+$ cells was observed also in the SPF Il10$^{Venus}$ mice treated with the antibiotics.

The colonization of *Clostridium* spp. strongly induced all regulatory T cell fractions of Venus$^+$ Foxp3$^-$, Venus$^+$ Foxp3$^+$, and Venus$^-$ Foxp3$^+$ in the colon, and the degrees of the induction thereof were equal to those in the SPF mice. In addition, it was found that the colonization of the three strains of *Lactobacillus* or the colonization of SFB had an extremely small influence on the number of Venus$^+$ and/or Foxp3$^+$ cells in the colon. Moreover, the colonization of 16 strains of *Bacteroides* spp. also induced Venus$^+$ cells, but the influence of the colonization was specific to Venus$^+$ Foxp3$^-$ Tr1-like cells. On the other hand, it was found that none of the bacterial species tested exerted any significant influence on the number of IL-10-producing cells in the small intestinal lamina propria (refer to FIG. 26).

Hence, it was shown that the genus *Clostridium* colonized in the colon or a physiologically active substance derived from the bacteria provided a signal for inducing the accumulation of IL-10$^+$ regulatory T cells in the colonic lamina propria or the expression of IL-10 in T cells. It was shown that the number of Venus$^+$ cells in the small intestine was not significantly influenced by the situation where no commensal bacteria were present or commensal bacteria were decreased, and that IL-10+ regulatory cells (Tr1-like cells) accumulated in the small intestinal lamina propria independently of commensal bacteria.

Example 14

It was investigated whether or not Venus+ cells induced by the genus *Clostridium* had an immunosuppressive function similar to that of Venus+ cells in the colon of SPF mice. Specifically, CD4+ CD25− cells (effector T cells, Teff cells) isolated from the spleen were seeded in a flat-bottomed 96-well plate at $2 \times 10^4$/well, and cultured for three days together with $2 \times 10^4$ splenic CD11c+ cells (antigen-representing cells) subjected to 30 Gy radiation irradiation treatment, 0.5 µg/ml of an anti-CD3 antibody, and a lot of Treg cells. In addition, for the last six hours, the CD4+ CD25− cells were cultured, with [$^3$H]-thymidine (1 µCi/well) was added thereto. Note that, Treg cells used in Example 14 were CD4+ GFP+ T cells isolated from the spleen of Foxp3$^{eGFP}$ reporter mice, or CD4+ Venus+ T cells in the colonic lamina propria of GF Il10$^{venus}$ mice in which *Clostridium* spp. were colonized or SPF Il10$^{venus}$ mice. Then, proliferation of the cells was determined based on the uptake amount of [$^3$H]-thymidine, and represented by a count per minute (cpm) value.

The results show that Venus+ CD4+ cells of the mice in which the genus *Clostridium* was colonized suppressed in vitro proliferation of CD25−CD4+ activated T cells. The suppression activity was slightly inferior to that of GFP+ cells isolated from the Foxp3$^{eGFP}$ reporter mice, but equal to that of Venus+ cells isolated from the SPF Il10$^{Venus}$ mice. Accordingly, it has been shown that the genus *Clostridium* induces IL-10-expressing T cells having sufficient immunosuppressive activities, and thereby plays a critical role in maintaining immune homeostasis in the colon.

Example 15

Next, the influence of the colonization of a large number of *Clostridium* on the local immune response and the resultant proliferation of Treg cells were investigated.

<Dextran Sulfate Sodium (DSS)-Induced Colitis Model>

First, the DSS-induced colitis model was prepared as described above, and the influence on the model mice of the inoculation of the *Clostridium* and the proliferation of Treg cells was investigated. Specifically, control mice and *Clostridium*-inoculated mice were treated with 2% DSS, then observed and measured for six days for body weight loss, the hardness of stool, and bleeding, and then were evaluated numerically. In addition, on day 6, the colons were collected, dissected, and analyzed histologically by HE staining.

The results show that the symptoms of the colitis such as body weight loss and rectal bleeding were significantly suppressed in the mice having a large number of *Clostridium* (hereinafter also referred to as "*Clostridium*-abundant mice") in comparison with the control mice (C57BL/6 mice grown in a conventional environment for six weeks and not inoculated with the fecal suspension). All the features typical for colonic inflammation, such as shortening of the colon, edema, and hemorrhage, were observed markedly in the control mice in comparison with the *Clostridium*-abundant mice. Moreover, histological features such as mucosal erosion, edema, cellular infiltration, and crypt loss were less severe in the DSS-treated *Clostridium*-abundant mice than in the control mice.

<Oxazolone-Induced Colitis Model>

Next, the oxazolone-induced colitis model was prepared as described above, and the influence on the model mice of the inoculation of *Clostridium* and the proliferation of Treg cells was investigated. Specifically, control mice and *Clostridium*-inoculated mice were sensitized with oxazolone, and subsequently the inside of the rectums thereof were treated with a 1% oxazolone/50% ethanol solution. Then, body weight loss was observed and measured. In addition, the colons were dissected, and analyzed histologically by HE staining.

The results show that the colitis proceeded along with persistent body weight loss in the control mice. Meanwhile, the body weight loss of the *Clostridium*-abundant mice was reduced. In addition, it was also revealed that portions having histological diseases such as mucosal erosion, edema, cellular infiltration, and hemorrhage were reduced in the colon of the *Clostridium*-abundant mice.

Example 16

Next, the influence, on the systemic immune response (systemic IgE production), of the colonization of a large number of *Clostridium* and the resultant proliferation of Treg cells was investigated. Specifically, as described above, control mice and *Clostridium*-inoculated mice were immunized by administering alum-absorbed ovalbumin (OVA) twice at a 2-week interval. Then, sera were collected from these mice, and the OVA-specific IgE level thereof was investigated by ELISA. In addition, splenic cells were collected from the mice in each group, and IL-4 and IL-10 production by in-vitro OVA restimulation was investigated.

Results show that the IgE level was significantly lower in the *Clostridium*-abundant mice than in the control mice. Moreover, the IL-4 production by the OVA restimulation was reduced and the IL-10 production thereby was increased in the splenic cells of the *Clostridium*-abundant mice sensitized with OVA and alum, in comparison with those of the control mice.

Accordingly, in consideration of the results shown in Example 15 in combination, the induction of Treg cells by *Clostridium* in the colon plays an important role in local and systemic immune responses.

Example 17

Next, GF Balb/c were colonized with three strains of *Clostridium* belonging to cluster IV (strains 22, 23 and 32 listed in FIG. 49). Three weeks later, colonic Foxp3+ Treg cells were analyzed by FACS. Results show that gnotobiotic mice colonized with three strains of *Clostridium* showed an intermediate pattern of Treg induction between GF mice and mice inoculated with all 46 strains.

Example 18

Next, it was investigated whether or not a spore-forming (for example, a chloroform resistant) fraction of a fecal sample obtained from humans had the effect of inducing proliferation or accumulation of regulatory T cells similar to the spore-forming fraction of the fecal sample obtained from mice.

Human stool from a healthy volunteer (Japanese, male, 29 years old) was suspended with phosphate-buffered saline (PBS), mixed with chloroform (final concentration 3%), and then incubated in a shaking water bath for 60 min. After evaporation of chloroform by bubbling with $N_2$ gas, the aliquots containing chloroform-resistant (for example, spore-forming) fraction of human intestinal bacteria were orally inoculated into germ-free (GF) mice (IQI, 8 weeks old). The treated mice were kept in a vinyl isolator for 3 weeks. The colon was collected and opened longitudinally, washed to remove fecal content, and shaken in Hanks' balanced salt solution (HBSS) containing 5 mM EDTA for 20 min at 37° C. After removing epithelial cells and fat tissue, the colon was cut into small pieces and incubated with RPMI1640 containing 4% fetal bovine serum, 1 mg/ml collagenase D, 0.5 mg/ml dispase and 40 µg/ml DNase I (all manufactured by Roche Diagnostics) for 1 hour at 37° C. in a shaking water bath. The digested tissue was washed with HBSS containing 5 mM EDTA, resuspended in 5 ml of 40% Percoll (manufactured by GE Healthcare) and overlaid on 2.5 ml of 80% Percoll in a 15-ml Falcon tube. Percoll gradient separation was performed by centrifugation at 780 g for 20 min at 25° C. The interface cells were collected and suspended in staining buffer containing PBS, 2% FBS, 2 mM EDTA and 0.09% NaN3 and stained for surface CD4 with Phycoerythrin-labeled anti-CD4 Ab (RM4-5, manufactured by BD Biosciences). Intracellular staining of Foxp3 was performed using the Alexa647-labeled anti-Foxp3 Ab (FJK-16s, manufactured by eBioscience) and Foxp3 Staining Buffer Set (manufactured by eBioscience). The percentage of Foxp3 positive cells within the CD4 positive lymphocyte population was analyzed by flow cytometry.

Results show that when the spore-forming (for example, the chloroform resistant) fraction of human intestinal bacteria was colonized in GF mice, the accumulation of Foxp3+ regulatory (Treg) cells in the colonic lamina propria of the mice was induced.

Next, it was investigated what species of bacteria grew by gavaging with chloroform-treated human stool.

Specifically, using a QIAamp DNA Stool mini kit (manufactured by QIAGEN), bacterial genomic DNA was isolated from the human stool from a healthy volunteer as described above (human stool) or fecal pellets from GF mice gavaged with chloroform-treated human stool (GF+Chloro.). Quantitative PCR analysis was carried out using a LightCycler 480 (manufactured by Roche). Relative quantity was calculated by the ΔCt method and normalized to the amount of total bacteria, dilution, and weight of the sample. The following primer sets were used:

```
total bacteria
                                    (SEQ ID NO: 62)
5'-GGTGAATACGTTCCCGG-3'
and (SEQ ID NO: 63)
5'-TACGGCTACCTTGTTACGACTT-3'

Clostridium cluster XIVa (Clostridium coccoides
subgroup)
                                    (SEQ ID NO: 64)
5'-AAATGACGGTACCTGACTAA-3'
and (SEQ ID NO: 65)
5'-CTTTGAGTTTCATTCTTGCGAA-3'

Clostridium cluster IV (Clostridium leptum)
                                    (SEQ ID NO: 66)
5'-GCACAAGCAGTGGAGT-3'
and
                                    (SEQ ID NO: 69)
5'-CTTCCTCCGTTTTGTCAA-3'
```

```
Bacteroides
                                    (SEQ ID NO: 67)
5'-GAGAGGAAGGTCCCCCAC-3'
and (SEQ ID NO: 68)
5'-CGCTACTTGGCTGGTTCAG-3'.
```

Results show that gavaged with chloroform-treated human stool had large amounts of spore-forming bacteria, such as *Clostridium* clusters XIVa and IV, and a severe decrease of non-spore-forming bacteria, such as *Bacteroides*, compared with the human stool before chloroform treatment.

Example 19

Human stool (2 g) from a healthy volunteer (Japanese, male, 29 y old) was suspended with 20 ml phosphate-buffered saline (PBS), mixed with or without chloroform (final concentration 3%), and incubated in a shaking water bath for 60 min. The chloroform was then evaporated by bubbling with N2 gas for 30 min. The suspensions of untreated human feces (designated as 'huUT') and chloroform-treated human feces (designated as 'huChloro') were orally inoculated into Germ-free (GF) mice (IQI, 8 week old) (250 µl/mouse). The suspension of huUT was inoculated into 4 GF mice, which were numbered from # A1 to # A4, and that of huChloro was inoculated into 4 GF mice numbered from # B1 to # B4. Such GF mice which were inoculated with suspensions of feces or the like are also referred to as "ex-GF mice" hereinafter. Each group of ex-GF mice was separately kept in a vinyl isolator to avoid further microbial contamination. After 3 weeks, the small intestinal and colonic lamina propria lymphocytes from each mouse were separately collected, and examined for the expressions of surface CD4 and intracellular Foxp3, Helios, IL-17 and IFN-γ by flow cytometry. For intracellular IL-17 and IFN-γ staining, isolated lymphocytes were stimulated in vitro with PMA and ionomycin for 4 hours. Foxp3 is the transcription factor essential for the differentiation and function of Treg cells. Helios is a member of the Ikaros transcription factor family and Helios– Foxp3+ Treg cells have been suggested to be Treg cells induced in the periphery [so called induced Treg (iTreg) cells]. As shown in FIGS. 1A-D, the percentages of Foxp3+ Treg cells within CD4+ T cells in the small intestinal and colonic lamina propria of both groups of ex-GF mice were increased, compared with those in GF mice. Marked increases were also observed for the percentage of Helios– cells among Foxp3+ Treg cells in small intestine and colon in both groups of ex-GF mice. Notably, besides Foxp3+ Treg cells, a significant accumulation of IL-17-expressing CD4+ cells (namely, Th17 cells) was observed in exGF+huUT mice, whereas it was only marginally observed in exGF+huChloro mice (FIGS. 1E, F). In both groups of mice, the percentages of IFN-γ+cells in CD4+ cells were unchanged (FIGS. 1E, G).

Example 20

To investigate whether dead bacteria also have an effect on the induction of Treg cells, the suspension of chloroform-treated human feces was autoclaved (121° C. for 20 min) and orally inoculated into GF mice (once a week for 4 weeks). After 4 weeks, mice were sacrificed, and the colonic lamina propria lymphocytes from each mouse were examined for the expression of CD4, Foxp3 and Helios by flow cytometry. As shown in FIG. 2, the inoculation of dead bacteria exhibited no effect on the numbers of Foxp3+ cells or Helios-Foxp3+ cells. These results do not rule out the possibility that the amount of dead bacteria inoculated was not sufficient, but suggest that live bacteria are required for the induction of Treg cells.

Example 21

Figure 3A:
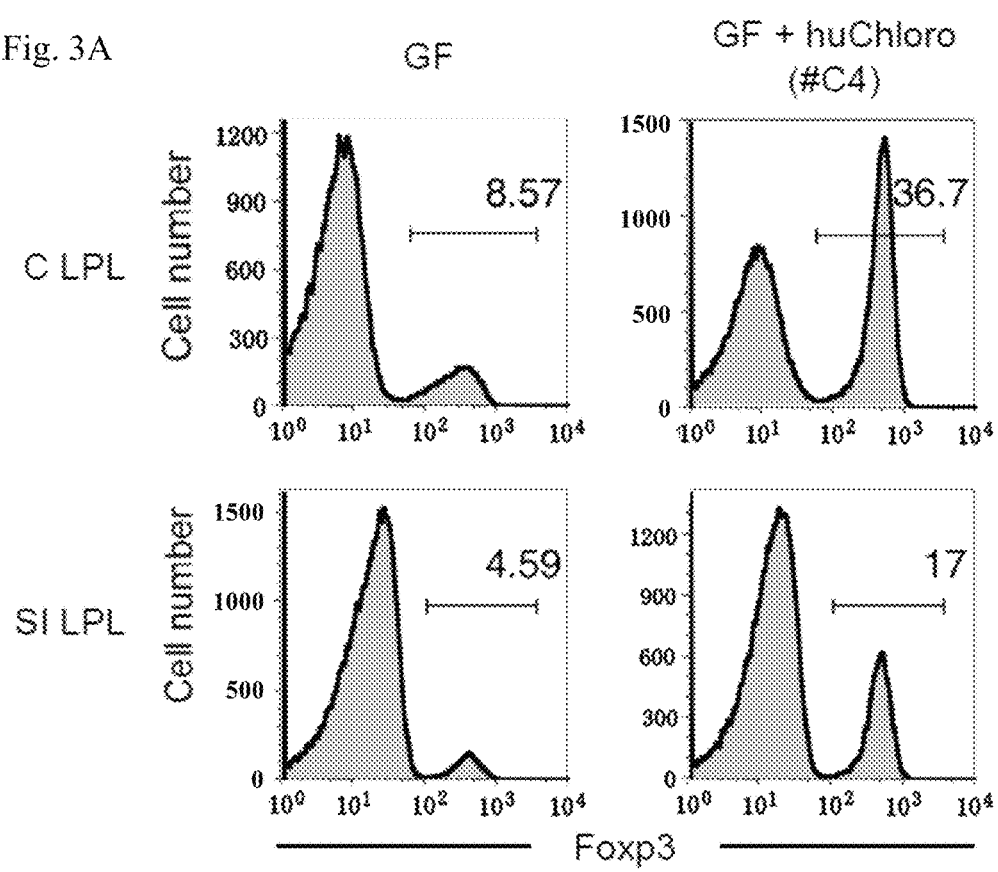
FIGS. 3A-3B shows representative plots (FIG. 3A, data of mouse # C4 is shown here) and combined data (FIG. 3B) for Foxp3 expression in CD4$^+$ cells from colonic and small intestinal lamina propria lymphocytes for GF mice and GF mice orally inoculated with chloroform-treated human feces (+huChloro, n=7, numbering from # C1 to # C7). Numbers above bracketed lines in FIG. 3A indicate the percentage of the population. Each circle in FIG. 3B represents a separate animal, and error bars indicate the SD. **$P<0.001$, unpaired t test.
Figure 3B:
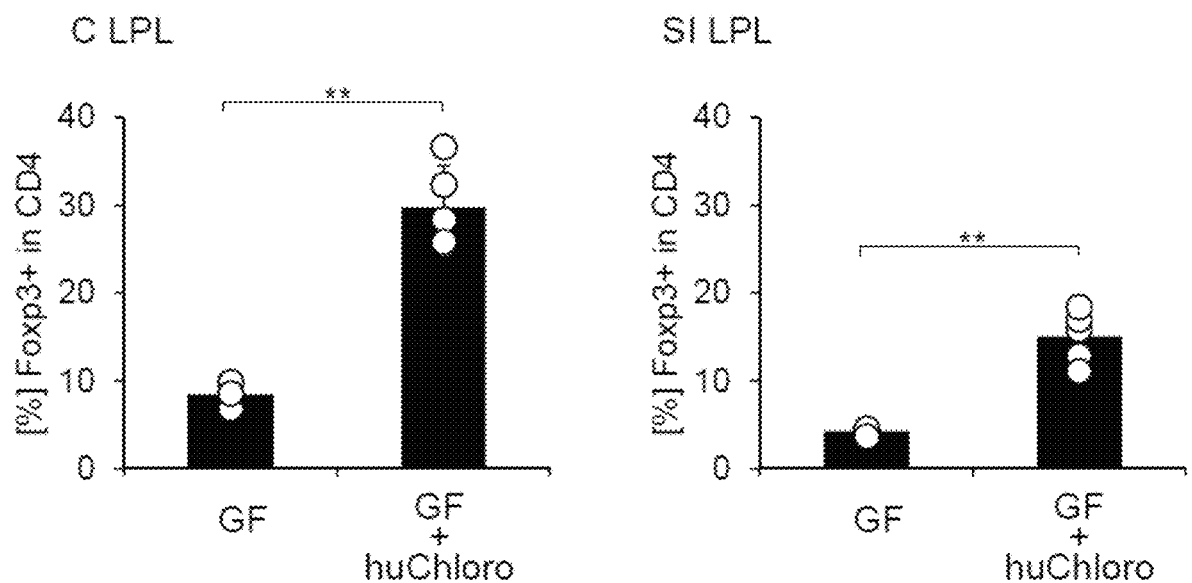

To confirm the induction of Treg cells by chloroform-resistant bacteria, another stool was obtained from the same person on a different day, treated with chloroform, and inoculated into IQI GF mice (7 mice, numbered from # C1 to C7). After 3-4 weeks, mice from # C1 to # C5 were sacrificed, and the small intestinal and colonic lamina propria lymphocytes from each mouse were separately collected, and examined for the expression of CD4 and Foxp3 by flow cytometry. Consistent with the findings in Example 19, colonization with chloroform-treated human feces significantly induced the accumulation of Foxp3$^+$ CD4$^+$ Treg cells in colonic and small intestinal lamina propria (FIG. 3). These results further support the notion that chloroform-resistant spore-forming bacteria can induce differentiation, proliferation and/or recruitment of Treg cells in intestinal lamina propria.

Example 22

Figure 4A:
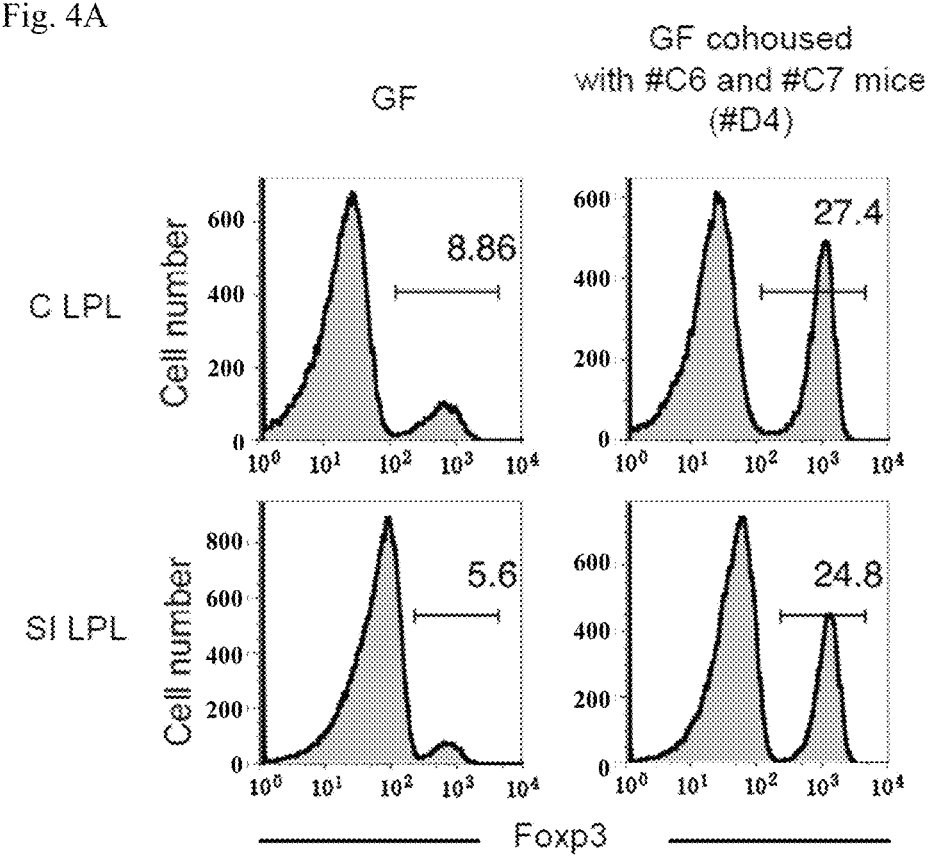
FIGS. 4A-4B shows representative plots (FIG. 4A) and combined data (FIG. 4B) for Foxp3 expression in CD4$^+$ cells from colonic lamina propria (C LPL) and small intestinal lamina propria (SI LPL) for GF mice and GF (numbering from # D1 to # D6) that were co-housed with # C6 and # C7 ex-GF mice colonized with chloroform-treated human feces. Numbers above bracketed lines in FIG. 4A indicate the percentage of the population. Each circle in FIG. 4B represents a separate animal, and error bars indicate the SD. **$P<0.001$, unpaired t test.
Figure 4B:
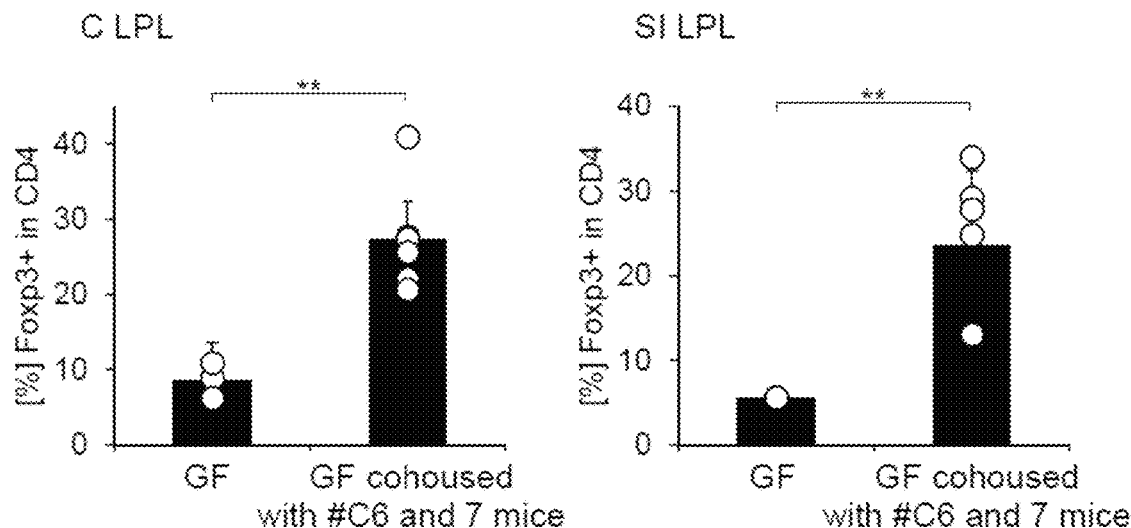

To test whether Treg cell induction by chloroform-resistant spore-forming fraction of human intestinal bacteria is horizontally transmissible, IQI GF mice (6 mice, numbered from # D1 to # D6) were cohoused for 4 weeks with mice # C6 and # C7 in the same cage in a vinyl isolator. Lamina propria lymphocytes from colon and small intestine were isolated and examined for CD4 and Foxp3. Cohoused mice exhibited a significant increase in the percentage of Foxp3+ cells among CD4+ cells (FIG. 4). Therefore, Treg cell induction by human intestinal bacteria is horizontally transmissible. These results let us assume a role of prominent components of the intestinal microbiota, rather than minor components, for the induction of Treg cells.

Example 23

Figure 5A:
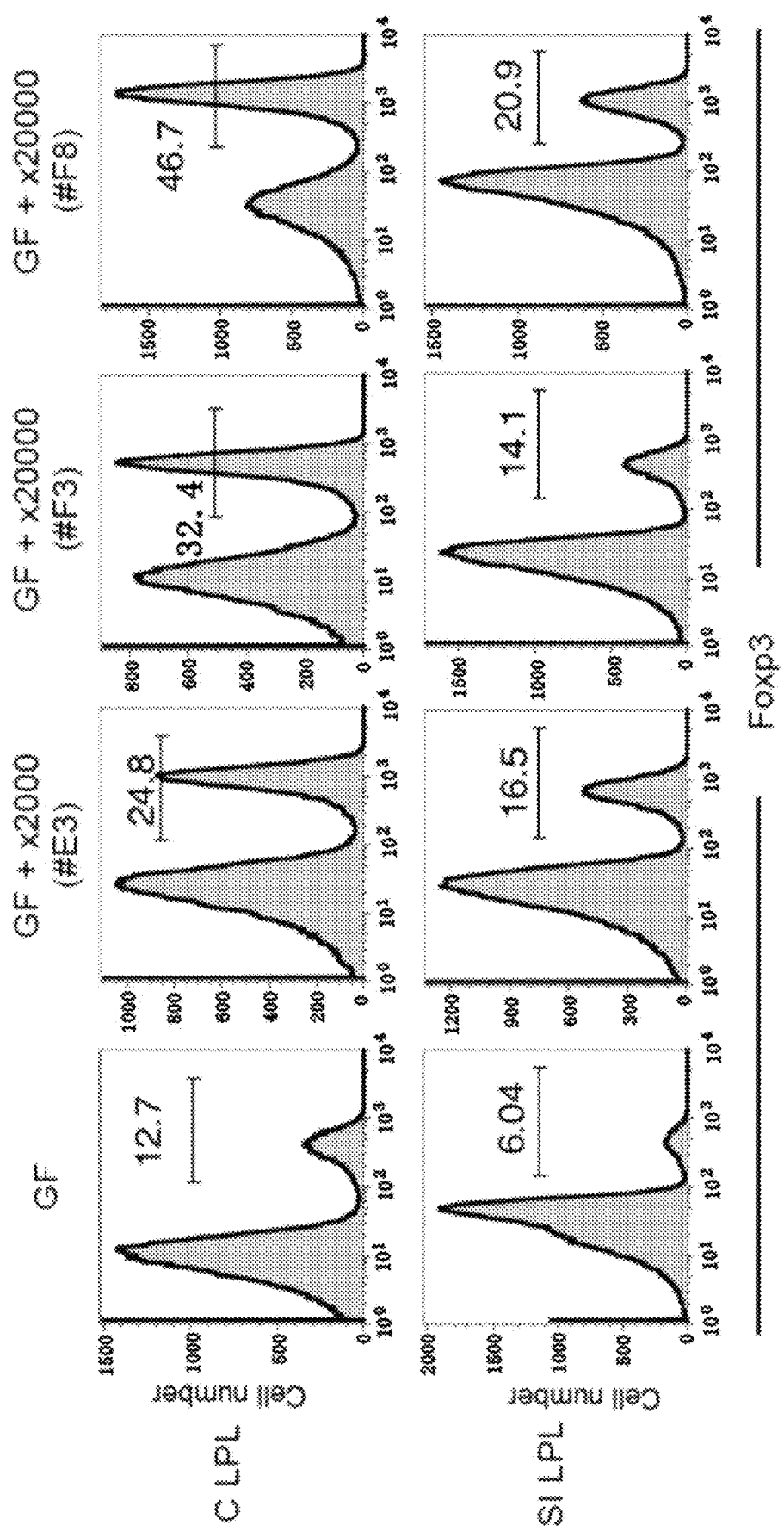
FIGS. 5A-5C shows representative plots and combined data for Foxp3 expression in CD4+ cells (FIGS. 5A, 5B), or Helios expression in Foxp3$^+$CD4$^+$ cells (FIG. 5C) from colonic lamina propria (C LPL) and small intestinal lamina propria (SI LPL) for GF mice, GF mice that were inoculated with 2000-fold (+x2000, n=4, numbering from # E1 to # E4) or 20000-fold (+x20000, n=8, numbering from # F1 to # F8) diluted fecal suspension from # C4 mouse. Numbers above bracketed lines in FIG. 5A indicate the percentage of the population. Each circle in FIG. 5B
Figure 5B:
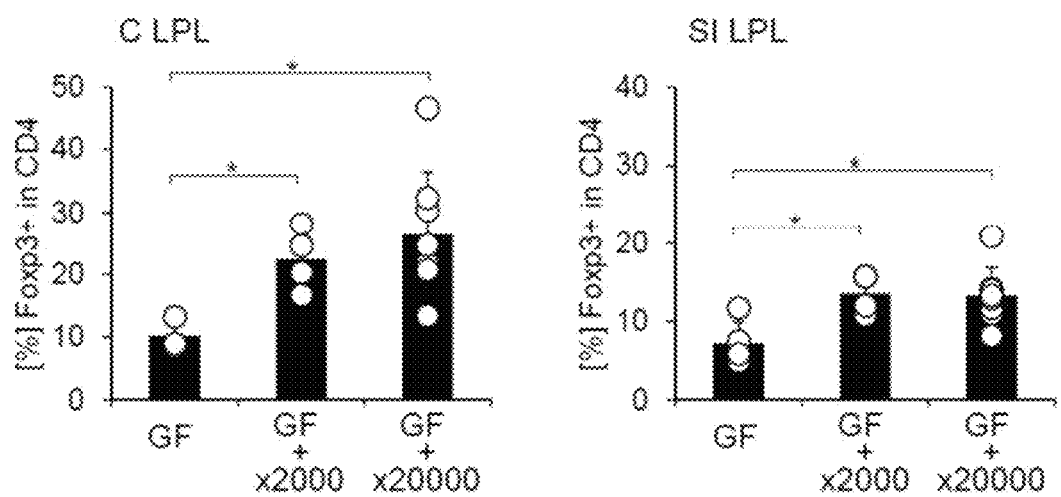
Figure 5C:
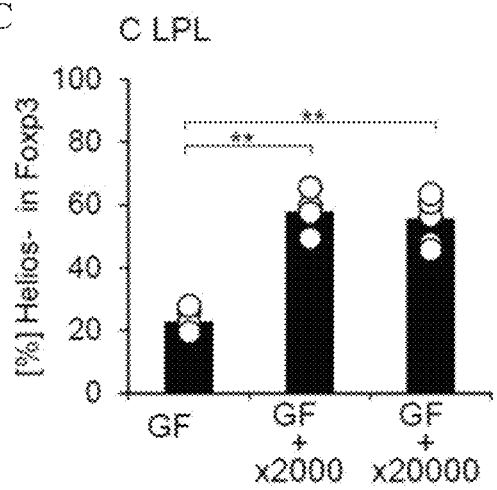

The frozen stock of cecal content from mouse # C4 was thawed, suspended in 10 times its volume (w/v) of PBS, and passed through a 70 µm cell strainer. The suspension was then treated with 3% chloroform, diluted 2000- or 20000-fold with PBS, and orally inoculated into GF IQI mice ($2.5 \times 10^5$ or $2.5 \times 10^4$ bacterial cells/250 µl/head, respectively). The 2000-fold diluted sample was orally inoculated into 4 mice (designated as exGF+2000, numbered from # E1 to # E4), whereas 20000-fold diluted sample was inoculated into 8 mice (designated as exGF+20000, numbered from # F1 to # F8). After 3 weeks, the intestinal lamina propria lymphocytes were isolated and examined for CD4, Foxp3 and Helios. Both 2000- and 20000-fold diluted samples similarly induced a marked accumulation of Foxp3+CD4+ cells in the intestinal lamina propria (FIG. 5). Therefore, the dose of bacteria for oral inoculation can be minimized to less than $2.5 \times 10^4$ bacterial cells.

Example 24

Figure 6C:
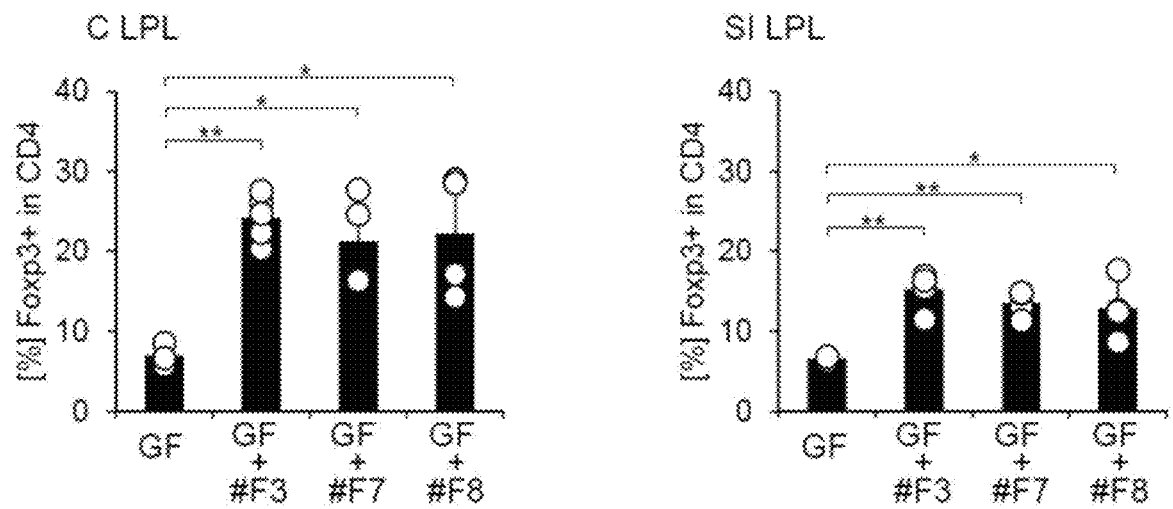
Figure 6D:
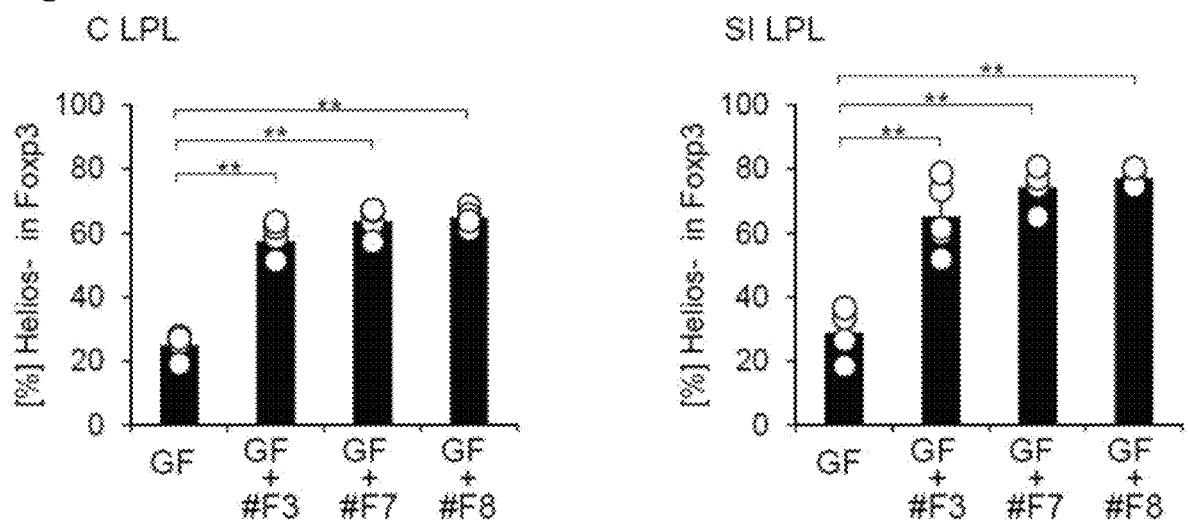

The frozen stock of cecal content from mouse # F3, # F7 or # F8 was suspended in 10 times its volume (w/v) of PBS, passed through a 70 µm cell strainer, and treated with 3% chloroform. Then, the fecal suspension from mouse # F3 was orally inoculated into 5 GF mice (numbered from # G1 to # G5), that from # F7 mouse into 4 GF mice (numbered from # H1 to # H4), and that from # F8 mouse into 4 GF mice (numbered from # I1 to # I4). After 4 weeks, lymphocytes from colonic and small intestinal lamina propria were isolated and examined for CD4, Foxp3 and Helios expression by flow cytometry. All # F, # G, and # H mice exhibited a significant increase in the percentage of Foxp3$^+$ cells among CD4$^+$ cells in the intestinal lamina propria compared with untreated GF mice (FIG. 6). Therefore, the Treg cell induction by human intestinal bacteria colonizing in exGF+ 20000 mice is also transmissible. Moreover, as shown in the later meta 16S rDNA sequencing data (FIG. 8), these mice commonly had bacteria having 16S rDNA sequence similarities with 16S rDNA sequence similarities with 20 species of known bacteria (*C. aminophilum, H. saccgarovorans, E. fissicatena, H. filiformis, C. clostridioforme, C. indolis, C. bolteae, Bacteroides* sp. MANG, *L. bacterium* DJF_VP30, *Ruminococcus* sp. ID8, *C. lavalense, C. symbiosum, E. contortum, C. saccharogumia, C. ramosum, F. plautii, C. scindens, Clostridium* sp. 2335, *Clostridium* sp. 14616 and cf *Clostridium* sp. MLG055).

Example 25

Figure 7A:
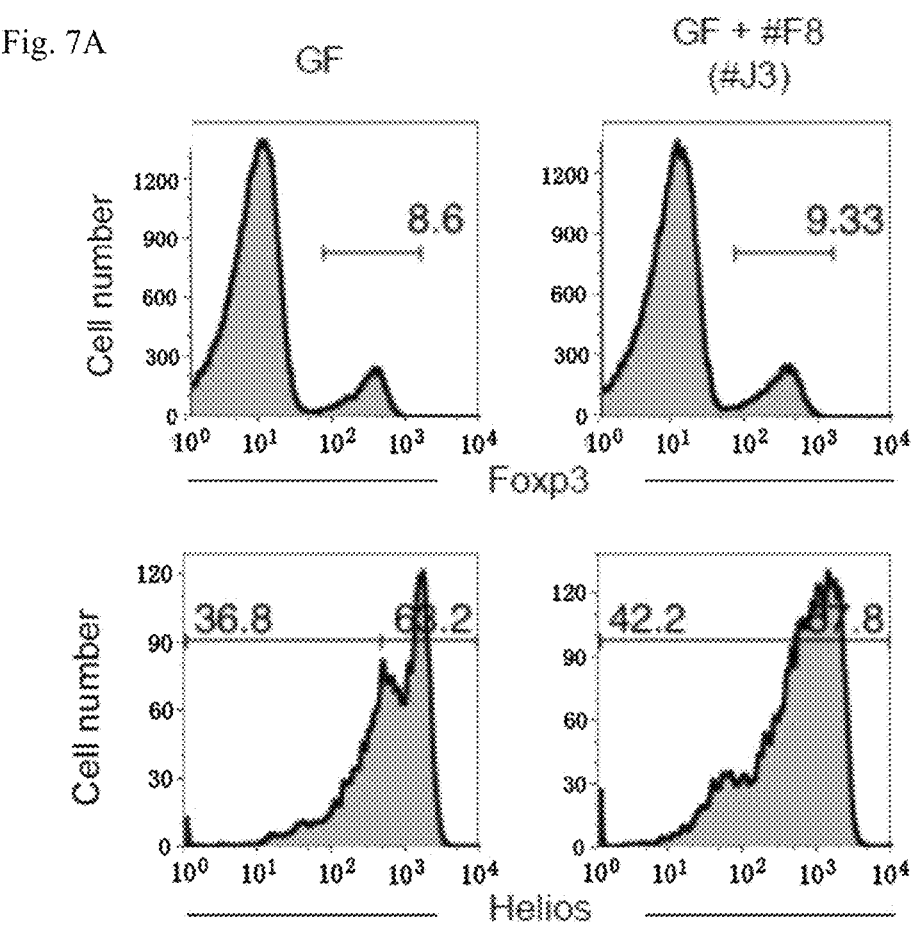
FIG. 7A-7C shows representative plots (FIG. 7A) and combined data (FIGS. 7B, 7C) for Foxp3 expression in CD4$^+$ cells (FIGS. 7A, 7B) or Helios expression in Foxp3$^+$CD4$^+$ cells for GF mice and GF mice that were inoculated with 3 isolated strains of bacteria from cecal content of # F8 mouse (n=4, numbering from # J1 to # J4). Numbers above bracketed lines in FIG. 7A indicate the percentage of the population. Each circle in FIG. 7B
Figure 7B:
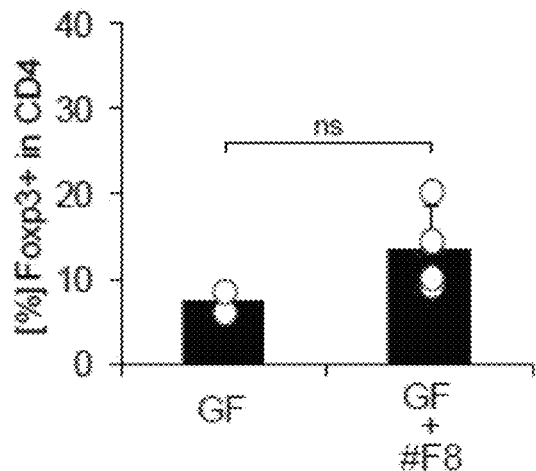
Figure 7C:
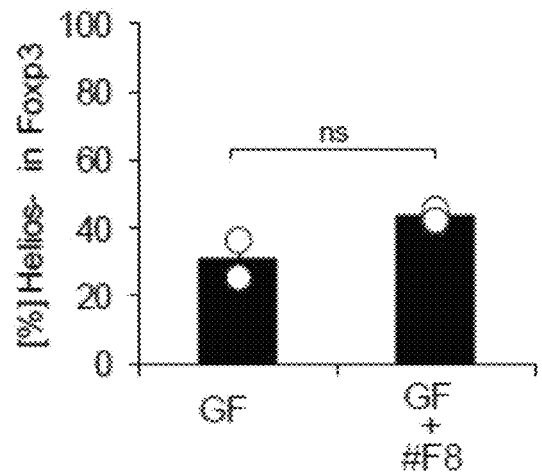

A frozen stock of the cecal content from # F8 mouse was serially diluted with 0.85% NaCl under an aerobic condition and plated onto BL agar. After culture at 37° C. for 2 or 4 days, 50 single colonies were observed. Of the 50 colonies, 29 were picked up, cultured for additional 2 or 4 days at 37° C. by ABCM broth, and stored in EG stock medium (10% DMSO) at −80° C. The genomic DNA from each colony was isolated, and 16S rRNA coding gene sequence was analyzed. The sequence of 16S rRNA of each colony revealed that the 29 colonies observed were represented by three strains, each having 100% similarity with *Clostridium ramosum*, 99.75% with *Clostridium saccharogumia*, 100% with *Flavonifractor plautii*, 99.17% with *Clostridium hathewayi*, 99.23% with *Clostridium scindens*, or 99.66% with *Clostridium* sp. 2335. Within the 29 colonies that were selected from the original 50 colonies, only *Clostridium saccharogumia, Clostridium ramosum*, and *Flavonifractor plautii* were present (25, 3, and 1 colonies, respectively). These 3 isolated strains were propagated, mixed and inoculated into GF IQI mice (4 mice, numbered from # J1 to J4). After 3-4 weeks, the colonic lamina propria lymphocytes were collected, and examined for the expressions of CD4, Foxp3, and Helios by flow cytometry. Foxp3+ cells or Helios− cells were not induced or only weakly induced by the colonization of these strains of bacteria in the colon (FIG. 7). These results suggest that the combination of *Clostridium saccharogumia* and *Clostridium ramosum* (both within cluster XVIII) were insufficient to induce Treg cells in the colon of mice. The effects of *Flavonifractor plautii* were not clear, since the strain was only represented by 1 of the 29 colonies that were selected.

Example 26

Figure 9A:
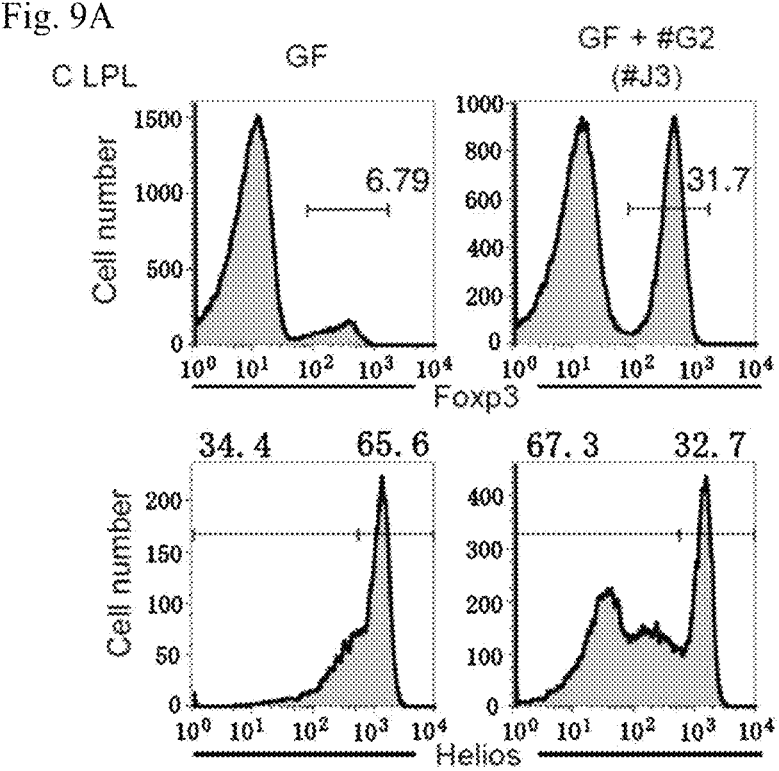
FIGS. 9A-9C shows representative plots (FIG. 9A) and combined data (FIGS. 9B, 9C) for Foxp3 expression in CD4$^+$ cells (FIGS. 9A, 9B), or Helios expression in Foxp3$^+$CD4$^+$ cells (FIGS. 9A, 9C) from colonic lamina propria (C LPL) and small intestinal lamina propria (SI LPL) for GF mice and GF mice that were inoculated with bacteria collections from culture plate of cecal content of # G2 mouse (n=4, numbering from # K1 to # K4. Numbers above bracketed lines in FIG. 9A indicate the percentage of the population. Each circle in FIG. 9B and FIG. 9C represents a separate animal, and error bars indicate the SD. *P<0.05; **P<0.001, unpaired t test.
Figure 9B:
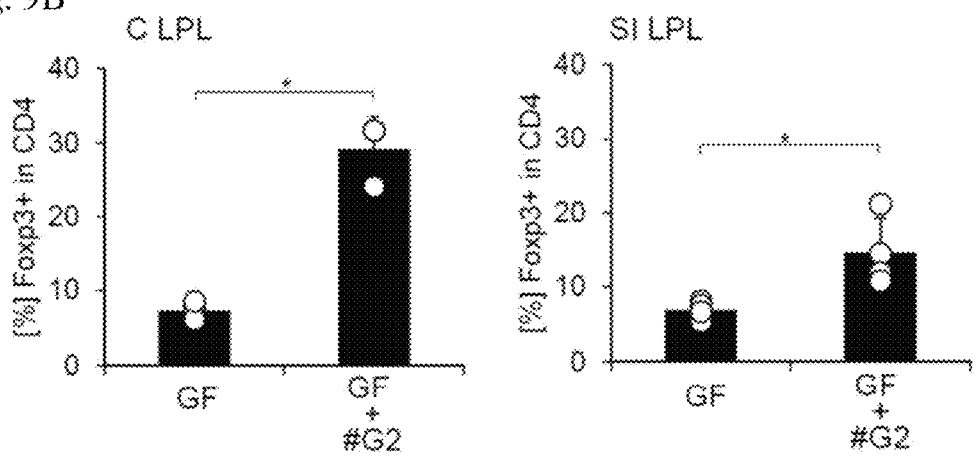
Figure 9C:
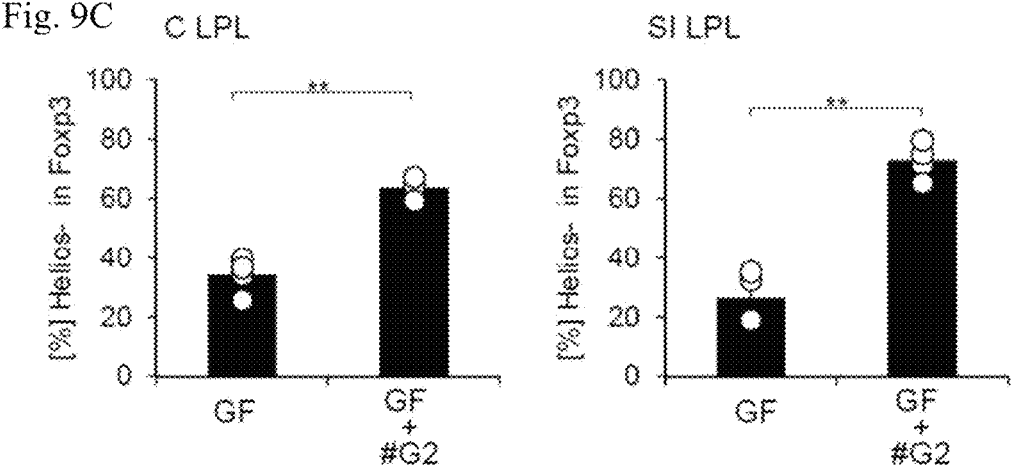

The frozen glycerol stock of cecal content from # G2 mouse was suspended with PBS, seeded onto BL agar plate, and incubated for 48 hours, similarly to the procedure done in Example 19. Different from Example 19, all bacteria on the plate were collected by scraping with a plate scraper, suspended in TS broth and inoculated into GF IQI mice (4 mice, numbering from # K1 to # K4). It should be noted that the bacterial suspension used in this experiment included bacteria that did not propagate but survived on the plate. After 4 weeks, lamina propria lymphocytes from colon and small intestine of K1~K4 mice were isolated and examined for CD4, Foxp3 and Helios expression. All 4 mice exhibited a significant increase in the percentages of Foxp3$^+$ cells among CD4$^+$ cells (FIGS. 9A, 9B) and Helios$^-$ cells among Foxp3$^+$ Treg cells (FIGS. 9A, 9C) in the intestinal lamina propria compared with untreated GF mice. Considering that the inoculation of mice with 6 strains of bacteria propagated on the BL agar plate failed to induce Treg cells, bacteria that did not propagate but survived on the plate might be responsible for the induction of Treg cells.

Example 27

Figure 8:
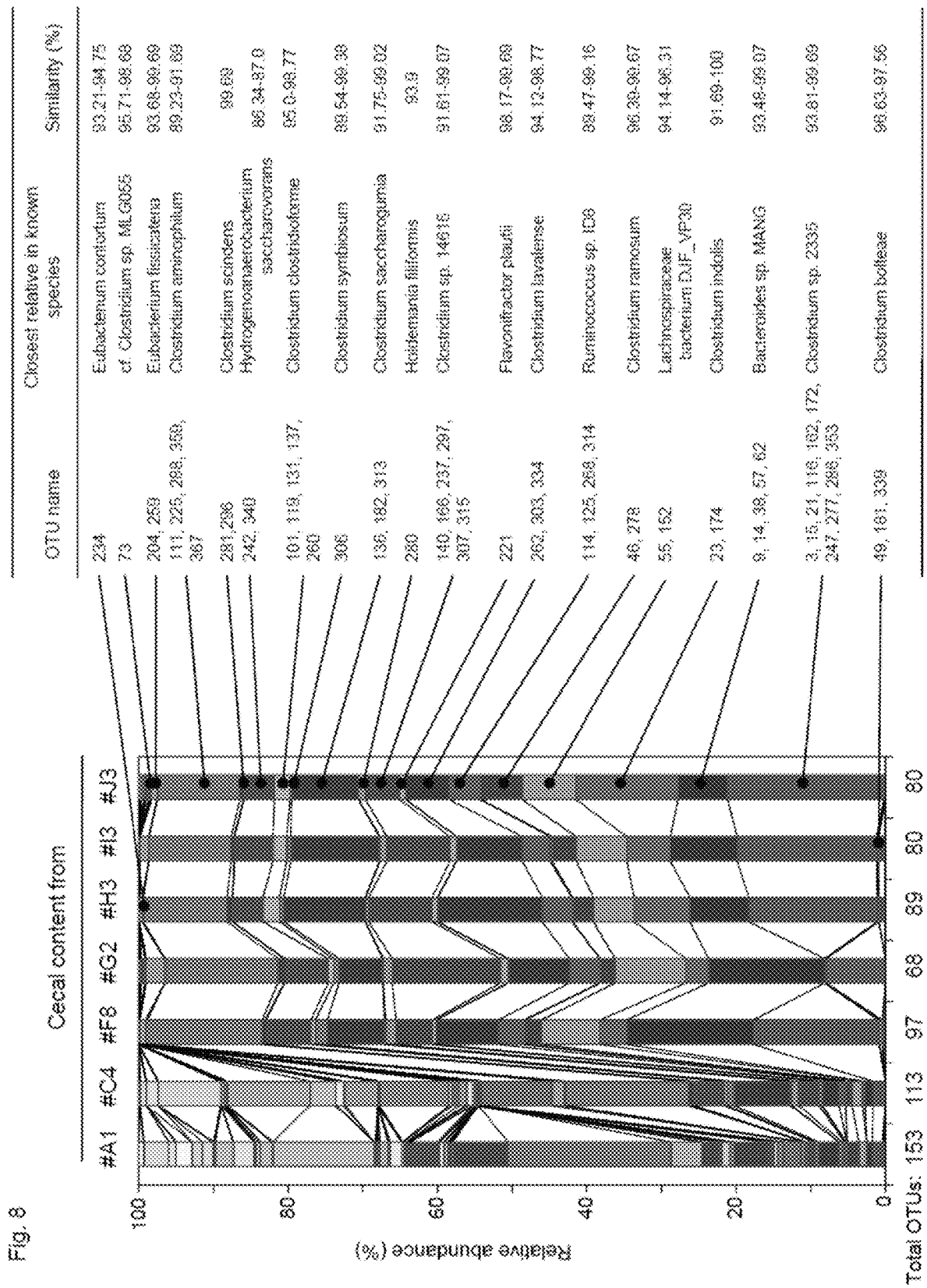
FIG. 8 shows the relative abundances of OTUs having the same closest relative in each cecal sample (bacterial DNA was extracted from the cecal contents of mouse # A1, # C4, # F8, # G2, # H3, # I3, # J3 and # K3, shown in the bars). Total number of OTUs detected in each sample is depicted below the bar. The detected OTU names in sample # H3, # I3 or # K3, their closest relative and their similarity with the closest relative are depicted in the right table.

Bacterial DNA was extracted from the cecal contents of mouse # A1, # C4, # F8, # G2, # H3, # I3, # J3 and # K3. Variable region 1-2 (V1-2) in bacterial 16S rRNA coding gene were amplified by PCR and used as template for metasequencing. Resulting sequences (3400 reads for each sample) were classified into operational taxonomic units (OTUs) on the basis of sequence similarity (>97% identity). Representative sequences from each OTU were compared with sequences in nucleic acid databases using BLAST to determine their closest relatives in known species. The numbers of detected reads and the closest relatives for each OTU are shown in Table 1. The relative abundances of OTUs having the same closest relative in each cecal sample are shown in FIG. 8. In mouse # A1, 153 OTUs (their closest relatives were 93 species) were identified and half of them were related to *Bacteroides* species. In contrast, in mouse # C4, 113 OTUs were identified and most of them were related to species belonging to the family Clostridiaceae. In mouse # F8, # G2, # H3, # I3, # J3 and # K3, 97-68 OTUs were identified. In these mice, in which Treg cell accumulation was observed in the intestine, the majority of bacteria consisted of bacteria having 16S rDNA sequence similarities with *C. aminophilum*, *H. saccgarovorans*, *E. fissicatena*, *H. filiformis*, *C. clostridioforme*, *C. indolis*, *C. bolteae*, *Bacteroides* sp. MANG, *L. bacterium* DJF_VP30, *Ruminococcus* sp. ID8, *C. lavalense*, *C. symbiosum*, *E. contortum*, *C. saccharogumia*, *C. ramosum*, *F. plautii*, *C. scindens*, *Clostridium* sp. 2335, *Clostridium* sp. 14616 and cf *Clostridium* sp. MLG055.

In mouse # J3, in which Treg accumulation was not observed, 3 OTUs were detected. Each has the 16S rDNA sequence similarity with *C. saccharogumia*, *C. ramosum* or *F. plautii*. These results suggest that the combination of these three species are insufficient to induce the intestinal Treg cells accumulation.

Example 28

Bacterial strains were isolated from the cecal contents of mouse # F8, # G2, # I1 and # K3 using BL agar or EG agar plates. Applicant picked-up 144 colonies from EG agar plates and 116 colonies from BL agar plates. BLAST search of 16S rRNA coding sequence of these clones revealed that they belonged to 17 species, and each had 93-100% similarities with *C. indolis*, *C. bolteae*, *Bacteroides* sp. MANG, *L. bacterium* DJF_VP30, *A. colihominis*, *Ruminococcus* sp. ID8, *C. lavalense*, *E. symbiosum*, *C. saccharogumia*, *C. ramosum*, *F. plautii*, *C. hathewayi*, *C. scindens*, *Clostridium* sp. 2335, *Clostridium* sp. 14616 and cf *Clostridium* sp. MLG055) (Table 2). They all belonged to *Clostridium* clusters IV, XIVa or XVIII (2 species of cluster IV, 12 of cluster XIVa, 1 of cluster XVI and 2 of cluster XVIII).

Example 29

Of the colonies selected in Example 28, additional colonies were picked and isolated and these strains were cultured using EG and BL media. BLAST search of 16S rRNA coding sequence of these clones revealed that they belonged to a total of 31 species (including the species mentioned in Example 28), and each had 93-100% similarities with *Clostridium saccharogumia*, *Clostridium ramosum* JCM1298, *Clostridium ramosum*, *Flavonifractor plautii*, *Pseudoflavonifractor capillosus* ATCC 29799, *Clostridium hathewayi*, *Clostridium saccharolyticum* WM1, *Bacteroides* sp. MANG, *Clostridium saccharolyticum*, *Clostridium scindens*, *Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis*, *Anaerostipes caccae*, *Clostridium bolteae*, *Lachnospiraceae bacterium* DJF_VP30, *Lachnospiraceae bacterium* 3_1_57FAA_CT1, *Anaerotruncus colihominis*, *Anaerotruncus colihominis* DSM 17241, *Ruminococcus* sp. ID8, *Lachnospiraceae bacterium* 2_1_46FAA, *Clostridium lavalense*, *Clostridium asparagiforme* DSM 15981, *Clostridium symbiosum*, *Clostridium symbiosum* WAL-14163, *Eubacterium contortum*, *Clostridium* sp. D5, *Oscillospiraceae bacterium* NML 061048, *Oscillibacter valericigenes*, *Lachnospiraceae bacterium* A4, *Clostridium* sp. 316002/08, and *Clostridiales bacterium* 1_7_47FAA, *Blautia cocoides*, *Anaerostipes caccae* DSM 14662 (Table 3). The stocks of bacterial strains were stored in 10% glycerol stock plus the media used to grow the cultures, and tubes were stored in a −80° C. freezer.

Example 30

Figure 10A:
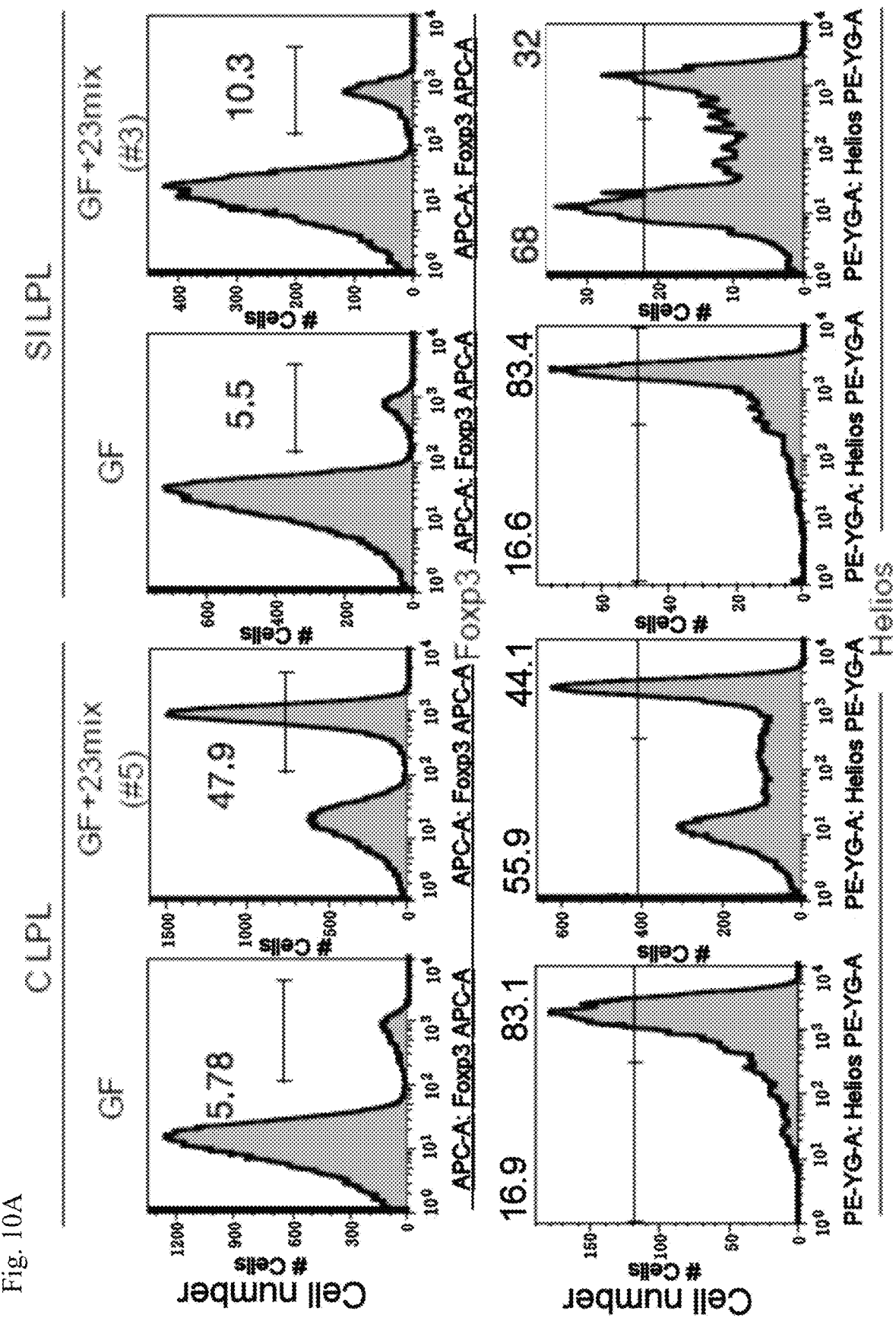
FIGS. 10A-10C shows representative plots (FIG. 10A) and combined data (FIGS. 10B, 10C) for Foxp3 expression in CD4$^+$ cells (FIG. 10A, 10B), or Helios expression in Foxp3$^+$CD4$^+$ cells (FIG. 10A, 10C) from colonic lamina propria (C LPL) and small intestinal lamina propria (SI LPL) for GF mice and GF mice that were inoculated with a mixture of 23 bacterial strains that were isolated and shown in Table 2 (23mix). Numbers above bracketed lines in FIG. 10A indicate the percentage of the population. Each circle in FIG. 10B
Figure 10B:
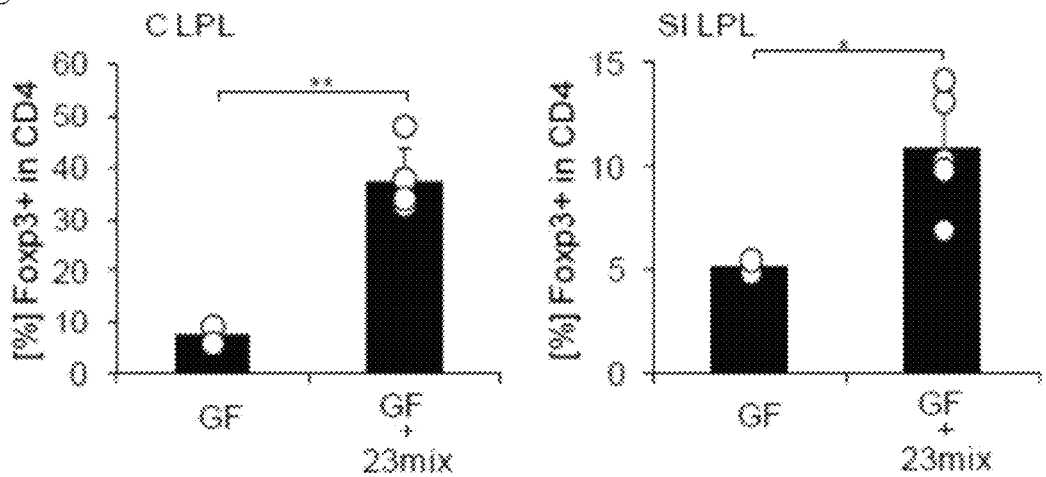
Figure 10C:
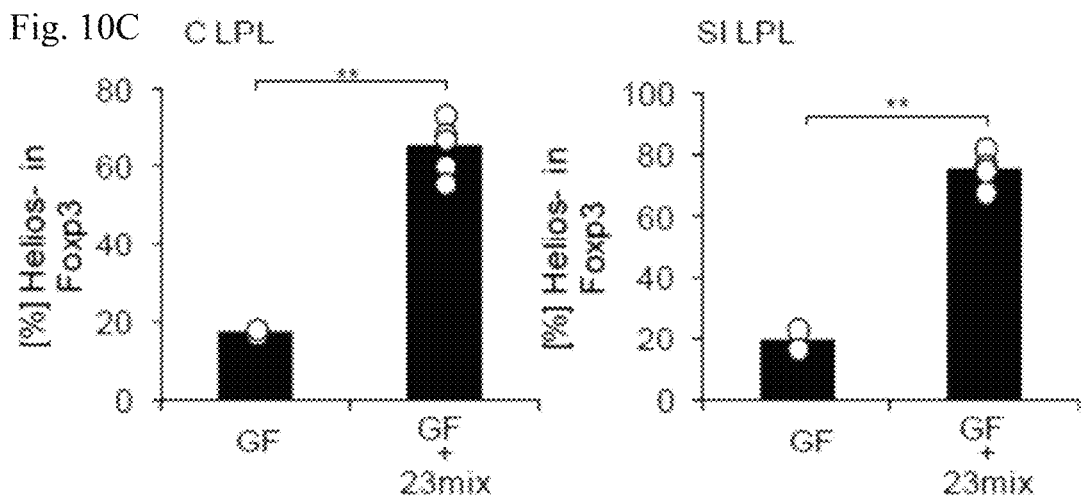

To investigate whether the strains in Example 29 have the ability to induce Tregs in GF mice, 31 strains on Table 3 were mixed at equal amounts of media volume using TS media and inoculated into GF mice. A detailed analysis of the 16S rRNA sequences revealed that 8 of the 31 strains overlapped with other strains (see Table 3, indicated by an asterisk), resulting in 23 distinct bacterial strains. As shown in FIG. 10, when orally administered to GF mice, the mixture of the 23 strains (23mix) induced very strong levels of Tregs (35-40% in the colon lamina propria, >10% in the small intestine; FIG. 10). These Tregs observed with colonization by 23mix were mostly Helios$^-$.

Example 31

Figure 11:
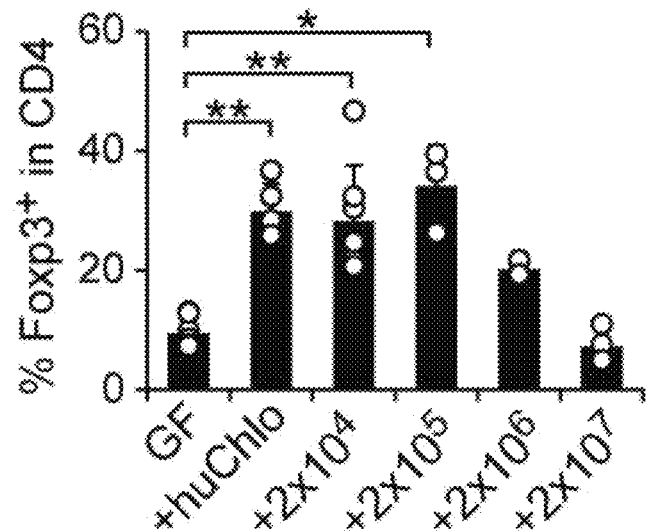
FIG. 11 shows a representative plot of the accumulation of Foxp3$^+$CD4$^+$ cells in adult GF mice that were inoculated with $2 \times 10^4$ to $2 \times 10^7$-fold diluted caecal samples from +huChlo mice. Experiments were performed more than twice. Error bars indicate SD. **P<0.01, *P<0.05, as calculated by Student's t-test.

To investigate whether the abundant members of the intestinal microbiota in the chloroform-resistant fraction of human intestinal bacteria, rather than the minor members, drive the induction of Treg cells, adult GF mice were inoculated with diluted caecal samples from mice that had been inoculated with the chloroform-resistant fraction of human intestinal bacteria (+huChlo mice) as described in example 19. As shown in FIG. 11, even when the huChlo mice cecal samples were diluted (diluted 2×10$^4$ and 2×10$^5$) to create +2×10$^4$ mice and 2×10$^5$ mice respectively, Tregs were induced in these adult GF mice.

Example 32

Figure 12:
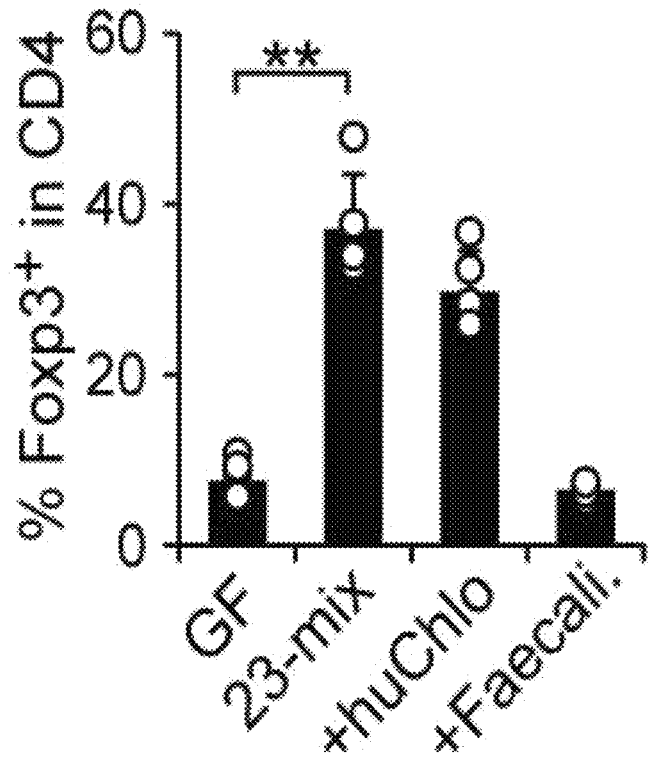
FIG. 12 shows a representative plot of the accumulation of Foxp3$^+$CD4$^+$ cells in the colon of adult GF mice that were inoculated with a mixture of 23 bacterial strains that were isolated and shown in Table 2 (23-mix), chloroform-treated human feces (+huChlo) and *Faecalibacterium prausnitzii* (+Faecali). Error bars indicate SD. **P<0.01, as calculated by Student's t-test.

To investigate whether the mix of 23 strains in Example 30 has the ability to induce Tregs in adult GF IQI mice more effectively than *Faecalibacterium prausnitzii*, a well-known human Clostridia strain characterized for enhancing regulatory cell functions, 23 strains in table 4 were mixed in equal amounts with media to make a cocktail, which was then administered to adult IQI GF mice. For comparison, *Faecalibacterium prausnitzii* was administered to another group of IQI GF mice. As shown in FIG. 12, when orally administered to adult IQI GF mice, the mixture of the 23 strains (23-mix) induced higher levels of Tregs than *Faecalibacterium prausnitzii*. *Faecalibacterium prausnitzii* (+Faecali.) showed negligible levels of Treg induction.

Example 33

Figure 13:
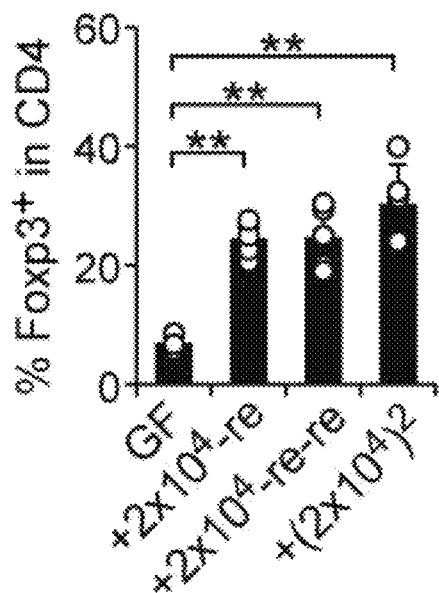
FIG. 13 shows a representative plot of the accumulation of Foxp3$^+$CD4$^+$ cells in adult GF mice that were the secondary ($+2 \times 10^4$-re) and tertiary ($+2 \times 10^4$-re-re) recipients of inoculations with the caecal content of $+2 \times 10^4$ mice, and adult GF mice inoculated with $2 \times 10^4$-fold diluted caecal samples from $+2 \times 10^4$ mice ($+(2 \times 10^4)^2$).

To investigate whether the microbiota communities in the +2×104 mice, described in example 31, were stable, serial oral inoculation of adult GF mice was performed to create +2×10$^4$-re mice (secondary inoculation) and +2×10$^4$-re-re (tertiary inoculation). As shown in FIG. 13 there was significant induction of Tregs in both the +2×10$^4$-re mice and the +2×10$^4$-re-re mice. To further eliminate nonessential components of the microbiota for Treg cell induction, the caecal content of +2×10$^4$ mice, described in example 31, was again diluted 2×10$^4$-fold and orally inoculated into another set of adult GF mice (+(2×10$^4$)$^2$ mice). As shown in FIG. 13, the +(2×10$^4$)$^2$ mice exhibited a marked accumulation of Treg cells in the colon.

Example 34

Figure 14:
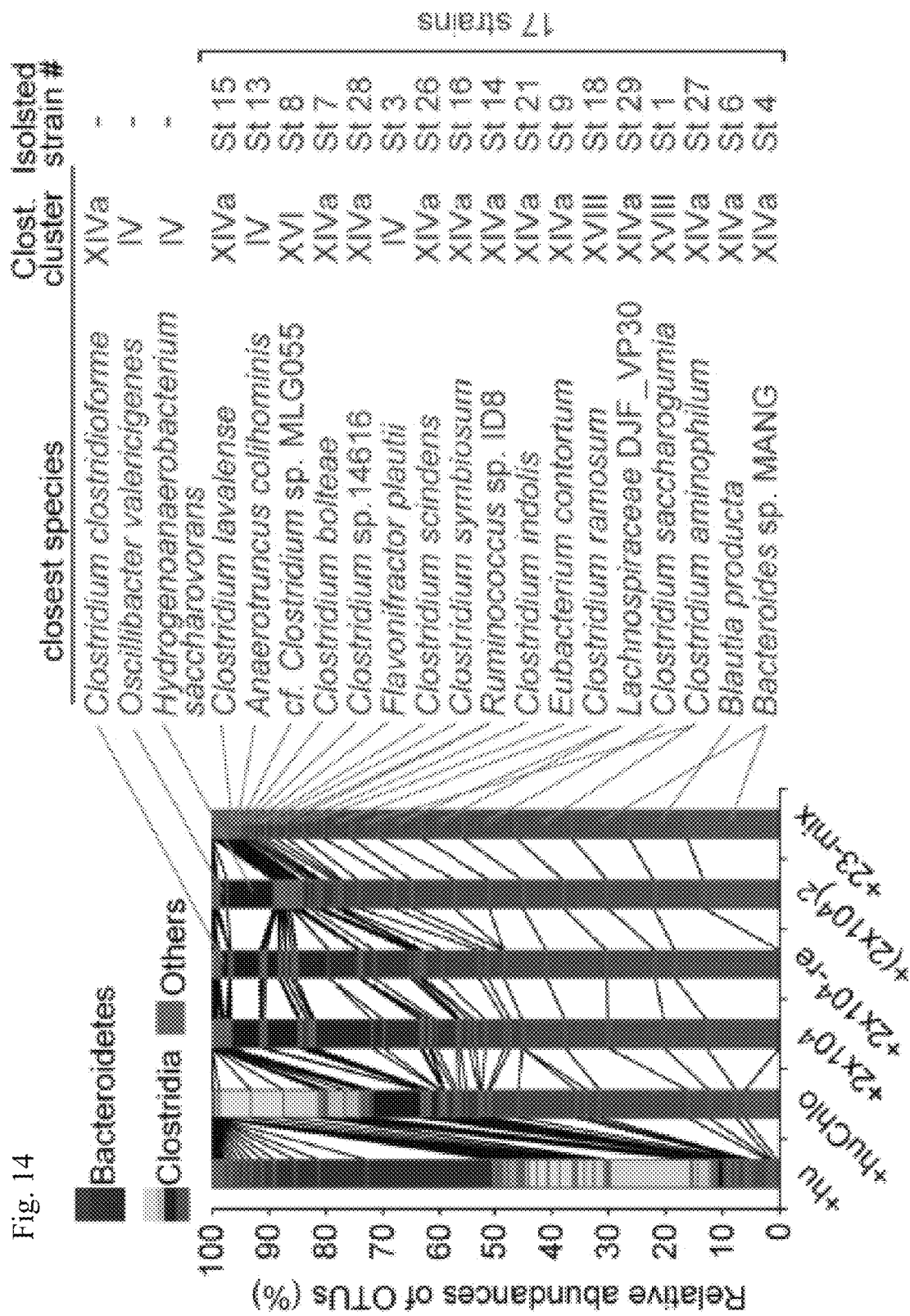
FIG. 14 shows the results of 16s rDNA pyrosequencing the caecal contents from the defined mice (+hu, +huChlo, $+2 \times 10^4$, $+2 \times 10^4$-re, $(+2 \times 10^4)^2$, +23-mix) using a 454 sequencer. The relative abundance of OTUs (%) in the caecal bacterial community in each mouse and the closest strains in the database and the corresponding isolated strain number for the indicated OTUs are shown.

To assess the composition of the gut microbiota in +huUT (+hu), +huChlo, +2×10$^4$, +2×10$^4$-re and +(2×10$^4$)$^2$, described in example 19, example 31, and example 33, bacterial DNA was extracted from the caecal contents of these adult mice. The variable region (V1-V2) of the bacterial 16S ribosomal DNA (rDNA) was amplified and metasequencing using a 454 sequencer was performed. The resulting sequences (3400 reads for each sample) were classified into operational taxonomic units (OTUs) based on sequence similarity (>96% identity). Representative sequences from each OTU were compared with sequences deposited in publicly available 16S and genome databases using BLAST to determine their closest species. As shown in FIG. 14, in +hu mice, OTUs belonging to Bacteroidetes accounted for about 50% of the caecal microbial community. In contrast, in most OTUs in +huChlo mouse were related to species belonging to Clostridia. In +2×10$^4$, +2×10$^4$-re and +(2×10$^4$)$^2$ mice, the majority of bacteria consisted of bacteria having 16S rDNA sequence similarities with about 20 species of Clostridia belonging to cluster XIVa (also referred to as *C. leptum* group), IV, XVI, and XVIII, listed in FIG. 14.

Example 35

Figure 15:
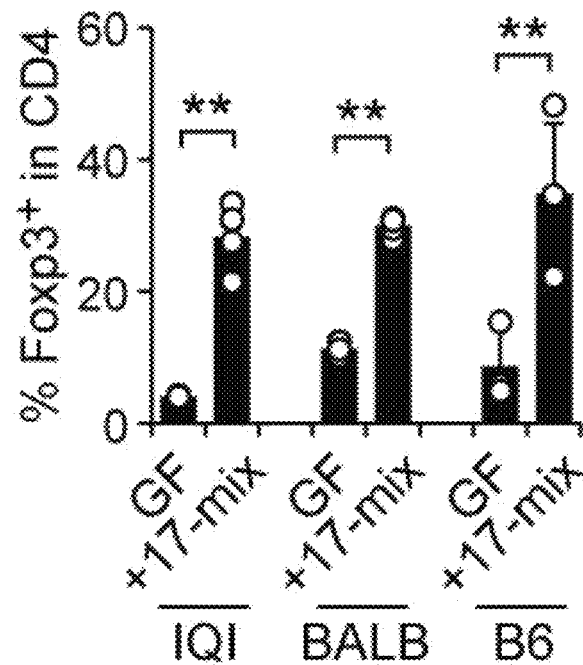
FIG. 15 shows a representative plot of the accumulation of Foxp3$^+$CD4$^+$ cells in the colons of adult IQI, BALB and B6 GF mice on inoculation with a mixture of 17 bacterial strains that were isolated and shown in Table 4 (17-mix), **P<0.01, as calculated by Student's t-test.

A meta analysis of 16S rDNA of caecal contents from mice inoculated with the 23 strains isolated in example 30 (+23-mix mice) confirmed the presence of 17 of the 23 strains listed in FIG. 14 and Table 4. To determine whether these 17 strains could induce Treg cells, a mixture of these 17 strains was inoculated into adult GF mice (+17-mix mice), Each bacterial strain was cultured in 2 mL EG liquid media and grown to confluence, and then these starter cultures were mixed into a 50 mL tube (2 mL×17 strains=34 mL). The bacteria were spun down into a pellet and resuspended in 10 mL PBS. A 200 uL aliquot, containing ~1×10$^6$-1×10$^7$ of each strain, was used to inoculate the adult GF mice. As shown in FIG. 15, when orally administered to adult IQI, BALB, and B6 mice, the mixture of 17 strains was able to induce Tregs in these three mouse models.

Example 36

Figure 16:
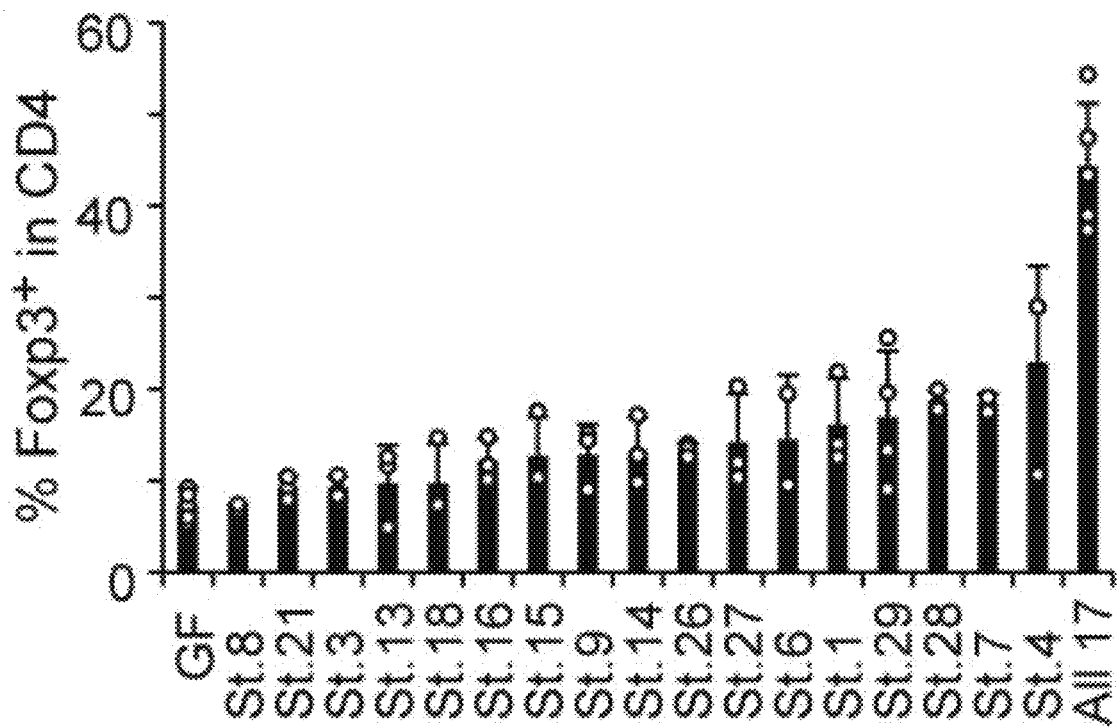
FIG. 16 shows a representative plot of the accumulation of Foxp3$^+$CD4$^+$ cells in adult IQI GF mice mono-colonized with each of the 17 strains listed in Table 4 (17-mix).

To investigate whether each of the 17 strains defined in example 35 could individually induce Tregs, adult GF mice were monocolonized with one of each of the 17 strains. As shown in FIG. 16, adult GF mice monocolonized with a single strain exhibited low to intermediate levels of Treg. Importantly, no single strain induced Tregs to the same extent as the mix of 17 strains.

Example 37

Figure 17:
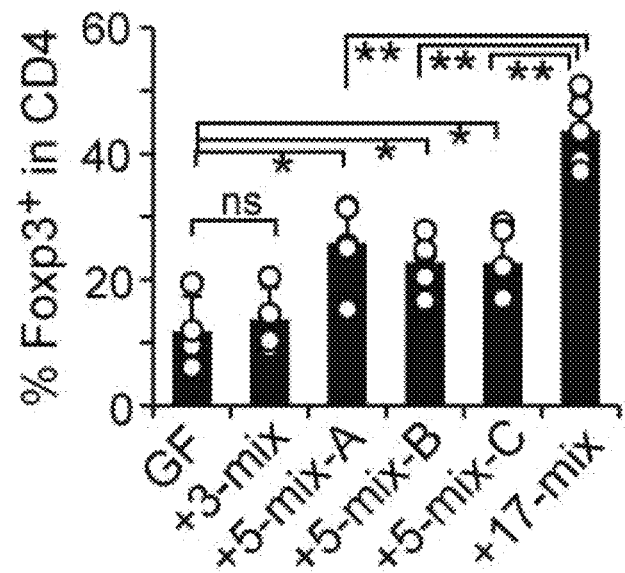
FIG. 17 shows a representative plot of the accumulation of Foxp3$^+$CD4$^+$ cells in adult IQI GF mice colonized with 3-mix, 5mix-A, 5-mix-B, 5-mix-C or 17-mix as listed in Table 4. Circles indicate individual animals. Experiments wasere performed more than twice with similar results. Error bars indicate SD. **P<0.01, *P<0.05, ns, not significant, as calculated by Student's t-test.

To investigate whether subsets of the 17 strains described in example 35 could induce Tregs, randomly selected combinations of 3-5 strains were made: 3-mix, 5mixA, 5-mix B, and 5-mix C, as shown in table 4, and used to inoculate adult GF mice. As shown in FIG. 17, only the 5-species mixes induced significant increases in the frequency of Treg cells, the magnitude of which was intermediate compared with that observed in +17-mix mice.

Example 38

Figure 18:
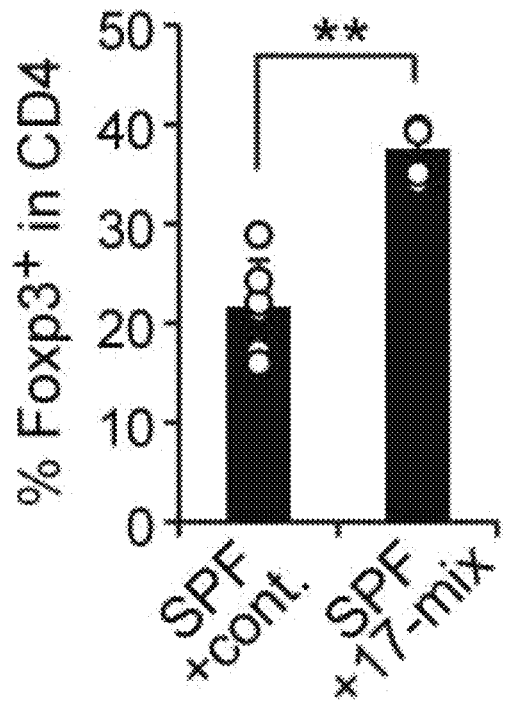
FIG. 18 shows a representative plot of the accumulation of Foxp3$^+$CD4$^+$ cells in adult SPF mice repeatedly inoculated with 17-mix (SPF+17mix; n=5) or control (SPF+cont; n=6). **P<0.01, as calculated by Student's t-test.

To investigate the benefits of administration of the mix of the 17 strains described in example 35 (17-mix), adult SPF mice were orally inoculated with either 17-mix or control media and assessed for the induction of Foxp3+ Treg cells three weeks later. As shown in FIG. 18, there was a significant increase in the frequency of colonic Foxp3$^+$ Treg (CD4) cells after three weeks of treatment.

Example 39

Figure 19:
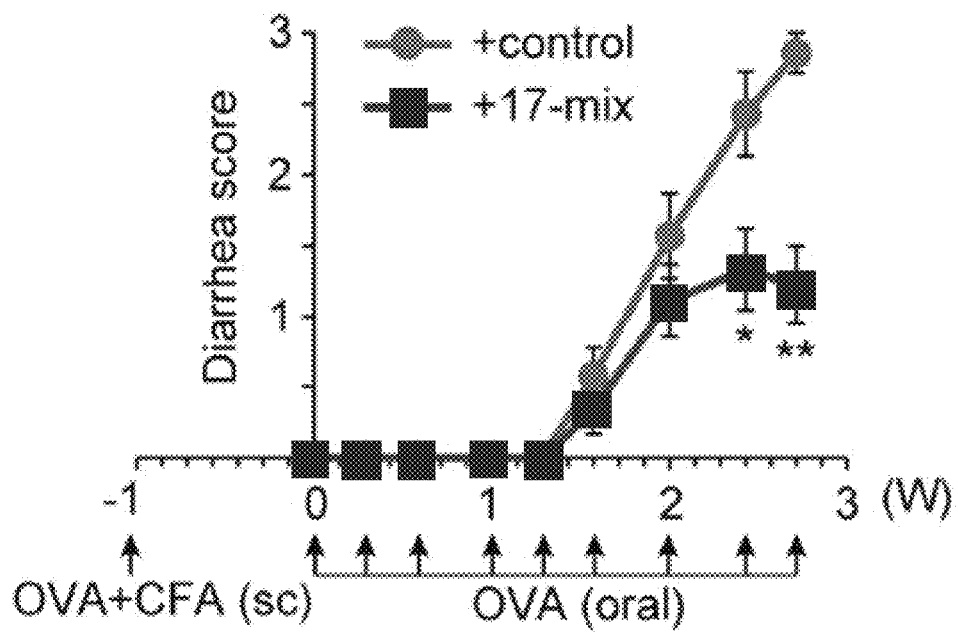
FIG. 19 shows the effects of inoculation with 17-mix on an OVA model of diarrhea, as measured by a qualitative diarrhea score. *P<0.05, as calculated by Student's t-test.

To evaluate the benefit of administration of 17-mix in an animal model of allergic diarrhea, adult SPF mice were orally inoculated with 17-mix or control media while being treated with ovalbumin (OVA), an inducer of allergic diarrhea. As shown in FIG. 19, the occurrence and severity of diarrhea (diarrhea score) was significantly reduced in mice fed 17-mix relative to control mice.

Example 40

Figure 20:
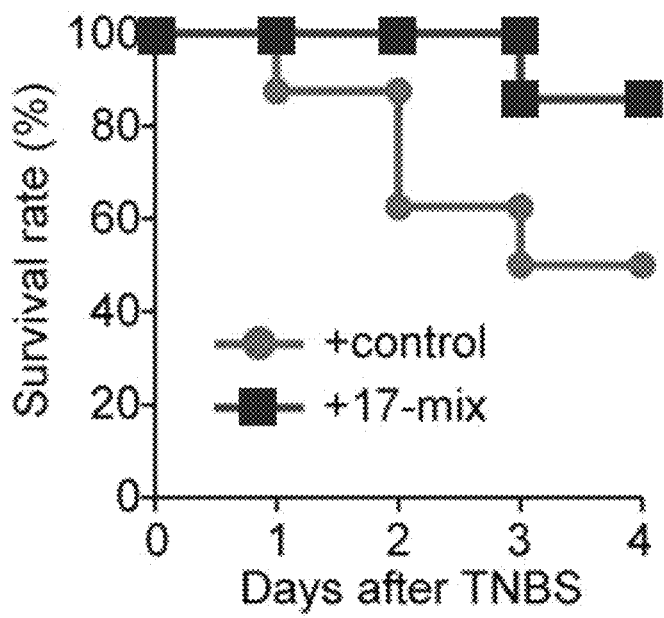
FIG. 20 shows the survival of adult mice inoculated with a mixture of 17 bacterial strains listed in Table 4 (17-mix) following exposure to trinitrobenzene sulfonic acid (TNBS), an agent used in experimental models of colitis.

To evaluate the benefit of administration of 17-mix in an animal model of colitis. Adult SPF mice were orally inoculated with either 17-mix or control media while being treated with trinitrobenzene sulfonic acid (TNBS), a frequently used experimental inducer of colitis. As shown in FIG. 20, SPF 17-mix mice demonstrated lower mortality than control mice on exposure to TNBS.

Example 41

Figure 21:
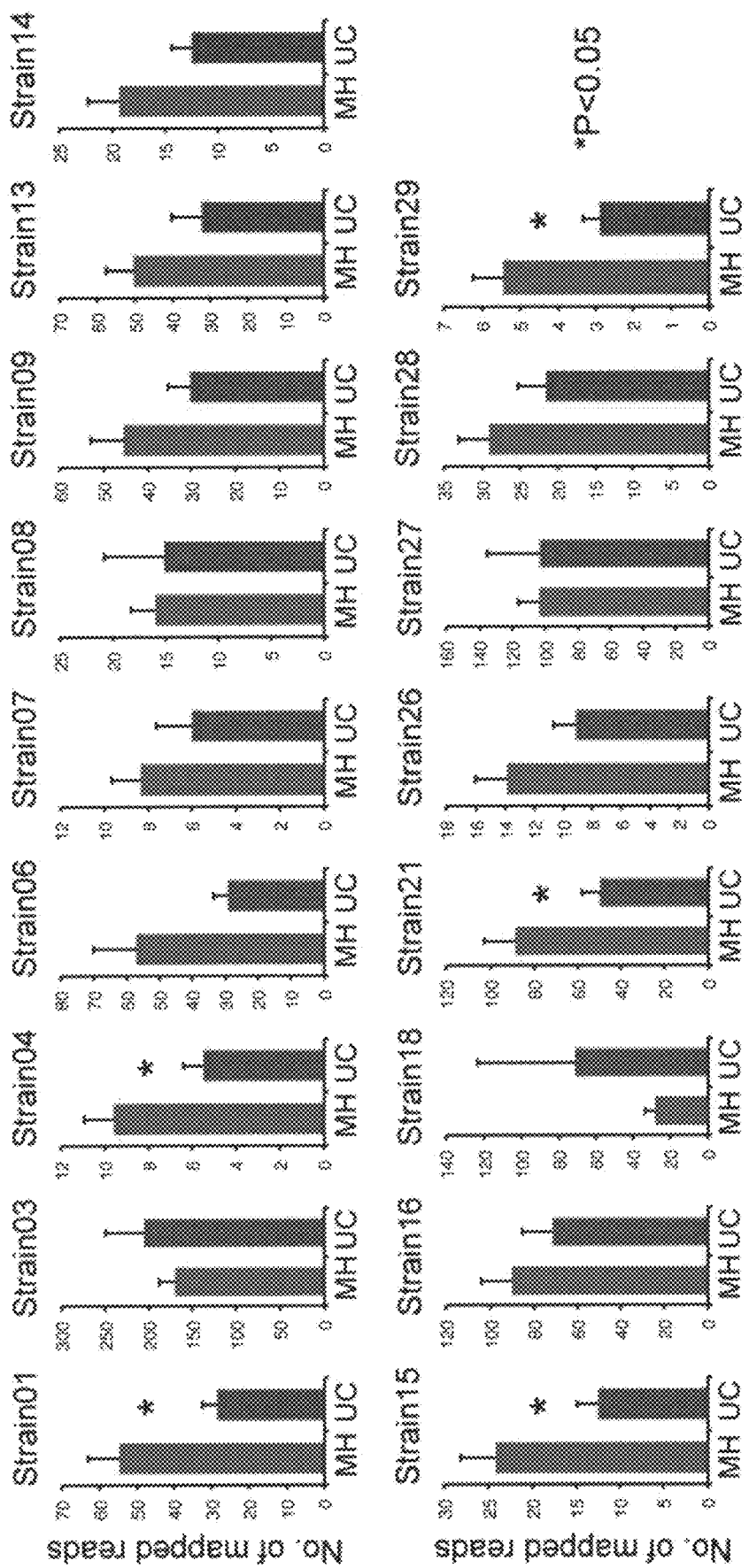
FIG. 21 shows the relative abundance of each of the 17-mix strains in the human fecal microbiota of ulcerative colitis and healthy subjects. The publically available reads of 15 healthy and 20 ulcerative colitis subjects in the MetaHIT database were aligned to the genome of the 17 strains. The mean numbers of mapped reads in healthy and UC groups for each of the 17 strain genomes are shown. Error bars represent SEM. *P<0.05, as calculated by the Student's t-test.

To evaluate the usefulness of the strains represented in 17-mix as a diagnostic and monitoring tool for ulcerative colitis, we examined the relative abundance of the 17 strains in healthy and ulcerative colitis (UC) human subjects using draft genomic sequences of the 17 strains and publicly available human faecal microbiome genomes generated through the European MetaHIT project. UC subjects (N=20) showed a a reduction of the 17 strains compared to healthy subjects (N=15), as shown in FIG. 21.

SEQ ID NOs.: OTU136; OTU46; OTU221; OTU9; OTU296; OTU21; OTU166; OTU73; OTU174; OTU14; OTU55; OTU337; OTU314; OTU195; OTU306; OTU87;

OTU86; OTU152; OTU253; OTU259; OTU281; OTU288; OTU334; OTU359; OTU362; or OTU367are SEQ ID NOs. 19-44, respectively.

INDUSTRIAL APPLICABILITY

As has been described above, the compositions and methods described herein make it possible to provide an excellent and well-characterized composition for inducing proliferation or accumulation of regulatory T cells (Treg cells) by utilizing certain human-derived bacteria belonging to the Clostridia class or a physiologically active substance or the like derived from the bacteria. Since the bacterial composition has immunosuppressive effects, the bacterial composition can be used, for example, to prevent or treat autoimmune diseases or allergic diseases, as well as to suppress immunological rejection in organ transplantation or the like. In addition, healthy individuals can easily and routinely ingest the bacterial composition, such as in food or beverage, (e.g., a health food), to improve their immune functions.

TABLE 1A

| | | The number of closest relative in known species | | | | | |
|---|---|---|---|---|---|---|---|
| OTU name | Close relative | #C4 | #F8 | #G2 | #H3 | #I3 | #J3 |
| 218 | bacterium ic1337 | 9 | 0 | 0 | 0 | 0 | 0 |
| 104 | bacterium ic1395 | 4 | 0 | 0 | 0 | 0 | 0 |
| 60 64 249 | Bacteroides uniformis | 0 | 0 | 0 | 0 | 0 | 1 |
| 16 | Bacteroides vulgatus | 0 | 0 | 0 | 0 | 0 | 1 |
| 233 | beta proteobacterium GMD 15D04 | 0 | 0 | 1 | 0 | 0 | 1 |
| 138 | Bifidobacterium pseudocatenulatum | 0 | 0 | 0 | 0 | 0 | 2 |
| 228 | butyrate-producing bacterium M104/1 | 0 | 0 | 1 | 0 | 0 | 3 |
| 31 73 | cf. Clostridium sp. MLG055 | 10 | 0 | 20 | 0 | 0 | 15 |
| 227 | Clostridiaceae bacterium bSSV31 | 2 | 0 | 0 | 0 | 0 | 0 |
| 311 | Clostridiaceae bacterium FH042 | 0 | 0 | 0 | 0 | 0 | 1 |
| 29 52 321 | Clostridiaceae bacterium NML 061030 | 3 | 0 | 3 | 0 | 0 | 8 |
| 33 156 | Clostridiaceae bacterium SH021 | 10 | 0 | 0 | 0 | 0 | 0 |
| 183 | Clostridiales bacterium DJF_B152 | 27 | 0 | 0 | 0 | 0 | 0 |
| 95 365 | Clostridium citroniae | 2 | 0 | 2 | 0 | 0 | 13 |
| 106 146 | Clostridium glycyrrhizinilyticum | 2 | 1 | 0 | 0 | 0 | 0 |
| 91 105 102 178 203 292 318 | Clostridium innocuum | 32 | 0 | 0 | 0 | 0 | 0 |
| 69 80 325 | Clostridium lactatifermentans | 32 | 0 | 0 | 0 | 0 | 0 |
| 47 335 | Clostridium methoxybenzovorans | 13 | 0 | 0 | 0 | 0 | 0 |
| 147 175 298 344 | Clostridium sp. CE6 | 317 | 0 | 0 | 0 | 0 | 1 |
| 209 | Clostridium sp. CYP2 | 1 | 0 | 0 | 0 | 0 | 0 |
| 322 | Clostridium sp. RT8 | 5 | 0 | 0 | 0 | 0 | 0 |
| 223 | Clostridium sp. SH-C52 | 0 | 1 | 0 | 0 | 0 | 0 |
| 48 | Clostridium xylanovorans | 0 | 0 | 0 | 0 | 0 | 1 |
| 352 | Desulfotomaculum sp. CYP1 | 1 | 0 | 0 | 0 | 0 | 0 |
| 132 154 283 | Dorea longicatena | 0 | 0 | 0 | 0 | 0 | 1 |
| 164 177 | Eggerthella lenta | 0 | 0 | 0 | 0 | 0 | 0 |
| 304 | Escherichia coli | 0 | 0 | 0 | 0 | 1 | 0 |
| 155 | Eubacterium dolichum | 150 | 0 | 0 | 0 | 0 | 0 |
| 66 | Eubacterium eligens | 7 | 0 | 0 | 0 | 0 | 0 |
| 81 219 | Eubacterium ramulus | 36 | 0 | 0 | 0 | 0 | 0 |
| 287 | Eubacterium siraeum | 0 | 0 | 0 | 0 | 1 | 0 |
| 53 | Eubacterium yurii | 0 | 0 | 0 | 1 | 0 | 0 |
| 41 71 212 222 320 | Faecalibacterium prausnitzii | 116 | 0 | 0 | 0 | 0 | 0 |
| 210 217 271 305 | Faecalibacterium sp. DJF_VR20 | 376 | 0 | 0 | 0 | 0 | 0 |
| 63 197 301 | Firmicutes bacterium DJF_VP44 | 5 | 0 | 0 | 0 | 0 | 0 |
| 324 | Fusobacterium periodonticum | 0 | 0 | 1 | 0 | 0 | 0 |
| 180 294 | Gram-negative bacterium cL10-2b-4 | 0 | 0 | 0 | 0 | 0 | 2 |
| 190 358 | human intestinal bacterium julong 601 | 8 | 0 | 0 | 0 | 0 | 0 |
| 153 184 198 265 | Lachnospiraceae bacterium DJF_RP14 | 2 | 0 | 0 | 0 | 0 | 1 |
| 171 | Lactobacillus murinus | 0 | 0 | 1 | 0 | 0 | 0 |
| 17 | Odoribacter splanchnicus | 13 | 0 | 0 | 0 | 0 | 0 |
| 267 | Porphyromonas catoniae | 0 | 0 | 1 | 0 | 0 | 0 |
| 145 | Prevotella melaninogenica | 0 | 0 | 0 | 0 | 0 | 1 |
| 8 | Prevotella nanceiensis | 0 | 0 | 1 | 0 | 0 | 0 |
| 243 | Prevotellaceae bacterium DJF_RP17 | 0 | 1 | 0 | 0 | 0 | 0 |
| 103 | Robinsoniella peoriensis | 1 | 0 | 0 | 0 | 0 | 4 |
| 98 127 | Ruminococcus gnavus | 286 | 0 | 0 | 0 | 0 | 0 |
| 43 99 102 159 275 | Ruminococcus sp. YE58 | 1 | 0 | 0 | 0 | 0 | 0 |
| 341 342 | Ruminococcus sp. ZS2-15 | 53 | 0 | 0 | 0 | 0 | 0 |
| 252 | Streptococcus australis | 0 | 0 | 1 | 0 | 0 | 0 |
| 130 191 272 | Subdoligranulum sp. DJF_VR33k2 | 27 | 0 | 0 | 0 | 0 | 0 |
| 351 | Subdoligranulum variabile | 1 | 0 | 0 | 0 | 0 | 0 |
| 56 | unidentified bacterium ZF3 | 6 | 0 | 0 | 0 | 0 | 0 |
| 257 282 284 327 329 332 | Ruminococcus sp. K-1 | 322 | 0 | 0 | 0 | 0 | 0 |
| 87 124 204 259 310 330 | Eubacterium fissicatena | 56 | 29 | 86 | 15 | 43 | 28 |
| 234 348 | Eubacterium contortum | 2 | 8 | 0 | 6 | 0 | 0 |
| 90 | Lachnospiraceae bacterium A4 | 2 | 0 | 0 | 0 | 0 | 0 |
| 2 61 82 92 111 163 225 266 288 312 336 355 359 367 | Clostridium aminophilum | 565 | 522 | 514 | 380 | 374 | 376 |

TABLE 1A-continued

| OTU name | Close relative | The number of closest relative in known species | | | | | |
|---|---|---|---|---|---|---|---|
| | | #C4 | #F8 | #G2 | #H3 | #I3 | #J3 |
| 281 296 | *Clostridium scindens* | 18 | 15 | 29 | 25 | 14 | 17 |
| 224 254 264 | *Roseburia hominis* | 2 | 1 | 0 | 0 | 1 | 0 |
| 350 | *Ruminococcus* sp. END-1 | 1 | 0 | 1 | 0 | 0 | 0 |
| 151 242 340 | *Hydrogenoanaerobacterium saccharovorans* | 141 | 205 | 199 | 138 | 175 | 140 |
| 44 101 110 119 131 135 137 214 260 | *Clostridium clostridioforme* | 12 | 20 | 25 | 75 | 62 | 71 |
| 54 77 97 121 179 187 202 261 306 326 345 366 | *Clostridium symbiosum* | 31 | 54 | 24 | 19 | 19 | 6 |
| 27 93 136 182 240 313 | *Clostridium saccharogumia* | 257 | 262 | 200 | 373 | 405 | 307 |
| 328 333 | *Bacteroides capillosus* | 3 | 6 | 3 | 1 | 3 | 0 |
| 280 | *Holdemania filiformis* | 33 | 46 | 41 | 15 | 31 | 33 |
| 100 120 140 143 166 194 229 237 276 297 307 315 319 354 | *Clostridium* sp. 14616 | 97 | 165 | 493 | 287 | 287 | 153 |
| 67 221 347 | *Flavonifractor plautii* | 12 | 17 | 34 | 25 | 30 | 29 |
| 85 107 | butyrate-producing *bacterium* T2-145 | 2 | 0 | 0 | 1 | 0 | 0 |
| 19 40 161 189 195 220 238 262 269 303 334 | *Clostridium lavalense* | 75 | 285 | 278 | 475 | 298 | 197 |
| 45 94 109 114 125 215 248 268 314 | *Ruminococcus* sp. ID8 | 30 | 114 | 140 | 135 | 127 | 141 |
| 337 | *Anaerotruncus colihominis* | 1 | 6 | 3 | 3 | 8 | 2 |
| 46 199 213 270 278 | *Clostridium ramosum* | 28 | 74 | 67 | 97 | 110 | 189 |
| 35 37 55 89 129 152 160 245 279 356 | *Lachnospiraceae bacterium* DJF_VP30 | 47 | 268 | 321 | 185 | 232 | 243 |
| 12 23 72 86 174 201 211 236 246 258 361 364 | *Clostridium indolis* | 13 | 121 | 104 | 253 | 198 | 467 |
| 4 9 13 14 22 28 38 57 62 76 78 144 186 231 241 362 | *Bacteroides* sp. MANG | 35 | 577 | 530 | 268 | 304 | 226 |
| 3 7 15 20 21 24 39 68 70 96 113 115 116 | *Clostridium* sp. 2335 | 57 | 574 | 1 | 587 | 637 | 712 |
| 49 117 181 302 339 | *Clostridium bolteae* | 0 | 13 | 0 | 30 | 32 | 0 |
| 74 126 208 251 285 | *Clostridium hathewayi* | 0 | 1 | 0 | 0 | 0 | 0 |
| 32 112 | *Clostridium* sp. 14774 | 0 | 0 | 268 | 0 | 0 | 0 |
| 50 155 196 253 | *Oscillibacter valericigenes* | 0 | 14 | 7 | 6 | 7 | 4 |
| 30 188 | *Ruminococcus* sp. M-1 | 0 | 0 | 0 | 0 | 0 | 3 |
| | Total: | 3400 | 3400 | 3400 | 3400 | 3400 | 3400 |

TABLE 1B

| OTU name | The closest relative in known species | Similarity (%) | The number OTU | | | | | | |
|---|---|---|---|---|---|---|---|---|---|
| | | | #A1 | #C4 | #F8 | #G2 | #H3 | #I3 | #J3 |
| 3 | *Clostridium* sp. 2335 | 98.46 | 1 | 0 | 13 | 18 | 10 | 13 | 8 |
| 9 | *Bacteroides* sp. MANG | 98.15 | 14 | 0 | 324 | 16 | 153 | 172 | 159 |
| 14 | *Bacteroides* sp. MANG | 99.07 | 4 | 34 | 46 | 401 | 28 | 27 | 14 |
| 15 | *Clostridium* sp. 2335 | 96.9 | 0 | 0 | 8 | 2 | 0 | 2 | 1 |
| 21 | *Clostridium* sp. 2335 | 99.69 | 19 | 53 | 325 | 322 | 376 | 410 | 358 |
| 23 | *Clostridium indolis* | 97.25 | 0 | 0 | 0 | 0 | 3 | 1 | 2 |
| 38 | *Bacteroides* sp. MANG | 96.26 | 0 | 0 | 6 | 0 | 1 | 1 | 4 |
| 46 | *Clostridium ramosum* | 99.67 | 47 | 28 | 70 | 67 | 85 | 101 | 188 |
| 49 | *Clostridium bolteae* | 95.98 | 1 | 0 | 7 | 0 | 17 | 28 | 0 |
| 55 | *Lachnospiraceae bacterium* DJF_VP30 | 95.53 | 12 | 45 | 120 | 289 | 72 | 85 | 106 |
| 57 | *Bacteroides* sp. MANG | 96.27 | 3 | 0 | 93 | 0 | 27 | 38 | 20 |
| 86 | *Clostridium indolis* | 98.78 | 1 | 0 | 22 | 0 | 43 | 43 | 0 |
| 87 | *Eubacterium fissicatena* | 99.69 | 1 | 40 | 11 | 39 | 4 | 8 | 0 |
| 89 | *Lachnospiraceae bacterium* DJF_VP30 | 95.18 | 1 | 0 | 4 | 0 | 0 | 2 | 0 |
| 92 | *Clostridium aminophilum* | 90.09 | 0 | 2 | 0 | 1 | 0 | 1 | 0 |
| 101 | *Clostridium clostridioforme* | 98.76 | 1 | 9 | 6 | 3 | 12 | 5 | 12 |
| 111 | *Clostridium aminophilum* | 91.64 | 0 | 1 | 0 | 0 | 0 | 1 | 1 |
| 114 | *Ruminococcus* sp. ID8 | 95.98 | 0 | 4 | 3 | 40 | 0 | 1 | 18 |
| 119 | *Clostridium clostridioforme* | 98.77 | 0 | 1 | 1 | 9 | 0 | 1 | 2 |
| 125 | *Ruminococcus* sp. ID8 | 97.25 | 0 | 0 | 11 | 12 | 13 | 15 | 43 |
| 131 | *Clostridium clostridioforme* | 97.23 | 1 | 0 | 1 | 3 | 2 | 1 | 9 |
| 136 | *Clostridium saccharogumia* | 97.02 | 10 | 1 | 23 | 16 | 36 | 43 | 12 |
| 137 | *Clostridium clostridioforme* | 98.15 | 1 | 0 | 12 | 10 | 28 | 51 | 47 |

TABLE 1B-continued

| OTU name | The closest relative in known species | Similarity (%) | #A1 | #C4 | #F8 | #G2 | #H3 | #I3 | #J3 |
|---|---|---|---|---|---|---|---|---|---|
| 144 | *Bacteroides* sp. MANG | 97.81 | 1 | 0 | 2 | 30 | 1 | 2 | 0 |
| 152 | *Lachnospiraceae bacterium* DJF_VP30 | 95.55 | 10 | 0 | 129 | 27 | 56 | 135 | 137 |
| 161 | *Clostridium lavalense* | 96.3 | 0 | 0 | 1 | 1 | 0 | 4 | 0 |
| 163 | *Clostridium aminophilum* | 90.74 | 0 | 0 | 3 | 0 | 1 | 2 | 0 |
| 165 | *Oscillibacter valericigenes* | 90.15 | 0 | 9 | 0 | 7 | 0 | 1 | 1 |
| 166 | *Clostridium* sp. 14616 | 98.45 | 2 | 35 | 14 | 44 | 26 | 32 | 26 |
| 173 | *Clostridium* sp. 2335 | 98.33 | 0 | 0 | 0 | 0 | 0 | 1 | 0 |
| 174 | *Clostridium indolis* | 100 | 0 | 13 | 98 | 103 | 205 | 152 | 465 |
| 181 | *Clostridium bolteae* | 97.56 | 0 | 0 | 5 | 0 | 12 | 2 | 0 |
| 182 | *Clostridium saccharogumia* | 94.37 | 0 | 2 | 1 | 0 | 3 | 1 | 1 |
| 189 | *Clostridium lavalense* | 94.12 | 0 | 0 | 0 | 0 | 0 | 1 | 0 |
| 195 | *Clostridium lavalense* | 98.47 | 0 | 0 | 47 | 0 | 33 | 31 | 0 |
| 196 | *Oscillibacter valericigenes* | 91.64 | 1 | 4 | 2 | 0 | 0 | 1 | 1 |
| 199 | *Clostridium ramosum* | 98.05 | 0 | 0 | 0 | 0 | 5 | 9 | 0 |
| 202 | *Clostridium symbiosum* | 97.52 | 0 | 0 | 0 | 0 | 0 | 1 | 0 |
| 204 | *Eubacterium fissicatena* | 96.62 | 0 | 14 | 4 | 30 | 0 | 16 | 15 |
| 211 | *Clostridium indolis* | 94.19 | 0 | 0 | 0 | 0 | 1 | 1 | 0 |
| 214 | *Clostridium clostridioforme* | 95.06 | 0 | 1 | 0 | 0 | 0 | 4 | 0 |
| 221 | *Flavonifractor plautii* | 99.69 | 6 | 11 | 17 | 34 | 25 | 30 | 29 |
| 224 | *Roseburia hominis* | 88.54 | 0 | 2 | 0 | 0 | 0 | 1 | 0 |
| 225 | *Clostridium aminophilum* | 90.8 | 0 | 13 | 10 | 8 | 7 | 2 | 1 |
| 237 | *Clostridium* sp. 14616 | 99.07 | 7 | 0 | 42 | 88 | 100 | 105 | 76 |
| 246 | *Clostridium indolis* | 95.11 | 0 | 0 | 1 | 1 | 0 | 1 | 0 |
| 253 | *Oscillibacter valericigenes* | 92.81 | 9 | 0 | 12 | 0 | 6 | 5 | 2 |
| 259 | *Eubacterium fissicatena* | 98.78 | 1 | 0 | 13 | 17 | 11 | 19 | 13 |
| 262 | *Clostridium lavalense* | 98.77 | 0 | 16 | 26 | 215 | 25 | 45 | 117 |
| 268 | *Ruminococcus* sp. ID8 | 97.82 | 0 | 0 | 36 | 0 | 4 | 100 | 41 |
| 269 | *Clostridium lavalense* | 97.27 | 0 | 0 | 1 | 0 | 2 | 2 | 0 |
| 277 | *Clostridium* sp. 2335 | 98.16 | 15 | 0 | 146 | 62 | 127 | 125 | 283 |
| 279 | *Lachnospiraceae bacterium* DJF_VP30 | 95.55 | 1 | 0 | 11 | 0 | 5 | 10 | 0 |
| 280 | *Holdemania filiformis* | 93.9 | 14 | 33 | 46 | 41 | 15 | 31 | 33 |
| 281 | *Clostridium scindens* | 99.69 | 0 | 11 | 6 | 22 | 15 | 11 | 10 |
| 286 | *Clostridium* sp. 2335 | 97.49 | 0 | 0 | 8 | 0 | 3 | 6 | 3 |
| 287 | *Eubacterium siraeum* | 87.3 | 0 | 0 | 0 | 0 | 0 | 1 | 0 |
| 288 | *Clostridium aminophilum* | 91.33 | 10 | 537 | 394 | 480 | 283 | 249 | 291 |
| 296 | *Clostridium scindens* | 99.69 | 0 | 7 | 9 | 7 | 10 | 3 | 7 |
| 297 | *Clostridium* sp. 14616 | 94.82 | 0 | 21 | 41 | 52 | 27 | 55 | 22 |
| 303 | *Clostridium lavalense* | 98.73 | 2 | 0 | 38 | 0 | 45 | 104 | 54 |
| 304 | *Escherichia coli* | 100 | 0 | 0 | 0 | 0 | 0 | 1 | 0 |
| 306 | *Clostridium symbiosum* | 99.38 | 0 | 28 | 50 | 22 | 1 | 17 | 6 |
| 307 | *Clostridium* sp. 14616 | 94.39 | 1 | 32 | 61 | 82 | 129 | 90 | 25 |
| 312 | *Clostridium aminophilum* | 91.69 | 0 | 0 | 0 | 0 | 0 | 1 | 0 |
| 313 | *Clostridium saccharogumia* | 98.01 | 5 | 254 | 238 | 184 | 127 | 361 | 294 |
| 314 | *Ruminococcus* sp. ID8 | 97.53 | 0 | 24 | 12 | 88 | 6 | 11 | 39 |
| 319 | *Clostridium* sp. 14616 | 93.19 | 0 | 0 | 1 | 0 | 0 | 5 | 0 |
| 326 | *Clostridium symbiosum* | 91.67 | 0 | 0 | 0 | 0 | 0 | 1 | 0 |
| 328 | *Bacteroides capillosus* | 92.9 | 1 | 3 | 4 | 3 | 1 | 2 | 0 |
| 333 | *Bacteroides capillosus* | 93.23 | 0 | 0 | 2 | 0 | 0 | 1 | 0 |
| 334 | *Clostridium lavalense* | 95.37 | 0 | 59 | 50 | 62 | 11 | 111 | 26 |
| 337 | *Anaerotruncus colihominis* | 99.38 | 2 | 1 | 6 | 3 | 3 | 8 | 2 |
| 339 | *Clostridium bolteae* | 96.63 | 0 | 0 | 0 | 0 | 1 | 2 | 0 |
| 340 | *Hydrogenoanaerobacterium saccharovorans* | 87 | 37 | 141 | 205 | 199 | 138 | 175 | 139 |
| 353 | *Clostridium* sp. 2335 | 96.63 | 7 | 3 | 59 | 87 | 63 | 80 | 54 |
| 359 | *Clostridium aminophilum* | 90.46 | 1 | 7 | 11 | 18 | 4 | 7 | 8 |
| 362 | *Bacteroides* sp. MANG | 98.14 | 3 | 0 | 100 | 79 | 55 | 64 | 29 |
| 367 | *Clostridium aminophilum* | 90.43 | 2 | 0 | 101 | 3 | 17 | 111 | 75 |

TABLE 2

| Strain | The corresponding OTU | The close relative | Max Similarity (%) | *Clostridiaceae* Cluster | Origin of mouse sample | Cultured Media |
|---|---|---|---|---|---|---|
| strain1 | OTU136 | *Clostridium saccharogumia* | 99 | XVIII | #F8 | BL |
| strain2 | OTU46 | *Clostridium ramosum* | 100 | XVIII | #F8, #G2, #J3 | BL, EG |
| strain3 | OTU221 | *Flavonifractor plautii* | 100 | IV | #F8, #G2 | BL |
| strain4 | OTU9 | *Clostridium hathewayi* | 99 | XlVa | #F8, #G2 | BL |

TABLE 2-continued

| Strain | The corresponding OTU | The close relative | Max Similarity (%) | Clostridiaceae Cluster | Origin of mouse sample | Cultured Media |
|---|---|---|---|---|---|---|
| strain5 | OTU296 | *Clostridium scindens* | 99 | XIVa | #F8 | BL |
| strain6 | OTU21 | *Clostridium* sp. 2335 | 99 | XIVa | #F8, #G2 | BL |
| strain7 | OTU166 OTU237 | *Clostridium* sp. 14616 | 99 | XIVa | #G2 | BL |
| strain8 | OTU73 | cf. *Clostridium* sp. MLG055 | 99 | XVI | #G2 | BL |
| strain9 | OTU174 | *Clostridium indolis* | 99 | XIVa | #G2, #J3 | EG |
| strain10 | OTU166 OTU181 | *Clostridium* sp. 14616 *Clostridium bolteae* | 97 98 | XIVa | #I1 | EG |
| strain11 | OTU14 | *Bacteroides* sp. MANG | 99 | XIVa | #I1 | EG |
| strain12 | OTU55 | *Lachnospiraceae bacterium* DJF_VP30 | 96 | XIVa | #I1 | EG |
| strain13 | OTU337 | *Anaerotruncus colihominis* | 99 | IV | #I1 | EG |
| strain14 | OTU314 | *Ruminococcus* sp. ID8 | 99 | XIVa | #I1 | EG |
| strain15 | OTU195 | *Clostridium lavalense* | 99 | XIVa | #I1 | EG |
| strain16 | OTU306 | *Clostridium symbiosum* | 99 | XIVa | #I1 | EG |
| strain17 | OTU87 | *Eubacterium contortum* | 99 | XIVa | #I1 | EG |

TABLE 3

| Strain | OTU | Sequenced length (bp) | Closest Strain | Similarity | BLAST | Similarity to other strains |
|---|---|---|---|---|---|---|
| Strain1 | 136 | 1179 | *Clostridium saccharogunia* | 99.75 | RDPiso | |
|  |  |  | *Clostridium ramosum* JCM1298 | 96.78 | genomeD | |
| Strain2 | 46 | 1184 | *Clostridium ramosum* | 100 | RDPiso | |
|  |  |  | *Clostridium ramosum* JCM1298 | 100 | genomeD | |
| Strain18 | 46 | 492 | *Clostridium ramosum* | 100 | DDBJ | Strain 2 |
|  |  |  | *Clostridium ramosum* | 100 | genomeDB | (>99%) |
| Strain3 | 221 | 1152 | *Flavonifractor plautii* | 100 | RDPiso | |
|  |  |  | *Pseudoflavonifractor capillosus* ATCC 29799 | 97.22 | genomeD | |
| Strain4 | 9 | 1154 | *Clostridium hathewayi* | 99.31 | RDPiso | |
|  |  |  | *Clostridium saccharolyticum* WM1 | 95.06 | genomeD | |
| Strain11 | 14 | 487 | *Bacteroides* sp. MANG | 99.33 | RDPiso | Strain 4 |
|  |  |  | *Clostridium saccharolyticum* WM1 | 94.9 | genomeDB | (>99%) |
| Strain19 | 9 | 474 | *Bacteroides* sp. MANG | 99 | DDBJ | Strain 4 |
|  |  |  | *Clostridium saccharolyticum* | 94.96 | genomeDB | (>99%) |
| Strain20 | 14 | 470 | *Bacteroides* sp. MANG | 99 | DDBJ | Strain 4 |
|  |  |  | *Clostridium saccharolyticum* | 95.81 | genomeDB | (>99%) |
| Strain30 | 362 | 478 | *Bacteroides* sp. MANG | 99 | DDBJ | Strain 4 |
|  |  |  | *Clostridium saccharolyticum* | 94.68 | genomeDB | (>99%) |
| Strain5 | 296 | 1182 | *Clostridium scindens* | 99.23 | RDPiso | |
|  |  |  | *Lachnospiraceae bacterium* 5_1_57FAA | 99.05 | genomeD | |
| Strain6 | 21 | 1203 | *Blautia coccoides* | 99.92 | RDPiso | |
|  |  |  | *Lachnospiraceae bacterium* 6_1_63FAA | 96.43 | genomeD | |
| Strain7 | 166 | 1149 | *Clostridium* sp. 14616 | 99.56 | RDPiso | |
|  |  |  | *Clostridium bolteae* ATCC BAA-613 | 99.56 | genomeD | |
| Strain8 | 73 | 1199 | cf. *Clostridium* sp. MLG055 | 99.42 | RDPiso | |
|  |  |  | *Erysipelotrichaceae bacterium* 2_2_44A | 92.71 | genomeD | |
| Strain9 | 174 | 1189 | *Clostridium indolis* | 99.24 | RDPiso | |
|  |  |  | *Anaerostripes caccae* DSM 14662 | 97.73 | genomeD | |
| Strain22 | 86 | 478 | *Clostridium indolis* | 100 | DDBJ | Strain 9 |
|  |  |  | *Anaerostripes caccae* | 96.96 | genomeDB | (>99%) |
| Strain10 | 166 | 491 | *Clostridium bolteae* | 98.03 | RDPiso | |
|  |  |  | *Clostridium bolteae* ATCC BAA-613 | 97.15 | genomeD | |
| Strain12 | 55 | 487 | *Lachnospiraceae bacterium* DJF_VP30 | 96.08 | RDPiso | |
|  |  |  | *Lachnospiraceae bacterium* 3_1_57FAA_CT1 | 99.12 | genomeD | |
| Strain13 | 337 | 490 | *Anaerotruncus colihominis* | 100 | RDPiso | |
|  |  |  | *Anaerotruncus colihominis* DSM 17241 | 100 | genomeD | |
| Strain14 | 314 | 487 | *Ruminococcus* sp. ID8 | 99.54 | RDPiso | |
|  |  |  | *Lachnospiraceae bacterium* 2_1_46FAA | 96.5 | genomeD | |
| Strain15 | 195 | 488 | *Clostridium lavalense* | 99.56 | RDPiso | |
|  |  |  | *Clostridium asparagiforme* DSM 15981 | 100 | genomeD | |
| Strain16 | 306 | 470 | *Clostridium symbiosum* | 99.78 | RDPiso | |
|  |  |  | *Clostridium symbiosum* WAL-14163 | 99.56 | genomeD | |
| Strain17 | 87 | 474 | *Eubacterium contortum* | 99.34 | RDPiso | |
|  |  |  | *Clostridium* sp. D5 | 99.12 | genomeD | |

TABLE 3-continued

| Strain | OTU | Sequenced length (bp) | Closest Strain | Similarity | BLAST | Similarity to other strains |
|---|---|---|---|---|---|---|
| Strain21 | 87 | 490 | *Eubacterium contortum* | 99 | DDBJ | Strain 17 |
| | | | *Clostridium* sp. D5 | 99.13 | genomeDB | (>99%) |
| Strain23 | 152 | 491 | *Lachnospiraceae bacterium* DJF_VP30 | 95 | DDBJ | |
| | | | *Lachnospiraceae bacterium* 3_1_57FAA_CT1 | 98.48 | genomeD | |
| Strain24 | 253 | 476 | *Oscillospiraceae bacterium* NML 061048 | 93 | DDBJ | |
| | | | *Oscillibacter valericigenes* | 93.23 | genomeD | |
| Strain25 | 259 | 491 | *Eubacterium contortum* | 99 | DDBJ | |
| | | | *Clostridium* sp. D5 | 99.78 | genomeD | |
| Strain26 | 281 | 490 | *Clostridium scindens* | 97 | DDBJ | |
| | | | *Lachnospiraceae bacterium* 5_1_57FAA | 98.03 | genomeD | |
| Strain27 | 288 | 488 | *Lachnospiraceae bacterium*A4 | 95 | DDBJ | |
| | | | *Lachnospiraceae bacterium* 3_1_57FAA_CT1 | 97.45 | genomeD | |
| Strain28 | 334 | 490 | *Clostridium* sp. 316002/08 | 98 | DDBJ | |
| | | | *Clostridiales bacterium* 1_7_47FAA | 99.56 | genomeD | |
| Strain29 | 359 | 488 | *Lachnospiraceae bacterium*A4 | 95 | DDBJ | |
| | | | *Lachnospiraceae bacterium* 3_1_57FAA_CT1 | 97.8 | genomeD | |
| Strain31 | 367 | 489 | *Lachnospiraceae bacterium*A4 | 95 | DDBJ | Strain 29 |
| | | | *Lachnospiraceae bacterium* 3_1_57FAA_CT1 | 97.8 | genomeDB | (>99%) |

TABLE 4

| Strain | Corresponding OTU | Sequenced length of 16S rDNA (bp) | Closest species | Clostridia Cluster | Similarity with the closest species (%) | Database used for BLAST | Similarity to other strain |
|---|---|---|---|---|---|---|---|
| strain1 | OTU136 | 1418 | *Clostridium saccharogumia* | XVIII | 99.75 | RDPiso | |
| | | | *Clostridium ramosum* JCM1298 | | 96.78 | genomeDB | |
| strain2 | OTU48 | 1184 | *Clostridium ramosum* | XVIII | 100 | RDPiso | strain 18 |
| | | | *Clostridium ramosum* JCM1298 | | 100 | genomeDB | >99% |
| strain3 | OTU221 | 1427 | *Flavonifractor plautii* | IV | 100 | RDPiso | |
| | | | *Pseudoflavonifractor capillosus* ATCC 29799 | | 97.22 | genomeDB | |
| strain4 | OTU9 | 1430 | *Clostridium hathewayi* | XIVa | 99.31 | RDPiso | |
| | | | *Clostridium saccharolyticum* WM1 | | 95.06 | genomeDB | |
| strain5 | OTU296 | 1433 | *Clostridium scindens* | XIVa | 99.23 | RDPiso | |
| | | | *Lachnospiraceae bacterium* 5 1 57FAA | | 99.05 | genomeDB | |
| strain6 | OTU21 | 1428 | *Blautia coccoides* | XIVa | 99.92 | RDPiso | |
| | | | *Lachnospiraceae bacterium* 6 1 63FAA | | 96.43 | genomeDB | |
| strain7 | OTU166 | 1432 | *Clostridium* sp. | XIVa | 99.56 | RDPiso | |
| | | | *Clostridium bolteae* ATCC BAA-613 | | 99.56 | genomeDB | |
| strain8 | OTU73 | 1433 | cf. *Clostridium* sp. MLG055 | XVI | 99.42 | RDPiso | |
| | | | *Erysipelotrichaceae bacterium* 2_2_44A | | 92.71 | genomeDB | |
| strain9 | OTU174 | 1434 | *Clostridium indolis* | XIVa | 99.24 | RDPiso | |
| | | | *Anaerostipes caccae* DSM 14662 | | 97.73 | genomeDB | |
| strain10 | OTU166 | 1431 | *Clostridium bolteae* | XIVa | 98.03 | RDPiso | |
| | | | *Clostridium bolteae* ATCC BAA-613 | | 97.15 | genomeDB | |
| strain11 | OTU14 | 1430 | *Bacteroides* sp. MANG | XIVa | 99.33 | RDPiso | strain 4 |
| | | | *Clostridium saccharolyticum* WM1 | | 94.9 | genomeDB | 99% |
| strain12 | OTU55 | 1431 | *Lachnospiraceae bacterium* DJF_VP30 | XIVa | 96.08 | RDPiso | |
| | | | *Lachnospiraceae bacterium* 3_1_57FAA_CT1 | | 99.12 | genomeDB | |
| strain13 | OTU337 | 1418 | *Anaerotruncus colihominis* | IV | 100 | RDPiso | |
| | | | *Anaerotruncus colihominis* DSM 17241 | | 100 | genomeDB | |
| strain14 | OTU314 | 1429 | *Ruminococcus* sp. ID8 | XIVa | 99.54 | RDPiso | |
| | | | *Lachnospiraceae bacterium* 2_1_46FAA | | 96.5 | genomeDB | |
| strain15 | OTU195 | 1430 | *Clostridium lavalense* | XIVa | 99.56 | RDPiso | |
| | | | *Clostridium asparagiforme* DSM 15981 | | 100 | genomeDB | |
| strain16 | OTU306 | 1430 | *Clostridium symbiosum* | XIVa | 99.78 | RDPiso | |
| | | | *Clostridium symbiosum* WAL-14163 | | 99.56 | genomeDB | |
| strain17 | OTU87 | 474 | *Eubacterium contortum* | XIVa | 99.34 | RDPiso | strain 22 |
| | | | *Clostridium* sp. D5 | | 99.12 | genomeDB | >99% |
| strain18 | OTU46 | 1422 | *Clostridium ramosum* | XVIII | 100 | DDBJ | |
| | | | *Clostridium ramosum* | | 100 | genomeDB | |
| strain19 | OTU9 | 474 | *Bacteroides* sp. MANG | XIVa | 99 | DDBJ | strain 4 |
| | | | *Clostridium saccharolyticum* | | 94.96 | genomeDB | >99% |
| strain20 | OTU14 | 1430 | *Bacteroides* sp. MANG | XIVa | 99 | DDBJ | strain 4 |
| | | | *Clostridium saccharolyticum* | | 95.81 | genomeDB | >99% |
| strain21 | OTU87 | 490 | *Eubacterium contortum* | XIVa | 99 | DDBJ | |
| | | | *Clostridium* sp. D5 | | 99.13 | genomeDB | |
| strain22 | OTU86 | 1424 | *Clostridium indolis* | XIVa | 100 | DDBJ | strain 9 |
| | | | *Anaerostipes caccae* | | 96.96 | genomeDB | >99% |
| strain23 | OTU152 | 1430 | *Lachnospiraceae bacterium* DJF_VP30 | XIVa | 95 | DDBJ | |
| | | | *Lachnospiraceae bacterium* 3_1_57FAA_CT1 | | 98.48 | genomeDB | |

TABLE 4-continued

| | | | | | | |
|---|---|---|---|---|---|---|
| strain24 | OTU253 | 1427 | *Oscillospiraceae bacterium* NML 061048 | IV | 93 | DDBJ |
| | | | *Oscillibacter valericigenes* | | 93.23 | genomeDB |
| strain25 | OTU259 | 491 | *Eubacterium contortum* | XIVa | 99 | DDBJ |
| | | | *Clostridium* sp. D5 | | 99.78 | genomeDB |
| strain26 | OTU281 | 1433 | *Clostridium scindens* | XIVa | 97 | DDBJ |
| | | | *Lachnospiraceae bacterium* 5_1_57FAA | | 98.03 | genomeDB |
| strain27 | OTU288 | 1431 | *Lachnospiraceae bacterium* A4 | XIVa | 95 | DDBJ |
| | | | *Lachnospiraceae bacterium* 3_1_57FAA_CT1 | | 97.45 | genomeDB |
| strain28 | OTU344 | 1429 | *Clostridium* sp. 316002/08 | XIVa | 98 | DDBJ |
| | | | *Clostridiales bacterium* 1_7_47FAA | | 99.56 | genomeDB |
| strain29 | OTU359 | 1430 | *Lachnospiraceae bacterium* A4 | XIVa | 95 | DDBJ |
| | | | *Lachnospiraceae bacterium* 3_1_57FAA_CT1 | | 97.8 | genomeDB |
| strain30 | OTU362 | 1430 | *Bacteroides* sp. MANG | XIVa | 99 | DDBJ strain 4 |
| | | | *Clostridium saccharolyticum* | | 94.68 | genomeDB >99% |
| strain31 | OTU367 | 1430 | *Lachnospiraceae bacterium* A4 | XIVa | 95 | DDBJ strain 29 |
| | | | *Lachnospiracee bacterium* 3_1_57AA_CT1 | | 97.8 | genomeDB >99% |

| Strain | 23-mix | 17-mix | 5-mix-A | 5-mix-B | 5-mix-C | 3-mix |
|---|---|---|---|---|---|---|
| strain1 | X | X | X | | | X |
| strain2 | | | | | X | X |
| strain3 | X | X | | | X | X |
| strain4 | X | X | X | | | |
| strain5 | X | | | | | |
| strain6 | X | X | | X | | |
| strain7 | X | X | | | X | |
| strain8 | X | X | | X | | |
| strain9 | X | X | | | X | |
| strain10 | X | | | | | |
| strain11 | | | | | | |
| strain12 | X | | | | | |
| strain13 | X | X | | X | | |
| strain14 | X | X | | X | | |
| strain15 | X | X | | | X | |
| strain16 | X | X | X | | | |
| strain17 | | | | | | |
| strain18 | X | X | | | | |
| strain19 | | | | | | |
| strain20 | | | | | | |
| strain21 | X | X | | | | |
| strain22 | | | | | | |
| strain23 | X | | | | | |
| strain24 | X | | | | | |
| strain25 | X | | | | | |
| strain26 | X | X | | X | | |
| strain27 | X | X | X | | | |
| strain28 | X | X | | | X | |
| strain29 | X | X | X | | | |
| strain30 | | | | | | |
| strain31 | | | | | | |

OTU3

(SEQ ID NO.: 70)
GATGAACGCTGGCGGCGTGCTTAACACATGCAAGTCGAGCGAAGCACTAA

GACGGATTTCTTCGGATTGAAGTCTTTGTGACTGAGCGGCGGACGGTGAG

TAACGCGTGGGTAACCTGCCTCATACAGGGGGATAACAGTTAGAAATGAC

TGCTAATACCGCATAAGCGCACAGGACCGCATGGTCTGGTGTGAAAAACT

CCGGTGGTATGAGATGGACCCGCGTCTGATTAGCTAGTTGGAGGGTAACG

GCCCACCGAAGGCGACGATCAGTAGCCGGCCTGAGAGGGTGAACGGCCAC

ATTGGGACTGAGACACGGCCCAG

OTU9

(SEQ ID NO.: 22)
GATGAACGCTGGCGGCGGTGCTTAACACATGCAAGTCGAGCGAAGCGGTT

TCGAGTGAAGTTTTGGATGGAATTGAAATTGACTTAGCGGCGGACGGGTG

AGTAACGCGTGGGTAACCTGCCTTACACTGGGGGATAACAGTTAGAAATG

ACTGCTAATACCGCATAAGCGCACAGGGCCGCATGGTCTGGTGCGAAAAA

CTCCGGTGGTGTAAGATGGACCCGCGTCTGATTAGGTAGTTGGTGGGGTA

ACGGCCCACCAAGCCGACGATCAGTAGCCGACCTGAGAGGGTGACCGGCC

ACATTGGGACTGAGACACGGCCCAA

OTU14

(SEQ ID NO.: 28)
GATGAACGCTGGCGGCGTGCTTAACACATGCAAGTCGAGCGAAGCGGTTT

CAATGAAGTTTTCGGATGGAATTGAAATTGACTTAGCGGCGGACGGGTGA

GTAACGCGTGGGTAACCTGCCTTACACTGGGGGATAACAGTTAGAAATGA

CTGCTAATACCGCATAAGCGCACAGGGCCGCATGGTCTGGTGTGAAAAAC

TCCGGTGGTGTAAGATGGACCCGCGTCTGATTAGGTAGTTGGTGGGGTAA

CGGCCACCAAGCCGACGATCAGTAGCCGACCTGAGAGGGTGACCGGCCAC

ATTGGGACTGAGACACGGCCCA

OTU15

(SEQ ID NO.: 71)
GATGAACGCTGGCGGCGTGCTTAACACATGCAAGTCGAGCGAAGCATTAA

GACAGATTTCTTCGGATTGAAGTCTTTGTGACTGAGCGGCGGACGGGTGA

GTAACGCGTGGGTAACCTGCCTCATACAGGGGATAACAGTTAGAAATGA

CTGCTAATACCGCATAAGCGCACAGGGCCGCATGGTCTGGTGTGAAAAAC

TCCGGTGGTGTAAGATGGACCCGCGTCTGATTAGGTAGTTGGTGGGGTAA

CGGCCCACCAAGCCGACGATCAGTAGCCGACCTGAGAGGGTGACCGGCCA

CATTGGGACTGAGACACGGCCCAA

OTU21

(SEQ ID NO.: 24)
GATGAACGCTGGCGGCGTGCTTAACACATGCAAGTCGAGCGAAGCGCTAA

GACAGATTTCTTCGGATTGAAGTCTTTGTGGCTGAGCGGCGGACGGGTGA

GTAACGCGTGGGTAACCTGCCTCATACAGGGGATAACAGTTAGAAATGA

CTGCTAATACCGCATAAGCGCACAGGACCGCATGGTCTGGTGTGAAAAAC

TCCGGTGGTATGAGATGGACCCGCGTCTGATTAGCTAGTTGGAGGGGTAA

CGGCCCACCAAGGCGACGATCAGTAGCCGGCCTGAGAGGGTGAACGGCCA

CATTGGGACTGAGACACGGCCCA

OTU23

(SEQ ID NO.: 72)
GATGAACGCTGGCGGCGTGCTTAACACATGCAAGTCGAACGAAGCATTTT

GGAAGGAAGTTTTCGGATGGAATTCCTTAATGACTGAGTGGCGGACGGGT

GAGTAACGCGTGGGGAACCTCCCTACTACAGGGGAGTAACAGCTGGAACG

GACTGCTAATACCGCATAAGCGCACAGAATCGCATGATTCGGTGTGAAAG

CTCCGGCAGTATAGGATGGTCCCGCGTCTGATTAGCTGGTTGGCGGGTAA

CGGCCCACCAAGGCGACGATCAGTAGCCGGCTTGAGAGAGTGGACGGCCA

CATTGGGACTGAGACACGGCCCAA

OTU38

(SEQ ID NO.: 73)
GATGAACGCTGGCGGCGTGCTTAACACATGCAAGTCGAGCGAAGCGGTTT

CAATGAAGTTTTCGGATGGAATTGAAATTGACTTAGCGGCGGACGGGTGA

GTAACGCGTGGGTAACCTGCCTCATACAGGGGGATAACAGTTAGAAATGA

CTGCTAATACCGCATAAGCGCACAGGACCGCATGGTCTGGTGTGAAAAAC

TCCGGTGGTATGAGATGGACCCGCGTCTGATTAGCTAGTTGGAGGGGTAA

CGGCCCACCAAGGCGACGATCAGTAGCCGGCCTGAGAGGGTGAACGGCCA

CATTGGGACTGAGACACGGCCCAG

OTU46

(SEQ ID NO.: 20)
GATGAACGCTGGCGGCGTGCCTAATACATGCAAGTCGAACGCGAGCACTT

GTGCTCGAGTGGCGAACGGGTGAGTAATACATAAGTAACCTGCCCTAGAC

AGGGGGATAACTATTGGAAACGATAGCTAAGACCGCATAGGTACGGACAC

TGCATGGTGACCGTATTAAAGTGCCTCAAAGCACTGGTAGAGGATGGACT

TATGGCGCATTAGCTGGTTGGCGGGGTAACGGCCCACCAAGGCGACGATG

CGTAGCCGACCTGAGAGGGTGACCGGCCACACTGGGACTGAGACACGGCC

CAG

OTU49

(SEQ ID NO.: 74)
GATGAACGCTGGCGGCGTGCCTAACACACGCAAGACGAACGAAGCAATTA

AAATGAAGTTTTCGGATGGATTTTTGATTGACTGAGTGGCGGACGGGTGA

GTAACGCGTGGATAACCTGCCTCACACTGGGGGGATAACAGTTAGAAATG

ACTGCTAATACCGCATAAGCGCACAGTACCGCATGGTACGTGTGAAAACT

ACCGGTGGTGTGAGATGGAGTCCCGCGTCTGATTAGCCAGTTGGCGGGGT

AACGGCCCACCAAAGCGACGATCAGTAGCCGACCTGAGAGGGTGACCGGC

CACATTGGGACTGAGACACGGGCCCAA

OTU55

(SEQ ID NO.: 29)
GATGAACGCTGGCGGCGTGCCTAACACATGCAAGTCGAACGAAGTTACAC

GGAGGAAGTTTTCGGATGGAATCGGTATAACTTAGTGGCGGACGGGTGAG

TAACGCGTGGGAAACCTGCCCTGTACCGGGGGATAACACTTAGAAATAGG

TGCTAATACCGCATAAGCGCACGGAACCGCATGGTTCCGTGTGAAAAACT

ACCGGTGGTACAGGATGGTCCCGCGTCTGATTAGCCAGTTGGCAGGGTAA

CGGCCTACCAAAGCGACGATCAGTAGCCGGCCTGAGAGGGTGAACGGCCA

CATTGGGACTGAGACACAGCCCA

OTU57

(SEQ ID NO.: 75)
GATGAACGCTGGCGGCGTGCTTAACACATGCAAGTCGAGCGAAGCGGTTT

CGATGAAGTTTTCGGATGGATTTGAAATCGACTTAGCGGCGGACGGGTGA

GTAACGCGTGGGTAACCTGCCTTACACTGGGGGATAACAGTTAGAAATGA

CTGCTAATACCGCATAAGCGCACAGGGCCGCATGGTCTGGTGCGAAAAAC

TCCGGTGGTGTAAGATGGACCCGCGTCTGATTAGCCAGTTGGCAGGGTAA

CGGCCTACCAAAGCGACGATCAGTAGCCGGCCTGAGAGGGTGAACGGCCA

CATTGGGACTGAGACACGGCCCAA

OTU73

(SEQ ID NO: 26)
GATGAACGCTGGCGGCATGCCTAATACATGCAAGTCGAACGAAGTGAAGA

TAGCTTGCTATCGGAGCTTAGTGGCGAACGGGTGAGTAACACGTAGATAA

CCTGCCTGTATGACCGGGATAACAGTTGGAAACGACTGCTAATACCGGAT

AGGCAGAGAGGAGGCATCTCTTCTCTGTTAAAGTTGGGATACAACGCAAA

CAGATGGATCTGCGGTGCATTAGCTAGTTGGTGAGGTAACGGCCCACCAA

GGCGATGATGCATAGCCGGCCTGAGAGGGCGAACGGCCACATTGGGACTG

AGACACGGCCCAA

OTU86

(SEQ ID NO.: 35)
GATGAACGCTGGCGGCGTGCTTAACACATGCAAGTCGAACGAAGCATTNT

TGGAAGGAAGTTTTCGGATGGAATTCCTTAATGACTGAGTGGCGGACGGGT

GAGTAACGCGTGGGGAACCTACCCTATACAGGGGGATAACAGCTGGAAAC

GGCTGCTAATACCGCATAAGCGCACAGAATCGCATGATTCGGTGTGAAAA

GCTCCGGCAGTATAGGATGGTCCCGCGTCTGATTAGCTGGTTGGCGGGTA

OTU87

(SEQ ID NO.: 34)
GATGAACGCTGGCGGCGTGCTTAACACATGCAAGTCGAGCGAAGCGCTTT

ACTTAGATTTCTTCGGATTGAAAGTTTTGCGACTGAGCGGCGGACGGGTG

AGTAACGCGTGGGTAACCTGCCTCATACAGGGGGATAACAGTTAGAAATG

ACTGCTAATACCGCATAAGACCACAGTACCGCATGGTACAGTGGGAAAAA

CTCCGGTGGTATGAGATGGACCCGCGTCTGATTAGCTAGTTGGTAAGGTA

ACGGCTTACCAAGGCGACGATCAGTAGCCGACCTGAGAGGGTGACCGGCC

ACATTGGGACTGAGACACGGCCCA

OTU89

(SEQ ID NO.: 76)
GATGAACGCTGGCGGCGTGCTTAACACATGCAAGTCGAACGAAGCATTTT

GGAAGGAAGTTTTCGGATGGAATCGGTATAACTTAGTGGCGGACGGGTGA

GTAACGCGTGGGAAACCTGCCCTGTACCGGGGGATAACACTTAGAAATAG

GTGCTAACACCGCATAAGCGCACGGAACCGCATGGTTCTGTGTGAAAAAA

CTCCGGTGGTACAGGATGGTCCCGCGTCTGATTAGCCAGTTGGCGAGGGT

AACGGCCTACCAAAGACGACGATCAGTAGCCGGCCTGAGAGGGTGAACGG

CCACATTGGGACTGAGACACGGCCCAA

OTU92

(SEQ ID NO.: 77)
GATGAACGCTGGCGGCGTGCCTAACACATGCAAGTCGAACGGAGTTATGC

AGAGGAAGTTTTCGGATGGAATCGGCGTAACTTAGTGGCGGACGGGTGAG

TAACGCGTGGGAAACCTGCCCTGTACCGGGGGATAACACTTAGAAATAGG

TGCTAATACCGCATAAGCGCACAGCTTCACATGAGGCAGTGTGAAAAACT

CCGGTGGTGTAAGATGGACCCGCGTCTGATTAGGTAGTTGGTGGGGTAAC

GGCCCACCAAGCCGACGATCAGTAGCCGACCTGAGAGGGTGACCGGCCAC

ATTGGGACTGAGACACGGCCCA

OTU101

(SEQ ID NO.: 78)
GATGAACGCTGGCGGCGTGCCTAACACATGCAAGTCGAACGAAGCAATTA

AGATGAAGTTTTCGGATGGAATCTTGATTGACTGAGTGGCGGACGGGTGA

GTAACGCGTGGATAACCTGCCTCACACTGGGGGATAACAGTTAGAAATGA

CTGCTAATACCGCATAAGCGCACAGTGCCGCATGGCAGTGTGTGAAAAAC

TCCGGTGGTGTGAGATGGATCCGCGTCTGATTAGCCAGTTGGCGGGGTAA

CGGCCACCGAAAGCGACGATCAGTAGCCGACCTGAGAGGGTGACCGGCCA

CACTGGGACTGAGACACGGCCCA

OTU111

(SEQ ID NO.: 79)
GATGAACGCTGGCGGCGTGCCTAACACATGCAAGTCGAACGAAGTTACAC

AGAGGAAGTTTTCGGATGGAATCGGTATAACTTAGTGGCGGACGGGTGAG

TAACGCGTGGGAAACCTGCCCTGTACCGGGGGATAACACTTAGAAATAGG

TGCTAATACCGCATAAGCGCACAGCTTCACATGAAGCAGTGTGAAAAACT

CCGGTGGTACAGGATGGTCCCGCGTCTGATTAGCTGGTTGGCGGGGTAAC

GGCCCACCAAGGCGACGATCAGTAGCCGGCTTGAGAGAGTGGACGGCCAC

ATTGGGACTGAGACACGGCCCA

OTU114

(SEQ ID NO.: 80)
GATGAACGCTGGCGGCGTGCCTAACACATGCAAGTCGAGCGAAGCGCTGT

TTTCAGAATCTTCGGAGGAAGAGGACAGTGACTGAGCGGCGGACGGGTGA

GTAACGCGTGGGCAACCTGCCTCATACAGGGGGATAACAGTTAGAAATGA

CTGCTAATACCGCATAAGCGCACAGGACCGCATGGTGTAGTGTGAAAAAC

TCCGGTGGTATGAGATGGACCCGCGTCTGATTAGCCAGTTGGCAGGGTAA

CGGCCTACCAAAGCGACGATCAGTAGCCGGCCTGAGAGGGTGAACGGCCA

CATTGGGACTGAGACACGGCCCA

OTU119

(SEQ ID NO.: 81)
GATGAACGCTGGCGGCGTGCCTAACACATGCAAGTCGAACGAAGCAATTA

AGATGAAGTTTTCGGATGGAATCTTGATTGACTGAGTGGCGGACGGGTGA

GTAACGCGTGGATAACCTGCCTCACACTGGGGGATAACAGTTAGAAATGA

CTGCTAATACCGCATAAGCGCACAGTGCCGCATGGCAGTGTGTGAAAAAC

TCCGGTGGTGTGAGATGGATCCGCGTCTGATTAGCCAGTTGCGGGGTAAC

GGCCCGACCAAAGCGACGATCAGTAGCCGACCTGAGAGGGTNACCGGCC

ACATTGGGACTGAGACACGGCCCA

OTU125

(SEQ ID NO.: 82)
GATGAACGCTGGCGGCGTGCCTAACACATGCAAGTCGAGCGAAGCGCTGT

TTTCAGAATCTTCGGAGGAAGAGGACAGTGACTGAGCGGCGGACGGGTGA

GTAACGCGTGGGCAACCTGCCTCATACAGGGGATAACAGTTAGAAATGA

CTGCTAATACCGCATAAGCGCACAGGACCGCATGGTGTAGTGTGAAAAAC

TCCGGTGGTATGAGATGGACCCGCGTCTGATTAGGTAGTTGGTGGGTAAA

GGCTACCGAAGCCGACGATCAGTAGCCGACCTGACGAGGGTGACCGGCCA

CGATTGGGACTGAGACACGGCCCAA

OTU131

(SEQ ID NO.: 83)
GATGAACGCTGGCGGCGTGCCTAACACATGCAAGTCGAACGAAGCAATTA

AGATGAAGTTTTCGGATGGAATCTTGATTGACTGAGTGGCGGACGGGTGA

GTAACGCGTGGATAACCTGCCTCACACTGGGGGATAACAGTTAGAAATGA

CTGCTAATACCGCATAAGCGCACAGTGCCGCATGGCAGTGTGTGAAAAAC

TCCGGTGGTGTGAGATGGATCCGCGTCTGATTAGCCAGTTGCGGGTAACG

GCCACCGAAAGCGACGATCAGTAGCCGACCTGACGAGGGTNACCGGCACA

TTGGGACTGAGACACGGCCCAA

OTU136

(SEQ ID NO.: 19)
GATGAACGCTGGCGGCGTGCCTAATACATGCAAGTCGAACGCGAGCACTT

GTGCTCGAGTGGCGAACGGGTGAGTAATACATAAGTAACCTGCCCTTTAC

AGGGGGATAACTATTGGAAACGATAGCTAAGACCGCATAGGTAAAGATAC

CGCATGGTAAGTTTATTAAAAGTGCCAAGGCACTGGTAGAGGATGGACTT

ATGGCGCATTAGCTAGTTGGTGAGGTAACGGCTCACCAAGGCGACGATGC

OTU137
(SEQ ID NO.: 84)
GATGAACGCTGGCGGCGTGCCTAACACATGCAAGTCGAACGAAGCAATTA
AGATGAAGTTTTCGGATGGAATCTTGATTGACTGAGTGGCGGACGGGTGA
GTAACGCGTGGATAACCTGCCTCACACTGGGGGGATAACAGTTAGAAATG
ACTGCTAATACCGCATAAGCGCACAGTGCCGCATGGCAGTGTGTGAAAAA
CTCCGGTGGTGTGAGATGGATCCGCGTCTGATTAGGTAGTTGGTGGGGTA
ACGGCCCACCAAGCCGACGATCAGTAGCCGACCTGAGAGGGTGACCGGCC
ACATTGGGACTGAGACACGGCCCAA

OTU144
(SEQ ID NO.: 85)
GATGAACGCTGGCGGCGTGCTTAACACATGCAAGTCGAGCGAAGCGGTTT
CGATGAAGTTTTTGGATGGAATTGAAATTGACTTAGCGGCGGACGGGTGA
GTAACGCGTGGGTAACCTGCCTTACACTGGGGGATAACAGTTAGAAATGA
CTGCTAATACCGCATAAGCGCACAGGGCCGCATGGTCTGGTGCGAAAAAC
TCCGGTGGTGTAAGATGGACCCGCGTCTGATTAGGTAGTTGGTGGGTAA
CGGCCCACCGAAGCCGACGATCAGTAGCCGACCTGAGAGGGTGACCGGCA
CATTGGGACCTGAGACACGGGCCCA

OTU152
(SEQ ID NO.: 36)
GATGAACGCTGGCGGCGTGCCTAACACATGCAAGTCGAACGAAGTTAGAC
AGAGGAAGTTTTCGGATGGAATCGGTATAACTTAGTGGCGGACGGGTGAG
TAACGCGTGGGAAACCTGCCCTGTACCGGGGGATAACACTTAGAAATAGG
TGCTAATACCGCATAAGCGCACGGAACCGCATGGGTTCTGTGTGAAAACT
CCGGTGGTACAGGATGGTCCCGCGTCTGATTAGCCAGTTGGCAGGGTAAC
GGCCTACCAAAGCGACGATCAGTAGCCGGCCTGAGAGGGTGAACGGCCAC
ATTGGGACTGAGACACGGCCCAA

OTU161
(SEQ ID NO.: 86)
GATGAACGCTGGCGGCGTGCCTAACACATGCAAGTCGAACGAAGCATTTT
AGATGAAGTTTTCGGATGGATTCTGAGATGACTGAGTGGCGGACGGGTGA
GTAACACGTGGATAACCTGCCTCACACTGGGGACAACAGTTAGAAATGA
CTGCTAATACCGCATAAGCGCACAGTACCGCATGGTACGGTGTGAAAAAC
TCCGGTGGTACAGGATGGTCCCGCGTCTGATTAGCCAGTTGGCAGGGTAA
CGGCCTACCAAAGCGACGATCAGTAGCCGGCCTGAGAGGGTGAACGGCCA
CATTGGGACTGAGACACGGCCCAA

OTU163
(SEQ ID NO.: 87)
GATGAACGCTGGCGGCGTGCCTAACACATGCAAGTCGAACGAAGTTACAC
GGAGGAAGTTTTCGGATGGAATCGGTATAACTTAGTGGCGGACGGGTGAG
TAACGCGTGGGAAACCTGCCCTGTACCGGGGGATAACACTTAGAAATAGG
TGCTAATACCGCATAAGCGCACGGAACCGCATGGTTCCGTGTGAAAACT
CCGGTGGTACAGGATGGTCCCGCGTCTGATTAGGTAGTTGGTGGGGTAAC
GGCCCACCAAGCCGACGATCAGTAGCCGACCTGAGAGGGTGACCGGCCAC
ATTGGGACTGAGACACGGCCCA

OTU165
(SEQ ID NO.: 88)
GATGAACGCTGGCGGCGTGCTTAACACATGCAAGTCGAACGGAGCACCCT
TGACTGAGGTTTCGGCCAAATGATAGGAATGCTTAGTGGCGGACTGGTGA
GTAACGCGTGAGGAACCTACCTTCCAGAGGGGACGAACAGTTGGAACGAC
TGCTAATACCGCATGACGCATGACCGGGGCGATCCCGGGCCGATGTCAAA
GATTTTATTCGCTGGAAGATGGCCTCGCGTCTGATTAGCTAGATGGTGGG
GTAACGGCCCACCATGGCGACGATCAGTAGCCGGACTGAGAGGTTGACCG
GCCACATTGGGACTGAGATACGGCCCA

OTU166
(SEQ ID NO.: 25)
GATGAACGCTGGCGGCGTGCCTAACACATGCAAGTCGAACGAAGCAATTA
AAATGAAGTTTCGGATGGATTTTGATTGACTGAGTGGCGGACGGGTGAGT
AACGCGTGGATAACCTGCCTCACACTGGGGGATAACAGTTAGAAATGACT
GCTAATACCGCATAAGCGCACAGTACCGCATGGTACGGTGTGAAAAACTC
CGGTGGTGTGAGATGGATCCGCGTCTGATTAGCCAGTTGGCGGGGTAACG
GCCCACCAAAGCGACGATCAGTAGCCGACCTGAGAGGGTGACCGGCCACG
ATTGGGACTGAGACACGGCCCA

OTU173
(SEQ ID NO.: 123)
GACGAACGCTGGCGGCGCGCCTAACACATGCAAGTCGAACGGAGTTGTGT
TGAAAGCTTGCTGGATATACAACTTAGTGGCGGACGGGTGAGTAACGCGT
GGGTAACCTGCCTCATACAGGGGGATAACAGTTAGAAATGACTGCTAATA
CCGCATAAGCGCACAGGATCGCATGGTCTGGTGTGAAAAACTCCGGTGGT
ATGAGATGGACCCGCGTCTGATTAACTAGTTGGAGGGGTAACGGCCCACC
AAGGCGACGAGTCAGTAGCCGGCCTGAGAGGGTGAACGGCCACGATTGGG
ACTGAGACACGGCCCAG

OTU174
(SEQ ID NO.: 27)
GATGAACGCTGGCGGCGTGCTTAACACATGCAAGTCGAACGAAGCATTTT
GGAAGGAAGTTTTCGGATGGAATTCCTTAATGACTGAGTGGCGGACGGGT
GAGTAACGCGTGGGGAACCTGCCCTATACAGGGGGATAACAGCTGGAAAC
GGCTGCTAATACCGCATAAGCGCACAGAATCGCATGATTCGGTGTGAAAA
GCTCCGGCAGTATAGGATGGTCCCGCGTCTGATTAGCTGGTTGGCGGGGT
AACGGCCCACCAAGGCGACGATCAGTAGCCGGCTTGAGAGAGTGGACGGC
CACATTGGGACTGAGACACGGCCCA

OTU181
(SEQ ID NO.: 89)
GATGAACGCTGGCGGCGTGCCTAACACATGCAAGTCGAACGAAGCAATTT
AAAATGAAGTTTTCGGATGGATTTTTGATTGACTGAGTGGCGGACGGGTG
AGTAACGCGTGGATAACCTGCCTCACGACTGGGGGATAACAGTTAGAAAT
GACTGCTAATACCGCATAAGCGCACAGTACCGCATGGTACGGTGTGAAAA
ACTCCGGTGGTGTGAGATGGATCCGCGTCTGATTAGCCAGTTGCGGGGTA

ACGGCCCACCGAAAGCGACGATCAGTAGCCGACCTGAGAGGGTGACCGGC
CACATTGGGACTGAGACACGGCCCAA

OTU182
(SEQ ID NO.: 90)
GATGAACGCTGGCGGCGTGCCTAATACATGCAAGTCGAACGCGGGCAGCA
ATGCCCGAGTGGCGAACGGGTGAGTAATACATAAGTAACCTGCCCTTTAC
AGGGGGATAACTATTGGAAACGATAGCTAAGACCGCATAGGTAAAGATAC
CGCATGGTAAGTTTATTAAAAGTGCCAAGGCACTACGAGGGAGTAGTGAT
ATGCGCATAGCTAGTTGGTGAGGTAACGGCTCACCAAGGCGACGATGCGT
AGCCGACCTGAGAGGGTGACCGGCCACACTGGGACTGAGACACGGCCCAG

OTU189
(SEQ ID NO.: 91)
GATGAACGCTGGCGGCGTGCCTAACACATGCAAGTCGAACGAAGCATTTT
AGATGAAGTTTTCGGATGGATTCTGAGATGACTGAGTGGCGGACGGGTGA
GTAACACGTGGATAACCTGCCTCACACTGGGGGACACAGTTAGAAATGAC
TGCTAATACCGCATAAGCGCACAGCTTCACATGAAGCAGTGTGAAAAACT
CCGGTGGTACAGGATGGTCCCGCGTCTGATTAGCCAGTTGGCAGGGTAAC
GGCCTACCAAAGCGACGATCAGTAGCCGGCCTGAGAGGGTGAACGGCCAC
ATTGGGACTGAGACACGGCCCAG

OTU195
(SEQ ID NO.: 32)
GATGAACGCTGGCGGCGTGCCTAACACATGCAAGTCGAACGAAGCATTTT
AGATGAAGTTTTCGGATGGATTCTGAGATGACTGAGTGGCGGACGGGTGA
GTAACACGTGGATAACCTGCCTCACACTGGGGACGAACAGTTAGAAATG
ACTGCTAATACCGCATAAGCGCACAGTACCGCATGGTACGGTGTGAAAAA
CTCCGGTGGTGTGAGATGGATCCGCGTCTGATTAGCCAGTTGGCGGGTAA
CGGCCCACCGAAAGCGACGATCAGTAGCCGACCTGAGAGGGTGACCGGCC
ACATTGGGACTGAGACACGGCCCAA

OTU196
(SEQ ID NO.: 92)
GACGAACGCTGGCGGCGTGCTTAACACATGCAAGTCGAACGGAGCACCCC
TGAATGAGGTTTCGGCCAAAGGAAGGGAATGCTTAGTGGCGGACTGGTGA
GTAACGCGTGAGGAACCTGCCTTTCAGAGGGGACAACAGTTGGAAACGAC
TGCTAATACCGCATGACACATGAATGGGGCATCCCATTGATGTCAAAGAT
TTATCGCTGAAAGATGGCCTCGCGTCCCATTAGCTAGTAGGCGGGGTAAC
GGCCCACCTAGGCGACGATGGGTAGCCGGACTGAGAGGTTGACCGGCCAC
ATTGGGACTGAGATACGGCCCA

OTU199
(SEQ ID NO.: 93)
GATGAACGCTGGCGGCGTGCCTAATACATGCAAGTCGAACGCGAGCACTT
GTGCTCGAGTGGCGAACGGGTGAGTAATACATAAGTAACCTGCCCTAGAC
AGGGGGAGTAACTATTGGAAACGATAGCTAAGACCGCATAGGTACGGACAC
TGCGTGGTGACCGTATTAAAAGTAGCCTCAAAGACACTGGTAGAGGATGG
ACTTATGGCGCATTAGCTGGTTGGCGGGGTAACGGCCCACCCAAGGCGAC

GATGCGTAGCCGACCTGAGAGGGTGACCGGCCACACTGGGACTGAGACAC
GGCCCAG

OTU202
(SEQ ID NO.: 94)
GATGAACGCTGGCGGCGTGCCTAACACATGCAAGTCGAACGAAGCAATTT
AACGGAAGTTTTCGGATGGAAGTTGAATTGACTGAGTGGCGGACGGGTGA
GTAACGCGTGGGTAACCTGCCTTGTACTGGGGGACAACAGTTAGAAATGA
CTGCTAATACCGCATAAGCGCACAGTATCGCATGATACAGTGTGAAAAAC
TCCGGTGGTACAAGATGGACCCGCGTCTGATTAGCTAGTTGGAGGGGTAA
CGGCCCACCAAGGCGACGATCAGTAGCCGGCCTGAGAGGGTGAACGGCCA
CATTGGGACTGAGACACGGCCCAG

OTU204
(SEQ ID NO.: 95)
GATGAACGCTGGCGGCGTGCTTAACACATGCAAGTCGAGCGAAGCACTAA
GACGGATTTCTTCGGATTGAAGTCTTTGTGACTGAGCGGCGGACGGGTGA
GTAACGCGTGGGTAACCTGCCTCATACAGGGGGATAACAGTTAGAAATGA
CTGCTAATACCGCATAAGACCACAGTACCGCATGGTACAGTGGGAAAAAC
TCCGGTGGTATGAGATGGACCCGCGTCTGATTAGCTAGTTGGTAAGGTAA
CGGCTTACCAAGGCGACGATCAGTAGCCGACCTGAGAGGGTGACCGGCCA
CATTGGGACTGAGACACGGCCCA

OTU211
(SEQ ID NO.: 96)
GATGAACGCTGGCGGCGTGCTTAACACATGCAAGTCGAGCGAAGCGGTTT
CGATGAAGTTTTCGGATGGATTTGAAATCGACTTAGCGGCGGACGGGTGA
GTAACGCGTGGGTAACCTGCCTTACACTGGGGGATAACAGCTGGAAACGG
CTGCTAATACCGCATAAGCGCACAGAATCGCATGATTCGGTGCGAAAAGC
TCCGGCAGTATAGGATGGTCCCGCGTCTGATTAGCTGGTTGGCGGGGTAA
CGGCCCACCAAGGCGACGATCAGTAGCCGGCTTGAGAGAGTGGACGGCCA
CATTGGGACTGAGACACGGCCCAA

OTU214
(SEQ ID NO.: 97)
GATGAACGCTGGCGGCGTGCCTAACACATGCAAGTCGAACGAAGCAATTA
AGATGAAGTTTTCGGATGGAATCTTGATTGACTGAGTGGCGGACGGGTGA
GTAACGCGTGGGTAACCTGCCTCATACAGGGGGAGTAACAGTTAGAAATG
ACTGCTAATACCGCATAAGCGCACAGGGCTGCATGGCCTGGTGTGAAAAA
CTCCGGTGGTATGAGATGGACCCGCGTCTGATTAGCTAGTTGGAGGGGTA
ACGGCCCACCAAGGCGACGATCAGTAGCCGGCCTGAGAGGGTGAACGGCC
ACATTGGGACTGAGACACGGCCCA

OTU221
(SEQ ID NO.: 21)
GATGAACGCTGGCGGCGTGCTTAACACATGCAAGTCGAACGGGGTGCTCA
TGACGGAGGATTCGTCCAACGGATTGAGTTACCCAGTGGCGGACGGGTGA
GTAACGCGTGAGGAACCTGCCTTGGAGAGGGGAATAACACTCCGAAGGA
GTGCTAATACCGCATGATGCAGTTGGGTCGCATGGCTCTGACTGCCAAAG
ATTTATCGCTCTGAGATGGCCTCGCGTCTGATTAGCTAGTAGGCGGGGTA

ACGGCCCACCTAGGCGACGATCAGTAGCCGGACTGAGAGGTTGACCGGCC

ACATTGGGACTGAGACACGGCCCA

OTU224

(SEQ ID NO.: 98)

GATGAACGCTGGCGGCGTGCTTAACACATGCAAGTCGAGCGAAGCACCTT

GGCGGATTTCTTCGGATTGAAGCCTTGGTGACTGAGCGGCGGACGGGTGA

GTAACGCGTGGGTAACCTGCCCTGTACCGGGGGATAACACTTAGAAATAG

GTGCTAATACCGCATAAGCGCACAGCTTCACATGAAGCAGTGTGAAAAAC

TCCGGCGGTACAGGATGGTCCCGCGTCTGATTAGCCAGTTGACAGGGTAA

CGGCCTACCAAAGCGACGATCAGTAGCCGGCCTGAGAGGGTGAACGGCCA

CATTGGGACTGAGACACGGCCCA

OTU225

(SEQ ID NO.: 99)

GATGAACGCTGGCGGCGTGCCTAACACATGCAAGTCGAACGGAAGTTATG

CAGAGGAAGTTTTCGGTATGGAATCGGCGTAACTTAGTGGCGGACGGGTG

AGTAACGCGTGGGAAACCTGCCCTGTACCGGGGGAGTAACACTTAGAATA

GGTGCTAATACCGCATAAGCGCACAGCTTCACATGAGGCAGTGTGAAAAA

CTCCGGTGGTACAGGATGGTCCCGCGTCTGATTAGCCAGTTGGCAGGGTA

ACGGCCTACCAAAGCGACGATCAGTAGCCGGCCTGAGAGGGTGAACGGCC

ACATTGGGACTGAGACACGGCCCA

OTU237

(SEQ ID NO.: 100)

GATGAACGCTGGCGGCGTGCCTAACACATGCAAGTCGAACGAAGCAATTG

AAGGAAGTTTTCGGATGGAATTCGATTGACTGAGTGGCGGACGGGTGAGT

AACGCGTGGATAACCTGCCTCACACTGGGGGATAACAGTTAGAAATGACT

GCTAATACCGCATAAGCGCACAGTGCCGCATGGTACGGTGTGAAAAACTC

CGGTGGTGTGAGATGGATCCGCGTCTGATTAGCCAGTTGGCGGGGTAACG

GCCCACCAAAGCGACGATCAGTAGCCGACCTGAGAGGGTGACCGGCCACA

TTGGGACTGAGACACGGCCCAA

OTU246

(SEQ ID NO.: 101)

GATGAACGCTGGCGGCGTGCCTAACACATGCAAGTCGAACGGAGTTATGC

AGAGGAAGTTTTCGGATGGAATCGGCGTAACTTAGTGGCGGACGGGTGAG

TAACGCGTGGGAAACCTGCCCTATACAGGGGGATAACAGCTGGAAACGGC

TGCTAATACCGCATAAGCGCACAGAATCGCATGATTCGGTGTGAAAAGCT

CCGGCAGTATAGGATGGTCCCGCGTCTGATTAGCTGGTTGGCGGGGTAAC

GGCCCACCAAGGCGACGATCAGTAGCCGGCTTGAGAGAGTGGACGGCCAC

ATTGGGACTGAGACACGGCCCAA

OTU253

(SEQ ID NO.: 37)

GACGAACGCTGGCGGCGTGCTTAACACATGCAAATCGAACGGAGCACCCT

TGACTGAGGTTTCGGCCAAATGATAGGAATGCTTAGTGGCGGACTGGTGA

GTAACGCGTGAGGAACCTGCCTTCCAGAGGGGGACAACAGTTGGAAACGA

CTGCTAATACCGCATGACGCATGACCGGGGCATCCCGGGCATGTCAAAGA

TTTTATCGCTGGAAGATGGCCTCGCGTCTGATTAGCTAGATGGTGGGGTA

ACGGCCCACCATGGCGACGATCAGTAGCCGGACTGAGAGGTTGACCGGCC

ACATTGGGACTGAGATACGGGCCCAG

OTU259

(SEQ ID NO.: 38)

GATGAACGCTGGCGGCGTGCTTAACACATGCAAGTCGAGCGAAGCGCTTT

ACTTAGATTTCTTCGGATTGAAAAGTTTTGCGACTGAGCGGCGGACGGGT

GAGTAACGCGTGGGTAACCTGCCTCATACAGGGGGATAACAGTTAGAAAT

GACTGCTAATACCGCATAAGACCACGGTACCGCATGGTACAGTGGGAAAA

ACTCCGGTGGTATGAGATGGACCCGCGTCTGATTAGCTAGTTGGTAAGGT

AACGGCTTACCAAGGCGACGATCAGTAGCCGACCTGAGAGGGTGACCGGC

ACATTGGGACCTGAGACACGGCCCAA

OTU262

(SEQ ID NO.: 102)

GATGAACGCTGGCGGCGTGCCTAACACATGCAAGTCGAACGAAGCATTTT

AGATGAAGTTTTCGGATGGATTCTGAGATGACTGAGTGGCGGACGGGTGA

GTAACACGTGGATAACCTGCCTCACACTGGGGGACAACAGTTAGAAATGA

CTGCTAATACCGCATAAGCGCACAGTACCGCATGGTACAGTGTGAAAAAC

TCCGGTGGTGTGAGATGGATCCGCGTCTGATTAGCCAGTTGGCGGGGTAA

CGGCCCACCAAAGCGACGATCAGTAGCCGACCTGAGAGGGTGACCGGCCA

CATTGGGGACCTGAGACACGGCCCA

OTU268

(SEQ ID NO.: 103)

GATGAACGCTGGCGGCGTGCCTAACACATGCAAGTCGAGCGAAGCGCTGT

TTTCAGAATCTTCGGAGGAAGAGGACAGTGACTGAGCGGCGGACGGGTGA

GTAACGCGTGGGCAACCTGCCTCATACAGGGGGATAACAGTTAGAAATGA

CTGCTAATACCGCATAAGCGCACAGGACCGCATGGTGTAGTGTGAAAAAC

TCCGGTGGTATGAGATGGACCCGCGTCTGATTAGGTAGTTGGTGGGGTAA

AGGCCTACCAAGCCGACGATCAGTAGCCGACCTGAGACGGGTGACCGGCA

CATTGGGGACTGAGACACGGGCCCAA

OTU269

(SEQ ID NO.: 104)

GATGAACGCTGGCGGCGTGCCTAACACATGCAAGTCGAACGAAGCATTTT

AGATGAAGTTTTCGGATGGATTCTGAGATGACTGAGTGGCGGACGGGTGA

GTAACACGTGGATAACCTGCCTCACACTGGGGGACAACAGTTAGAAATA

GACTGCTAATACCGCATAAGCGCACAGTACCGCATGGTACAGTGTGAAAA

ACTACCGGTGGTGTGAGATGGATCCGCGCTGATTAGTCCAGTTGGCGGGG

TAACGGCCGACCAAAGCGACGATCAGTAGCCGACCTGAGAGGGTGACCGG

CCGACAGTTGGGACTGAGACACGGCCCAA

OTU277

(SEQ ID NO.: 105)

GATGAACGCTGGCGGCGTGCTTAACACATGCAAGTCGAGCGAAGCACTAA

GACGGATTTCTTTGGATTGAAGTCTTTGTGACTGAGCGGCGGACGGGTGA

GTAACGCGTGGGTAACCTGCCTCATACAGGGGGATAACAGTTAGAAATGA

CTGCTAATACCGCATAAGCGCACAGGATCGCATGGTCTGGTGTGGAAAAA

CTCCGGTGGTATGAGATGGACCCGCGTCTGATTAGCTAGTTGGAGGGGTA

ACGGCCCACCAAGGCGACGATCAGTAGCCGGCCTGAGAGGGTGAACGGCC

ACGATTGGGACTGAGACACGGCCCAG

OTU279

(SEQ ID NO.: 106)

GATGAACGCTGGCGGCGTGCCTAACACATGCAAGTCGAACGAAGTTAGAC

AGAGGAAGTTTTCGGATGGAATCGGTATAACTTAGTGGCGGACGGGTGAG

TAACGCGTGGGAACCTGCCCTGTACCGGGGGAGTAACACTTAGAAATAGG

TGCTAATACCGCATAAGCGCACGGAACCGCATGGTTCTGTGTGAAAAACT

ACCGGTGGTACAGGATGGTCCCGCGTCTGATTAGCCAGTTGGCAGGGTAA

CGGCCTACCAAAGCGACGATCAGTAGCCGGCCTGAGAGGGTGAACGGCCA

CATTGGGACTGAGACACGGCCCA

OTU280

(SEQ ID NO.: 107)

GATGAACGCTGGCGGCGTGCCTAATACATGCAAGTCGAACGCTTTGTAAA

GGAGCTTGCTTCTTTACGAGGAGTGGCGAACGGGTGAGTAATACATAAGC

AATCTGCCCATCGGCCTGGGATAACAGTTGGAAACGACTGCTAATACCGG

ATAGGTTAGTTTCTGGCATCAGGGACTAATTAAAGTTGGGATACAACACG

GATGGATGAGCTTATGCGTATTAGCTAGTAGGTGAGGTAACGGCCCACC

TAGGCGATGATACGTAGCCGACCTGAGAGGGTGACCGGCCACATTGGGAC

TGAGACACGGCCCAA

OTU281

(SEQ ID NO.: 39)

GATGAACGCTGGCGGCGTGCCTAACACATGCAAGTCGAACGAAGCGCTTC

CGCCTGATTTTCTTCGGAGATGAAGGCGGCTGCGACTGAGTGGCGGACGG

GTGAGTAACGCGTGGGCAACCTGCCTTGCACTGGGGGATAACAGCCAGAA

ATGGCTGCTAATACCGCATAAGACCGAAGCGCCGCATGGCGCTGCGGCCA

AAGCCCCGGCGGTGCAAGATGGGCCCGCGTCTGATTAGGTAGTTGGCGGG

GTAACGGCCCACCAAGCCGACGATCAGTAGCCGACCTGAGAGGGTGACCG

GCCACATTGGGACTGAGACACGGCCCA

OTU286

(SEQ ID NO.: 108)

GATGAACGCTGGCGGCGTGCTTAACACATGCAAGTCGAGCGAAGCACTAA

GACGGATTTCTTCGGATTGAAGTCTTTGTGACTGAGCGGCGGACGGGTGA

GTAACGCGTGGGTAACCTGCCTCATACAGGGGGATAACAGTTAGAAATGA

CTGCTAATACCGCATAAGCGCACAGGATCGCATGGTCTGGTGTGAAAAAC

TCCGGTGGTATGAGATGGACCCGCGTCTGATTAGCCAGTTGGCAGGGTAA

CGGCCTACCAAAGCGACGATCAGTAGCCGGCCTGAGAGGGTGAACGGCCA

CATTGGGACTGAGACACGGCCCAA

OTU287

(SEQ ID NO.: 109)

GACGAACGCTGGCGGCGCGCCTAACACATGCAAGTCGAACGGACACATCC

GACGGAATAGCTTGCTAGGAAGATGGATGTTGTTAGTGGCGGACGGGTGA

GTAACACGTGAGCAACCTGCCTCGGAGTGGGGGACAACAGTTGGAAACGA

CTGCTAATACCGCATACGGTGGTCGGGGGACATCCCCTGGCCAAGAAGG

ATTATATCCGCTCTGAGATGGGCTCGCGTCTGATTAGCTAGTTGGCGGGT

AATGGCCCGACCGAAGGCAACGATCAGTAGCCGGACTGAGAGGTTGAACG

GCCACATTGGGACTGAGACACGGCCCCAG

OTU288

(SEQ ID NO.: 40)

GATGAACGCTGGCGGCGTGCCTAACACATGCAAGTCGAACGGAGTTATGC

AGAGGAAGTTTTCGGATGGAATCGGCGTAACTTAGTGGCGGACGGGTGAG

TAACGCGTGGGAAACCTGCCCTGTACCGGGGGATAACACTTAGAAATAGG

TGCTAATACCGCATAAGCGCACAGCTTCACATGAAGCAGTGTGAAAAACT

CCGGTGGTACAGGATGGTCCCGCGTCTGATTAGCCAGTTGGCAGGGTAAC

GGCCTACCAAAGCGACGATCAGTAGCCGGCCTGAGAGGGTGAACGGCCAC

ATTGGGACTGAGACACGGCCCA

OTU296

(SEQ ID NO.: 23)

GATGAACGCTGGCGGCGTGCCTAACACATGCAAGTCGAACGAAGCGCCTG

GCCCCGACTTCTTCGGAACGAGGAGCCTTGCGACTGAGTGGCGGACGGGT

GAGTAACGCGTGGGCAACCTGCCTTGCACTGGGGGATAACAGCCAGAAAT

GGCTGCTAATACCGCATAAGACCGAAGCGCCGCATGGCGCAGCGGCCAAA

GCCCCGGCGGTGCAAGATGGGCCCGCGTCTGATTAGGTAGTTGGCGGGGT

AACGGCCCACCAAGCCGACGATCAGTAGCCGACCTGAGAGGGTGACCGGC

CACATTGGGACTGAGACACGGCCCA

OTU297

(SEQ ID NO.: 110)

GATGAACGCTGGCGGCGTGCCTAACACATGCAAGTCGAACGAAGCATCTTA

TAGGAAGTTTTCGGATGGAATATGGGATGACTGAGTGGCGGACGGGTGAG

TAACGCGTGGATAACCTGCCTCACACTGGGGGAGTAACAGTTAGAAATGG

CTGCTAATACCCCACTAAGCGCACGGTACCGCATGGTACGGTGTGAAAAA

CCCAGGTGGTGTGAGATGGATCCGCGTCTGATTAGCCAGTTGGCGGGGTA

ACGGCCCGACCAAACGCGACGATCAGTAGCCGACCTGAGAGGGTGACCGG

CCGACATTGGGACTGAGACACGGCCCA

OTU303

(SEQ ID NO.: 111)

GATGAACGCTGGCGGCGTGCCTAACACATGCAAGTCGAACGAAGCATTT

TAGATGAAGTTTTCGGATGGATTCTGAGATGACTGAGTGGCGGACGGGTG

AGTAACACGTGGATAACCTGCCTCACACTGGGGGACAACAGTTAGAAATG

ACTGCTAATACCGCATAAGCGCACAGTACCGCATGGTACAGCGTGAAAAA

CTCCGGTGGTGTGAGATGGATCCGCGTCTGATTAGCCAGTTGGCGGGGTA

ACGGCCCACCAAAGCGACGATCAGTAGCCGACCTGAGAGGGTGACCGGCA

CATTGGGACTGAGACCACGGGCCCAA

OTU304

(SEQ ID NO.: 112)

ATTGAACGCTGGCGGCAGGCCTAACACATGCAAGTCGAACGGTAACAGGA

AGCAGCTTGCTGCTTTGCTGACGAGTGGCGGACGGGTGAGTAATGTCTGG

GAAACTGCCCGATGGAGGGGGATAACTACTGGAAACGGTAGCTAATACCG

CATAACGTCGCAAGACCAAAGAGGGGGACCTTAGGGCCTCTTGCCATCGG

ATGTGCCCAGATGGGATTAGCTAGTAGGTGGGGTAAAGGCTCACCTAGGC

OTU306 (SEQ ID NO.: 33)
GATGAACGCTGGCGGCGTGCCTAACACATGCAAGTCGAACGAAGCGACTT
AACGGAAGTTTTCGGATGGAAGTTGAATTGACTGAGTGGCGGACGGGTGA
GTAACGCGTGGGTAACCTGCCTTGTACTGGGGGACGAACAGTTAGAAATG
ACTGCTAATACCGCATAAGCGCACAGTATCGCATGATACAGTGTGAAAAA
CTCCGGTGGTACAAGATGGACCCGCGTCTGATTAGCTAGTTGGTAAGGTA
ACGGCTTACCAAGGCGACGATCAGTAGCCGACCTGAGAGGGTGACCGGCC
ACATTGGGACTGAGACACGGCCCA

OTU307 (SEQ ID NO.: 113)
GATGAACGCTGGCGGCGTGCCTAACACATGCAAGTCGAACGAAGCATCTT
ATAGGAAGTTTTCGGATGGAATATGGGATGACTGAGTGGCGGACGGGTGA
GTAACGCGTGGAGTAACCTGCCTCACACTGGGGGATAACAGTTAGAAATG
GCTGCTAATACCCCATAAGCGCACAGTACCGCATGGTACGGTGTGAAAAA
CCCAGGTGGTGTGAGATGGATCCGCGTCTGATTAGCCAGTTGGCGGGTAA
CGGCCGACCAAAGCGACGATCAGTAGCCGACCTGAGAGGGTGACCGGCAC
GATTGGGACCTGAGACACGGGCCCA

OTU312 (SEQ ID NO.: 114)
GATGAACGCTGGCGGCGTGCCTAACACATGCAAGTCGAACGAAGTTATAT
CGAGGAAGTTTTCGGATGGAATCAGTATAACTTAGTGGCGGACGGGTGAG
TAACGCGTGGGAAACCTGCCCTGTACCGGGGGATAACACTTAGAAATAGG
TGCTAATACCGCATAAGCGCACAGCTTCACATGAAGCAGTGTGAAAAACT
CCGGTGGTATGAGATGGACCCGCGTCTGATTAGCTAGTTGGAGGGGTAAC
GGCCCACCAAGGCGACGATCAGTAGCCGGCCTGAGAGGGTGAACGGCCAC
ATTGGGACTGAGACACGGCCCAG

OTU313 (SEQ ID NO.: 115)
GATGAACGCTGGCGGCGTGCCTAATACATGCAAGTCGAACGCGGGCAGCA
ATGCCCGAGTGGCGAACGGGTGAGTAATACATAAGTAACCTGCCCTTTAC
AGGGGGATAACTATTGGAAACGATAGCTAAGACCGCATAGGTAAAGATAC
CGCATGGTAAGTTTATTAAAGTGCCAAGGCACTGGTAGAGGATGGACTTA
TGGCGCATTAGCTAGTTGGTGAGGTAACGGCTCACCAAGGCGACGATGCG
TAGCCGACCTGAGAGGGTGACCGGCCACACTGGGACTGAGACACGGCCCA
A

OTU314 (SEQ ID NO.: 31)
GATGAACGCTGGCGGCGTGCCTAACACATGCAAGTCGAGCGAAGCGCTGT
TTTCAGAATCTTCGGAGGAAGAGGACAGTGACTGAGCGGCGGACGGGTGA
GTAACGCGTGGGCAACCTGCCTCATACAGGGGGATAACAGTTAGAAATGA
CTGCTAATACCGCATAAGCGCACAGGACCGCATGGTGTAGTGTGAAAAAC
TCCGGTGGTATGAGATGGACCCGCGTCTGATTAGGTAGTTGGTGGGGTAA

GGCCGTACCAAGCCGACGATCAGTAGCCGACCTGAGAGGGTGACCGGCCA
CATTGGGACTGAGACACGGCCCA

OTU319 (SEQ ID NO.: 116)
GATGAACGCTGGCGGCGTGCCTAACACATGCAAGTCGAACGAAGTTAGAC
AGAGGAAGTTTTCGGATGGAATCGGTATAACTTAGTGGCGGACGGGTGAG
TAACGCGTGGGAAACCTGCCCTGTACCGGGGGATAACACTTAGAAATGAC
TGCTAATACCGCATAAGCGCACAGTACCGCATGGTACAGTGTGAAAAACT
CCGGTGGTGTGAGATGGATCCGCGTCTGATTAGCCAGTTGGCGGGGTAAC
GGCCCACCAAAGCGACGATCAGTAGCCGACCTGAGAGGGTGACCGGCACA
TTGGGACTGAGACACGGCCCAA

OTU326 (SEQ ID NO.: 117)
GATGAACGCTGGCGGCGTGCCTAACACATGCAAGTCGAACGAAGCAATTA
AAATGAAGTTTTCGGATGGATTTTTGATTGACTGAGTGGCGGACGGGTGA
GTAACGCGTGGATAACCTGCCTCACACTGGGGGATAACAGTTAGAAATGA
CTGCTAATACCGCATAAGCGCACAGCTTCACATGAAGCAGTGTGAAAAAC
TCCGGTGGTACAGGATGGTCCCGCGTCTGATTAGCCAGTTGGCAGGGTAA
CGGCCTACCAAAGCGACGATCAGTAGCCGGCCTGAGAGGGTGAACGGCCA
CATTGGGACTGAGACACGGCCCAA

OTU328 (SEQ ID NO.: 118)
GATGAACGCTGGCGGCGTGCTTAACACATGCAAGTCGAACGGAGTGCCTT
AGAAAGAGGATTCGTCCAATTGATAAGGTTACTTAGTGGCGGACGGGTGA
GTAACGCGTGAGGAACCTGCCTCGGAGTGGGGAATAACAGACCGAAAGGT
CTGCTAATACCGCATGATGCAGTTGGACCGCATGGTCCTGACTGCCAAAG
ATTTATCGCTCTGAGATGGCCTCGCGTCTGATTAGCTTGTTGGCGGGGTA
ATGGCCCACCAAGGCGACGATCAGTAGCCGGACTGAGAGGTTGGCCGGCC
ACATTGGGACTGAGACACGGCCCA

OTU333 (SEQ ID NO.: 119)
GATGAACGCTGGCGGCGTGCTTAACACATGCAAGTCGAACGGAGTGCTCA
TGACAGAGGATTCGTCCAATGGAGTGAGTTACTTAGTGGCGGACGGGTGA
GTAACGCGTGAGTAACCTGCCTTGGAGTGGGGAATAACAGGTGGAAACAT
CTGCTAATACCGCATGATGCAGTTGGGTCGCATGGCTCTGACTGCCAAAG
ATTTATCGCTCTGAGATGGACTCGCGTCTGATTAGCTGGTTGGCGGGTAA
CGGCCACCAAGGCGACGATCAGTAGCCGGACTGAGAGGTTGGCCGGCCAC
ATTGGGACTGAGACACGGCCCAG

OTU334 (SEQ ID NO.: 41)
GATGAACGCTGGCGGCGTGCCTAACACATGCAAGTCGAACGAAGCATCCC
ATAGGAAGTTTTCGGATGGAATATGGGATGACTGAGTGGCGGACGGGTGA
GTAACGCGTGGATAACCTGCCTCACACTGGGGGATAACAGTTAGAAATGG
CTGCTAATACCGCATAAGCGCACAGTACCGCATGGTACGGTGTGAAAAAC
CCAGGTGGTGTGAGATGGATCCGCGTCTGATTAGCCAGTTGGCGGGGTAA

CGGCCCACCAAAGCGACGATCAGTAGCCGACCTGAGAGGGTGACCGGCCA
CATTGGGGACTGAGACACGGCCCA

OTU337
(SEQ ID NO.: 30)
GACGAACGCTGGCGGCGCGCCTAACACATGCAAGTCGAACGGAGCTTACG
TTTTGAAGTTTTCGGATGGATGAATGTAAGCTTAGTGGCGGACGGGTGAG
TAACACGTGAGCAACCTGCCTTTCAGAGGGGGATAACAGCCGGAAACGGC
TGCTAATACCGCATGATGTTGCGGGGGCACATGCCCCTGCAACCAAAGGA
GCAATCCGCTGAAAGATGGGCTCGCGTCCGATTAGCCAGTTGGCGGGGTA
ACGGCCCACCAAAGCGACGATCGGTAGCCGGACTGAGAGGTTGAACGGCC
ACATTGGGACTGAGACACGGCCCAG

OTU339
(SEQ ID NO.: 120)
GATGAACGCTGGCGGCGTGCCTAACACATGCAAGTCGAACGAAGCAATTA
AAATGAAGTTTTCGGATGGATTTTTGATTGACTGAGTGGCGGACGGGTGA
GTAACGCGTGGATAACCTGCCTCACACTGGGGATAACAGTTAGAAATGAC
TGCTAATACCGCATAAGCGCACAGTACCGCATGGTACGGTGTGAAAAACT
CCGGTGGTGTGAGATGGATCCGCGTCTGATTAGCCAGTTGCGGGGTAACG
GCCCGACCAAGCGACGATCAGTAGCCGACCGTGAGAGGTGACCGGCCCAC
ATTGGGACTGAGACACGGCCCAA

OTU340
(SEQ ID NO.: 121)
GACGAACGCTGGCGGCGCGCCTAACACATGCAAGTCGAACGGAGTTGTGT
TGAAAGCTTGCTGGATATACAACTTAGTGGCGGACGGGTGAGTAACACGT
GAGTAACCTGCCTCTCAGAGTGGAATAACGTTTGGAAACGAACGCTAATA
CCGCATAACGTGAGAAGAGGGCATCCTCTTTTTACCAAAGATTTATCGCT
GAGAGATGGGCTCGCGGCCGATTAGGTAGTTGGTGAGATAACAGCCCACC
AAGCCGACGATCGGTAGCCGGACTGAGAGGTTGATCGGCCACATTGGGAC
TGAGACACGGCCCAG

OTU353
(SEQ ID NO.: 122)
GATGAACGCTGGCGGCGTGCTTAACACATGCAAGTCGAGCGAAGCACCTT
GACGGATTCTTCGGATTGAAGCCTTGGTGACTGAGCGGCGGACGGGTGAG

TAACGCGTGGGTAACCTGCCTCATACAGGGGGGATAAACAGTTAGAAATG
ACTGCTAATACCGCATAAGCGCACAGGACCGCATGGTCTGGTGTGAAAAA
CTCCGGTGGTATGAGATGGACCCGCGTCTGATTAGCTAGTTGGAGGGGTA
ACGGCCCACCAAGGCGACGATCAGTAGCCGGCCTGAGAGGGTGAACGGCC
ACATTGGGACTGAGGACACGGCCCA

OTU359
(SEQ ID NO.: 42)
GATGAACGCTGGCGGCGTGCCTAACACATGCAAGTCGAACGAAGTTATAT
CGAGGAAGTTTTCGGATGGAATCAGTATAACTTAGTGGCGGACGGGTGAG
TAACGCGTGGGAAACCTGCCCTGTACCGGGGGATAACACTTAGAAATAGG
TGCTAATACCGCATAAGCGCACAGCTTCACATGAAAGCAGTGTGAAAAAC
TCCGGTGGTACAGGATGGTCCCGCGTCTGATTAGCCAGTTGGCAGGGTAA
CGGCCTACCAAAGCGACGATCAGTAGCCGGCCTGGAGAGGGTGAACGGCC
ACATTGGGACTGAGACACGGCCCG

OTU362
(SEQ ID NO.: 43)
GATGAACGCTGGCGGCGTGCTTAACACATGCAAGTCGAGCGAAGCGGTTT
CGATGAAGTTTTCGGATGGATTTGAAATCGACTTAGCGGCGGACGGGTGA
GTAACGCGTGGGTAACCTGCCTTACACTGGGGATAACAGTTAGAAATGAC
TGCTAATACCGCATAAGCGCACAGGGCCGCATGGTCCGGTGTGAAAACTC
CGGTGGTGTAAGATGGACCCGCGTCTGATTAGGTAGTTGGTGGGTAACGG
CCCACCAAGCCGACGATCAGTAGCCGACCTGAGAGGGTGACCGGCCACAT
TGGGACTGAGACACGGCCCAA

OTU367
(SEQ ID NO.: 44)
GATGAACGCTGGCGGCGTGCCTAACACATGCAAGTCGAACGAAGTTACAC
AGAGGAAGTTTTCGGATGAATCGGTATAACTTAGTGGCGGACGGGTGAG
TAACGCGTGGGAAACCCGCCCTGTACCGGGGGATAACACTTAGAAATAGG
TGCTAATACCGCATAAGCGCACAGCTTCACATGAAGCAGTGTGAAAACTC
CGGTAGGTACAGGATGGTCCCGCGTCTGATTAGCCAGTTGGCAGGGTAAC
GGCCTACCAAAGCGACGATCAGTAGCCGGCCTGAGAGGGTCAACGGCCAC
ATTGGGACTGAGACACGGCCCAA

What is claimed is:

1. A pharmaceutical composition comprising a purified bacterial mixture comprising three or more bacterial strains selected from the group consisting of *Clostridium saccharogumia* or *Clostridium ramosum* JCM1298,

*Flavonifractor plautii* or *Pseudoflavonifractor capillolus* ATCC 29799,

*Clostridium hathewayi* or *Clostridium saccharolyticum* WM1,
*Blautia coccoides* or *Lachnospiraceae bacterium* 6_1_63FAA,
*Clostridium* sp. or *Clostridium bolteae* ATCC BAA-613,
cf. *Clostridium* sp. MLGO55 or *Erysipelotrichaceae bacterium* 2_2_44A
*Clostridium indolis* or *Anaerostipes caccae* DSM 14662,
*Anaerotruncus colihominis* or *Anaerotruncus colihominis* DSM 17241,
*Ruminococcus* sp. ID8 or *Lachnospiraceae bacterium* 2_1_46FAA,
*Clostridium lavalense* or *Clostridium asparagiforme* DSM 15981,
*Clostridium symbiosum* or *Clostridium symbiosum* WAL-14163,
*Clostridium ramosum*,
*Eubacterium contortum* or *Clostridium* sp. D5,
*Clostridium scindens* or *Lachnospiraceae bacterium* 5_1_57FAA,
*Lachnospiraceae bacterium* A4 or *Lachnospiraceae bacterium* 3_1_57FAA_CT1,
*Clostridium* sp. 316002/008 or *Clostridiales bacterium* 1_7_47FAA, and
*Lachnospiraceae bacterium* A4 or *Lachnospiraceae bacterium* 3_1_57FAA_CT1; and one or more enteric polymers.

2. The composition of claim 1, wherein the purified bacterial mixture comprises at least 4, at least 5, at least 6, at least 7, at least 8, at least 9, at least 10, at least 11, at least 12, at least 13, at least 14, at least 15, at least 16 or at least 17 bacterial strains.

3. The pharmaceutical composition of claim 1, wherein the bacterial strains are human-derived bacteria.

4. The pharmaceutical composition of claim 1, wherein the bacterial strains are human commensal bacteria.

5. The pharmaceutical composition of claim 1, wherein one or more of the bacterial strains are in spore-form.

6. The pharmaceutical composition of claim 1, further comprising a pharmaceutically acceptable excipient.

7. The pharmaceutical composition of claim 1, wherein the pharmaceutical composition is formulated for oral administration.

8. The pharmaceutical composition of claim 1, wherein the pharmaceutical composition is formulated for delivery to the intestine or colon.

9. A pharmaceutical composition comprising a purified bacterial mixture consisting of the following 17 bacterial strains:

*Clostridium saccharogumia* or *Clostridium ramosum* JCM1298,
*Flavonifractor plautii* or *Pseudoflavinofractor capillolus* ATCC 29799,
*Clostridium hathewayi* or *Clostridium saccharolyticum* WM1,
*Blautia coccoides* or *Lachnospiraceae bacterium* 6_1_63FAA,
*Clostridium* sp. or *Clostridium bolteae* ATCC BAA-613,
cf. *Clostridium* sp. MLGO55 or *Erysipelotrichaceae bacterium* 2_2_44A,
*Clostridium indolis* or *Anaerostipes caccae* DSM 14662,
*Anaerotruncus colihominis* or *Anaerotruncus colihominis* DSM 17241,
*Ruminococcus* sp. ID8 or *Lachnospiraceae bacterium* 2_1_46FAA,
*Clostridium lavalense* or *Clostridium asparagiforme* DSM 15981,
*Clostridium symbiosum* or *Clostridium symbiosum* WAL-14163,
*Clostridium ramosum*,
*Eubacterium contortum* or *Clostridium* sp. D5,
*Clostridium scindens* or *Lachnospiraceae bacterium* 5_1_57FAA,
*Lachnospiraceae bacterium* A4 or *Lachnospiraceae bacterium* 3_1_57FAA_CT1,
*Clostridium* sp. 316002/008 or *Clostridiales bacterium* 1_7_47FAA, and
*Lachnospiraceae bacterium* A4 or *Lachnospiraceae bacterium* 3_1_57FAA_CT1; and one or more enteric polymers.

10. The pharmaceutical composition of claim 9, wherein the bacterial strains are human-derived bacteria.

11. The pharmaceutical composition of claim 9, wherein the bacterial strains are human commensal bacteria.

12. The pharmaceutical composition of claim 9, wherein one or more of the bacterial strains are in spore-form.

13. The pharmaceutical composition of claim 9, further comprising a pharmaceutically acceptable excipient.

14. The pharmaceutical composition of claim 9, wherein the pharmaceutical composition is formulated for oral administration.

15. The pharmaceutical composition of claim 9, wherein the pharmaceutical composition is formulated for delivery to the intestine or colon.

\* \* \* \* \*

SEQUENCE LISTING

<160> NUMBER OF SEQ ID NOS: 123

<210> SEQ ID NO 1
<211> LENGTH: 23
<212> TYPE: DNA
<213> ORGANISM: Artificial Sequence
<220> FEATURE:
<223> OTHER INFORMATION: Primer, Foxp3

<400> SEQUENCE: 1
ggcaatagtt ccttcccaga gtt                                          23

<210> SEQ ID NO 2
<211> LENGTH: 22

```
<212> TYPE: DNA
<213> ORGANISM: Artificial Sequence
<220> FEATURE:
<223> OTHER INFORMATION: Primer, Foxp3

<400> SEQUENCE: 2
gggtcgcata ttgtggtact tg                                              22

<210> SEQ ID NO 3
<211> LENGTH: 23
<212> TYPE: DNA
<213> ORGANISM: Artificial Sequence
<220> FEATURE:
<223> OTHER INFORMATION: Primer, CTLA4

<400> SEQUENCE: 3 cctttttgtag ccctgctcac tct                                            23

<210> SEQ ID NO 4
<211> LENGTH: 21
<212> TYPE: DNA
<213> ORGANISM: Artificial Sequence
<220> FEATURE:
<223> OTHER INFORMATION: Primer, CTLA4

<400> SEQUENCE: 4
gggtcacctg tatggcttca g                                               21

<210> SEQ ID NO 5
<211> LENGTH: 21
<212> TYPE: DNA
<213> ORGANISM: Artificial Sequence
<220> FEATURE:
<223> OTHER INFORMATION: Primer, GITR

<400> SEQUENCE: 5
tcagtgcaag atctgcaagc a                                               21

<210> SEQ ID NO 6
<211> LENGTH: 19
<212> TYPE: DNA
<213> ORGANISM: Artificial Sequence
<220> FEATURE:
<223> OTHER INFORMATION: Primer, GITR

<400> SEQUENCE: 6
acaccggaag ccaaacaca                                                  19

<210> SEQ ID NO 7
<211> LENGTH: 27
<212> TYPE: DNA
<213> ORGANISM: Artificial Sequence
<220> FEATURE:
<223> OTHER INFORMATION: Primer, IL-10

<400> SEQUENCE: 7
gattttaata agctccaaga ccaaggt                                         27

<210> SEQ ID NO 8
<211> LENGTH: 27
<212> TYPE: DNA
<213> ORGANISM: Artificial Sequence
<220> FEATURE:
<223> OTHER INFORMATION: Primer, IL-10

<400> SEQUENCE: 8
```
cttctatgca gttgatgaag atgtcaa                                    27

<210> SEQ ID NO 9
<211> LENGTH: 21
<212> TYPE: DNA
<213> ORGANISM: Artificial Sequence
<220> FEATURE:
<223> OTHER INFORMATION: Primer, GAPDH

<400> SEQUENCE: 9
cctcgtcccg tagacaaaat g                                          21

<210> SEQ ID NO 10
<211> LENGTH: 20
<212> TYPE: DNA
<213> ORGANISM: Artificial Sequence
<220> FEATURE:
<223> OTHER INFORMATION: Primer, GAPDH

<400> SEQUENCE: 10
tctccacttt gccactgcaa                                            20

<210> SEQ ID NO 11
<211> LENGTH: 20
<212> TYPE: DNA
<213> ORGANISM: Artificial Sequence
<220> FEATURE:
<223> OTHER INFORMATION: Primer, Mmp2

<400> SEQUENCE: 11
ggacattgtc tttgatggca                                            20

<210> SEQ ID NO 12
<211> LENGTH: 20
<212> TYPE: DNA
<213> ORGANISM: Artificial Sequence
<220> FEATURE:
<223> OTHER INFORMATION: Primer, Mmp2

<400> SEQUENCE: 12
cttgtcacgt ggtgtcactg                                            20

<210> SEQ ID NO 13
<211> LENGTH: 20
<212> TYPE: DNA
<213> ORGANISM: Artificial Sequence
<220> FEATURE:
<223> OTHER INFORMATION: Primer, Mmp9

<400> SEQUENCE: 13
tctctggacg tcaaatgtgg                                            20

<210> SEQ ID NO 14
<211> LENGTH: 19
<212> TYPE: DNA
<213> ORGANISM: Artificial Sequence
<220> FEATURE:
<223> OTHER INFORMATION: Primer, Mmp9

<400> SEQUENCE: 14
gctgaacagc agagccttc                                             19

<210> SEQ ID NO 15
<211> LENGTH: 20
<212> TYPE: DNA
<213> ORGANISM: Artificial Sequence

```
<220> FEATURE:
<223> OTHER INFORMATION: Primer, Mmp13

<400> SEQUENCE: 15
aggtctggat cactccaagg                                                  20

<210> SEQ ID NO 16
<211> LENGTH: 19
<212> TYPE: DNA
<213> ORGANISM: Artificial Sequence
<220> FEATURE:
<223> OTHER INFORMATION: Primer, Mmp13

<400> SEQUENCE: 16
tcgcctggac cataaagaa                                                   19

<210> SEQ ID NO 17
<211> LENGTH: 20
<212> TYPE: DNA
<213> ORGANISM: Artificial Sequence
<220> FEATURE:
<223> OTHER INFORMATION: Primer, Ido1

<400> SEQUENCE: 17
agaggatgcg tgactttgtg                                                  20

<210> SEQ ID NO 18
<211> LENGTH: 20
<212> TYPE: DNA
<213> ORGANISM: Artificial Sequence
<220> FEATURE:
<223> OTHER INFORMATION: Primer, Ido1

<400> SEQUENCE: 18
atacagcaga ccttctggca                                                  20

<210> SEQ ID NO 19
<211> LENGTH: 302
<212> TYPE: DNA
<213> ORGANISM: Artificial Sequence
<220> FEATURE:
<223> OTHER INFORMATION: OTU136

<400> SEQUENCE: 19
gatgaacgct ggcggcgtgc ctaatacatg caagtcgaac gcgagcactt gtgctcgagt       60
ggcgaacggg tgagtaatac ataagtaacc tgccctttac aggggataa ctattggaaa       120 cgatagctaa gaccgcatag gtaaagatac cgcatggtaa gtttattaaa agtgccaagg      180
cactggtaga ggatggactt atggcgcatt agctagttgg tgaggtaacg gctcaccaag      240
gcgacgatgc gtagccgacc tgagagggtg accggccaca ctgggactga gacacggccc     300
ag                                                                    302

<210> SEQ ID NO 20
<211> LENGTH: 303
<212> TYPE: DNA
<213> ORGANISM: Artificial Sequence
<220> FEATURE:
<223> OTHER INFORMATION: OTU46

<400> SEQUENCE: 20
gatgaacgct ggcggcgtgc ctaatacatg caagtcgaac gcgagcactt gtgctcgagt       60
ggcgaacggg tgagtaatac ataagtaacc tgccctagac aggggataa ctattggaaa      120
```

```
cgatagctaa gaccgcatag gtacggacac tgcatggtga ccgtattaaa gtgcctcaaa        180
gcactggtag aggatggact tatggcgcat tagctggttg gcggggtaac ggcccaccaa        240
ggcgacgatg cgtagccgac ctgagagggt gaccggccac actgggactg agacacggcc        300
cag                                                                     303

<210> SEQ ID NO 21
<211> LENGTH: 324
<212> TYPE: DNA
<213> ORGANISM: Artificial Sequence
<220> FEATURE:
<223> OTHER INFORMATION: OTU221

<400> SEQUENCE: 21
gatgaacgct ggcggcgtgc ttaacacatg caagtcgaac ggggtgctca tgacggagga        60
ttcgtccaac ggattgagtt acccagtggc ggacgggtga gtaacgcgtg aggaacctgc        120
cttggagagg ggaataacac tccgaaagga gtgctaatac cgcatgatgc agttgggtcg        180
catggctctg actgccaaag atttatcgct ctgagatggc ctcgcgtctg attagctagt        240
aggcggggta acggcccacc taggcgacga tcagtagccg gactgagagg ttgaccggcc        300
acattgggac tgagacacgg ccca                                              324

<210> SEQ ID NO 22
<211> LENGTH: 325
<212> TYPE: DNA
<213> ORGANISM: Artificial Sequence
<220> FEATURE:
<223> OTHER INFORMATION: OTU9

<400> SEQUENCE: 22
gatgaacgct ggcggcggtg cttaacacat gcaagtcgag cgaagcggtt tcgagtgaag        60
ttttggatgg aattgaaatt gacttagcgg cggacgggtg agtaacgcgt gggtaacctg        120
ccttacactg ggggataaca gttagaaatg actgctaata ccgcataagc gcacagggcc        180
gcatggtctg gtgcgaaaaa ctccggtggt gtaagatgga cccgcgtctg attaggtagt        240
tggtggggta acggcccacc aagccgacga tcagtagccg acctgagagg gtgaccggcc        300
acattgggac tgagacacgg cccaa                                             325

<210> SEQ ID NO 23
<211> LENGTH: 325
<212> TYPE: DNA
<213> ORGANISM: Artificial Sequence
<220> FEATURE:
<223> OTHER INFORMATION: OTU296

<400> SEQUENCE: 23
gatgaacgct ggcggcgtgc ctaacacatg caagtcgaac gaagcgcctg ccccgacttc        60
cttcggaacg aggagccttg cgactgagtg gcggacgggt gagtaacgcg tgggcaacct        120
gccttgcact gggggataac agccagaaat ggctgctaat accgcataag accgaagcgc        180
cgcatggcgc agcggccaaa gccccggcgg tgcaagatgg gcccgcgtct gattaggtag        240
ttggcggggt aacggcccac caagccgacg atcagtagcc gacctgagag ggtgaccggc        300
cacattggga ctgagacacg gccca                                             325

<210> SEQ ID NO 24
<211> LENGTH: 323
<212> TYPE: DNA
<213> ORGANISM: Artificial Sequence
```

```
<220> FEATURE:
<223> OTHER INFORMATION: OTU21

<400> SEQUENCE: 24
gatgaacgct ggcggcgtgc ttaacacatg caagtcgagc gaagcgctaa gacagatttc     60
ttcggattga agtctttgtg gctgagcggc ggacgggtga gtaacgcgtg ggtaacctgc    120
ctcatacagg gggataacag ttagaaatga ctgctaatac cgcataagcg cacaggaccg    180
catggtctgg tgtgaaaaac tccggtggta tgagatggac ccgcgtctga ttagctagtt    240
ggaggggtaa cggcccacca aggcgacgat cagtagccgg cctgagaggg tgaacggcca    300
cattgggact gagacacggc cca                                            323

<210> SEQ ID NO 25
<211> LENGTH: 322
<212> TYPE: DNA
<213> ORGANISM: Artificial Sequence
<220> FEATURE:
<223> OTHER INFORMATION: OTU166

<400> SEQUENCE: 25
gatgaacgct ggcggcgtgc ctaacacatg caagtcgaac gaagcaatta aaatgaagtt     60
tcggatggat tttgattgac tgagtggcgg acgggtgagt aacgcgtgga taacctgcct    120
cacactgggg gataacagtt agaaatgact gctaataccg cataagcgca cagtaccgca    180
tggtacggtg tgaaaaactc cggtggtgtg agatggatcc gcgtctgatt agccagttgg    240
cggggtaacg gcccaccaaa gcgacgatca gtagccgacc tgagagggtg accggccacg    300
attgggactg agacacggcc ca                                             322

<210> SEQ ID NO 26
<211> LENGTH: 313
<212> TYPE: DNA
<213> ORGANISM: Artificial Sequence
<220> FEATURE:
<223> OTHER INFORMATION: OTU73

<400> SEQUENCE: 26
gatgaacgct ggcggcatgc ctaatacatg caagtcgaac gaagtgaaga tagcttgcta     60
tcggagctta gtggcgaacg ggtgagtaac acgtagataa cctgcctgta tgaccgggat    120
aacagttgga aacgactgct aataccggat aggcagagag gaggcatctc ttctctgtta    180
aagttgggat acaacgcaaa cagatggatc tgcggtgcat tagctagttg gtgaggtaac    240
ggcccaccaa ggcgatgatg catagccggc ctgagagggc gaacggccac attgggactg    300
agacacggcc caa                                                       313

<210> SEQ ID NO 27
<211> LENGTH: 325
<212> TYPE: DNA
<213> ORGANISM: Artificial Sequence
<220> FEATURE:
<223> OTHER INFORMATION: OTU174

<400> SEQUENCE: 27
gatgaacgct ggcggcgtgc ttaacacatg caagtcgaac gaagcattt ggaaggaagt     60 tttcggatgg aattccttaa tgactgagtg gcggacgggt gagtaacgcg tggggaacct    120
gccctataca gggggataac agctggaaac ggctgctaat accgcataag cgcacagaat    180
cgcatgattc ggtgtgaaaa gctccggcag tataggatgg tcccgcgtct gattagctgg    240
```

```
ttggcggggt aacggcccac caaggcgacg atcagtagcc ggcttgagag agtggacggc    300
cacattggga ctgagacacg gccca                                          325
```

<210> SEQ ID NO 28
<211> LENGTH: 323
<212> TYPE: DNA
<213> ORGANISM: Artificial Sequence
<220> FEATURE:
<223> OTHER INFORMATION: OTU14

<400> SEQUENCE: 28

```
gatgaacgct ggcggcgtgc ttaacacatg caagtcgagc gaagcggttt caatgaagtt    60
ttcggatgga attgaaattg acttagcggc ggacgggtga gtaacgcgtg ggtaacctgc   120
cttacactgg gggataacag ttagaaatga ctgctaatac cgcataagcg cacagggccg   180
catggtctgg tgtgaaaaac tccggtggtg taagatggac ccgcgtctga ttaggtagtt   240
ggtggggtaa cggccaccaa gccgacgatc agtagccgac ctgagagggt gaccggccac   300
attggggact gagacacggc cca                                           323
```

<210> SEQ ID NO 29
<211> LENGTH: 323
<212> TYPE: DNA
<213> ORGANISM: Artificial Sequence
<220> FEATURE:
<223> OTHER INFORMATION: OTU55

<400> SEQUENCE: 29

```
gatgaacgct ggcggcgtgc ctaacacatg caagtcgaac gaagttacac ggaggaagtt    60
ttcggatgga atcggtataa cttagtggcg gacgggtgag taacgcgtgg gaaacctgcc   120
ctgtaccggg ggataacact tagaaatagg tgctaatacc gcataagcgc acggaaccgc   180
atggttccgt gtgaaaaact accggtggta caggatggtc ccgcgtctga ttagccagtt   240
ggcagggtaa cggcctacca aagcgacgat cagtagccgg cctgagaggg tgaacggcca   300
cattgggact gagacacagc cca                                           323
```

<210> SEQ ID NO 30
<211> LENGTH: 325
<212> TYPE: DNA
<213> ORGANISM: Artificial Sequence
<220> FEATURE:
<223> OTHER INFORMATION: OTU337

<400> SEQUENCE: 30

```
gacgaacgct ggcggcgcgc ctaacacatg caagtcgaac ggagcttacg ttttgaagtt    60
ttcggatgga tgaatgtaag cttagtggcg gacgggtgag taacacgtga gcaacctgcc   120
tttcagaggg ggataacagc cggaaacggc tgctaatacc gcatgatgtt gcggggggcac  180 atgcccctgc aaccaaagga gcaatccgct gaaagatggg ctcgcgtccg attagccagt   240
tggcggggta acggcccacc aaagcgacga tcggtagccg gactgagagg ttgaacggcc   300
acattgggac tgagacacgg cccag                                         325
```

<210> SEQ ID NO 31
<211> LENGTH: 324
<212> TYPE: DNA
<213> ORGANISM: Artificial Sequence
<220> FEATURE:
<223> OTHER INFORMATION: OTU314

<400> SEQUENCE: 31

```
gatgaacgct ggcggcgtgc ctaacacatg caagtcgagc gaagcgctgt tttcagaatc    60
ttcggaggaa gaggacagtg actgagcggc ggacgggtga gtaacgcgtg ggcaacctgc   120
ctcatacagg gggataacag ttagaaatga ctgctaatac cgcataagcg cacaggaccg   180
catggtgtag tgtgaaaaac tccggtggta tgagatggac ccgcgtctga ttaggtagtt   240
ggtggggtaa ggccgtacca agccgacgat cagtagccga cctgagaggg tgaccggcca   300 cattgggggac tgagacacgg ccca                                         324
```

```
<210> SEQ ID NO 32
<211> LENGTH: 325
<212> TYPE: DNA
<213> ORGANISM: Artificial Sequence
<220> FEATURE:
<223> OTHER INFORMATION: OTU195

<400> SEQUENCE: 32
gatgaacgct ggcggcgtgc ctaacacatg caagtcgaac gaagcatttt agatgaagtt    60
ttcggatgga ttctgagatg actgagtggc ggacgggtga gtaacacgtg gataacctgc   120
ctcacactgg gggacgaaca gttagaaatg actgctaata ccgcataagc gcacagtacc   180
gcatggtacg gtgtgaaaaa ctccggtggt gtgagatgga tccgcgtctg attagccagt   240
tggcgggtaa cggcccaccg aaagcgacga tcagtagccg acctgagagg gtgaccggcc   300
acattgggac tgagacacgg cccaa                                         325
```

```
<210> SEQ ID NO 33
<211> LENGTH: 324
<212> TYPE: DNA
<213> ORGANISM: Artificial Sequence
<220> FEATURE:
<223> OTHER INFORMATION: OTU306

<400> SEQUENCE: 33
gatgaacgct ggcggcgtgc ctaacacatg caagtcgaac gaagcgactt aacggaagtt    60
ttcggatgga agttgaattg actgagtggc ggacgggtga gtaacgcgtg ggtaacctgc   120
cttgtactgg gggacgaaca gttagaaatg actgctaata ccgcataagc gcacagtatc   180 gcatgatcaca gtgtgaaaaa ctccggtggt acaagatgga cccgcgtctg attagctagt   240
tggtaaggta acggcttacc aaggcgacga tcagtagccg acctgagagg gtgaccggcc   300
acattgggac tgagacacgg ccca                                          324
```

```
<210> SEQ ID NO 34
<211> LENGTH: 324
<212> TYPE: DNA
<213> ORGANISM: Artificial Sequence
<220> FEATURE:
<223> OTHER INFORMATION: OTU87

<400> SEQUENCE: 34
gatgaacgct ggcggcgtgc ttaacacatg caagtcgagc gaagcgcttt acttagattt    60
cttcggattg aaagttttgc gactgagcgg cggacgggtg agtaacgcgt gggtaacctg   120
cctcatacag ggggataaca gttagaaatg actgctaata ccgcataaga ccacagtacc   180
gcatggtaca gtgggaaaaa ctccggtggt atgagatgga cccgcgtctg attagctagt   240
tggtaaggta acggcttacc aaggcgacga tcagtagccg acctgagagg gtgaccggcc   300
acattgggac tgagacacgg ccca                                          324
```

<210> SEQ ID NO 35
<211> LENGTH: 325
<212> TYPE: DNA
<213> ORGANISM: Artificial Sequence
<220> FEATURE:
<223> OTHER INFORMATION: OTU86
<220> FEATURE:
<221> NAME/KEY: misc_feature
<222> LOCATION: (49)..(49)
<223> OTHER INFORMATION: n is a, c, g, or t

<400> SEQUENCE: 35

```
gatgaacgct ggcggcgtgc ttaacacatg caagtcgaac gaagcattnt tggaaggaag      60
tttcggatgg aattccttaa tgactgagtg gcggacgggt gagtaacgcg tggggaacct     120
accctataca gggggataac agctggaaac ggctgctaat accgcataag cgcacagaat     180
cgcatgattc ggtgtgaaaa gctccggcag tataggatgg tcccgcgtct gattagctgg     240
ttggcgggta acggcccacc aaggcgacga tcagtagccg gcttgagaga gtggacggcc     300
acattgggac tgagacacgg cccaa                                           325
```

<210> SEQ ID NO 36
<211> LENGTH: 323
<212> TYPE: DNA
<213> ORGANISM: Artificial Sequence
<220> FEATURE:
<223> OTHER INFORMATION: OTU152

<400> SEQUENCE: 36

```
gatgaacgct ggcggcgtgc ctaacacatg caagtcgaac gaagttagac agaggaagtt      60
ttcggatgga atcggtataa cttagtggcg gacgggtgag taacgcgtgg gaaacctgcc     120
ctgtaccggg ggataacact tagaaatagg tgctaatacc gcataagcgc acggaaccgc     180
atgggttctg tgtgaaaact ccggtggtac aggatggtcc cgcgtctgat tagccagttg     240
gcagggtaac ggcctaccaa agcgacgatc agtagccggc tgagagggt gaacggccac      300 attgggactg agacacggcc caa                                             323
```

<210> SEQ ID NO 37
<211> LENGTH: 326
<212> TYPE: DNA
<213> ORGANISM: Artificial Sequence
<220> FEATURE:
<223> OTHER INFORMATION: OTU253

<400> SEQUENCE: 37

```
gacgaacgct ggcggcgtgc ttaacacatg caaatcgaac ggagcaccct tgactgaggt      60
ttcggccaaa tgataggaat gcttagtggc ggactggtga gtaacgcgtg aggaacctgc     120
cttccagagg gggacaacag ttggaaacga ctgctaatac cgcatgacgc atgaccgggg     180
catcccgggc atgtcaaaga ttttatcgct ggaagatggc ctcgcgtctg attagctaga     240
tggtggggta acggcccacc atggcgacga tcagtagccg gactgagagg ttgaccggcc     300
acattgggac tgagatacgg cccag                                           326
```

<210> SEQ ID NO 38
<211> LENGTH: 326
<212> TYPE: DNA
<213> ORGANISM: Artificial Sequence
<220> FEATURE:
<223> OTHER INFORMATION: OTU259

<400> SEQUENCE: 38

```
gatgaacgct ggcggcgtgc ttaacacatg caagtcgagc gaagcgcttt acttagattt      60
cttcggattg aaaagttttg cgactgagcg gcggacgggt gagtaacgcg tgggtaacct     120
gcctcataca gggggataac agttagaaat gactgctaat accgcataag accacggtac     180
cgcatggtac agtgggaaaa actccggtgg tatgagatgg acccgcgtct gattagctag     240
ttggtaaggt aacggcttac caaggcgacg atcagtagcc gacctgagag ggtgaccggc     300
acattgggac ctgagacacg gcccaa                                          326

<210> SEQ ID NO 39
<211> LENGTH: 327
<212> TYPE: DNA
<213> ORGANISM: Artificial Sequence
<220> FEATURE:
<223> OTHER INFORMATION: OTU281

<400> SEQUENCE: 39
gatgaacgct ggcggcgtgc ctaacacatg caagtcgaac gaagcgcttc cgcctgattt      60
tcttcggaga tgaaggcggc tgcgactgag tggcggacgg gtgagtaacg cgtgggcaac     120
ctgccttgca ctgggggata acagccagaa atggctgcta ataccgcata agaccgaagc     180
gccgcatggc gctgcggcca agccccggc ggtgcaagat gggcccgcgt ctgattaggt      240
agttggcggg gtaacggccc accaagccga cgatcagtag ccgacctgag agggtgaccg     300
gccacattgg gactgagaca cggccca                                         327

<210> SEQ ID NO 40
<211> LENGTH: 322
<212> TYPE: DNA
<213> ORGANISM: Artificial Sequence
<220> FEATURE:
<223> OTHER INFORMATION: OTU288

<400> SEQUENCE: 40
gatgaacgct ggcggcgtgc ctaacacatg caagtcgaac ggagttatgc agaggaagtt      60
ttcggatgga atcggcgtaa cttagtggcg gacgggtgag taacgcgtgg gaaacctgcc     120
ctgtaccggg ggataacact tagaaatagg tgctaatacc gcataagcgc acagcttcac     180
atgaagcagt gtgaaaaact ccggtggtac aggatggtcc cgcgtctgat tagccagttg     240
gcagggtaac ggcctaccaa agcgacgatc agtagccggc tgagagggt gaacggccac      300 attgggactg agacacggcc ca                                              322

<210> SEQ ID NO 41
<211> LENGTH: 324
<212> TYPE: DNA
<213> ORGANISM: Artificial Sequence
<220> FEATURE:
<223> OTHER INFORMATION: OTU334

<400> SEQUENCE: 41
gatgaacgct ggcggcgtgc ctaacacatg caagtcgaac gaagcatccc ataggaagtt      60
ttcggatgga atatgggatg actgagtggc ggacgggtga gtaacgcgtg gataacctgc     120
ctcacactgg gggataacag ttagaaatgg ctgctaatac cgcataagcg cacagtaccg     180
catggtacgg tgtgaaaaac ccaggtggtg tgagatggat ccgcgtctga ttagccagtt     240
ggcggggtaa cggcccacca aagcgacgat cagtagccga cctgagaggg tgaccggcca    300 cattgggac tgagacacgg ccca                                             324
```

```
<210> SEQ ID NO 42
<211> LENGTH: 324
<212> TYPE: DNA
<213> ORGANISM: Artificial Sequence
<220> FEATURE:
<223> OTHER INFORMATION: OTU359

<400> SEQUENCE: 42
gatgaacgct ggcggcgtgc ctaacacatg caagtcgaac gaagttatat cgaggaagtt      60
ttcggatgga atcagtataa cttagtggcg gacgggtgag taacgcgtgg gaaacctgcc     120
ctgtaccggg ggataacact tagaaatagg tgctaatacc gcataagcgc acagcttcac     180
atgaaagcag tgtgaaaaac tccggtggta caggatggtc ccgcgtctga ttagccagtt     240
ggcagggtaa cggcctacca aagcgacgat cagtagccgg cctggagagg gtgaacggcc     300
acattgggac tgagacacgg cccg                                           324

<210> SEQ ID NO 43
<211> LENGTH: 321
<212> TYPE: DNA
<213> ORGANISM: Artificial Sequence
<220> FEATURE:
<223> OTHER INFORMATION: OTU362

<400> SEQUENCE: 43
gatgaacgct ggcggcgtgc ttaacacatg caagtcgagc gaagcggttt cgatgaagtt      60
ttcggatgga tttgaaatcg acttagcggc ggacgggtga gtaacgcgtg ggtaacctgc     120
cttacactgg ggataacagt tagaaatgac tgctaatacc gcataagcgc acagggccgc     180
atggtccggt gtgaaaactc cggtggtgta agatggaccc gcgtctgatt aggtagttgg     240
tgggtaacgg cccaccaagc cgacgatcag tagccgacct gagagggtga ccggccacat     300
tgggactgag acacggccca a                                             321

<210> SEQ ID NO 44
<211> LENGTH: 323
<212> TYPE: DNA
<213> ORGANISM: Artificial Sequence
<220> FEATURE:
<223> OTHER INFORMATION: OTU367

<400> SEQUENCE: 44
gatgaacgct ggcggcgtgc ctaacacatg caagtcgaac gaagttacac agaggaagtt      60
ttcggatgga atcggtataa cttagtggcg gacgggtgag taacgcgtgg gaaacccgcc     120
ctgtaccggg ggataacact tagaaatagg tgctaatacc gcataagcgc acagcttcac     180
atgaagcagt gtgaaaactc cggtaggtac aggatggtcc cgcgtctgat tagccagttg     240
gcagggtaac ggcctaccaa agcgacgatc agtagccggc ctgagagggt caacggccac     300
attgggactg agacacggcc caa                                            323

<210> SEQ ID NO 45
<211> LENGTH: 17
<212> TYPE: DNA
<213> ORGANISM: Artificial Sequence
<220> FEATURE:
<223> OTHER INFORMATION: Primer, total bacteria

<400> SEQUENCE: 45
ggtgaatacg ttcccgg                                                   17
```

```
<210> SEQ ID NO 46
<211> LENGTH: 22
<212> TYPE: DNA
<213> ORGANISM: Artificial Sequence
<220> FEATURE:
<223> OTHER INFORMATION: Primer, total bacteria

<400> SEQUENCE: 46
tacggctacc ttgttacgac tt                                              22

<210> SEQ ID NO 47
<211> LENGTH: 20
<212> TYPE: DNA
<213> ORGANISM: Artificial Sequence
<220> FEATURE:
<223> OTHER INFORMATION: Primer, Clostridium cluster XIVa (Clostridium
      coccoides subgroup)

<400> SEQUENCE: 47
aaatgacggt acctgactaa                                                 20

<210> SEQ ID NO 48
<211> LENGTH: 22
<212> TYPE: DNA
<213> ORGANISM: Artificial Sequence
<220> FEATURE:
<223> OTHER INFORMATION: Primer, Clostridium cluster XIVa (Clostridium
      coccoides subgroup)

<400> SEQUENCE: 48
ctttgagttt cattcttgcg aa                                              22

<210> SEQ ID NO 49
<211> LENGTH: 18
<212> TYPE: DNA
<213> ORGANISM: Artificial Sequence
<220> FEATURE:
<223> OTHER INFORMATION: Primer, Clostridium cluster IV (Clostridium
      leptum)

<400> SEQUENCE: 49
ccttccgtgc cgsagtta                                                   18

<210> SEQ ID NO 50
<211> LENGTH: 26
<212> TYPE: DNA
<213> ORGANISM: Artificial Sequence
<220> FEATURE:
<223> OTHER INFORMATION: Primer, Clostridium cluster IV (Clostridium
      leptum)

<400> SEQUENCE: 50
gaattaaacc acatactcca ctgctt                                          26

<210> SEQ ID NO 51
<211> LENGTH: 18
<212> TYPE: DNA
<213> ORGANISM: Artificial Sequence
<220> FEATURE:
<223> OTHER INFORMATION: Primer, Bacteroides

<400> SEQUENCE: 51
gagaggaagg tcccccac                                                   18

<210> SEQ ID NO 52
<211> LENGTH: 19
<212> TYPE: DNA
```

```
<213> ORGANISM: Artificial Sequence
<220> FEATURE:
<223> OTHER INFORMATION: Primer, Bacteroides

<400> SEQUENCE: 52
cgctacttgg ctggttcag                                               19

<210> SEQ ID NO 53
<211> LENGTH: 20
<212> TYPE: DNA
<213> ORGANISM: Artificial Sequence
<220> FEATURE:
<223> OTHER INFORMATION: Primer, Bifidobacterium

<400> SEQUENCE: 53
cgggtgagta atgcgtgacc                                              20

<210> SEQ ID NO 54
<211> LENGTH: 18
<212> TYPE: DNA
<213> ORGANISM: Artificial Sequence
<220> FEATURE:
<223> OTHER INFORMATION: Primer, Bifidobacterium

<400> SEQUENCE: 54
tgataggacg cgacccca                                                18

<210> SEQ ID NO 55
<211> LENGTH: 50
<212> TYPE: DNA
<213> ORGANISM: Artificial Sequence
<220> FEATURE:
<223> OTHER INFORMATION: Modified primer 8F
<220> FEATURE:
<221> NAME/KEY: misc_feature
<222> LOCATION: (30)..(31)
<223> OTHER INFORMATION: barcode

<400> SEQUENCE: 55
ccatctcatc cctgcgtgtc tccgactcag agrgtttgat ymtggctcag             50

<210> SEQ ID NO 56
<211> LENGTH: 49
<212> TYPE: DNA
<213> ORGANISM: Artificial Sequence
<220> FEATURE:
<223> OTHER INFORMATION: Modified Primer 338R

<400> SEQUENCE: 56
cctatcccct gtgtgccttg gcagtctcag tgctgcctcc cgtaggagt              49

<210> SEQ ID NO 57
<211> LENGTH: 19
<212> TYPE: DNA
<213> ORGANISM: Artificial Sequence
<220> FEATURE:
<223> OTHER INFORMATION: KOD FX (TOYOBO), 16S rRNA gene-specific primer,
      8F

<400> SEQUENCE: 57
gagtttgatc mtggctcag                                               19

<210> SEQ ID NO 58
<211> LENGTH: 16
<212> TYPE: DNA
<213> ORGANISM: Artificial Sequence
<220> FEATURE:
```

<223> OTHER INFORMATION: KOD FX (TOYOBO), 16S rRNA gene-specific primer, 519R

<400> SEQUENCE: 58
attaccgcgg ckgctg                                                    16

<210> SEQ ID NO 59
<211> LENGTH: 21
<212> TYPE: DNA
<213> ORGANISM: Artificial Sequence
<220> FEATURE:
<223> OTHER INFORMATION: KOD FX (TOYOBO), 16S rRNA gene-specific primer, 1513R

<400> SEQUENCE: 59
acggctacct tgttacgact t                                              21

<210> SEQ ID NO 60
<211> LENGTH: 20
<212> TYPE: DNA
<213> ORGANISM: Artificial Sequence
<220> FEATURE:
<223> OTHER INFORMATION: 16S rRNA gene-specific primer

<400> SEQUENCE: 60
agagtttgat cmtggctcag                                                20

<210> SEQ ID NO 61
<211> LENGTH: 16
<212> TYPE: DNA
<213> ORGANISM: Artificial Sequence
<220> FEATURE:
<223> OTHER INFORMATION: 16S rRNA gene-specific

<400> SEQUENCE: 61
attaccgcgg ckgctg                                                    16

<210> SEQ ID NO 62
<211> LENGTH: 17
<212> TYPE: DNA
<213> ORGANISM: Artificial Sequence
<220> FEATURE:
<223> OTHER INFORMATION: Primer, total bacteria

<400> SEQUENCE: 62
ggtgaatacg ttcccgg                                                   17

<210> SEQ ID NO 63
<211> LENGTH: 22
<212> TYPE: DNA
<213> ORGANISM: Artificial Sequence
<220> FEATURE:
<223> OTHER INFORMATION: Primer, total bacteria

<400> SEQUENCE: 63
tacggctacc ttgttacgac tt                                             22

<210> SEQ ID NO 64
<211> LENGTH: 20
<212> TYPE: DNA
<213> ORGANISM: Artificial Sequence
<220> FEATURE:
<223> OTHER INFORMATION: Primer, Clostridium cluster XIVa (Clostridium coccoides subgroup)

<400> SEQUENCE: 64

-continued aaatgacggt acctgactaa                                          20

<210> SEQ ID NO 65
<211> LENGTH: 22
<212> TYPE: DNA
<213> ORGANISM: Artificial Sequence
<220> FEATURE:
<223> OTHER INFORMATION: Clostridium cluster XIVa (Clostridium coccoides
      subgroup)

<400> SEQUENCE: 65
ctttgagttt cattcttgcg aa                                       22

<210> SEQ ID NO 66
<211> LENGTH: 16
<212> TYPE: DNA
<213> ORGANISM: Artificial Sequence
<220> FEATURE:
<223> OTHER INFORMATION: Primer, Clostridium cluster IV (Clostridium
      leptum)

<400> SEQUENCE: 66
gcacaagcag tggagt                                              16

<210> SEQ ID NO 67
<211> LENGTH: 18
<212> TYPE: DNA
<213> ORGANISM: Artificial Sequence
<220> FEATURE:
<223> OTHER INFORMATION: Primer, Bacteroides

<400> SEQUENCE: 67
gagaggaagg tcccccac                                            18

<210> SEQ ID NO 68
<211> LENGTH: 19
<212> TYPE: DNA
<213> ORGANISM: Artificial Sequence
<220> FEATURE:
<223> OTHER INFORMATION: Primer, Bacteroides

<400> SEQUENCE: 68
cgctacttgg ctggttcag                                           19

<210> SEQ ID NO 69
<211> LENGTH: 18
<212> TYPE: DNA
<213> ORGANISM: Artificial Sequence
<220> FEATURE:
<223> OTHER INFORMATION: Primer, Clostridium cluster IV (Clostridium
      leptum)

<400> SEQUENCE: 69
cttcctccgt tttgtcaa                                            18

<210> SEQ ID NO 70
<211> LENGTH: 323
<212> TYPE: DNA
<213> ORGANISM: Artificial Sequence
<220> FEATURE:
<223> OTHER INFORMATION: OTU3

<400> SEQUENCE: 70
gatgaacgct ggcggcgtgc ttaacacatg caagtcgagc gaagcactaa gacggatttc    60
ttcggattga agtctttgtg actgagcggc ggacggtgag taacgcgtgg gtaacctgcc   120

```
tcatacaggg ggataacagt tagaaatgac tgctaatacc gcataagcgc acaggaccgc      180
atggtctggt gtgaaaaact ccggtggtat gagatggacc cgcgtctgat tagctagttg      240
gagggtaacg gcccaccgaa ggcgacgatc agtagccggc ctgagagggt gaacggccac      300
attgggactg agacacggcc cag                                              323

<210> SEQ ID NO 71
<211> LENGTH: 324
<212> TYPE: DNA
<213> ORGANISM: Artificial Sequence
<220> FEATURE:
<223> OTHER INFORMATION: OTU15

<400> SEQUENCE: 71
gatgaacgct ggcggcgtgc ttaacacatg caagtcgagc gaagcattaa gacagatttc       60
ttcggattga agtctttgtg actgagcggc ggacgggtga gtaacgcgtg ggtaacctgc      120
ctcatacagg gggataacag ttagaaatga ctgctaatac cgcataagcg cacagggccg      180
catggtctgg tgtgaaaaac tccggtggtg taagatggac ccgcgtctga ttaggtagtt      240
ggtggggtaa cggcccacca agccgacgat cagtagccga cctgagaggg tgaccggcca      300
cattgggact gagacacggc ccaa                                             324

<210> SEQ ID NO 72
<211> LENGTH: 324
<212> TYPE: DNA
<213> ORGANISM: Artificial Sequence
<220> FEATURE:
<223> OTHER INFORMATION: OTU23

<400> SEQUENCE: 72
gatgaacgct ggcggcgtgc ttaacacatg caagtcgaac gaagcatttt ggaaggaagt       60
tttcggatgg aattccttaa tgactgagtg gcggacgggt gagtaacgcg tggggaacct      120
ccctactaca ggggagtaac agctggaacg gactgctaat accgcataag cgcacagaat      180
cgcatgattc ggtgtgaaag ctccggcagt ataggatggt cccgcgtctg attagctggt      240
tggcgggtaa cggcccacca aggcgacgat cagtagccgg cttgagagag tggacggcca      300
cattgggact gagacacggc ccaa                                             324

<210> SEQ ID NO 73
<211> LENGTH: 324
<212> TYPE: DNA
<213> ORGANISM: Artificial Sequence
<220> FEATURE:
<223> OTHER INFORMATION: OTU38

<400> SEQUENCE: 73
gatgaacgct ggcggcgtgc ttaacacatg caagtcgagc gaagcggttt caatgaagtt       60
ttcggatgga attgaaattg acttagcggc ggacgggtga gtaacgcgtg ggtaacctgc      120
ctcatacagg gggataacag ttagaaatga ctgctaatac cgcataagcg cacaggaccg      180
catggtctgg tgtgaaaaac tccggtggta tgagatggac ccgcgtctga ttagctagtt      240
ggaggggtaa cggcccacca aggcgacgat cagtagccgg cctgagaggg tgaacggcca      300
cattgggact gagacacggc ccag                                             324

<210> SEQ ID NO 74
<211> LENGTH: 328
<212> TYPE: DNA
<213> ORGANISM: Artificial Sequence
```

```
<220> FEATURE:
<223> OTHER INFORMATION: OTU49

<400> SEQUENCE: 74
gatgaacgct ggcggcgtgc ctaacacacg caagacgaac gaagcaatta aaatgaagtt      60
ttcggatgga tttttgattg actgagtggc ggacgggtga gtaacgcgtg gataacctgc     120
ctcacactgg ggggataaca gttagaaatg actgctaata ccgcataagc gcacagtacc    180
gcatggtacg tgtgaaaact accggtggtg tgagatggag tcccgcgtct gattagccag    240
ttggcggggt aacggcccac caaagcgacg atcagtagcc gacctgagag ggtgaccggc    300
cacattgggg actgagacac gggcccaa                                       328

<210> SEQ ID NO 75
<211> LENGTH: 324
<212> TYPE: DNA
<213> ORGANISM: Artificial Sequence
<220> FEATURE:
<223> OTHER INFORMATION: OTU57

<400> SEQUENCE: 75
gatgaacgct ggcggcgtgc ttaacacatg caagtcgagc gaagcggttt cgatgaagtt     60
ttcggatgga tttgaaatcg acttagcggc ggacgggtga gtaacgcgtg ggtaacctgc    120
cttacactgg gggataacag ttagaaatga ctgctaatac cgcataagcg cacagggccg    180
catggtctgg tgcgaaaaac tccggtggtg taagatggac ccgcgtctga ttagccagtt    240
ggcagggtaa cggcctacca aagcgacgat cagtagccgg cctgagaggg tgaacggcca    300
cattgggact gagacacggc ccaa                                           324

<210> SEQ ID NO 76
<211> LENGTH: 327
<212> TYPE: DNA
<213> ORGANISM: Artificial Sequence
<220> FEATURE:
<223> OTHER INFORMATION: OTU89

<400> SEQUENCE: 76
gatgaacgct ggcggcgtgc ttaacacatg caagtcgaac gaagcatttt ggaaggaagt     60
tttcggatgg aatcggtata acttagtggc ggacgggtga gtaacgcgtg ggaaacctgc    120
cctgtaccgg gggataacac ttagaaatag gtgctaacac cgcataagcg cacggaaccg    180
catggttctg tgtgaaaaaa ctccggtggt acaggatggt cccgcgtctg attagccagt    240
tggcgagggt aacggcctac caaagacgac gatcagtagc cggcctgaga gggtgaacgg    300
ccacattggg actgagacac ggcccaa                                        327

<210> SEQ ID NO 77
<211> LENGTH: 322
<212> TYPE: DNA
<213> ORGANISM: Artificial Sequence
<220> FEATURE:
<223> OTHER INFORMATION: OTU92

<400> SEQUENCE: 77
gatgaacgct ggcggcgtgc ctaacacatg caagtcgaac ggagttatgc agaggaagtt     60
ttcggatgga atcggcgtaa cttagtggcg gacgggtgag taacgcgtgg gaaacctgcc    120
ctgtaccggg ggataacact tagaaatagg tgctaatacc gcataagcgc acagcttcac    180
atgaggcagt gtgaaaaact ccggtggtgt aagatggacc cgcgtctgat taggtagttg    240
```

```
gtggggtaac ggcccaccaa gccgacgatc agtagccgac ctgagagggt gaccggccac    300
attgggactg agacacggcc ca                                             322

<210> SEQ ID NO 78
<211> LENGTH: 323
<212> TYPE: DNA
<213> ORGANISM: Artificial Sequence
<220> FEATURE:
<223> OTHER INFORMATION: OTU101

<400> SEQUENCE: 78
gatgaacgct ggcggcgtgc ctaacacatg caagtcgaac gaagcaatta agatgaagtt    60
ttcggatgga atcttgattg actgagtggc ggacgggtga gtaacgcgtg gataacctgc    120
ctcacactgg gggataacag ttagaaatga ctgctaatac cgcataagcg cacagtgccg    180
catggcagtg tgtgaaaaac tccggtggtg tgagatggat ccgcgtctga ttagccagtt    240
ggcggggtaa cggccaccga aagcgacgat cagtagccga cctgagaggg tgaccggcca    300
cactgggact gagacacggc cca                                            323

<210> SEQ ID NO 79
<211> LENGTH: 322
<212> TYPE: DNA
<213> ORGANISM: Artificial Sequence
<220> FEATURE:
<223> OTHER INFORMATION: OTU111

<400> SEQUENCE: 79
gatgaacgct ggcggcgtgc ctaacacatg caagtcgaac gaagttacac agaggaagtt    60
ttcggatgga atcggtataa cttagtggcg gacgggtgag taacgcgtgg gaaacctgcc    120
ctgtaccggg ggataacact tagaaatagg tgctaatacc gcataagcgc acagcttcac    180
atgaagcagt gtgaaaaact ccggtggtac aggatggtcc cgcgtctgat tagctggttg    240
gcggggtaac ggcccaccaa ggcgacgatc agtagccggc ttgagagagt ggacggccac    300
attgggactg agacacggcc ca                                             322

<210> SEQ ID NO 80
<211> LENGTH: 323
<212> TYPE: DNA
<213> ORGANISM: Artificial Sequence
<220> FEATURE:
<223> OTHER INFORMATION: OTU114

<400> SEQUENCE: 80
gatgaacgct ggcggcgtgc ctaacacatg caagtcgagc gaagcgctgt tttcagaatc    60
ttcggaggaa gaggacagtg actgagcggc ggacgggtga gtaacgcgtg ggcaacctgc    120
ctcatacagg gggataacag ttagaaatga ctgctaatac cgcataagcg cacaggaccg    180
catggtgtag tgtgaaaaac tccggtggta tgagatggac ccgcgtctga ttagccagtt    240
ggcagggtaa cggcctacca aagcgacgat cagtagccgg cctgagaggg tgaacggcca    300
cattgggact gagacacggc cca                                            323

<210> SEQ ID NO 81
<211> LENGTH: 324
<212> TYPE: DNA
<213> ORGANISM: Artificial Sequence
<220> FEATURE:
<223> OTHER INFORMATION: OTU119
<220> FEATURE:
<221> NAME/KEY: misc_feature
```

```
<222> LOCATION: (293)..(293)
<223> OTHER INFORMATION: n is a, c, g, or t

<400> SEQUENCE: 81
gatgaacgct ggcggcgtgc ctaacacatg caagtcgaac gaagcaatta agatgaagtt    60
ttcggatgga atcttgattg actgagtggc ggacgggtga gtaacgcgtg gataacctgc   120
ctcacactgg gggataacag ttagaaatga ctgctaatac cgcataagcg cacagtgccg   180
catggcagtg tgtgaaaaac tccggtggtg tgagatggat ccgcgtctga ttagccagtt   240
gcggggtaac ggcccgacca aagcgacgga tcagtagccg acctgagagg gtnaccggcc   300
acattgggac tgagacacgg ccca                                          324

<210> SEQ ID NO 82
<211> LENGTH: 325
<212> TYPE: DNA
<213> ORGANISM: Artificial Sequence
<220> FEATURE:
<223> OTHER INFORMATION: OTU125

<400> SEQUENCE: 82
gatgaacgct ggcggcgtgc ctaacacatg caagtcgagc gaagcgctgt tttcagaatc    60
ttcggaggaa gaggacagtg actgagcggc ggacgggtga gtaacgcgtg ggcaacctgc   120
ctcatacagg gggataacag ttagaaatga ctgctaatac cgcataagcg cacaggaccg   180
catggtgtag tgtgaaaaac tccggtggta tgagatggac ccgcgtctga ttaggtagtt   240
ggtgggtaaa ggctaccgaa gccgacgatc agtagccgac ctgacgaggg tgaccggcca   300
cgattgggac tgagacacgg cccaa                                         325

<210> SEQ ID NO 83
<211> LENGTH: 322
<212> TYPE: DNA
<213> ORGANISM: Artificial Sequence
<220> FEATURE:
<223> OTHER INFORMATION: OTU131
<220> FEATURE:
<221> NAME/KEY: misc_feature
<222> LOCATION: (291)..(291)
<223> OTHER INFORMATION: n is a, c, g, or t

<400> SEQUENCE: 83
gatgaacgct ggcggcgtgc ctaacacatg caagtcgaac gaagcaatta agatgaagtt    60
ttcggatgga atcttgattg actgagtggc ggacgggtga gtaacgcgtg gataacctgc   120
ctcacactgg gggataacag ttagaaatga ctgctaatac cgcataagcg cacagtgccg   180
catggcagtg tgtgaaaaac tccggtggtg tgagatggat ccgcgtctga ttagccagtt   240
gcgggtaacg gccaccgaaa gcgacgatca gtagccgacc tgacgagggt naccggcaca   300
ttgggactga gacacggccc aa                                            322

<210> SEQ ID NO 84
<211> LENGTH: 325
<212> TYPE: DNA
<213> ORGANISM: Artificial Sequence
<220> FEATURE:
<223> OTHER INFORMATION: OTU137

<400> SEQUENCE: 84
gatgaacgct ggcggcgtgc ctaacacatg caagtcgaac gaagcaatta agatgaagtt    60
ttcggatgga atcttgattg actgagtggc ggacgggtga gtaacgcgtg gataacctgc   120
```

```
ctcacactgg ggggataaca gttagaaatg actgctaata ccgcataagc gcacagtgcc      180
gcatggcagt gtgtgaaaaa ctccggtggt gtgagatgga tccgcgtctg attaggtagt      240
tggtggggta acggcccacc aagccgacga tcagtagccg acctgagagg gtgaccggcc      300
acattgggac tgagacacgg cccaa                                            325

<210> SEQ ID NO 85
<211> LENGTH: 325
<212> TYPE: DNA
<213> ORGANISM: Artificial Sequence
<220> FEATURE:
<223> OTHER INFORMATION: OTU144

<400> SEQUENCE: 85
gatgaacgct ggcggcgtgc ttaacacatg caagtcgagc gaagcggttt cgatgaagtt      60
tttggatgga attgaaattg acttagcggc ggacgggtga gtaacgcgtg ggtaacctgc      120
cttacactgg gggataacag ttagaaatga ctgctaatac cgcataagcg cacagggccg      180
catggtctgg tgcgaaaaac tccggtggtg taagatggac ccgcgtctga ttaggtagtt      240
ggtggggtaa cggcccaccg aagccgacga tcagtagccg acctgagagg gtgaccggca      300
cattgggacc tgagacacgg gccca                                            325

<210> SEQ ID NO 86
<211> LENGTH: 324
<212> TYPE: DNA
<213> ORGANISM: Artificial Sequence
<220> FEATURE:
<223> OTHER INFORMATION: OTU161

<400> SEQUENCE: 86
gatgaacgct ggcggcgtgc ctaacacatg caagtcgaac gaagcatttt agatgaagtt      60
ttcggatgga ttctgagatg actgagtggc ggacgggtga gtaacacgtg gataacctgc      120
ctcacactgg gggacaacag ttagaaatga ctgctaatac cgcataagcg cacagtaccg      180
catggtacgg tgtgaaaaac tccggtggta caggatggtc ccgcgtctga ttagccagtt      240
ggcagggtaa cggcctacca aagcgacgat cagtagccgg cctgagaggg tgaacggcca      300
cattgggact gagacacggc ccaa                                             324

<210> SEQ ID NO 87
<211> LENGTH: 322
<212> TYPE: DNA
<213> ORGANISM: Artificial Sequence
<220> FEATURE:
<223> OTHER INFORMATION: OTU163

<400> SEQUENCE: 87
gatgaacgct ggcggcgtgc ctaacacatg caagtcgaac gaagttacac ggaggaagtt      60
ttcggatgga atcggtataa cttagtggcg gacgggtgag taacgcgtgg gaaacctgcc      120
ctgtaccggg ggataacact tagaaatagg tgctaatacc gcataagcgc acggaaccgc      180
atggttccgt gtgaaaaact ccggtggtac aggatggtcc cgcgtctgat taggtagttg      240
gtggggtaac ggcccaccaa gccgacgatc agtagccgac ctgagagggt gaccggccac      300
attgggactg agacacggcc ca                                               322

<210> SEQ ID NO 88
<211> LENGTH: 327
<212> TYPE: DNA
<213> ORGANISM: Artificial Sequence
```

<220> FEATURE:
<223> OTHER INFORMATION: OTU165

<400> SEQUENCE: 88

```
gatgaacgct ggcggcgtgc ttaacacatg caagtcgaac ggagcaccct tgactgaggt    60
ttcggccaaa tgataggaat gcttagtggc ggactggtga gtaacgcgtg aggaacctac   120
cttccagagg ggacgaacag ttggaacgac tgctaatacc gcatgacgca tgaccggggc   180
gatcccgggc cgatgtcaaa gattttattc gctggaagat ggcctcgcgt ctgattagct   240
agatggtggg gtaacggccc accatggcga cgatcagtag ccggactgag aggttgaccg   300
gccacattgg gactgagata cggccca                                       327
```

<210> SEQ ID NO 89
<211> LENGTH: 327
<212> TYPE: DNA
<213> ORGANISM: Artificial Sequence
<220> FEATURE:
<223> OTHER INFORMATION: OTU181

<400> SEQUENCE: 89

```
gatgaacgct ggcggcgtgc ctaacacatg caagtcgaac gaagcaattt aaaatgaagt    60
tttcggatgg attttttgatt gactgagtgg cggacgggtg agtaacgcgt ggataacctg   120
cctcacgact gggggataac agttagaaat gactgctaat accgcataag cgcacagtac   180
cgcatggtac ggtgtgaaaa actccggtgg tgtgagatgg atccgcgtct gattagccag   240
ttgcggggta acggcccacc gaaagcgacg atcagtagcc gacctgagag ggtgaccggc   300
cacattgggg actgagacac ggcccaa                                       327
```

<210> SEQ ID NO 90
<211> LENGTH: 300
<212> TYPE: DNA
<213> ORGANISM: Artificial Sequence
<220> FEATURE:
<223> OTHER INFORMATION: OTU182

<400> SEQUENCE: 90

```
gatgaacgct ggcggcgtgc ctaatacatg caagtcgaac gcgggcagca atgcccgagt    60
ggcgaacggg tgagtaatac ataagtaacc tgcccttttac aggggggataa ctattggaaa   120
cgatagctaa gaccgcatag gtaaagatac cgcatgtaa gtttattaaa agtgccaagg   180
cactacgagg gagtagtgat atgcgcatag ctagttggtg aggtaacggc tcaccaaggc   240
gacgatgcgt agccgacctg agagggtgac cggccacact gggactgaga cacggcccag   300
```

<210> SEQ ID NO 91
<211> LENGTH: 323
<212> TYPE: DNA
<213> ORGANISM: Artificial Sequence
<220> FEATURE:
<223> OTHER INFORMATION: OTU189

<400> SEQUENCE: 91

```
gatgaacgct ggcggcgtgc ctaacacatg caagtcgaac gaagcatttt agatgaagtt    60
ttcggatgga ttctgagatg actgagtggc ggacgggtga gtaacacgtg gataacctgc   120
ctcacactgg gggacacagt tagaaatgac tgctaatacc gcataagcgc acagcttcac   180
atgaagcagt gtgaaaaact ccggtggtac aggatggtcc cgcgtctgat tagccagttg   240
gcagggtaac ggcctaccaa agcgacgatc agtagccggc ctgagagggt gaacggccac   300
```
attgggactg agacacggcc cag                                         323

<210> SEQ ID NO 92
<211> LENGTH: 322
<212> TYPE: DNA
<213> ORGANISM: Artificial Sequence
<220> FEATURE:
<223> OTHER INFORMATION: OTU196

<400> SEQUENCE: 92
gacgaacgct ggcggcgtgc ttaacacatg caagtcgaac ggagcacccc tgaatgaggt     60
ttcggccaaa ggaagggaat gcttagtggc ggactggtga gtaacgcgtg aggaacctgc    120 cttttcagagg ggacaacagt tggaaacgac tgctaatacc gcatgacaca tgaatggggc   180
atcccattga tgtcaaagat ttatcgctga aagatggcct cgcgtcccat tagctagtag   240
gcggggtaac ggcccaccta ggcgacgatg ggtagccgga ctgagaggtt gaccggccac   300
attgggactg agatacggcc ca                                            322

<210> SEQ ID NO 93
<211> LENGTH: 307
<212> TYPE: DNA
<213> ORGANISM: Artificial Sequence
<220> FEATURE:
<223> OTHER INFORMATION: OTU199

<400> SEQUENCE: 93
gatgaacgct ggcggcgtgc ctaatacatg caagtcgaac gcgagcactt gtgctcgagt    60
ggcgaacggg tgagtaatac ataagtaacc tgccctagac aggggagta actattggaa    120 cgatagctaa gaccgcatag gtacggacac tgcgtggtga ccgtattaaa agtagcctca   180
aagacactgg tagaggatgg acttatggcg cattagctgg ttggcggggt aacggcccac   240
ccaaggcgac gatgcgtagc cgacctgaga gggtgaccgg ccacactggg actgagacac   300
ggcccag                                                              307

<210> SEQ ID NO 94
<211> LENGTH: 324
<212> TYPE: DNA
<213> ORGANISM: Artificial Sequence
<220> FEATURE:
<223> OTHER INFORMATION: OTU202

<400> SEQUENCE: 94
gatgaacgct ggcggcgtgc ctaacacatg caagtcgaac gaagcaattt aacggaagtt    60
ttcggatgga agttgaattg actgagtggc ggacgggtga gtaacgcgtg ggtaacctgc   120
cttgtactgg gggacaacag ttagaaatga ctgctaatac cgcataagcg cacagtatcg   180
catgatacag tgtgaaaaac tccggtggta caagatggac ccgcgtctga ttagctagtt   240
ggaggggtaa cggcccacca aggcgacgat cagtagccgg cctgagaggg tgaacggcca   300
cattgggact gagacacggc ccag                                          324

<210> SEQ ID NO 95
<211> LENGTH: 323
<212> TYPE: DNA
<213> ORGANISM: Artificial Sequence
<220> FEATURE:
<223> OTHER INFORMATION: OTU204

<400> SEQUENCE: 95
gatgaacgct ggcggcgtgc ttaacacatg caagtcgagc gaagcactaa gacggatttc    60

```
ttcggattga agtctttgtg actgagcggc ggacgggtga gtaacgcgtg ggtaacctgc    120
ctcatacagg gggataacag ttagaaatga ctgctaatac cgcataagac cacagtaccg    180
catggtacag tgggaaaaac tccggtggta tgagatggac ccgcgtctga ttagctagtt    240
ggtaaggtaa cggcttacca aggcgacgat cagtagccga cctgagaggg tgaccggcca    300
cattgggact gagacacggc cca                                            323

<210> SEQ ID NO 96
<211> LENGTH: 324
<212> TYPE: DNA
<213> ORGANISM: Artificial Sequence
<220> FEATURE:
<223> OTHER INFORMATION: OTU211

<400> SEQUENCE: 96
gatgaacgct ggcggcgtgc ttaacacatg caagtcgagc gaagcggttt cgatgaagtt    60
ttcggatgga tttgaaatcg acttagcggc ggacgggtga gtaacgcgtg ggtaacctgc    120
cttacactgg gggataacag ctggaaacgg ctgctaatac cgcataagcg cacagaatcg    180
catgattcgg tgcgaaaagc tccggcagta taggatggtc ccgcgtctga ttagctggtt    240
ggcggggtaa cggcccacca aggcgacgat cagtagccgg cttgagagag tggacggcca    300
cattgggact gagacacggc ccaa                                           324

<210> SEQ ID NO 97
<211> LENGTH: 324
<212> TYPE: DNA
<213> ORGANISM: Artificial Sequence
<220> FEATURE:
<223> OTHER INFORMATION: OTU214

<400> SEQUENCE: 97
gatgaacgct ggcggcgtgc ctaacacatg caagtcgaac gaagcaatta agatgaagtt    60
ttcggatgga atcttgattg actgagtggc ggacgggtga gtaacgcgtg ggtaacctgc    120
ctcatacagg gggagtaaca gttagaaatg actgctaata ccgcataagc gcacagggct    180
gcatggcctg gtgtgaaaaa ctccggtggt atgagatgga cccgcgtctg attagctagt    240
tggaggggta acggcccacc aaggcgacga tcagtagccg gcctgagagg gtgaacggcc    300
acattgggac tgagacacgg ccca                                           324

<210> SEQ ID NO 98
<211> LENGTH: 323
<212> TYPE: DNA
<213> ORGANISM: Artificial Sequence
<220> FEATURE:
<223> OTHER INFORMATION: OTU224

<400> SEQUENCE: 98
gatgaacgct ggcggcgtgc ttaacacatg caagtcgagc gaagcacctt ggcggatttc    60
ttcggattga agccttggtg actgagcggc ggacgggtga gtaacgcgtg ggtaacctgc    120
cctgtaccgg gggataacac ttagaaatag gtgctaatac cgcataagcg cacagcttca    180
catgaagcag tgtgaaaaac tccggcgtta caggatggtc ccgcgtctga ttagccagtt    240
gacagggtaa cggcctacca aagcgacgat cagtagccgg cctgagaggg tgaacggcca    300
cattgggact gagacacggc cca                                            323

<210> SEQ ID NO 99
```

```
<211> LENGTH: 324
<212> TYPE: DNA
<213> ORGANISM: Artificial Sequence
<220> FEATURE:
<223> OTHER INFORMATION: OTU225

<400> SEQUENCE: 99
gatgaacgct ggcggcgtgc ctaacacatg caagtcgaac ggaagttatg cagaggaagt    60
tttcggtatg gaatcggcgt aacttagtgg cggacgggtg agtaacgcgt gggaaacctg   120
ccctgtaccg ggggagtaac acttagaata ggtgctaata ccgcataagc gcacagcttc   180
acatgaggca gtgtgaaaaa ctccggtggt acaggatggt cccgcgtctg attagccagt   240
tggcagggta acggcctacc aaagcgacga tcagtagccg gcctgagagg gtgaacggcc   300
acattgggac tgagacacgg ccca                                          324

<210> SEQ ID NO 100
<211> LENGTH: 322
<212> TYPE: DNA
<213> ORGANISM: Artificial Sequence
<220> FEATURE:
<223> OTHER INFORMATION: OTU237

<400> SEQUENCE: 100
gatgaacgct ggcggcgtgc ctaacacatg caagtcgaac gaagcaattg aaggaagttt    60
tcggatggaa ttcgattgac tgagtggcgg acgggtgagt aacgcgtgga taacctgcct   120
cacactgggg gataacagtt agaaatgact gctaataccg cataagcgca cagtgccgca   180
tggtacggtg tgaaaaactc cggtggtgtg agatggatcc gcgtctgatt agccagttgg   240
cggggtaacg gcccaccaaa gcgacgatca gtagccgacc tgagagggtg accggccaca   300
ttgggactga gacacggccc aa                                            322

<210> SEQ ID NO 101
<211> LENGTH: 323
<212> TYPE: DNA
<213> ORGANISM: Artificial Sequence
<220> FEATURE:
<223> OTHER INFORMATION: OTU246

<400> SEQUENCE: 101
gatgaacgct ggcggcgtgc ctaacacatg caagtcgaac ggagttatgc agaggaagtt    60
tcggatggaa tcggcgtaac ttagtggcg gacgggtgag taacgcgtgg gaaacctgcc   120
ctatacaggg ggataacagc tggaaacggc tgctaatacc gcataagcgc acagaatcgc   180
atgattcggt gtgaaaagct ccggcagtat aggatggtcc cgcgtctgat tagctggttg   240
gcggggtaac ggcccaccaa ggcgacgatc agtagccggc ttgagagagt ggacggccac   300
attgggactg agacacggcc caa                                           323

<210> SEQ ID NO 102
<211> LENGTH: 325
<212> TYPE: DNA
<213> ORGANISM: Artificial Sequence
<220> FEATURE:
<223> OTHER INFORMATION: OTU262

<400> SEQUENCE: 102
gatgaacgct ggcggcgtgc ctaacacatg caagtcgaac gaagcattt agatgaagtt    60 tcggatggaa ttctgagatg actgagtggc ggacgggtga gtaacacgtg gataacctgc   120
ctcacactgg gggacaacag ttagaaatga ctgctaatac cgcataagcg cacagtaccg   180
```

```
catggtacag tgtgaaaaac tccggtggtg tgagatggat ccgcgtctga ttagccagtt    240
ggcggggtaa cggcccacca aagcgacgat cagtagccga cctgagaggg tgaccggcca    300
cattggggac ctgagacacg gccca                                          325

<210> SEQ ID NO 103
<211> LENGTH: 326
<212> TYPE: DNA
<213> ORGANISM: Artificial Sequence
<220> FEATURE:
<223> OTHER INFORMATION: OTU268

<400> SEQUENCE: 103
gatgaacgct ggcggcgtgc ctaacacatg caagtcgagc gaagcgctgt tttcagaatc    60
ttcggaggaa gaggacagtg actgagcggc ggacgggtga gtaacgcgtg ggcaacctgc   120
ctcatacagg gggataacag ttagaaatga ctgctaatac cgcataagcg cacaggaccg   180
catggtgtag tgtgaaaaac tccggtggta tgagatggac ccgcgtctga ttaggtagtt   240
ggtggggtaa aggcctacca agccgacgat cagtagccga cctgagacgg gtgaccggca   300
cattggggac tgagacacgg gcccaa                                         326

<210> SEQ ID NO 104
<211> LENGTH: 329
<212> TYPE: DNA
<213> ORGANISM: Artificial Sequence
<220> FEATURE:
<223> OTHER INFORMATION: OTU269

<400> SEQUENCE: 104
gatgaacgct ggcggcgtgc ctaacacatg caagtcgaac gaagcatttt agatgaagtt    60
ttcggatgga ttctgagatg actgagtggc ggacgggtga gtaacgcgtg gataacctgc   120
ctcacactgg gggacgaaca gttagaaata gactgctaat accgcataag cgcacagtac   180
cgcatggtac agtgtgaaaa actaccggtg gtgtgagatg gatccgcgct gattagtcca   240
gttggcgggg taacggccga ccaaagcgac gatcagtagc cgacctgaga gggtgaccgg   300
ccgacagttg ggactgagac acggcccaa                                      329

<210> SEQ ID NO 105
<211> LENGTH: 326
<212> TYPE: DNA
<213> ORGANISM: Artificial Sequence
<220> FEATURE:
<223> OTHER INFORMATION: OTU277

<400> SEQUENCE: 105
gatgaacgct ggcggcgtgc ttaacacatg caagtcgagc gaagcactaa gacggatttc    60
tttggattga agtctttgtg actgagcggc ggacgggtga gtaacgcgtg ggtaacctgc   120
ctcatacagg gggataacag ttagaaatga ctgctaatac cgcataagcg cacaggatcg   180
catggtctgg tgtggaaaaa ctccggtggt atgagatgga cccgcgtctg attagctagt   240
tggaggggta acggcccacc aaggcgacga tcagtagccg gcctgagagg gtgaacggcc   300
acgattggga ctgagacacg gcccag                                         326

<210> SEQ ID NO 106
<211> LENGTH: 323
<212> TYPE: DNA
<213> ORGANISM: Artificial Sequence
<220> FEATURE:
```

<223> OTHER INFORMATION: OTU279

<400> SEQUENCE: 106

| gatgaacgct ggcggcgtgc ctaacacatg caagtcgaac gaagttagac agaggaagtt | 60 |
| ttcggatgga atcggtataa cttagtggcg gacgggtgag taacgcgtgg gaacctgccc | 120 |
| tgtaccgggg gagtaacact tagaaatagg tgctaatacc gcataagcgc acggaaccgc | 180 |
| atggttctgt gtgaaaaact accggtggta caggatggtc ccgcgtctga ttagccagtt | 240 |
| ggcagggtaa cggcctacca aagcgacgat cagtagccgg cctgagaggg tgaacggcca | 300 |
| cattgggact gagacacggc cca | 323 |

<210> SEQ ID NO 107
<211> LENGTH: 315
<212> TYPE: DNA
<213> ORGANISM: Artificial Sequence
<220> FEATURE:
<223> OTHER INFORMATION: OTU280

<400> SEQUENCE: 107

| gatgaacgct ggcggcgtgc ctaatacatg caagtcgaac gctttgtaaa ggagcttgct | 60 |
| tctttacgag gagtggcgaa cgggtgagta atacataagc aatctgccca tcggcctggg | 120 |
| ataacagttg gaaacgactg ctaataccgg ataggttagt ttctggcatc agggactaat | 180 |
| taaagttggg atacaacacg gatggatgag cttatgcgt attagctagt aggtgaggta | 240 |
| acggcccacc taggcgatga tacgtagccg acctgagagg gtgaccggcc acattgggac | 300 |
| tgagacacgg cccaa | 315 |

<210> SEQ ID NO 108
<211> LENGTH: 325
<212> TYPE: DNA
<213> ORGANISM: Artificial Sequence
<220> FEATURE:
<223> OTHER INFORMATION: OTU286

<400> SEQUENCE: 108

| gatgaacgct ggcggcgtgc ttaacacatg caagtcgagc gaagcactaa gacggatttc | 60 |
| ttcggattga agtctttgtg actgagcggc ggacgggtga gtaacgcgtg ggtaacctgc | 120 |
| ctcatacagg gggataacag ttagaaatga ctgctaatac cgcataagcg cacaggatcg | 180 |
| catggtctgg tgtgaaaaac tccggtggta tgagatggac ccgcgtctga ttagccagtt | 240 |
| ggcagggtaa cggcctacca aagcgacgat cagtagccgg cctgagaggg tgaacggcca | 300 |
| cattgggact gagacacggg cccaa | 325 |

<210> SEQ ID NO 109
<211> LENGTH: 329
<212> TYPE: DNA
<213> ORGANISM: Artificial Sequence
<220> FEATURE:
<223> OTHER INFORMATION: OTU287

<400> SEQUENCE: 109

| gacgaacgct ggcggcgcgc ctaacacatg caagtcgaac ggacacatcc gacggaatag | 60 |
| cttgctagga agatggatgt tgttagtggc ggacgggtga gtaacacgtg agcaacctgc | 120 |
| ctcggagtgg gggacaacag ttggaaacga ctgctaatac cgcatacggt ggtcggggga | 180 |
| catcccctgg ccaagaaagg attatatccg ctctgagatg ggctcgcgtc tgattagcta | 240 |
| gttggcgggt aatggcccga ccgaaggcaa cgatcagtag ccggactgag aggttgaacg | 300 |

```
gccacattgg gactgagaca cggccccag                                          329

<210> SEQ ID NO 110
<211> LENGTH: 328
<212> TYPE: DNA
<213> ORGANISM: Artificial Sequence
<220> FEATURE:
<223> OTHER INFORMATION: OTU297

<400> SEQUENCE: 110
gatgaacgct ggcggcgtgc ctaacacatg caagtcgaac gaagcatctt ataggaagtt         60
ttcggatgga atatgggatg actgagtggc ggacgggtga gtaacgcgtg gataacctgc        120
ctcacactgg gggagtaaca gttagaaatg ctgctaata ccccactaag cgcacggtac         180
cgcatggtac ggtgtgaaaa acccaggtgg tgtgagatgg atccgcgtct gattagccag        240
ttggcggggt aacggcccga ccaaacgcga cgatcagtag ccgacctgag agggtgaccg        300
gccgacattg ggactgagac acggccca                                           328

<210> SEQ ID NO 111
<211> LENGTH: 326
<212> TYPE: DNA
<213> ORGANISM: Artificial Sequence
<220> FEATURE:
<223> OTHER INFORMATION: OTU303

<400> SEQUENCE: 111
gatgaacgct ggcggcgtgc ctaacacatg caagtcgaac gaagcatttt agatgaagtt         60
ttcggatgga ttctgagatg actgagtggc ggacgggtga gtaacacgtg gataacctgc        120
ctcacactgg gggacaacag ttagaaatga ctgctaatac cgcataagcg cacagtaccg        180
catggtacag cgtgaaaaac tccggtggtg tgagatggat ccgcgtctga ttagccagtt        240
ggcggggtaa cggcccacca aagcgacgat cagtagccga cctgagaggg tgaccggcac        300
attggggact gagaccacgg gcccaa                                             326

<210> SEQ ID NO 112
<211> LENGTH: 310
<212> TYPE: DNA
<213> ORGANISM: Artificial Sequence
<220> FEATURE:
<223> OTHER INFORMATION: OTU304

<400> SEQUENCE: 112
attgaacgct ggcggcaggc ctaacacatg caagtcgaac ggtaacagga agcagcttgc         60
tgctttgctg acgagtggcg gacgggtgag taatgtctgg gaaactgccc gatggagggg        120
gataactact ggaaacggta gctaataccg cataacgtcg caagaccaaa gagggggacc        180
ttagggcctc ttgccatcgg atgtgcccag atgggattag ctagtaggtg gggtaaaggc        240
tcacctaggc gacgatccct agctggtctg agaggatgac cagccacact ggaactgaga        300
cacggtccag                                                               310

<210> SEQ ID NO 113
<211> LENGTH: 325
<212> TYPE: DNA
<213> ORGANISM: Artificial Sequence
<220> FEATURE:
<223> OTHER INFORMATION: OTU307

<400> SEQUENCE: 113
```

```
gatgaacgct ggcggcgtgc ctaacacatg caagtcgaac gaagcatctt ataggaagtt      60
ttcggatgga atatgggatg actgagtggc ggacgggtga gtaacgcgtg gagtaacctg     120
cctcacactg ggggataaca gttagaaatg gctgctaata ccccataagc gcacagtacc     180
gcatggtacg gtgtgaaaaa cccaggtggt gtgagatgga tccgcgtctg attagccagt     240
tggcgggtaa cggccgacca aagcgacgat cagtagccga cctgagaggg tgaccggcac     300
gattgggacc tgagacacgg gccca                                           325

<210> SEQ ID NO 114
<211> LENGTH: 323
<212> TYPE: DNA
<213> ORGANISM: Artificial Sequence
<220> FEATURE:
<223> OTHER INFORMATION: OTU312

<400> SEQUENCE: 114
gatgaacgct ggcggcgtgc ctaacacatg caagtcgaac gaagttatat cgaggaagtt      60
ttcggatgga atcagtataa cttagtggcg gacgggtgag taacgcgtgg gaaacctgcc     120
ctgtaccggg ggataacact tagaaatagg tgctaatacc gcataagcgc acagcttcac     180
atgaagcagt gtgaaaaact ccggtggtat gagatgaccc gcgtctgat  tagctagttg     240 gaggggtaac ggcccaccaa ggcgacgatc agtagccggc ctgagagggt aacggccac      300 attgggactg agacacggcc cag                                             323

<210> SEQ ID NO 115
<211> LENGTH: 301
<212> TYPE: DNA
<213> ORGANISM: Artificial Sequence
<220> FEATURE:
<223> OTHER INFORMATION: OTU313

<400> SEQUENCE: 115
gatgaacgct ggcggcgtgc ctaatacatg caagtcgaac gcgggcagca atgcccgagt      60
ggcgaacggg tgagtaatac ataagtaacc tgcccttta  aggggataa  ctattggaaa     120 cgatagctaa gaccgcatag gtaaagatac cgcatggtaa gtttattaaa gtgccaaggc     180
actggtagag gatggactta tggcgcatta gctagttggt gaggtaacgg ctcaccaagg     240
cgacgatgcg tagccgacct gagagggtga ccggccacac tgggactgag acacggccca     300
a                                                                     301

<210> SEQ ID NO 116
<211> LENGTH: 322
<212> TYPE: DNA
<213> ORGANISM: Artificial Sequence
<220> FEATURE:
<223> OTHER INFORMATION: OTU319

<400> SEQUENCE: 116
gatgaacgct ggcggcgtgc ctaacacatg caagtcgaac gaagttagac agaggaagtt      60
ttcggatgga atcggtataa cttagtggcg gacgggtgag taacgcgtgg gaaacctgcc     120
ctgtaccggg ggataacact tagaaatgac tgctaatacc gcataagcgc acagtaccgc     180
atggtacagt gtgaaaaact ccggtggtgt gagatggatc cgcgtctgat tagccagttg     240
gcggggtaac ggcccaccaa agcgacgatc agtagccgac ctgagagggt gaccggcaca     300
ttgggactga gacacggccc aa                                              322
```

```
<210> SEQ ID NO 117
<211> LENGTH: 324
<212> TYPE: DNA
<213> ORGANISM: Artificial Sequence
<220> FEATURE:
<223> OTHER INFORMATION: OTU326

<400> SEQUENCE: 117
gatgaacgct ggcggcgtgc ctaacacatg caagtcgaac gaagcaatta aaatgaagtt      60
ttcggatgga tttttgattg actgagtggc ggacgggtga gtaacgcgtg gataacctgc     120
ctcacactgg gggataacag ttagaaatga ctgctaatac cgcataagcg cacagcttca     180
catgaagcag tgtgaaaaac tccggtggta caggatggtc ccgcgtctga ttagccagtt     240
ggcagggtaa cggcctacca aagcgacgat cagtagccgg cctgagaggg tgaacggcca     300
cattgggact gagacacggc ccaa                                             324

<210> SEQ ID NO 118
<211> LENGTH: 324
<212> TYPE: DNA
<213> ORGANISM: Artificial Sequence
<220> FEATURE:
<223> OTHER INFORMATION: OTU328

<400> SEQUENCE: 118
gatgaacgct ggcggcgtgc ttaacacatg caagtcgaac ggagtgcctt agaaagagga      60
ttcgtccaat tgataaggtt acttagtggc ggacgggtga gtaacgcgtg aggaacctgc     120
ctcggagtgg ggaataacag accgaaaggt ctgctaatac cgcatgatgc agttggaccg     180
catggtcctg actgccaaag atttatcgct ctgagatggc ctcgcgtctg attagcttgt     240
tggcggggta atggcccacc aaggcgacga tcagtagccg gactgagagg ttggccggcc     300
acattgggac tgagacacgg ccca                                             324

<210> SEQ ID NO 119
<211> LENGTH: 323
<212> TYPE: DNA
<213> ORGANISM: Artificial Sequence
<220> FEATURE:
<223> OTHER INFORMATION: OTU333

<400> SEQUENCE: 119
gatgaacgct ggcggcgtgc ttaacacatg caagtcgaac ggagtgctca tgacagagga      60
ttcgtccaat ggagtgagtt acttagtggc ggacgggtga gtaacgcgtg agtaacctgc     120
cttggagtgg ggaataacag gtggaaacat ctgctaatac cgcatgatgc agttgggtcg     180
catggctctg actgccaaag atttatcgct ctgagatgga ctcgcgtctg attagctggt     240
tggcgggtaa cggccaccaa ggcgacgatc agtagccgga ctgagaggtt ggccggccac     300
attgggactg agacacggcc cag                                              323

<210> SEQ ID NO 120
<211> LENGTH: 323
<212> TYPE: DNA
<213> ORGANISM: Artificial Sequence
<220> FEATURE:
<223> OTHER INFORMATION: OTU339

<400> SEQUENCE: 120
gatgaacgct ggcggcgtgc ctaacacatg caagtcgaac gaagcaatta aaatgaagtt      60
ttcggatgga tttttgattg actgagtggc ggacgggtga gtaacgcgtg gataacctgc     120
```

```
ctcacactgg ggataacagt tagaaatgac tgctaatacc gcataagcgc acagtaccgc    180
atggtacggt gtgaaaaact ccggtggtgt gagatggatc cgcgtctgat tagccagttg    240
cggggtaacg gcccgaccaa gcgacgatca gtagccgacc gtgagaggtg accggcccac    300
attgggactg agacacggcc caa                                             323

<210> SEQ ID NO 121
<211> LENGTH: 315
<212> TYPE: DNA
<213> ORGANISM: Artificial Sequence
<220> FEATURE:
<223> OTHER INFORMATION: OTU340

<400> SEQUENCE: 121
gacgaacgct ggcggcgcgc ctaacacatg caagtcgaac ggagttgtgt tgaaagcttg     60
ctggatatac aacttagtgg cggacgggtg agtaacacgt gagtaacctg cctctcagag    120
tggaataacg tttggaaacg aacgctaata ccgcataacg tgagaagagg gcatcctctt    180
tttaccaaag atttatcgct gagagatggg ctcgcgccg attaggtagt tggtgagata     240 acagccacc aagccgacga tcggtagccg gactgagagg ttgatcggcc acattgggac     300
tgagacacgg cccag                                                     315

<210> SEQ ID NO 122
<211> LENGTH: 325
<212> TYPE: DNA
<213> ORGANISM: Artificial Sequence
<220> FEATURE:
<223> OTHER INFORMATION: OTU353

<400> SEQUENCE: 122
gatgaacgct ggcggcgtgc ttaacacatg caagtcgagc gaagcacctt gacggattct     60
tcggattgaa gccttggtga ctgagcggcg gacgggtgag taacgcgtgg gtaacctgcc    120
tcatacaggg gggataaaca gttagaaatg actgctaata ccgcataagc gcacaggacc    180
gcatggtctg gtgtgaaaaa ctccggtggt atgagatgga cccgcgtctg attagctagt    240
tggaggggta acggcccacc aaggcgacga tcagtagccg gcctgagagg gtgaacggcc    300
acattgggac tgaggacacg gccca                                          325

<210> SEQ ID NO 123
<211> LENGTH: 317
<212> TYPE: DNA
<213> ORGANISM: Artificial Sequence
<220> FEATURE:
<223> OTHER INFORMATION: OTU173

<400> SEQUENCE: 123
gacgaacgct ggcggcgcgc ctaacacatg caagtcgaac ggagttgtgt tgaaagcttg     60
ctggatatac aacttagtgg cggacgggtg agtaacgcgt gggtaacctg cctcatacag    120
ggggataaca gttagaaatg actgctaata ccgcataagc gcacaggatc gcatggtctg    180
gtgtgaaaaa ctccggtggt atgagatgga cccgcgtctg attaactagt tggaggggta    240
acggcccacc aaggcgacga gtcagtagcc ggcctgagag ggtgaacggc cacgattggg    300
actgagacac ggcccag                                                   317
```